US010016363B2

(12) United States Patent
Bromley

(10) Patent No.: US 10,016,363 B2
(45) Date of Patent: *Jul. 10, 2018

(54) PRE-SPRAY EMULSIONS AND POWDERS CONTAINING NON-POLAR COMPOUNDS

(71) Applicant: VIRUN, INC., Walnut, CA (US)

(72) Inventor: Philip J. Bromley, Fullerton, CA (US)

(73) Assignee: Virun, Inc., Pomona, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/866,717

(22) Filed: Sep. 25, 2015

(65) Prior Publication Data

US 2016/0081927 A1    Mar. 24, 2016

Related U.S. Application Data

(63) Continuation of application No. PCT/US2015/051097, filed on Sep. 18, 2015.

(60) Provisional application No. 62/052,433, filed on Sep. 18, 2014, provisional application No. 62/052,450, filed on Sep. 18, 2014.

(51) Int. Cl.

| | |
|---|---|
| A61K 9/16 | (2006.01) |
| A61K 35/60 | (2006.01) |
| A61K 31/201 | (2006.01) |
| A61K 31/202 | (2006.01) |
| A61K 31/23 | (2006.01) |
| A61K 31/05 | (2006.01) |
| A61K 31/4375 | (2006.01) |
| A61K 31/36 | (2006.01) |
| A61K 31/12 | (2006.01) |
| A61K 31/685 | (2006.01) |
| A61K 31/355 | (2006.01) |
| A61K 31/385 | (2006.01) |
| A61K 31/352 | (2006.01) |
| A61K 31/475 | (2006.01) |
| A61K 47/22 | (2006.01) |
| A61K 47/36 | (2006.01) |
| A61K 36/82 | (2006.01) |
| A61K 36/324 | (2006.01) |
| A61K 45/06 | (2006.01) |
| A61K 9/107 | (2006.01) |
| A23P 10/40 | (2016.01) |
| A23L 33/10 | (2016.01) |
| A23L 33/12 | (2016.01) |
| A23L 33/15 | (2016.01) |

(52) U.S. Cl.
CPC ............. *A61K 9/107* (2013.01); *A23L 33/10* (2016.08); *A23L 33/12* (2016.08); *A23L 33/15* (2016.08); *A23P 10/40* (2016.08); *A61K 9/1617* (2013.01); *A61K 31/05* (2013.01); *A61K 31/12* (2013.01); *A61K 31/201* (2013.01); *A61K 31/202* (2013.01); *A61K 31/23* (2013.01); *A61K 31/352* (2013.01); *A61K 31/355* (2013.01); *A61K 31/36* (2013.01); *A61K 31/385* (2013.01); *A61K 31/4375* (2013.01); *A61K 31/475* (2013.01); *A61K 31/685* (2013.01); *A61K 35/60* (2013.01); *A61K 36/324* (2013.01); *A61K 36/82* (2013.01); *A61K 45/06* (2013.01); *A61K 47/22* (2013.01); *A61K 47/36* (2013.01)

(58) Field of Classification Search
CPC .. A61K 2300/00; A61K 36/324; A61K 36/82; A61K 31/00; A61K 31/05; A61K 31/12; A61K 31/201; A61K 31/202; A61K 31/23; A61K 31/352; A61K 31/355; A61K 31/36; A61K 31/385; A61K 31/4375; A61K 31/475; A61K 31/685; A61K 35/60; A61K 45/06; A61K 47/22; A61K 47/36; A61K 9/107; A61K 9/1617; A23L 33/10; A23L 33/12; A23L 33/15; A23P 10/40

See application file for complete search history.

(56) References Cited

U.S. PATENT DOCUMENTS

| | | | |
|---|---|---|---|
| 2,680,749 A | 6/1954 | Cawley et al. | 549/410 |
| 3,102,078 A | 8/1963 | Robeson et al. | 514/458 |
| 3,480,616 A | 11/1969 | Osipow et al. | 536/119 |
| 3,538,119 A | 11/1970 | Grant | 549/410 |
| 3,644,333 A | 2/1972 | Osipow et al. | 536/119 |
| 3,714,144 A | 1/1973 | Feuge et al. | 536/119 |
| 3,917,859 A | 11/1975 | Terada et al. | 426/602 |
| 4,353,365 A | 10/1982 | Hallworth et al. | 128/203.15 |
| 4,524,769 A | 6/1985 | Wetterlin et al. | 128/203.15 |

(Continued)

FOREIGN PATENT DOCUMENTS

| | | |
|---|---|---|
| WO | WO 95/31217 | 11/1995 |
| WO | WO 1996/36316 | 11/1996 |

(Continued)

OTHER PUBLICATIONS

Letter/Written Disclosure of the Supplemental Information Disclosure Statement for the above-referenced application, filed herewith on Dec. 16, 2015, 2 pages.

Goddeeris et al., "Free flowing solid dispersions of the anti-HIV drug UC 781 with Poloxamer 407 and a maximum amount of TPGS 1000: investigating the relationship between physicochemical characteristics and dissolution behaviour." Eur. J. Pharm. Sci. 35:104-113 (2008).

Gordon, A. and Shaughnessy, A. "Saw palmetto for prostate disorders," American Family Physician 67(6):1281-1283 (2003).

Griffin, W., "Classification of surface-reactive agents by HLB," J. Soc. Cos. Chem. 1:311-326 (1949).

(Continued)

*Primary Examiner* — Michael B. Pallay
(74) *Attorney, Agent, or Firm* — Dentons US LLP; Stephanie Seidman

(57) ABSTRACT

Provided are compositions and methods for producing water-soluble powders that contain additives such as essential fatty acids, including omega-3 fatty acids, omega-6 fatty acids, conjugated fatty acids, and other fatty acids; phytochemicals, including phytosterols; other oils; and coenzymes, including coenzyme Q10, and other oil-based additives.

32 Claims, No Drawings

(56) References Cited

U.S. PATENT DOCUMENTS

| | | | |
|---|---|---|---|
| 4,572,915 A | 2/1986 | Crooks | 514/458 |
| 4,665,204 A | 5/1987 | Wirth | 549/410 |
| 4,670,285 A | 6/1987 | Clandinin et al. | 426/602 |
| 4,710,567 A | 12/1987 | Kea et al. | 536/119 |
| 4,835,002 A | 5/1989 | Wolf et al. | 426/590 |
| 4,849,227 A | 7/1989 | Cho | 424/498 |
| 4,867,986 A | 9/1989 | Desai et al. | 424/464 |
| 4,898,935 A | 2/1990 | Nakamura et al. | 536/119 |
| 4,916,163 A | 4/1990 | Shah et al. | 514/593 |
| 4,995,911 A | 2/1991 | Matsumoto et al. | 127/48 |
| 4,996,309 A | 2/1991 | Matsumoto et al. | 536/119 |
| 5,011,922 A | 4/1991 | Matsumoto et al. | 536/119 |
| 5,017,697 A | 5/1991 | Matsumoto et al. | 536/127 |
| 5,035,237 A | 7/1991 | Newell et al. | 128/203.15 |
| 5,179,122 A | 1/1993 | Greene et al. | 514/458 |
| 5,234,695 A | 8/1993 | Hobbs et al. | 424/489 |
| 5,239,993 A | 8/1993 | Evans et al. | 128/203.15 |
| 5,397,591 A | 3/1995 | Kyle et al. | 426/602 |
| 5,407,957 A | 4/1995 | Kyle et al. | 514/547 |
| 5,415,162 A | 5/1995 | Caspser et al. | 128/203.12 |
| 5,430,021 A | 7/1995 | Rudnic et al. | 514/10.1 |
| 5,492,938 A | 2/1996 | Kyle et al. | 514/786 |
| 5,583,105 A | 12/1996 | Kovacs et al. | 514/20.5 |
| 5,597,595 A | 1/1997 | Dewille et al. | 426/74 |
| 5,711,983 A | 1/1998 | Kyle et al. | 426/635 |
| 5,715,810 A | 2/1998 | Armstrong et al. | 128/230.15 |
| 5,798,333 A | 8/1998 | Sherman et al. | 514/11 |
| 5,843,891 A | 12/1998 | Sherman et al. | 514/11 |
| 5,891,469 A | 4/1999 | Amselem | 424/451 |
| 6,045,826 A | 4/2000 | Borowy-Borowski et al. | 424/451 |
| 6,048,566 A | 4/2000 | Behnam et al. | 426/590 |
| 6,056,971 A | 5/2000 | Goldman | 424/439 |
| 6,136,851 A | 10/2000 | Bonte et al. | 424/455 |
| 6,162,474 A | 12/2000 | Chen et al. | 426/72 |
| 6,180,130 B1 | 1/2001 | Chen et al. | 424/439 |
| 6,184,255 B1 | 2/2001 | Mae et al. | 514/720 |
| 6,193,985 B1 | 2/2001 | Sonne et al. | 424/400 |
| 6,248,363 B1 | 6/2001 | Patel et al. | 424/497 |
| 6,265,717 B1 | 7/2001 | Sakata et al. | 250/289 |
| 6,267,985 B1 | 7/2001 | Chen et al. | 424/451 |
| 6,284,268 B1 | 9/2001 | Mishra et al. | 424/455 |
| 6,378,519 B1 | 4/2002 | Davies et al. | 128/203.21 |
| 6,426,362 B1 | 7/2002 | Miller et al. | 514/458 |
| 6,441,050 B1 | 8/2002 | Chopra | 514/675 |
| 6,509,044 B2 | 1/2003 | Van Den Braak et al. | 426/2 |
| 6,534,085 B1 | 3/2003 | Zeligs | 424/451 |
| 6,589,516 B1 | 7/2003 | Eyre et al. | 424/70.1 |
| 6,632,443 B2 | 10/2003 | Borowy-Borowski et al. | 424/400 |
| 6,761,903 B2 | 7/2004 | Chen et al. | 424/451 |
| 6,870,077 B2 | 3/2005 | Kenaschuk | 800/298 |
| 6,977,166 B1 | 12/2005 | Ratledge et al. | 435/134 |
| 6,982,282 B2 | 1/2006 | Lambert et al. | 424/405 |
| 7,026,361 B2 | 4/2006 | Minemura et al. | 516/75 |
| 7,906,140 B2 | 3/2011 | Bromley et al. | 424/450 |
| 8,252,323 B2 | 8/2012 | Bromley | 424/450 |
| 8,282,977 B2 | 10/2012 | Bromley | 426/72 |
| 8,337,931 B2 | 12/2012 | Bromley | 426/602 |
| 8,414,914 B2 | 4/2013 | Bromley et al. | 424/450 |
| 8,741,373 B2 | 6/2014 | Bromley | 514/560 |
| 8,765,661 B2 | 7/2014 | Bromley | 514/1 |
| 9,320,295 B2 | 4/2016 | Bromley | 424/94.1 |
| 9,351,517 B2 * | 5/2016 | Bromley | A23C 9/158 |
| 9,693,574 B2 * | 7/2017 | Bromley | A23L 29/212 |
| 2001/0025058 A1 | 9/2001 | Borowy-Borowski et al. | 541/772.4 |
| 2003/0072798 A1 | 4/2003 | Schwarz | 424/456 |
| 2004/0072330 A1 | 4/2004 | Ratledge et al. | 435/258.1 |
| 2004/0086619 A1 | 5/2004 | Zhong et al. | 426/590 |
| 2004/0115287 A1 | 6/2004 | Chen et al. | 424/731 |
| 2004/0121043 A1 | 6/2004 | Behnam | 514/458 |
| 2004/0191296 A1 * | 9/2004 | Sternberg | A61K 33/00 424/439 |
| 2004/0219274 A1 | 11/2004 | Cook | 426/590 |
| 2005/0002992 A1 | 1/2005 | McCleary et al. | 424/439 |
| 2005/0008581 A1 | 1/2005 | Parkhideh | 424/46 |
| 2005/0208082 A1 | 9/2005 | Papas et al. | 424/400 |
| 2005/0281772 A1 | 12/2005 | Bromley et al. | 424/70.14 |
| 2006/0088558 A1 | 4/2006 | Jandzinski et al. | 424/400 |
| 2006/0134299 A1 | 6/2006 | Lahteenmaki | 426/590 |
| 2006/0165735 A1 | 7/2006 | Abril | 426/601 |
| 2006/0165769 A1 | 7/2006 | Hyatt et al. | 424/450 |
| 2007/0003614 A1 | 1/2007 | Chen et al. | 424/456 |
| 2007/0087104 A1 | 4/2007 | Chanamai | 426/602 |
| 2007/0104780 A1 | 5/2007 | Lipari et al. | 424/456 |
| 2007/0141203 A1 | 6/2007 | Cook et al. | 426/72 |
| 2007/0141224 A1 | 6/2007 | Zawistowski | 426/611 |
| 2007/0160738 A1 | 7/2007 | Van Bokkelen et al. | 426/601 |
| 2007/0166411 A1 | 7/2007 | Anthony et al. | 424/750 |
| 2007/0184117 A1 | 8/2007 | Gregory et al. | 424/489 |
| 2007/0213234 A1 | 9/2007 | Yaghmur | 508/110 |
| 2007/0298083 A1 | 12/2007 | Mehansho et al. | 426/590 |
| 2007/0298156 A1 | 12/2007 | Mehansho et al. | 426/590 |
| 2008/0058418 A1 | 3/2008 | D'Angelo et al. | 514/560 |
| 2008/0070981 A1 | 3/2008 | Borowy-Borowski et al. | 514/458 |
| 2008/0233056 A1 | 9/2008 | Berl | 424/49 |
| 2008/0254188 A1 | 10/2008 | Borowy-Borowski et al. | 424/400 |
| 2008/0311255 A1 | 12/2008 | Feltes et al. | 426/98 |
| 2009/0018186 A1 | 1/2009 | Chen et al. | 426/590 |
| 2009/0297491 A1 | 12/2009 | Bromley | 424/94.1 |
| 2009/0297665 A1 | 12/2009 | Bromley | 426/72 |
| 2009/0317532 A1 | 12/2009 | Bromley | 426/590 |
| 2010/0041622 A1 | 2/2010 | Bromley et al. | 514/52 |
| 2010/0080785 A1 | 4/2010 | Berl | 424/94.1 |
| 2010/0104730 A1 | 4/2010 | Mehansho et al. | 426/590 |
| 2010/0136175 A1 | 6/2010 | Skiff et al. | 426/72 |
| 2010/0166915 A1 | 7/2010 | Mathisen et al. | 426/477 |
| 2010/0279413 A1 | 11/2010 | Fain | 435/406 |
| 2010/0284987 A1 | 11/2010 | Diguet et al. | 424/94.4 |
| 2011/0008305 A1 | 1/2011 | Yu et al. | 424/94.1 |
| 2011/0015266 A1 | 1/2011 | Hanefeld et al. | 252/363.5 |
| 2011/0081330 A1 | 4/2011 | Hitzfeld et al. | 424/94.1 |
| 2011/0118351 A1 | 5/2011 | Berl | 514/560 |
| 2611/0117184 | 5/2011 | Bromley | 424/450 |
| 2011/0130562 A1 | 6/2011 | Berl | 540/604 |
| 2011/0135745 A1 | 6/2011 | Mathisen et al. | 424/522 |
| 2011/0184194 A1 | 7/2011 | Bed | 549/410 |
| 2011/0236364 A1 | 9/2011 | Bromley | 424/94.1 |
| 2012/0016026 A1 * | 1/2012 | Bromley | A23D 7/0053 514/560 |
| 2012/0093998 A1 | 4/2012 | Voelker et al. | 426/590 |
| 2012/0128815 A1 | 5/2012 | Poulos et al. | 426/74 |
| 2012/0251685 A1 | 10/2012 | Wang-Nolan et al. | 426/250 |
| 2012/0308644 A1 | 12/2012 | Bromley et al. | 424/450 |
| 2013/0017183 A1 | 1/2013 | Bromley | 424/94.1 |
| 2013/0017295 A1 | 1/2013 | Bromley | 426/66 |
| 2013/0309362 A1 | 11/2013 | Bromley | 424/72 |
| 2014/0039052 A1 | 2/2014 | Borowy-Borowski et al. | 514/560 |
| 2014/0086993 A1 | 3/2014 | Guth et al. | 424/489 |
| 2014/0227242 A1 | 8/2014 | Bromley et al. | 424/94.1 |
| 2014/0242055 A1 | 8/2014 | Bromley | 424/94.1 |
| 2014/0271593 A1 | 9/2014 | Bromley | 424/94.1 |
| 2015/0110924 A1 | 4/2015 | Bromley | 426/72 |
| 2016/0081975 A1 | 3/2016 | Bromley | 424/464 |
| 2016/0081976 A1 | 3/2016 | Bromley | 424/456 |
| 2016/0193146 A1 | 7/2016 | Bromley | 424/94.1 |
| 2016/0227832 A1 | 8/2016 | Bromley | 424/94.1 |
| 2017/0182133 A1 | 6/2017 | Bromley et al. | 424/450 |

FOREIGN PATENT DOCUMENTS

| | | |
|---|---|---|
| WO | WO 98/08490 | 3/1998 |
| WO | WO 00/23545 | 4/2000 |
| WO | WO 02/017879 | 3/2002 |
| WO | WO 02/076970 | 10/2002 |
| WO | WO 2004/098311 | 11/2004 |
| WO | WO 2005/112654 | 12/2005 |
| WO | WO 2007/080515 | 7/2007 |
| WO | WO 2007/082149 | 7/2007 |

(56) References Cited

FOREIGN PATENT DOCUMENTS

| | | |
|---|---|---|
| WO | WO 2007/149591 | 12/2007 |
| WO | WO 2008/134766 | 11/2008 |
| WO | WO 2009/029046 | 3/2009 |
| WO | WO 2009/115175 | 9/2009 |
| WO | WO 2009/117151 | 9/2009 |
| WO | WO 2009/117152 | 9/2009 |
| WO | WO 2010/008475 | 1/2010 |
| WO | WO 2010/008762 | 1/2010 |
| WO | WO 2010/021820 | 2/2010 |
| WO | WO 2011/040141 | 4/2011 |
| WO | WO 2011/119228 | 9/2011 |
| WO | WO 2011/149854 | 12/2011 |
| WO | WO 2013/032934 | 3/2013 |
| WO | WO 2013/120025 | 8/2013 |
| WO | WO 2014/151109 | 9/2014 |
| WO | WO 2016/044813 | 3/2016 |

OTHER PUBLICATIONS

Gutmann, V., "Solvent effects on the reactivities of organometallic compounds," Coord. Chem. Rev. 18:225-255 (1976).

Higgins, K.T., "Emerging Plant Technologies Help Processors Make Better Beverages," Food Processing, found at: http://www.foodprocessing.com/articles/2013/beverage-technology/?show=all [accessed Dec. 17, 2013], 3 pages.

Ju et al., "Cancer-preventive activities of tocopherols and tocotrienols." Carcinogenesis 31(4):533-542 (2010).

Kong et al., "Direct quantification of mono- and di-D-α-tocopherol polyethylene glycol 1000 succinate by high performance liquid chromatography." J. Chromatography A 1218:8664-8671 (2011).

Kosower, E., "2.6 Solvent polarity: Empirical Measures," found in an Introduction to Physical Organic Chemistry, New York:Wiley, p. 293 (1969).

Landfester, K., "Miniemulsions for Nanoparticle Synthesis: Formation of particles in inverse microemulsion," Colloid Cheimstry II, vol. 227. Ed. M. Antionietti. New York: Springer, 2003 pp. 97-99.

Lands, W., "Biochemistry and physiology of n-3 fatty acids," The FASEB Journal, 6(8):2530-2536 (1992).

Li et al., "δ-tocopherol is more active than α- or γ-tocopherol in inhibiting lung tumorigenesis in vivo." Cancer Prev. Res. (Phila.) 4(3):404-413 (2011).

Lipshutz et al. "TPGS-750-M: a second-generation amphiphile for metal-catalyzed cross-couplings in water at room temperature." J. Org. Chem. 76(11):4379-4391 (2011).

Lowery et al., "2.4 Solutions," found in Mechanism and Theory in Organic Chemistry, Harper Collins Publishers, 3rd ed., p. 177 (1987).

NutraBIOsciences™ food-beverage technology evolved product brochure, published May 21, 2014 [online] [available at http://www.beveragedaily.com/smartlead/view/918190/4/NutraBIOsciences-food-beverage-technology-evolved] [accessed on Jun. 2, 2014], 3 pages.

Offer for Sale, "Kaneka Liquid CoQ10" formulation, to Kaneka Nutrients L.P., Pasadena, TX, on Jun. 22-27, 2007, 2 pages.

Okamoto et al., "Effect of sucrose fatty acid esters on transdermal permeation of lidocaine and ketoprofen," Biol. Pharm. Bull., 28(9):1689-1694 (2005).

Partial Translation of Ling, X., "Research on the preparation of natural vitamin E derivatives," Wufang Database, published Sep. 18, 2006, 15 pages.

Perry, R. and D. Green, *Perry's Chemical Engineers' Handbook*, Sixth Edition, New York:McGraw-Hill, pp. 20-54 to 20-57 (1984).

Press Release: "DSM: 'Consumers are searching for new ways to add omega-3s into their diet'" Jul. 27, 2015 [online] [Retrieved from:<URL:nutraingredients-usa.com/content/view/print/1145391] [accessed on Nov. 4, 2015], 2 pages.

Press Release: "Hormel Foods Specialty Products Division and VIRUN®, Granted U.S. Pat. No. 8,741,373" Jul. 9, 2014 [online] [retrieved at http://www.pr.com/press-release/569191] [accessed on Aug. 20, 2014], 2 pages.

Press Release, "OmegaH2O® clear shelf stable Omega-3, CoQ10 and other non polar compounds U.S. Appl. No. 12/383,244 approved in Europe and Notice of Allowance in U.S.," Published on Jun. 4, 2012 [online] Retrieved from:<URL:prcom/press-release/417599 [4 pages].

Press Release: "The State of California Invests in VIRUN® NutraBIOsciences™; VIRUN® Receives Two More Patent Grants in China While Premiering Esolv® Vitamin E Encapsulator" Apr. 7, 2015 [online] [retrieved at http://pdf.pr.com/press-release/pr-613759.pdf] [accessed on Nov. 4, 2015], 4 pages.

Press Release: "Virun and Vital Pharmaceuticals expand operations," Published on Oct. 31, 2013, Retrieved from:<URL:bevnet.com/news/supplier-news/2013/virun-and-vital-pharmaceuticals-expand-operations/, accessed on Dec. 17, 2013, 2 pages.

Press Release: "VIRUN NutraBIOsciences™, Leader in Cognitive-Functional-Ingredients, to Sponsor Cognitive Health Forum at NutraIngredients-USA" May 13, 2014 [online] [retrieved at http://www.pr.com/press-release/557966] [accessed on Jun. 2, 2014], 3 pages.

Press Release: "VIRUN® & Pacific Deep Ocean Biotech Combine Natural Mineral Complexes with OmegaH2O® EPA and DHA for Foods, Beverages & Supplements" Jun. 18, 2014 [online] [retrieved at http://www.pr.com/press-release/565168] [accessed on Aug. 20, 2014], 2 pages.

Ross et al., "Omega-3 fatty acids as treatments for mental illness: which disorder and which fatty acid?," Lipids in Health and Disease 6:21 pp. 1-19 (2007).

Schultz, H., "PQQ set to make splash in sports nutrition beverages," nutraingredients-usa.com Aug. 6, 2013 [online] Retrieved from:<URL:nutraingredients-usa.com/content/view/print/807624] [accessed on Aug. 16, 2013], 2 pages.

Scientific Panel of the European Food Safety Authority, "Opinion of the Scientific Panel on Food Additives, Flavourings, Processing Aids and Materials in Contact with Food on a request from the Commission related to D-alpha-tocopheryl polyethylene glycol 1000 succinate (TPGS) in use for food for partic ular nutritional purposes." EFSA J. 490:1-20 (2007).

Sheu et al.,"Influence of micelle solubilization by tocopheryl polyethylene glycol succinate (TPGS) on solubility enhancement and percutaneous penetration of estradiol," J. Controlled Release 88:355-368 (2003).

Snyder, L., "Classification of the solvent properties of common liquids," J. Chromatography A 92:223-230 (1974).

Sokol et al., "Improvement of cyclosporin absorption in children after liver transplantation by means of water-soluble vitamin E." Lancet 338:212-215 (1991).

Starling, S., "Virun debuts shelf-stable, H20 soluble, nanotech omega-3," Published on Mar. 12, 2009 [online] Retrieved from:<URL:beveragedaily.com/Products/Virun-debuts-shelf-stable-H20-soluble-nanotech-omega-3, 2 pages.

Stojkovic et al., "Coenzyme Q10 in submicron-sized dispersion improves development, hatching, cell proliferation, and adenosine triphosphate content of in vitro-produced bovine embryos," 61:541-547 (1999).

Swern, D., *Bailey's Industrial Oil and Fat Products*, vol. 1, 4th edition. John Wiley & Sons, New York, p. 387-391, 424-428 (1979).

Traber et al. "Absorption of water-miscible forms of vitamin E in a patient with cholestasis and in thoracic duct-cannulated rats." Am. J. Clin. Nutr. 44:914-923 (1986).

US Pharmacopeia NF-30, Vitamin E Polyethylene Glycol Succinate, pp. 2013-2015 (2012).

Varma et al. "Enhanced oral paclitaxel absorption with vitamin E-TPGS: effect on solubility and permeability in vitro, in situ and in vivo." Eur. J. Pharm. Sci. 25(4-5):445-453 (2005).

Virun Clear Water Soluble Omega-3 DHA, EPA & ALA for Foods & Beverages found at: www.slideshare.net/virun/virun-food-beverage-division-v2 [accessed on May 11, 2009], 6 pages.

Virun Esolv technology Webpage, Retrieved from:<URL:virun.com/omega2.htm [accessed on Jun. 2, 2014], 1 page.

Virun Facebook Webpage, Retrieved from:<URL:facebook.com/pages/Virun/168007462662 [accessed on Aug. 16, 2013], 8 pages.

Virun Facebook Webpage, Retrieved from:<URL:facebook.com/pages/Virun/168007462662 [accessed on Jun. 2, 2014], 14 pages.

(56) References Cited

OTHER PUBLICATIONS

Virun Facebook Page, [online] Retrieved from:<URL:facebook.com/pages/Virun/168007462662, [retrieved on Mar. 10, 2015] 11 pages.
Virun Facebook Webpage, Retrieved from:<URL:facebook.com/pages/Virun/168007462662 [accessed on Dec. 17, 2013], 6 pages.
Virun Facebook Webpage, Retrieved from:<URL:facebook.com/Virun-168007462662/?fref=ts [accessed on Nov. 4, 2015], 18 pages.
Letter/Written Disclosure of the Information Disclosure Statement for the above-referenced application, filed herewith on Dec. 15, 2015, 2 pages.
"Alpha-Tocopherol Polyethylene glycol Succinate (TPGS)," Pure Matters website [online][retrieved on Feb. 26, 2013] Retrieved from:<URL: resources.purematters.com/herbs-supplements/a/alpha-tocopherol-polyethylene-glycol-succinate-tpgs [2 pages.].
Analytical Chemistry an Introduction 6th Ed., Douglas A. Skoog et al., Chapters 22, "Applications of molecular absorption spectroscopy," (pp. 421-442) and 27, "Applications of chromatography," (pp. 509-530) (1994).
Antares Health Products "Vitamin-E TPGS," product brochure distributed at SupplySide Trade Show Oct. 22, 2008, 2 pages.
Argao et al., "d-Alpha-tocopheryl polyethylene glycol-1000 succinate enhances the absorption of vitamin D in chronic cholestatic liver disease of infancy and childhood," Ped. Res. 31(2):146-150 (1992).
Boukley, B., "'Next Generation' Omega-3 sports drink set to hydrate America" Beveragedaily.com Aug. 1, 2013 [online] [retrieved at http://www.beveragedaily.com/content/view/print/804977] [accessed on Aug. 16, 2013 ], 2 pages.
Boukley, B., "Runaway Omega-3 beverage demand 'can be scary'— Virun CEO" Beveragedaily.com Dec. 20, 2012 [online] [retrieved at http://www.beveragedaily.com/content/view/print/711158] [accessed on Aug. 16, 2013], 2 pages.
Boukley, B., "Searching for the Holy Grail: Science-backed functional beverages," Beveragedaily.com Mar. 3, 2013 [online] [retrieved at http://www.beveragedaily.com/content/view/print/749075] [accessed on Aug. 16, 2013], 2 pages.
Bromley, P., "Nanotechnology and nonpolar active compounds in functional foods: an application note," in *Bio-Nanotechnology: A Revolution in Food, Biomedical and Health Sciences* (eds D. Bagchi et al.), Blackwell Publishing Ltd., Oxford, UK, pp. 697-703 (2013).
Brouwers et al., "Intraluminal drug and formulation behavior and integration in in vitro permeability estimation: a case study with amprenavir," J. Pharm. Sci. 95:372-383 (2006).
Certified English translation of German patent DE 10 2005 049664, published Apr. 19, 2007, entitled: "Liquid Composition and Method for its Production," Inventor—Haller, 9 pages.
Christiansen et al., "Investigating the stability of the nonionic surfactants tocopheryl polyethylene glycol succinate and sucrose laurate by HPLC-MS, DAD, and CAD." J. Pharm. Sci. 100(5):1773-1782 (2011).
Certified English translation of International Patent WO 2011/040141, published Apr. 7, 2011, entitled: "Composition Containing Fat-soluble Vitamin," Inventor—Kondo, 17 pages.
Collnot et al., "Influence of vitamin E TPGS poly(ethylene glycol) chain length on apical efflux transporters in Caco-2 cell monolayers." J. Controlled Release 111:35-40 (2006).
Constantinides et al., "Advances in the use of tocols as drug delivery vehicles." Pharm. Res. 23(2):243-255 (2006).
Covington, M., "Omega-3 fatty acids," American Family Physician 70(1):133-140 (2004).
CRC Handbook of Chemistry and Physics, Lide, D., ed., 82nd edition, Cleveland, OH:CRC Press 15(14)-15(18) (2001).
Daniells, S. "Huge demand for omega-3 liquid products driving delivery innovations: Virun CEO," Nutraingredients-usa.com Mar. 20, 2014 [online] [retrieved at http://www.nutraingredients-usa.com/content/view/print/899348] [accessed on Jun. 2, 2014], 2 pages.

Ernst, E., "The risk-benefit profile of commonly used herbal therapies: Ginkgo, St. John's Wort, Ginseng, Echinacea, Saw Palmetto, and Kava," Ann Intern Med. 136(1):42-53 (2002).
Fan, Y. and Chapkin R., "Importance of dietary γ-linolenic acid in human health and nutrition," Journal of Nutrition 128(9):1411-1414 (1998).
Fulzele et al., "Inhalation delivery and anti-tumor activity of celecoxib in human orthotopic non-small cell lung cancer xenograft model." 23(9):2094-2106 (2006).
Gelo-Pujic et al., "Synthesis of new antioxidant conjugates and their in vitro hydrolysis with Stratum corneum enzymes." Int. J. Cosmet. Sci. 30(3):195-204 (2008).
Giddings et al., "High pressure gas chromatography of nonvolatile species. Compressed gas is used to cause migration of intractable solutes," Science, 162:67-73 (1968).
Letter/Written Disclosure of the Supplemental Information Disclosure Statement for the above-referenced application, filed herewith on Aug. 31, 2017, 2 pages.
Virun Static blog, "Three Separations of Product Brands and Distribution from a Developer," Published on Nov. 8, 2016 [online] Retreived from <URL: virun.com/blog [retrieved on Nov. 22, 2016], 2 pages.
Brief of Appellant, filed Feb. 1, 2016, in connection with U.S. Reexamination No. 90/012,700, 78 pages.
Brief of Appellee, filed Apr. 22, 2016, in connection with U.S. Reexamination No. 90/012,700, 52 pages.
Appellant's Reply Brief, filed Jun. 8, 2016, in connection with U.S. Reexamination No. 90/012,700, 42 pages.
Office Action, dated Aug. 29, 2016, in connection with Chinese Patent Application No. 201480027972.8 [Original document in Chinese and English translation], 36 pages.
Communication pursuant to Rule 94(3) EPC, dated Oct. 6, 2016, in connection with European Patent Application No. 14726228.1 [D1=WO2013/120025, D2=US2011/236364, D4=US2008/254188], 4 pages.
Office Action, dated Nov. 29, 2016, in connection with Japanese Patent Application No. 2016-501718 [English summary, original document in Japanese, and English translation], 11 pages.
Office Action, dated Dec. 14, 2016, in connection with U.S. Appl. No. 14/866,808, 11 pages.
International Preliminary Report on Patentability, dated Dec. 15, 2016, in connection with International Patent Application No. PCT/US2015/051083, 11 pages.
Response, filed Feb. 7, 2017, to Examination Report, dated Oct. 6, 2016, in connection with European Patent Application No. 14726228.1, 9 pages.
International Preliminary Report on Patentability, dated Feb. 7, 2017, in connection with International Patent Application No. PCT/US2015/051097, 7 pages.
Office Action, dated Mar. 8, 2017, in connection with U.S. Appl. No. 14/866,724, 9 pages.
Notice of Intent to Issue Ex Parte Reexamination Certificate, issued Mar. 10, 2017, in connection with U.S. Reexamination No. 90/012,700, 5 pages.
Response, filed Mar. 13, 2017, to Office Action, dated Aug. 29, 2016, in connection with Chinese Patent Application No. 201480027972.8 [Document as filed in Chinese, claims in English, and English instructions], 34 pages.
International Search Report and Wntten Opinion, dated Mar. 8, 2017, in connection with International Patent Application No. PCT/US2016/052256, 19 pages.
Notice of Allowance, dated Mar. 24, 2017, in connection with U.S. Appl. No. 14/449,880, 24 pages.
Decision to Grant, dated Mar. 28, 2017, in connection with Japanese Patent Application No. 2016-501718, [Original document in Japanese and English notification letter], 4 pages.
Ex Parte Reexamination Certificate, issued Apr. 14, 2017, in connection with U.S. Reexamination No. 90/012,700, 2 pages.
Notice of Allowance, dated May 1, 2017, in connection with U.S. Appl. No. 14/449,880, 21 pages.
Notice of Acceptance, dated May 9, 2017, in connection with Australian Patent Application No. 2014235283, 3 pages.

(56) References Cited

OTHER PUBLICATIONS

Office Action, dated May 24, 2017, in connection with Chinese Patent Application No. 201480027972.8 [Original document in the Chinese language and English translation], 30 pages.
Response, filed Jun. 14, 2017, to Office Action, dated Dec. 14, 2016, in connection with U.S. Appl. No. 14/866,808, 12 pages.
Intention to Grant (Communication under Rule 71(3) EPC), dated Jun. 22, 2017, in connection with European Patent Application No. 14726228.1, 5 pages.
Notice of Allowance, dated Aug. 28, 2017, in connection with U.S. Appl. No. 14/866,808, 14 pages.
U.S. Appl. No. 60/887,754, filed Feb. 1, 2007, Borowy-Borowski et al.
Letter/Written Disclosure of the Supplemental Information Disclosure Statement for the above-referenced.application, filed herewith on Nov. 30, 2016, 2 pages.
Bromley, P., "Inside Virun: Manufacturing the next generation of supplements, foods and beverages," presented at the 2016 Beverage Innovation: Online Summit, Feb. 18, 2016, Retrieved from: <URL:vts.inxpo.com/scripts/Server.
nxp?LASCmd=AI:1;S:17;F:QP!14100&EventKey=178592 &EventAttendeeKey=14661401&RandomValue=1456260156563 [retrieved on Feb. 23, 2016], 70 pages.
DK Ester Sucrose Esters Applications, Montello Inc., [online] retrieved from <URL: montelloinc.com/dk_ester2.htm [retrieved Sep. 24, 2008], 1 page.
DK Ester Sucrose Esters Properties, Montello Inc., [online] retrieved from <URL: montelloinc.com/dk_ester.htm [retrieved Sep. 24, 2008], 2 pages.
DK Ester Sucrose Esters Specifications, Montello Inc., [online] retrieved from <URL: montelloinc.com/dk_ester3.htm [retrieved Sep. 24, 2008], 1 page.
Eastman PCI-102B Publication, "Vitamin E TPGS NF—Applications and Properties," Eastman Chemical Company, Oct. 2005, 24 pages.
Gander, P. "Sea changes," published Nov. 5, 2013, [online] retrieved from <URL: foodmanufacture.co.uk/content/view/print/843822 [retrieved Dec. 17, 2013], 2 pages.
Idris et al., "Characterisation of gum from Acacia senegal trees of different age and location using multidetection gel permeation chromatography," Food Hydrocolloids 12(4):379-388 (1998).
Ling, X., "Research on the Preparation of Natural Vitamin E Derivatives," Wufang Database, published Sep. 18, 2006 [English abstract and main document in Chinese], 67 pages.
Surfhope SE Pharma, Mitsubishi-Kagaku Foods Corporation, [online] retrieved from <URL: mfc.co.jp/english/se_pharma/ sepharma.htm [retrieved on Sep. 25, 2008], 3 pages.
Tadros, T. "Emulsion Science and Technology: A General Introduction." Emulsion Science and Technology. Ed. T. Tadros. Wienheim: Wiley-VCH, 2009, pp. 1-56.
Virus Esolv—functional beverages cognitive ingredients, Product Pamphlet, Published on Feb. 10, 2016 [online] Retrieved from: <URL:vts.inxpo.com/scripts/Server.
nxp?LASCmd=AI:1;S:41008;F:LBSATTACH!V&AttachmentKey=1309416 [retrieved on Feb. 23, 2016], 4 pages.
Virun Facebook Page [online] Retrieved from: <URL: facebook. com/Virun-168007462662/?fref=ts [retrieved on May 31, 2016], 6 pages.
Response, filed Dec. 3, 2015, to Communication pursuant to Rules 161(1) and 162 EPC, dated Oct. 22, 2015, in connection with European Patent Application No. 14726228.1, 16 pages.
International Search Report and Written Opinion, dated Dec. 15, 2015, in connection with International Patent Application No. PCT/US2015/051083, 15 pages.
International Search Report and Written Opinion, dated Jan. 5, 2016, in connection with International Patent Application No. PCT/US2015/051097, 12 pages.
Response, filed Jul. 15, 2016, to International Search Report and Written Opinion, dated Jan. 5, 2016, in connection with International Patent Application No. PCT/US2015/051097, 52 pages.
Response, dated Jul. 18, 2016, to International Search Report and Written Opinion, dated Dec. 15, 2015, in connection with International Patent Application No. PCT/US2015/051083, 35 pages.
Written Opinion, dated Sep. 2, 2016, in connection with International Patent Application No. PCT/US2015/051083, 11 pages.
Written Opinion, dated Sep. 26, 2016, in connection with International Patent Application No. PCT/US2015/051097, 7 pages.
Response, dated Nov. 2, 2016, to Written Opinion, dated Sep. 2, 2016, in connection with International Patent Application No. PCT/US2015/051083, 28 pages.
Judgment, filed Nov. 10, 2016, in connection with U.S. Reexamination No. 90/012,700, U.S. Court of Appeals for the Federal Circuit, Appeal No. 16/1280, in re: Virun, Inc., 5 pages.
Response, dated Nov. 28, 2016, to Written Opinion, dated Sep. 26, 2016, in connection with International Patent Application No. PCT/US2015/051097, 49 pages.
Letter/Written Disclosure of the Supplemental Information Disclosure Statement for the above-referenced application, filed herewith on Dec. 17, 2015, 2 pages.
Virun home Webpage found at www.virun.com [ accessed on Mar. 24, 2011], 49 pages.
Virun home Webpage found at: www.virun.com [accessed on May 1, 2013], 22 pages.
Virun Improving Life Through Safe & Effective Oral Delivery found at: www.slideshare.net/virun/virun-improving-life-throughsafe-effective-oral-delivery [accessed on Aug. 13, 2009], 15 pages.
Virun Intricate Science; found at www.slideshare.net/virun/virunintricate-science [accessed May 25, 2011], 22 pages.
Virun on slideshare.net, Philip Bromley's Presentations on SlideShare found at: www.slideshare.net/virun [accessed on May 8, 2009], 5 pages.
Virun Pharmaceutical & Food Beverage Divisions: www.slideshare. net/virun/virun-food-beverage-divisions [accessed on Aug. 12, 2009], 9 pages.
Virun Product Sheet "Clear oils for water based beverages," Jan. 16, 2009, 4 pages.
Virun, "Virun Omega 3 Fortified Foods and Beverages," retrieved from the Internet:<URL: slideshare.net/virun/virun-omega-3-fortified-foods-and-beverages, [retrieved on May 7, 2010] [15 pages].
Vraka et al. "Synthesis and study of the cancer cell growth inhibitory properties of alpha-, gamma-tocopheryl and ganuna-tocotrienyl 2-phenylselenyl succinates." Bioorg. Med. Chem. 14(8):2684-2696(2006).
Watson, E., "Think you need to pop pills to get a decent dose of omega-3? Think again, say Hormel and Virun" Jul. 16, 2014[online] [retrieved from http://www.foodnavigator-usa.com/Suppliers2/ Hormel-Virun-patent-new-way-to-add-omega-3s-to-foods-beverages] [accessed on Aug. 20, 2014] 5 pages.
Youan et al., "Evaluation of sucrose esters as alternative surfactants in microencapsulation of proteins by the solvent evaporation method," AAPS PharmSci., 5(2):1-9 (2003).
Yu et al. "Vitamin E-TPGS increases absorption flux of an HIV protease inhibitorby enhancing its solubility and permeability," Pharm. Res. 16:1812-1817 (1999).
Zhao et al. "Enhanced oral bioavailability of paclitaxel formulated in vitamin E-TPGS emulsified nanoparticles of biodegradable polymers: in vitro and in vivo studies," J. Pharm. Sci. 99(8):3552-3560 (2010).
International Search Report and Written Opinion, dated Aug. 12, 2014, in connection with International Patent Application No. PCT/US2014/025006, 13 pages.
Response to International Search Report and Written Opinion, dated Jan. 13, 2015, in connection with International Patent Application No. PCT/US2014/025006, 31 pages.
Voluntary Amendment, dated Feb. 26, 2015, in connection with International Patent Application No. PCT/US2014/025006, 27 pages.
International Preliminary Report on Patentability, dated Mar. 23, 2015, in connection with International Patent Application No. PCT/US2014/025006, 6 pages.
Non-final Office Action, dated Jun. 26, 2015, in connection with U.S. Appl. No. 14/207,310, 12 pages.

(56) References Cited

OTHER PUBLICATIONS

Voluntary Amendment (part 1), dated Aug. 18, 2015, in connection with Australian Patent Application No. 2014235283, 289 pages.
Amendment and Response, dated Aug. 26, 2015, to Non-final Office Action, dated Jun. 26, 2015, in connection U.S. Appl. No. 14/207,310, 16 pages.
Final Office Action, dated Dec. 1, 2015, in connection with U.S. Appl. No. 14/207,310, 7 pages.
Response, filed Dec. 4, 2015, to Communication pursuant to Rules 161(1) and 162 EPC, dated Oct. 22, 2015, in connection with European Application No. 14726228.1, 16 pages.
Response, filed Dec. 4, 2015, to Final Office Action, dated Dec. 1, 2015, in connection with U.S. Appl. No. 14/207,310, 10 pages.
Voluntary Amendment (part 2), dated Aug. 18, 2015, in connection with Australian Patent Application No. 2014235283, 294 pages.
Letter/Written Disclosure of the Supplemental Information Disclosure Statement for the above-referenced application, filed herewith on Dec. 21, 2017, 2 pages.
Response, filed Sep. 22, 2017, to Communication pursuant to Rules 161(1) and 162 EPC, dated Apr. 25, 2017, in connection with corresponding European Patent Application No. 15772165.5, 36 pages.
Response, filed Oct. 9, 2017, to Office Action, dated May 24, 2017, in connection with Chinese Patent Application No. 201480027972.8 [English instructions and original document as filed in Chinese], 27 pages.
Response, filed Oct. 27, 2017, to Written Opinion, dated Aug. 30, 2017, in connection with International Patent Application No. PCT/US2016/052256, 40 pages.

\* cited by examiner

PRE-SPRAY EMULSIONS AND POWDERS CONTAINING NON-POLAR COMPOUNDS

RELATED APPLICATIONS

This application is a continuation of International PCT Application No. PCT/US2015/051097, filed Sep. 18, 2015, entitled "PRE-SPRAY EMULSIONS AND POWDERS CONTAINING NON-POLAR COMPOUNDS," to Philip J. Bromley, which claims priority to U.S. Provisional Application Ser. No. 62/052,433, filed Sep. 18, 2014, entitled "PRE-SPRAY EMULSIONS AND POWDERS CONTAINING NON-POLAR COMPOUNDS," to Philip J. Bromley, and to U.S. Provisional Application Ser. No. 62/052,450, filed Sep. 18, 2014, entitled "FORMULATIONS OF WATER-SOLUBLE DERIVATIVES OF VITAMIN E AND SOFT GEL COMPOSITIONS, CONCENTRATES AND POWDERS CONTAINING SAME," to Philip J. Bromley.

This application is related to U.S. application Ser. No. 14/866,808, filed the same day herewith, entitled "FORMULATIONS OF WATER-SOLUBLE DERIVATIVES OF VITAMIN E AND SOFT GEL COMPOSITIONS, CONCENTRATES AND POWDERS CONTAINING SAME," to Philip J. Bromley. U.S. application Ser. No. 14/866,808 also claims priority to U.S. Provisional Application Ser. No. 62/052,450, filed Sep. 18, 2014, entitled "FORMULATIONS OF WATER-SOLUBLE DERIVATIVES OF VITAMIN E AND SOFT GEL COMPOSITIONS, CONCENTRATES AND POWDERS CONTAINING SAME," to Philip J. Bromley.

This application also is related to U.S. patent application Ser. No. 14/207,310, filed Mar. 12, 2014, published as US-2014-0271593-A1 on Sep. 18, 2014, entitled "FORMULATIONS OF WATER-SOLUBLE DERIVATIVES OF VITAMIN E AND COMPOSITIONS CONTAINING SAME," which claims priority to U.S. Provisional Application Ser. No. 61/852,243, filed Mar. 15, 2013, entitled "FORMULATIONS OF PEG DERIVATIVES OF VITAMIN E AND COMPOSITIONS CONTAINING SAME," to Philip Bromley, and International PCT Application No. PCT/US2014/25006, filed Mar. 12, 2014, published as WO 2014/151109 on Sep. 25, 2014, entitled "FORMULATIONS OF WATER-SOLUBLE DERIVATIVES OF VITAMIN E AND COMPOSITIONS CONTAINING SAME," which also claims priority to U.S. Provisional Application Ser. No. 61/852,243, filed Mar. 15, 2013, entitled "FORMULATIONS OF PEG DERIVATIVES OF VITAMIN E AND COMPOSITIONS CONTAINING SAME" and to U.S. Provisional Application Ser. No. 61/863,732, filed Aug. 8, 2013, entitled "FORMULATIONS OF WATER-SOLUBLE DERIVATIVES OF VITAMIN E AND COMPOSITIONS CONTAINING SAME," each to Philip Bromley.

The subject matter of each of the above-referenced applications is incorporated by reference in its entirety.

FIELD OF THE INVENTION

Provided herein are emulsions and dry powders that contain high concentrations and amounts of non-polar ingredients that are or contain one or more non-polar compounds. Also provided are products containing the emulsions and dry powders, including aqueous beverage compositions for human consumption, and methods for preparing the products. Methods for preparing the emulsions, dry powders, and products are provided.

BACKGROUND

Non-polar compounds and ingredients are not easily dissolved in aqueous solutions, such as water or other polar solvents. A number of non-polar compounds and ingredients are used in compositions for human ingestion. These include, for example, pharmaceuticals, nutraceuticals and/or dietary supplements. Exemplary of non-polar compounds and ingredients are vitamins and minerals, fatty acids, and other non-polar compounds and non-polar ingredients. Because of poor water solubility, inclusion of non-polar compounds in products for human consumption, for example, in supplements, foods and beverages, can be problematic, and the amount of non-polar compound that can be included is limited.

Available products containing non-polar compounds, particularly products for human consumption, such as food and beverage products containing non-polar compounds, and methods for formulating such products, are limited. In addition, the amount, or concentration, of non-polar compounds in available food and beverage products is limited due to the display of undesirable organoleptic properties when the amount of non-polar compound is increased. Thus, there is a need to develop products for human consumption, such as food and beverage products, that contain non-polar compounds and methods for making the products. There is an additional need to develop products for human consumption, such as food and beverage products, that contain a higher amount of non-polar compound than is offered in available food and beverage products. There also is a need to develop products for human consumption, such as food and beverage products, that retain their organoleptic properties when they contain a higher amount of non-polar compound. Accordingly, it is among the objects herein to provide food and beverage products containing non-polar compounds, in particular, food and beverage products containing more non-polar compounds than available products, that retain desirable organoleptic properties, and methods for making the products.

SUMMARY

Provided herein is a water-soluble powder containing a mixture of sugar fatty acid ester and a binder, a polyethylene glycol (PEG) derivative of vitamin E, and a non-polar ingredient containing non-polar compounds other than the PEG derivative of vitamin E. The total amount of sugar fatty acid ester and binder in the powder is between 5% and 60%, or 7% and 55%, or 10% and 50%, by weight, of the powder, wherein the mixture of sugar fatty acid ester and binder contains at least 5% sugar fatty acid ester. The polyethylene glycol (PEG) derivative of vitamin E is present in the powder in an amount of from between 0.1% and 20%, or 0.1% and 25%, or 2% and 15%, by weight, of the powder. The non-polar ingredient containing non-polar compounds, other than the PEG derivative of vitamin E, is present in the powder in an amount of from between 10% and 55%, by weight, of the powder.

In any of the examples of a water-soluble powder provided herein, the sugar fatty acid ester has an HLB value of between 12 or about 12 and 20 or about 20, inclusive, or between 16 or about 16 and 18 or about 18, inclusive, or between 15 or about 15 and 18 or about 18 inclusive, or at least 15, or at least 16. In any of the examples of a water-soluble powder provided herein, the sugar fatty acid ester is a sucrose fatty acid ester or a sucrose fatty acid ester blend. For example, the sucrose fatty acid ester blend contains a sucrose fatty acid monoester. In examples of the water-soluble powder, the sucrose fatty acid ester blend can contain any one or more of sucrose stearate, sucrose laurate, sucrose palmitate, sucrose oleate, sucrose caprylate, sucrose decanoate, sucrose myristate, sucrose pelargonate, sucrose undecanoate, sucrose tridecanoate, sucrose pentadeconoate and sucrose heptadecanoate or homologs thereof. For example, the sucrose fatty acid ester blend contains any one or more of sucrose monostearate, sucrose monolaurate, sucrose monooleate or sucrose monopalmitate. The sucrose fatty acid ester blend can contain at least at or about 50%, by weight, at least at or about 60%, by weight, at least at or about 70%, by weight, at least at or about 80%, by weight, or at least at or about 90%, by weight, sucrose monoester. The sucrose fatty acid ester or sucrose fatty acid ester blend can contain a sucrose fatty acid ester having a carbon chain length of 12, 14, 16 or 18 carbons.

In any of the examples of a water-soluble powder provided herein, the total amount of sugar fatty acid ester is: between 5% or about 5% and 40% or about 40%, inclusive; or between 7% or about 7% and 30% or about 30%, inclusive; or between 7% or about 7% and 20% or about 20%, inclusive; or 7% or about 7%; or 8% or about 8%; or 10% or about 10%; or 12% or about 12%; or 15% or about 15%; or 17% or about 17%; or 19% or about 19%; or 20% or about 20%; or 25% or about 25%; or 30% or about 30%; or 35% or about 35%; or 40% or about 40%; or 50% or about 50%; or 60% or about 60%, by weight, of the powder. For example, the amount of sugar fatty acid ester is from 5% to 10%, inclusive, or is 12% to 17%, inclusive, or is 15% to 20%, inclusive, or is at least 5%, 7%, 10%, 12%, 15%, 17%, 19%, 20%, 25%, 30%, 35%, 40%, 45%, 50%, 55%, 60%, inclusive, by weight of the powder.

In any of the examples of a water-soluble powder provided herein, the binder can be one or more of polysaccharides, polyols, starches or gums. The binder can be a dextrin. For example, the binder can be maltodextrin, fish collagen, lactose, sucrose, starch, polyethylene glycol, hypromellose, methylcellulose, macrocrystalline cellulose, sorbitol, or pectin.

In any of the examples of a water-soluble powder provided herein, the mixture of sugar fatty acid ester and a binder is from 5% to 10%, inclusive, or is 15% to 20%, inclusive, or is 25% to 40%, inclusive, or is 35% to 45%, inclusive, or is 40% to 50%, inclusive, or is at least 5%, 7%, 10%, 12%, 15%, 17%, 19%, 20%, 25%, 30%, 35%, 36%, 40%, 44%, 45%, 46%, 49%, 50%, 55%, 60%, inclusive, by weight of the powder.

In any of the examples of a water-soluble powder provided herein, the PEG derivative of vitamin E contains a PEG moiety having a molecular weight from between or between about 100 Da and 20,000 Da, 200 Da and 10,000 Da, 200 Da and 8000 Da, 200 Da and 6000 Da, 200 Da and 5000 Da, 200 Da and 3000 Da, 200 Da and 1000 Da, 200 Da and 800 Da, 200 Da and 600 Da, 200 Da and 400 Da, 400 Da and 20,000 Da, 400 Da and 10,000 Da, 400 Da and 8000 Da, 400 Da and 6000 Da, 400 Da and 5000 Da, 400 Da and 3000 Da, 400 Da and 1000 Da, 400 Da and 800 Da, 400 Da and 600 Da, 600 Da and 20,000 Da, 600 Da and 10,000 Da, 600 Da and 8000 Da, 600 Da and 6000 Da, 600 Da and 5000 Da, 600 Da and 3000 Da, 600 Da and 1000 Da, 600 Da and 800 Da, 800 Da and 20,000 Da, 800 Da and 10,000 Da, 800 Da and 8000 Da, 800 Da and 6000 Da, 800 Da and 5000 Da, 800 Da and 3000 Da, 800 Da and 1000 Da, 1000 Da and 20,000 Da, 1000 Da and 10,000 Da, 1000 Da and 8000 Da, 1000 Da and 6000 Da, 1000 Da and 5000 Da, 1000 Da and 3000 Da, 3000 Da and 20,000 Da, 3000 Da and 10,000 Da, 3000 Da and 8000 Da, 3000 Da and 6000 Da, 3000 Da and 5000 Da, 5000 Da and 20,000 Da, 5000 Da and 10,000 Da, 5000 Da and 8000 Da, 5000 Da and 6000 Da, 6000 Da and 20,000 Da, 6000 Da and 10,000 Da, 6000 Da and 8000 Da, 8000 Da and 20,000 Da, 8000 Da and 10,000 Da or 10000 Da and 20,000 Da, or has a molecular weight of 100, 200, 238, 300, 400, 500, 600, 750, 800, 1000, 1200, 1500, 2000, 2500, 3000, 3400, 3500, 4000, 6000, 8000, 10,000, 12,000 or 20,000 Da.

In any of the examples of a water-soluble powder provided herein, the PEG derivative of vitamin E can be a tocopheryl polyethylene glycol succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate.

In any of the examples of a water-soluble powder provided herein, the PEG derivative of vitamin E is a tocopheryl polyethylene glycol succinate (TPGS), tocopheryl sebacate polyethylene glycol, tocopheryl dodecanodioate polyethylene glycol, tocopheryl suberate polyethylene glycol, tocopheryl azelaate polyethylene glycol, tocopheryl citraconate polyethylene glycol, tocopheryl methylcitraconate polyethylene glycol, tocopheryl itaconate polyethylene glycol, tocopheryl maleate polyethylene glycol, tocopheryl glutarate polyethylene glycol, tocopheryl glutaconate polyethylene glycol and tocopheryl phthalate polyethylene glycol, TPGS analog or TPGS homolog. For example, the vitamin E derivative is D-α-tocopheryl polyethylene glycol succinate (TPGS), such as D-α-tocopheryl polyethylene glycol succinate 1000 (TPGS 1000).

In any of the examples of a water-soluble powder provided herein, the polyalkylene glycol derivative of vitamin E is a high dimer containing mixture containing a water-soluble vitamin E derivative composition. The water-soluble vitamin E derivative is a high dimer containing mixture that is a high dimer PEG derivative of vitamin E composition. For example, the water-soluble vitamin E derivative is a high dimer containing mixture that is a high dimer D-α-tocopheryl polyethylene glycol succinate (TPGS) composition.

In any of the examples of a water-soluble powder provided herein, the PEG derivative of vitamin E is present in an amount between 1% and 15%, inclusive, by weight of the powder. For example, the amount of PEG derivative of vitamin E is from 0.5% to 2%, inclusive, or is 3% to 6%, inclusive, or is 5% to 8%, inclusive, or is 10% to 13%, inclusive, or is at least 0.1%, 0.5%, 1%, 1.5%, 2%, 2.5%, 5%, 7%, 10%, 12%, 15%, 17%, 19%, 20%, inclusive, by weight of the powder. In any of the examples of a water-soluble powder provided herein, the amount of the mixture of sugar fatty acid ester and binder is greater than the amount of the polyethylene glycol (PEG) derivative of vitamin E.

In any of the examples of a water-soluble powder provided herein, the non-polar ingredient is a non-polar compound or contains a mixture of non-polar compounds. For example, the non-polar ingredient contains a non-polar compound that is a polyunsaturated fatty acids (PUFAs), medium chain triglycerides, phospholipids, coenzyme Q compounds, flavonoids, carotenoids, micronutrients, alkaloids, antioxidants, or mixtures thereof. In one example, the non-polar ingredient contains a PUFA from among fish oil, algae (algal) oil, flaxseed oil, borage oil, saw palmetto extract, safflower oil, coconut oil, soybean oil, or conjugated linoleic acid (CLA)-containing compounds. The PUFA can be an omega-3 fatty acid, omega-6 fatty acid, omega-9 fatty acid, or conjugated fatty acid. For example, the PUFA is one or more of a docosahexaenoic acid (DHA), an eicosapentaenoic acid (EPA), an alpha-linolenic acid (ALA), a gamma-linolenic acid (GLA), a conjugated linoleic acid (CLA), or an oleic acid.

In other examples of the powders provided herein, the non-polar ingredient can be one or more of: a flavonoid that is selected from among resveratrol and quercetin; an alkaloid that is vinpocetine; a coenzyme Q10 that is selected from among ubiquinol, ubidecarenone, and ubisemiquinone; an oil-soluble vitamin that is selected from among vitamin B12, vitamin D3, vitamin A palmitate, vitamin E, vitamin B1, vitamin B3, vitamin B5, vitamin B6, vitamin C, vitamin K2, and mixtures thereof; a carotenoid-containing compound that is selected from among astaxanthin, lycopene, lutein, zeaxanthin, and mixtures thereof; an antioxidant that is selected from among sesamin, alpha-lipoic acid, pyrroloquinoline quinone (PQQ), a turmeric/curcumin composition that is 95% curcumin, and mixtures thereof; an omega-5 fatty acid derivative that is cetyl myristoleate (CMO); or a phospholipid that is a phosphatidylserine.

In any of the examples of a water-soluble powder provided herein, the non-polar ingredient is between 10% and 60%, or 10% and 55%, or 15% and 60%, or 16% and 60%, or 20% and 55%, or 25% and 55%, by weight of the powder. For example, the non-polar ingredient is from 15% to 30%, inclusive, or is 25% to 35%, inclusive, or is 30% to 40%, inclusive, or is 35% to 45%, inclusive, or is at least 10%, 12%, 15%, 17%, 19%, 20%, 25%, 26%, 30%, 33%, 35%, 36%, 38%, 40%, 45%, 50%, 55%, inclusive, by weight of the powder, such as greater than 50% by weight of the powder.

In any of the examples of a water-soluble powder provided herein, the powder can further contain a stabilizer selected from among one or more of a carbonate, bicarbonate, vitamin C, and green tea extract. In any of the examples of a water-soluble powder provided herein, the powder can further contain a preservative in an amount sufficient to preserve the powder, such as benzyl alcohol. In any of the examples of a water-soluble powder provided herein, the powder can further contain an emulsion stabilizer selected from among one or more of a blend of xanthan gum, guar gum and sodium alginate; modified gum acacia; ester gum; whey protein; and green tea extract containing epigallocatechin gallate (EGCG) or epicatechin gallate (ECG). In any of the examples of a water-soluble powder provided herein, the powder can further contain a pH adjuster present in an amount of less than 1% by weight, such as citric acid or phosphoric acid.

For example, among water-soluble powders provided herein is a powder that contains: a mixture of sugar fatty acid ester and a binder, where the sugar fatty acid ester is sucrose fatty acid ester and the binder is maltodextrin, the total amount of sucrose fatty acid ester and maltodextrin in the mixture is between 36% and 60%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS) in an amount between 1% and 13%, inclusive, by weight of the powder; and a non-polar ingredient in an amount between 12% and 39%, inclusive, by weight of the powder, wherein the non-polar ingredient is one or more of algal oil, fish oil, MCT oil, resveratrol, vinpocetine, sesamin, turmeric/curcumin, phosphatidylserine, alpha-lipoic acid, PQQ, or flaxseed oil; a stabilizer that is one or more of potassium bicarbonate, vitamin C, and mixtures thereof; an emulsion stabilizer that is one or more of a blend of xanthan gum, guar gum or sodium alginate; and a co-emulsifier that is saponin.

Also among water-soluble powders provided herein is a powder that contains: a mixture of sugar fatty acid ester and a binder, where the sugar fatty acid ester is sucrose fatty acid ester and the total amount of the mixture of sucrose fatty acid ester and binder is between 7% and 20%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS) in an amount between 1% and 3%, inclusive, by weight of the powder; a non-polar ingredient in an amount between 12% and 39%, inclusive, by weight of the powder, wherein the non-polar ingredient is algal oil or MCT oil; a stabilizer that is one or more of potassium bicarbonate, vitamin C, and mixtures thereof; an emulsion stabilizer that is one or more of a blend of xanthan gum, guar gum or sodium alginate; whey protein; a green tea extract containing epigallocatechin gallate (EGCG) and/or epicatechin gallate (ECG); and a co-emulsifier that is saponin.

Among water-soluble powders provided herein is a powder containing: a mixture of sugar fatty acid ester and a binder, wherein the sugar fatty acid ester is sucrose fatty acid ester and the binder is maltodextrin, the total amount of sucrose fatty acid ester and maltodextrin in the mixture is between 15% and 20%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS) in an amount between 1% and 5%, inclusive, by weight of the powder; a non-polar ingredient in an amount between 42% and 48%, inclusive, by weight of the powder, wherein the non-polar ingredient is a CLA oil or MCT oil; a stabilizer that is one or more of potassium bicarbonate, vitamin C, or mixtures thereof; an emulsion stabilizer that is a blend of xanthan gum, guar gum or sodium alginate; a co-surfactant that is fish collagen; and a co-emulsifier that is saponin.

Among water-soluble powders provided herein is a powder containing: a mixture of sugar fatty acid ester and a binder, wherein the sugar fatty acid ester is sucrose fatty acid ester and the total amount of sucrose fatty acid ester and binder in the mixture is between 7% and 20%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS), in an amount between 1% and 3%, inclusive, by weight of the powder; a non-polar ingredient in an amount between 42% and 48%, inclusive, by weight of the powder, wherein the non-polar ingredient is a CLA oil or MCT oil; a stabilizer that is one or more of potassium bicarbonate, vitamin C, and mixtures thereof; and an emulsion stabilizer that is a blend of xanthan gum, guar gum and sodium alginate or whey protein.

Among water-soluble powders provided herein is a powder containing: a mixture of sugar fatty acid ester and a binder, wherein the sugar fatty acid ester is sucrose fatty acid ester and the total amount of sucrose fatty acid ester and binder in the mixture is between 18% and 56%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS), in an amount between 1% and 13%, inclusive, by weight of the powder; a non-polar ingredient; a stabilizer that is a potassium bicarbonate or a mixture of potassium bicarbonate and vitamin C; an emulsion stabilizer that is a blend of xanthan gum, guar gum and/or sodium alginate; and a co-emulsifier that is saponin. The non-polar ingredient can be algal oil in an amount between 35% and 40%, inclusive, by weight of the powder, a CLA oil in an amount between 43% and 46%, inclusive, by weight of the powder, an MCT oil in an amount between 43% and 46%, inclusive, by weight of the powder, phosphatidylserine in an amount between 25% and 28%, inclusive, by weight of the powder, a mixture of MCT oil and phosphatidylserine in an amount between 32% and 35%, inclusive, by weight of the powder, vitamin E acetate in an amount between 35% and 38%, inclusive, by weight of the powder, or a mixture of fish oil and flaxseed oil in an amount between 28% and 32%, inclusive, by weight of the powder.

Among the water-soluble powder compositions provided herein is a powder containing: a mixture of sugar fatty acid ester and a binder, wherein the sugar fatty acid ester is sucrose fatty acid ester and the total amount of sucrose fatty acid ester and binder in the mixture is between 7% and 20%, inclusive, by weight of the powder, and the mixture contains at least 7% sucrose fatty acid ester; a polyethylene glycol (PEG) derivative of vitamin E that is D-α-tocopheryl polyethylene glycol succinate (TPGS), in an amount between 1% and 3%, inclusive, by weight of the powder; a non-polar ingredient; a stabilizer that is a mixture of potassium bicarbonate and vitamin C; and an emulsion stabilizer that is a blend of xanthan gum, guar gum and sodium alginate. In such a powder, the powder can further contain whey protein. The non-polar ingredient can be CLA oil in an amount between 43% and 47%, inclusive, by weight of the powder, or MCT oil in an amount between 43% and 47%, inclusive, by weight of the powder. Any of such powders can further contain saponin. The powder can further contain saponin and a green tea extract containing epigallocatechin gallate (EGCG) and epicatechin gallate (ECG). In examples of the powders, the non-polar ingredient is algal oil in an amount between 43% and 47%, inclusive, by weight of the powder.

Provided herein is a powder containing: a mixture of sucrose fatty acid ester and a binder, wherein the total amount of sucrose fatty acid ester and binder is between 5% to 10%, inclusive, or is 15% to 20%, inclusive, or is 25% to 40%, inclusive, or is 35% to 45%, inclusive, or is 40% to 50%, inclusive, or is at least 5%, 7%, 10%, 12%, 15%, 17%, 19%, 20%, 25%, 30%, 35%, 36%, 40%, 44%, 45%, 46%, 49%, 50%, 55%, 60%, inclusive, by weight of the powder, and the mixture of sucrose fatty acid ester and binder contains at least 5% sugar fatty acid ester; a polyethylene glycol (PEG) derivative of vitamin E in an amount from 0.5% to 2%, inclusive, or is 3% to 6%, inclusive, or is 5% to 8%, inclusive, or is 10% to 13%, inclusive, or is at least 0.1%, 0.5%, 1%, 1.5%, 2%, 2.5%, 5%, 7%, 10%, 12%, 15%, 17%, 19%, 20%, inclusive, by weight of the powder; and a non-polar ingredient containing non-polar compounds, other than the PEG derivative of vitamin E, present in an amount from 15% to 30%, inclusive, or is 25% to 35%, inclusive, or is 30% to 40%, inclusive, or is 35% to 45%, inclusive, or is at least 10%, 12%, 15%, 17%, 19%, 20%, 25%, 26%, 30%, 33%, 35%, 36%, 38%, 40%, 45%, 50%, 55%, inclusive, by weight of the powder. In any of such examples, the non-polar ingredient can be selected from among one or more of: a PUFA selected from among fish oil, algae (algal) oil, flaxseed oil, borage oil, saw palmetto extract, safflower oil, coconut oil, soybean oil and conjugated linoleic acid (CLA)-containing compounds; a flavonoid that is selected from among resveratrol and quercetin; an alkaloid that is vinpocetine; a coenzyme Q10 compound that is selected from among ubiquinol, ubidecarenone, and ubisemiquinone; an oil-soluble vitamin that is selected from among vitamin B12, vitamin D3, vitamin A palmitate, vitamin E, vitamin B1, vitamin B3, vitamin B5, vitamin B6, vitamin C, vitamin K2, and mixtures thereof; a carotenoid-containing compound that is selected from among astaxanthin, lycopene, lutein, zeaxanthin, and mixtures thereof; an antioxidant that is selected from among sesamin, alpha-lipoic acid, pyrroloquinoline quinone (PQQ), a turmeric/curcumin composition that is 95% curcumin, and mixtures thereof; an omega-5 fatty acid derivative that is cetyl myristoleate (CMO); and a phospholipid that is a phosphatidylserine.

Also provided herein are emulsions that can be used to make any of the above powders.

Provided herein is an emulsion containing a mixture of sugar fatty acid ester and a binder, a polyethylene glycol (PEG) derivative of vitamin E, a non-polar ingredient containing non-polar compounds other than the PEG derivative of vitamin E, and a polar solvent. In such emulsions, the total amount of sugar fatty acid ester and binder is between 5% and 40%, by weight, of the emulsion, and the mixture of sugar fatty acid ester and binder contains at least 1% sugar fatty acid ester; the polyethylene glycol (PEG) derivative of vitamin E is present in an amount from between 1% and 40%, by weight, of the emulsion; and a non-polar ingredient containing non-polar compounds, other than the PEG derivative of vitamin E, is present in an amount from between 5% and 30%, by weight, of the emulsion. In any of the emulsions, the polar solvent is a polar protic solvent, such as water or an edible alcohol and mixtures thereof. For example, the polar solvent is one or more of water, glycerin, propylene glycol, ethylene glycol, tetraethylene glycol, triethylene glycol and trimethylene glycol. The amount of polar solvent can be present in an amount of from between more than 25% to 70% by weight of the emulsion.

Provided herein is a method of making any of the above powders or emulsions by steps including: a) mixing and heating initial ingredients in a vessel, wherein the initial ingredients include a polyethylene glycol (PEG) derivative of vitamin E and a non-polar ingredient other than the PEG derivative of vitamin E; b) adding one or more additional ingredients to the vessel, wherein the one or more additional ingredients include a mixture of sugar fatty acid ester and a binder, a polar solvent, and one or more ingredients selected from among stabilizers, emulsion stabilizers, pH adjusters and co-emulsifiers; c) homogenizing the ingredients; d) cooling the mixed ingredients, whereby the mixed ingredients become waxy in consistency, thereby generating the emulsion. The method can include further: e) removing the polar solvent from the emulsion by drying, thereby generating the powder. The drying method can be by spray drying, freeze drying, evaporation, lyophilization, and absorption plating.

Provided herein are compositions that contain water-soluble vitamin E derivative mixtures (compositions) and a non-polar ingredient and optionally, additional ingredients. The water-soluble vitamin E derivative mixtures (compositions) contain a relatively high percentage, such as at least 13%, typically greater than 25%, 29%, 35%, 45%, 48%, 49%, 50%, 51%, 52%, or 53%, up to 60-65%, of the dimer form of the vitamin E derivative, generally a PEG-derivative of vitamin E. The remainder of the water-soluble vitamin E derivative composition is the monomer form with a small percentage, less than 5%, 4%, 3%, 2%, 1% of contaminants, such as higher order polymers and reagents, such as vitamin E. Previously, water-soluble vitamin E derivative compositions have been prepared to have as high as possible monomer concentration and typically have at least 87% or more monomer.

It is shown herein that the water-soluble vitamin E derivative mixtures (compositions) that contain the high dimer-containing compositions impart advantageous properties to compositions that contain the water-soluble vitamin E derivative composition. Hence, provided herein are compositions that contain a water-soluble vitamin E derivative composition and a non-polar ingredient, such as polyunsaturated fatty acids, coenzyme Q10 compounds, phytosterols, non-polar small molecule drugs, vitamins and other nutraceuticals and other such compounds.

Hence provided herein are compositions, which can be used as concentrates for providing soluble forms of non-polar compounds, for dilution into aqueous beverages and other foods and beverages, or can be formulated for direct consumption. The compositions, referred to herein as concentrates (although they can be formulated not only for dilution, but for direct consumption), that contain a non-polar compound and a water-soluble vitamin E derivative composition that contains at least 13%, typically, at least 20%, 25%, 29%, 30%, 40%, 45%, 50% or more, typically up to 60-65%, of the dimer form of the vitamin E derivative product. One advantageous property of the higher dimer-containing water-soluble vitamin E derivative compositions is that, when diluted into foods and beverages, the resulting products have greater clarity and stability than products produced by addition of the same concentrates, except that the concentrates contain a water-soluble vitamin E derivative composition that contains less than 13% dimer.

Generally, vitamin E derivative compositions have been prepared to contain as much monomer form as possible and contain dimer only as an undesired byproduct in low concentration. The water-soluble vitamin E derivative mixtures (compositions) provided herein can be used in as the PEG-derivatives of vitamin E, such as TPGS, and in addition to or in place of another surfactant, such as a polysorbate in any composition or formulation that contains a PEG-derivative of vitamin E, such as TPGS.

The water-soluble vitamin E derivative mixtures (compositions) described and used herein are manufactured to contain higher amounts of the dimer form and, consequently, lower amounts of the monomer form of the vitamin E derivative. For example, aqueous beverages that contain these higher content dimer water-soluble vitamin E derivative mixtures (compositions) have substantially greater clarity, typically they are about 2-fold less turbid when measured with a nephelometer in Nephelometric Turbidity Units (NTUs), compared to the same beverages and concentrates that differ only in the water-soluble vitamin E derivative composition that is used. Amounts and particulars of the compositions and the concentrates and resulting liquid dilution compositions, such as aqueous beverages, are described herein. Reference is made to the description and claims set forth below.

Previously, water-soluble vitamin E derivative compositions have been prepared to have as high as possible monomer concentration and typically have at least 87% or more monomer. It is shown herein that the water-soluble vitamin E derivative mixtures (compositions) that contain high amounts of dimer impart advantageous properties to compositions that contain the water-soluble vitamin E derivative composition. Hence, provided herein are compositions that contain a water-soluble vitamin E derivative mixture (composition) and a non-polar ingredient, such as polyunsaturated fatty acids, coenzyme Q10 compounds, phytosterols, non-polar small molecules, drugs, vitamins and other nutraceuticals, and other such compounds.

Provided herein are compositions that include concentrates and liquid dilution compositions produced from the concentrates, compositions for direct consumption, and dilutions of the concentrates, such as beverages, that contain water-soluble vitamin E derivative mixtures (compositions) and a non-polar ingredient and optionally, additional ingredients. The water-soluble vitamin E derivative mixtures (compositions) contain a relatively high percentage, at least 13%, typically greater than 25%, 29%, 35%, 45%, 48%, 49%, 50%, 51%, 52%, 53%, up to 60-65%, of the dimer form of the vitamin E derivative, generally a PEG-derivative of vitamin E. The remainder of the water-soluble vitamin E derivative composition is the monomer form and a small percentage, less than 5%, 4%, 3%, 2%, or 1% of contaminants, such as higher order polymers and reagents, such as vitamin E.

These high dimer-containing water-soluble vitamin E derivative compositions (mixtures) are employed for the preparation of compositions that contain the water-soluble vitamin E mixtures and one or more non-polar ingredients, such as a fatty acids, vitamins, phytosterols, other nutraceuticals, drugs, and bioactive components. The water-soluble vitamin E derivative mixtures (compositions) contain a high percentage, greater than or at least 13%, by weight, of the dimer form of the vitamin E derivative and the remainder is predominantly the monomer form, with up to 5% other components, such as trace amounts of reagents, other forms of vitamin E, and other minor contaminants. Thus, the water-soluble vitamin E derivative mixture (composition) provides a mixture of the dimer form and monomer form of the water-soluble vitamin E derivative and contains a relatively high concentration of dimer form. These mixtures (or compositions) also are referred to as high-dimer vitamin E derivative mixtures, because they are manufactured to be a mixture of forms, with greater than 13%, typically greater than 20%, dimer form. This mixture has advantageous properties, particularly compared to the same derivative of vitamin E that has been used that contains much lower concentrations of dimer, if any, and at least 87% monomer form. The high dimer containing water-soluble derivatives of vitamin E mixtures are employed to solubilize non-polar ingredients. Thus provided are compositions that contain high dimer containing water-soluble derivatives of vitamin E mixtures and a non-polar compound. In particular the compositions, which include compositions for direct consumption and concentrates, including nanoemulsion concentrates, contain: a water-soluble vitamin E derivative mixture (composition) in an amount of from between 1% to 99%, inclusive, by weight, of the resulting composition, where the water-soluble vitamin E derivative mixture contains at least 13 wt % water-soluble vitamin E derivative dimer and up to 87 wt % monomer; and a non-polar compound other than the water-soluble vitamin E derivative mixture. In some embodiments, the water-soluble vitamin E derivative mixture contains at least 20%, 25% or 29%, by weight, vitamin E derivative dimer, or the water-soluble vitamin E derivative mixture contains up to 75%, 70%, 69%, 62%, 55%, 50%, 45%, 40%, 35% dimer or 29%-69%, inclusive, of dimer; and/or contains less than 70%, 65%, 63%, 62%, 61%, 55%, 50%, 48%, by weight, of the vitamin E derivative monomer in the water-soluble vitamin E derivative mixture. In some embodiments, the amount of dimer is greater than 29% and the total amount of dimer and monomer in the water-soluble vitamin E derivative mixture is greater than 95%, 96%, 97%, 98%, or 99%.

The dimer form of the water-soluble vitamin E derivative is present in an amount between or between about 13% and 15%, 13% and 20%, 13% and 25%, 13% and 30%, 13% and 35%, 13% and 40%, 13% and 45%, 13% and 50%, 13% and 55%, 13% and 60%, 13% and 65%, 13% and 70%, 13% and 75%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 25% and 30%, 25% and 35%, 25% and 40%, 25% and 45%, 25% and 50%, 25% and 55%, 25% and 60%, 25% and 65%, 25% and 70%, 25% and 75%, 30% and 35%, 30% and 40%, 30% and 45%, 30% and 50%, 29% and 52%, 30% and 55%, 30% and 60%, 30% and 65%, 30% and 70%, 30% and 75%, 35% and 40%, 35% and 45%, 35% and 50%, 35% and 55%, 35% and 60%, 35% and 65%, 35% and 70%, 35% and 75%, 40% and 45%, 40% and 50%, 40% and 55%, 40% and 60%, 40% and 65%, 40% and 70%, 40% and 75%, 45% and 50%, 45% and 55%, 45% and 60%, 45% and 65%, 45% and 70%, 45% and 75%, 50% and 55%, 50% and 60%, 50% and 65%, 50% and 69%, 55% and 60%, 55% and 65%, 55% and 70%, 55% and 75%, 60% and 65%, 60% and 70%, 60% and 75%, 65% and 70%, 65% and 75%, or 70% and 75%, by weight, of the water-soluble vitamin E derivative mixture or is or is at least or at least about 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% or 74%, up to 75%, by weight, of the water-soluble vitamin E derivative mixture.

The monomer is present in the high dimer containing water-soluble derivatives of vitamin E mixtures in an amount from between or between about 25% and 30%, 25% and 35%, 25% and 40%, 25% and 45%, 25% and 50%, 25% and 55%, 25% and 60%, 25% and 65%, 30% and 35%, 30% and 40%, 30% and 45%, 30% and 50%, 30% and 55%, 30% and 60%, 30% and 65%, 30% and 69%, 35% and 40%, 35% and 45%, 35% and 50%, 35% and 55%, 35% and 60%, 35% and 65%, 35% and 69%, 40% and 45%, 40% and 50%, 40% and 55%, 40% and 60%, 40% and 65%, 40% and 69%, 45% and 50%, 45% and 55%, 45% and 60%, 45% and 65%, 45% and 69%, 50% and 55%, 50% and 60%, 50% and 65%, 50% and 69%, 55% and 60%, 55% and 65%, 55% and 69%, 60% and 65%, 60% and 69%, or 65% and 69%, by weight, of the water-soluble vitamin E derivative mixture or is or is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, up to and including 69%, by weight, of the water-soluble vitamin E derivative mixture.

In the high dimer containing water-soluble derivatives of vitamin E mixtures, the monomer comprises between or between about 35% and 65%, inclusive, by weight, of the water-soluble vitamin E derivative mixture and the dimer comprises between or between about 25% and 65%, by weight, of the water-soluble vitamin E derivative mixture, or the dimer comprises between or between about 29% and 61% or 62%, by weight, of the water-soluble vitamin E derivative mixture, and the monomer and dimer comprise at least 70%, by weight, of the water-soluble vitamin E mixture in the composition.

The water-soluble vitamin E derivative is any suitable derivative of vitamin E that renders it more soluble than in its absence, and can result in mixtures of dimers and monomers. Exemplary of such derivatives are polyalkylene glycol derivatives of vitamin E, such as, but not limited to, polyethylene glycol (PEG) derivatives of vitamin E. PEG derivatives include those in which the PEG derivative of vitamin E contains a PEG moiety having a molecular weight between or between about 100 Da and 20,000 Da, inclusive, including between 200 Da and 10,000 Da, 200 Da and 8000 Da, 200 Da and 6000 Da, 200 Da and 5000 Da, 200 Da and 3000 Da, 200 Da and 1000 Da, 200 Da and 800 Da, 200 Da and 600 Da, 200 Da and 400 Da, 400 Da and 20,000 Da, 400 Da and 10,000 Da, 400 Da and 8000 Da, 400 Da and 6000 Da, 400 Da and 5000 Da, 400 Da and 3000 Da, 400 Da and 1000 Da, 400 Da and 800 Da, 400 Da and 600 Da, 600 Da and 20,000 Da, 600 Da and 10,000 Da, 600 Da and 8000 Da, 600 Da and 6000 Da, 600 Da and 5000 Da, 600 Da and 3000 Da, 600 Da and 1000 Da, 600 Da and 800 Da, 800 Da and 20,000 Da, 800 Da and 10,000 Da, 800 Da and 8000 Da, 800 Da and 6000 Da, 800 Da and 5000 Da, 800 Da and 3000 Da, 800 Da and 1000 Da, 1000 Da and 20,000 Da, 1000 Da and 10,000 Da, 1000 Da and 8000 Da, 1000 Da and 6000 Da, 1000 Da and 5000 Da, 1000 Da and 3000 Da, 3000 Da and 20,000 Da, 3000 Da and 10,000 Da, 3000 Da and 8000 Da, 3000 Da and 6000 Da, 3000 Da and 5000 Da, 5000 Da and 20,000 Da, 5000 Da and 10,000 Da, 5000 Da and 8000 Da, 5000 Da and 6000 Da, 6000 Da and 20,000 Da, 6000 Da and 10,000 Da, 6000 Da and 8000 Da, 8000 Da and 20,000 Da, 8000 Da and 10,000 Da or 10000 Da and 20,000 Da, or has a molecular weight of at least 100, 200, 238, 300, 400, 500, 600, 750, 800, 1000, 1200, 1500, 2000, 2500, 3000, 3400, 3500, 4000, 6000, 8000, 10,000, 12,000, 14,000, 16,000, or 18,000, up to and including 20,000 Da.

Among the PEG derivatives of vitamin E are, for example, tocopheryl polyethylene glycol succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate.

In some embodiments the vitamin E derivative is selected from among tocopheryl polyethylene glycol succinate (TPGS), tocopheryl sebacate polyethylene glycol and other TPGS analogs and TPGS homologs, tocopheryl dodecanodioate polyethylene glycol, tocopheryl suberate polyethylene glycol, tocopheryl azelaate polyethylene glycol, tocopheryl citraconate polyethylene glycol, tocopheryl methylcitraconate polyethylene glycol, tocopheryl itaconate polyethylene glycol, tocopheryl maleate polyethylene glycol, tocopheryl glutarate polyethylene glycol, tocopheryl glutaconate polyethylene glycol and tocopheryl phthalate polyethylene glycol. Exemplary of TPGS, is D-α-tocopheryl polyethylene glycol succinate (TPGS).

The compositions provided herein contain in addition to the high dimer containing water-soluble derivatives of vitamin E mixtures an additional ingredient, which typically is a bioactive ingredient, such as a drug, vitamin or nutraceutical. Generally such ingredients are non-polar ingredients and are rendered soluble by the high dimer containing water-soluble derivatives of vitamin E mixture. As provided and shown herein, the high dimer containing water-soluble derivatives of vitamin E mixtures are more effective than vitamin E derivative compositions that contain high amounts of monomer and low amounts, if any, of dimer.

Among the non-polar ingredients are those that contain a non-polar active ingredient, such as, but not limited to, polyunsaturated fatty acids (PUFA), coenzyme Q, phytosterols, resveratrol, carotenoids, micronutrients, alpha lipoic acid and oil-soluble vitamins. Exemplary of such compounds are non-polar compounds that contain PUFAs, such as fish oil, algae (algal) oil, flaxseed oil, borage oil, saw palmetto extract, safflower oil, coconut oil, soybean oil and conjugated linoleic acid (CLA)-containing compounds. These include omega-3 fatty acids, omega-6 fatty acids, omega-9 fatty acids and conjugated fatty acids, such as, but not limited to, docosahexaenoic acid (DHA), eicosapentaenoic acid (EPA), alpha-linolenic acid (ALA), gamma-linolenic acid (GLA), conjugated linoleic acid (CLA) and oleic acid compounds. Among these are coenzyme Q10; an oil-soluble vitamin that is selected from among vitamin B12, vitamin D3, vitamin A palmitate, vitamin E, vitamin B1, vitamin B3, vitamin B5, vitamin B6, vitamin C and mixtures thereof; a carotenoid-containing compound that is selected from among lycopene, lutein, zeaxanthin and mixtures of lutein and zeaxanthin; and a micronutrient-containing compound that is selected from among yerba mate, *ginkgo biloba* and *ginseng*.

The concentration of non-polar compound in the composition depends upon the particular compound and desired dosage or amount to be administered and also whether the composition is intended for direct administration or is a concentrate for dilution or consumption in a capsule. Hence, the concentration of non-polar compound can be present in an amount from 0.1%-99%, by weight, of the composition, such as 0.5% or 1% to 75%, by weight, of the composition, or, for example, 0.1% to 10%, 1%-5%, 5%-10%, 5%-12%, 5%-15%, 5%-20%, 5%-25%, 10%-14%, 10%-12%, 10%-15%, 10%-20%, 10%-25%, 5%-30%, 1%-30% or 1%-15%, inclusive, by weight, of the composition.

Other ingredients in the compositions include a preservative in an amount sufficient to preserve the composition. The preservative, for example, can contain benzyl alcohol.

The compositions can also include a non-polar solvent that dissolves the non-polar compound and is different therefrom and is present in an amount sufficient to dissolve the non-polar compound. Exemplary non-polar solvents include, for example, a vitamin E oil, a flaxseed oil, an oat oil and mixtures thereof.

The compositions can include a polar solvent, such as a polar protic solvent. Exemplary polar solvents include water and consumable alcohols and mixtures thereof, such as, but not limited to, water, glycerin, propylene glycol, ethylene glycol, tetraethylene glycol, triethylene glycol and trimethylene glycol. The amount of polar solvent depends upon the particular composition and whether it is a concentrate or for direct consumption. Hence, the concentration can be for example, from more than 0.5% or 1% to 95%, by weight, of the composition, such as from 45% to 80%, or 60%-80%, by weight, of the composition.

The compositions also can contain a co-surfactant present in an amount sufficient to increase stability of the composition compared to the absence of a co-surfactant. Co-surfactants for use with the high dimer-containing water-soluble vitamin E derivative mixtures include, for example, a phospholipid, such as phosphatidyl choline, a sucrose fatty acid ester, a polysorbate and a polysorbate analog.

The compositions also can include an emulsion stabilizer, such as a modified starch and gum mixture. These include, for example, one or more of a blend of xanthan gum, guar gum and sodium alginate; modified gum acacia; and ester gum.

The compositions include other optional ingredients, such as a pH adjuster, present to adjust the pH of the composition to between 2.0 and 4.0. Typically, the pH adjuster is present in an amount of less than 1% by weight. Exemplary pH adjusters include citric acid and phosphoric acid. Other ingredients include a flavor or flavoring agent and/or sweeteners, particularly in the compositions for direct administration. Flavors can be imparted by beverage bases as well as flavoring agents.

The amount of the water-soluble vitamin E derivative mixture is from 16% to 30%, inclusive, or is 1%-95%, inclusive, or is 10% to 40%, inclusive, or 10%-50%, inclusive, or 15%-25%, inclusive, by weight, of the composition, or is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95%, inclusive, by weight, of the composition, such as greater than 1%, 2%, 3%, 4%, 5%, 10%, 15% or 20% or about 20%, greater than 30% or about 30%, between 30% or about 30% and 55% or about 55%, between 16% and 30%, between 30% or about 30% and 50% or about 50%, between 30% or about 30% and 45% or about 45%, or at least 10%, 12%, 15%, 17%, 20%, 22%, 24%, 27%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55%, up to at least 60%, 65%, 70%, 75%, 80%, 85%, 90%, 95%, 97%, 98%, or 99%, all by weight, of the composition. For example, for concentrates, the vitamin E derivative mixture can be present in an amount of about at least 15%, 15%-30%, at least 40% or about 40%, 50% or about 50%, or greater than 60% or about 60%, greater than 65% or about 65%, for example, greater than 70% or about 70%, for example, a starting concentration within the concentration range of between 50% or about 50% and 95% or about 95%, between 60% or about 60% and 95% or about 95%, between 65% or about 65% and 90% or about 90%, for example, between 69% or about 69% and 90% or about 90%, between 69% or about 69% and 89% or about 89%, for example, at least 65%, 66%, 67%, 68%, 69%, 69.5%, 69.9%, 70%, 71%, 72%, 73%, 74%, 75%, 76%, 77%, 78%, 79%, 79.5%, 79.9%, 80%, 81%, 82%, 83%, 84%, 85%, 86%, 87%, 88%, 89%, 89.5%, 89.9%, or 90%, by weight, of the composition.

Exemplary compositions, particularly concentrates, include a composition that contains a water-soluble vitamin E derivative mixture present in an amount from 5% to 95%, by weight, of the composition, wherein the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; and a preservative, present in an amount sufficient to preserve the composition.

Another composition contains a water-soluble vitamin E derivative mixture present in an amount from 5% to 95%, by weight, of the composition, where: the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; a preservative, present in an amount sufficient to preserve the composition; and a non-polar solvent that differs from the non-polar compound and is present in an amount sufficient to dissolve the non-polar compound.

Another exemplary composition contains a water-soluble vitamin E derivative mixture, present in an amount from 5% to 95%, by weight, of the composition, where: the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; a preservative, present in an amount sufficient to preserve the composition; a polar solvent, present in an amount from 45% to 80%, by weight, of the composition; and a pH adjuster, present in an amount sufficient to adjust the pH of the composition to between 2.0 and 4.0.

The compositions provided herein can be concentrates or can be for direct consumption. Among those for direct consumption are dilution compositions, such as beverage compositions, into which any of the concentrates provide herein have been diluted. Also included are the pre-gel compositions and soft gel compositions that contain a surfactant and non-polar ingredient(s) for direct consumption.

The compositions provided herein also can contain additional ingredients such as sweeteners, stabilizers, pH adjusters and antifoaming agents. Sweeteners include any known to those of skill in the art, including, but not limited to, sucralose, sucrose, lactose, fructose, an acesulfame salt, aspartame, saccharin, stevia, stevioside and xylitol. Stabilizers include, but are not limited to, carbonates, bicarbonates, acids and antioxidants. The carbonates, bicarbonates, acids and antioxidants can be included in the compositions for direct consumption, as they stabilize the compositions as consumed and packaged. Such compositions also are packaged in a sealed container, which can contain nitrogen to displace oxygen from the sealed container. Such compositions include, but are not limited to, juice, water, sports drinks and sodas.

Also provided are emulsion compositions that can be used to form dry powders. Also provided are soft gel compositions that contain a non-polar ingredient, a high dimer water-soluble vitamin E derivative composition, such as a the PEG-derivative of vitamin E composition, such as a high dimer TPGS composition, and a relatively high concentration greater than 1%, typically greater than 7%, 10%, 15%, of a non-aqueous solvent, such as an alkyl alcohol, such as benzyl alcohol, in an amount greater than 1% and up to 25%, are provided. The claims set forth below directed to each of these compositions is herein incorporated by reference. Also, incorporated by reference are the subject matter, and all claims in U.S. Provisional Application Ser. No. 62/052, 433, filed Sep. 18, 2104, entitled "SOFT GEL COMPOSITIONS AND PRE-GEL CONCENTRATES" to Philip J. Bromley, and U.S. Provisional Application Ser. No. 62/052, 433, filed Sep. 18, 2014, entitled "PRE-SPRAY EMULSIONS AND POWDERS CONTAINING NON-POLAR COMPOUNDS" to Philip J. Bromley. It is understood that for purposes herein, the water-soluble vitamin E derivative compositions in the incorporated claims are the high dimer compositions as described herein. Provided are powders and pre-spray emulsions. The pre-spray emulsions comprise the ingredients of the powders plus a polar solvent. The capsules, tables and soft gel capsules are for administering to a subject to provide a non-polar compound to the subject, such as for supplementation to provide a nutrient or nutraceutical or a bioactive compound for treating or lowering the risk of a disease. The powders, which are soluble, can be introduced into a beverage of choice to provide the non-polar compound or sprinkled on food.

Exemplary of the non-polar ingredients in all of the compositions provided herein are the following:

Omega-3 EPA and DHA; Resveratrol; Sesamin; Curcumin; *Boswellia* (Boswellic Acids); lipoic acid, such as Alpha Lipoic Acids, Capsaicinoids; PQQ, carotenoids, such as Astaxanthin, Zeaxanthin; Lutein, Beta Carotene, and Lycopene; and vitamins, such as Vitamin A, Vitamin D and Vitamin E complexes; Vitamin K1 and Vitamin K as MK7

Methods for preparing the compositions, particularly those that are concentrates, are provided. These methods include steps of: (a) mixing and heating initial ingredients in a vessel, where the initial ingredient(s) comprise: a water-soluble vitamin E derivative mixture present in an amount from 5% to 95%, by weight, of the concentrate; and the water-soluble vitamin E derivative mixture comprises from 25 wt % to 69 wt % water-soluble vitamin E monomer and from 13 wt % to 75 wt % water-soluble vitamin E dimer; and then (b) adding one or more additional ingredients to the vessel, where the one or more additional ingredients comprise: a non-polar compound at an amount from 1% to 75%, by weight, of the concentrate; and then (c) homogenizing the ingredients; and (d) cooling the mixed ingredients, whereby, for compositions with high levels of vitamin E derivatives, the mixed ingredients become waxy in consistency, and lower levels form an emulsion, thereby generating the composition.

Methods for preparing a beverage, soft gel, and other composition for direct consumption containing a non-polar compound also are provided. The beverages are prepared by adding the composition provided herein, such as a nanoemulsion concentrate, to a beverage base. The concentrate is added at a predetermined concentration to produce a beverage supplemented with the active ingredient in the concentrate at an effective or intended concentration. The beverage base comprises the other components of the resulting beverage, including, but not limited to, water, juice, soda, a sports drink and/or a nutritional drink. Soft gel compositions are prepared by introducing a pre-gel composition into to soft gel shell or capsule.

DETAILED DESCRIPTION

| Outline |
|---|
| A. Definitions |
| B. Compositions containing non-polar compounds |
|   1. Pre-emulsion concentrates containing non-polar compounds |
|     a. Formulating the pre-emulsion concentrates containing non-polar compounds |
|     b. Polyalkylene glycol derivatives of vitamin E |
|       i. Tocopherols and tocotrienols |
|       ii. Linkers |
|       iii. PEG moieties |
|       iv. Tocopheryl polyalkylene glycol derivatives |
|         (a) Synthesis |
|         (b) Water-soluble vitamin E derivative mixtures (compositions) |

| Outline |
| --- |
| v. Methods for making water-soluble vitamin E derivatives |
|    (a) Reaction mixture |
|      (i) Vitamin E succinate |
|      (ii) Polyethylene glycol |
|      (iii) Catalyst |
|      (iv) Solvent |
|      (v) Exemplary reaction mixtures |
|    (b) Exemplary methods |
|      (i) Preparation of a crude water-soluble vitamin E derivative mixture |
|      (ii) Processing the reaction mixture to obtain a crude water-soluble vitamin E derivative mixture |
|      (iii) Purification of the crude water-soluble vitamin E derivative mixture to obtain a purified high dimer-containing water-soluble vitamin E derivative mixture |
| c. Non-polar compounds |
|   i. Polyunsaturated fatty acid (PUFA)-containing non-polar compounds |
|    (a) Omega-3 fatty acid compounds |
|      (1) DHA/EPA |
|        (i) Fish oils |
|        (ii) Algae oil |
|      (2) Flaxseed oil-omega 3 (ALA) |
|    (b) Omega-6 compounds |
|    (c) Saw palmetto extract |
|    (d) Conjugated linoleic acid (CLA) |
|   ii. Phytochemical-containing non-polar compounds |
|    (a) Phytosterols |
|    (b) Flavonoids |
|   iii. Micronutrient-containing compounds |
|    (a) Vitamins |
|   iv. Alkaloids |
|   v. Cannabinoids |
|   vi. Hops-containing compounds |
|   vii. Antioxidants |
|   viii. Coenzyme Q compounds |
|   ix. Carotenoid-containing compounds |
|    (a) Carotenes |
|    (b) Xanthophylls |
|   x. *Boswellia* extracts |
|   xi. Phospholipids |
| d. Preservatives and sterilizers |
| 2. Pre-spray emulsions containing non-polar compounds |
|   a. Formulating the pre-spray emulsions |
|   b. Exemplary ingredients and typical concentration ranges |
|    i. Pre-emulsion concentrates |
|    ii. Surfactants |
|      (a) Sucrose fatty acid ester surfactants |
|      (b) Production of sucrose esters |
|    iii. Stabilizers |
|      (a) Bicarbonates or carbonates |
|      (b) Acids |
|      (c) Antioxidants |
|    iv. Polar solvents |
|    v. Binders |
|    vi. Co-surfactants (emulsifiers) |
|      (a) Phospholipids |
|      (b) PEG-derived surfactants |
|    vii. Emulsion stabilizers (co-emulsifiers) |
|    viii. pH adjusters |
| 3. Powder compositions containing non-polar compounds |
|   a. Formulating the powder composition |
|   b. Exemplary ingredients and concentration ranges |
| C. Exemplary methods for preparing compositions containing non-polar compounds |
| 1. Equipment employed in the methods |
|   a. Scales |
|   b. Purifiers |
|   c. Vessels |
|   d. Mixers |
|   e. Heating/cooling apparatuses |
|   f. Transfer devices |
|   g. Evaluation equipment |
| 2. General methods for producing the compositions |
|   a. Oil phase ingredients |
|   b. Oil phase production |
|   c. Water phase ingredients |
|   d. Water phase production |
|   e. Combining phases |
|   f. Cooling |
|   g. Spray drying |
|   h. Filtration, additions, evaluation and packaging |
|   i. Cleaning the equipment |
| D. Examples |

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "vitamin E" refers to any naturally occurring or synthetic form of vitamin E, for example, tocopherols and tocotrienols, and can refer to a single form of the compound or a mixture of forms.

As used herein, "water-soluble vitamin E derivative composition," "water-soluble vitamin E derivative," "water-soluble vitamin E derivative surfactant," "water-soluble vitamin E surfactant," and "water-soluble derivative of vitamin E mixture," which are to be used interchangeably, refer to compositions that contain mixtures of water-soluble forms of vitamin E (vitamin E derivatized with moieties, such as polyalkylene glycol that increase the water solubility of the water-insoluble vitamin E). A "polyalkylene glycol derivative of vitamin E" is thus a water-soluble vitamin E derivative composition that contains a mixture of water-soluble forms of vitamin E and is derivatized with a polyalkylene glycol moiety.

The mixtures can contain dimers and monomers of the vitamin E derivatives. The water-soluble vitamin E derivative mixtures (compositions) include vitamin E (natural or synthetic forms of vitamin E), such as tocopherol derivatives and tocotrienol derivatives. Generally, vitamin E derivative mixtures contain predominantly or primarily monomer forms. Derivatives of vitamin E, such as polyethylene glycol (PEG) derivatives previously produced, are manufactured to contain as much monomer form as possible, and to contain minimal amounts of any dimer form (see, e.g., Christiansen et al. (2011) J. Pharm. Sci. 100(5):1773-1782). All are intended to be included in the compositions herein.

In contrast, "high dimer-containing" (or "high dimer") vitamin E derivative mixtures, such as PEG derivative of vitamin E compositions (also referred to herein as high dimer PEG derivatives of vitamin E mixtures) can be employed herein. These mixtures are manufactured to contain dimer forms, and they contain at least 13%, particularly at least or at least about 20%, 25%, 29%, or more, of the dimer form of the water-soluble vitamin E derivative. In particular, the water-soluble vitamin E derivative mixtures (compositions) are manufactured to contain between or between about 13 wt % and about or up to 95%, 90%, 85%, 80%, or 75 wt %, particularly at least 29% to 75% or 80%, inclusive, of the water-soluble vitamin E dimer form. In general, the high dimer-containing vitamin E derivative mixtures, such as PEG derivatives of vitamin E mixtures, such as a high dimer-containing TPGS composition, contain 30% to 60%, particularly 35% to 52%, dimer, and the remainder is the monomer form and other trace components, such as unreacted reagents, such as vitamin E and the hydrophilic derivatizing moiety.

In general, for the high dimer-containing vitamin E derivative mixtures, the mixtures contain at least 13% of the dimer form and up to 87% monomer form, in particular, at least 25% of the dimer form and up to 70% of the monomer form, such as between or between about 25 wt % and 69%, inclusive, of the monomer. Hence, the water-soluble vitamin E derivative mixtures (compositions) (high dimer-containing compositions) contain a substantial amount (i.e., 13% or more, particularly 25%, 29%, 35%, 48%, 52%, or more) of the dimer form compared to commercially available forms that are manufactured to provide the monomer form.

As manufactured, the high dimer-containing vitamin E derivative mixtures can include other forms and unreacted components, hence the total amount of dimer and monomer do not necessarily total 100%, by weight, of the composition. It is shown herein that inclusion of at least 13%, 20%, 25%, 29%, or more of the dimer form, and some monomer form, about less than 87%, 69%, 65%, 60%, 55%, or 50% of the monomer with at least 13% dimer, confers advantageous properties on these water-soluble vitamin E derivative mixtures (compositions) not possessed by such compositions that contain lower amounts of the dimer form.

Examples of water-soluble vitamin E derivatives are those formed by covalently attaching a vitamin E moiety, e.g., a tocopherol or tocotrienol, to a hydrophilic moiety, for example, an alkylene glycol, such as a polyethylene glycol (PEG) moiety, via a linker. The compositions include those that are commercially available, manufactured to maximize the concentration of monomer (such as those sold by Eastman), and those that are manufactured so that the resulting water-soluble vitamin E derivative mixtures (compositions) include a mixture of monomers and dimers of the water-soluble vitamin E derivatives (see, e.g., U.S. patent application Ser. No. 14/207,310, and International Application No. PCT/US2014/25006, now published as US-2014-0271593-A1 and WO 2014/151109, respectively, which describes such mixtures), and contain a substantial amount (compared to prior art preparations), i.e., 13% to 95%, inclusive, such as at least 13%, 20%, 25%, or 29%, up to as much as 75%, 80%, 85%, 90%, 95%, by weight, of the dimer form and generally less than 70%, 65%, 63%, 62%, 61% or 60%, or less, of the monomer form. Water-soluble vitamin E derivative mixtures (compositions) include, for example, polyalkylene glycol derivatives of tocopherol, e.g., polyethylene glycol (PEG) derivatives of tocopherol, and polyalkylene glycol derivatives of tocotrienol, e.g., polyethylene glycol (PEG) derivatives of tocotrienol. The water-soluble vitamin E derivatives can include, for example, polyalkylene glycol derivatives of vitamin E, such as polyethylene glycol derivatives of vitamin E, e.g., vitamin E TPGS (D-α-tocopheryl polyethylene glycol succinate), TPGS analogs, TPGS homologs and TPGS derivatives.

As used herein, "tocopherol" and "tocotrienol" refer to any naturally occurring or synthetic form of vitamin E, and can refer to a single compound or a mixture of tocopherols and tocotrienols. Examples of tocopherols include, for example, α-tocopherol, D-α-tocopherol, β-tocopherol, γ-tocopherol and δ-tocopherol. Examples of tocotrienols include, for example, α-tocotrienol, β-tocotrienol, γ-tocotrienol and δ-tocotrienol.

As used herein, a "PEG derivative of vitamin E" or "vitamin E-PEG conjugate" or "vitamin E-PEG derivative," is a compound containing one or more vitamin E moieties (e.g., a tocopherol or tocotrienol) joined by a covalent bond, for example, an ester, ether, amide or thioester bond, to one or more polyethylene glycol (PEG) moieties, via a linker, such as a dicarboxylic or tricarboxylic acid. Exemplary of PEG derivatives of vitamin E are D-α-tocopheryl polyethylene glycol succinate (TPGS), TPGS analogs, TPGS homologs and TPGS derivatives.

As used herein, "tocopheryl polyethylene glycol succinate," "TPGS," "tocopheryl polyethylene glycol succinate surfactant" and "TPGS surfactant" refer to tocopheryl polyethylene glycol conjugates that are formed by covalently joining tocopherol succinate, an ester formed through esterification of tocopherol and succinic acid, to a polyethylene glycol (PEG) moiety via an esterification reaction. The PEG moiety of the TPGS surfactant can be any PEG moiety, for example, a PEG moiety with a molecular weight of between or between about 200 Da and 20,000 Da or about 20,000 Da, for example, PEG moieties having a molecular weight of or about 200, 300, 400, 500, 600, 800, 1000, 3000, 5000, 6000, 8000, 10,000, 20,000 Da, or more; or PEG analogs, including, for example, PEG-NHS (N-hydroxysuccinimide), PEG-aldehyde, PEG-SH, PEG-NH$_2$, PEG-CO$_2$H, and branched PEGs.

Exemplary of a TPGS surfactant is TPGS-1000, which has a PEG moiety with a molecular weight of 1000 Da. The TPGS can be any natural, water-soluble, tocopherol polyethylene glycol succinate, for example, the food grade TPGS sold under the name Eastman Vitamin E TPGS®, food grade, by Eastman Chemical Company, Kingsport, Tenn. This TPGS is a water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. TPGS typically has a reported HLB value of between 12 or 13 or about 12 or 13 and 18 or about 18.

As used herein, "analog" refers to a chemical compound that is structurally similar to another compound (referred to as a parent compound), but differs slightly in composition, for example, due to the variation, addition or removal of an atom, one or more units (e.g., methylene units, —(CH$_2$)$_n$—) or one or more functional groups. The analog can have different chemical or physical properties compared with the original compound and/or can have improved biological and/or chemical activity. Alternatively, the analog can have similar or identical chemical or physical properties compared with the original compound and/or can have similar or identical biological and/or chemical activity. For example, the analog can be more hydrophilic or it can have altered reactivity as compared to the parent compound. The analog can mimic the chemical and/or biological activity of the parent compound (i.e., it can have similar or identical activity), or, in some cases, can have increased or decreased activity. The analog can be a naturally or non-naturally occurring (e.g., synthetic) variant of the original compound. Other types of analogs include isomers (e.g., enantiomers, diastereomers) and other types of chiral variants of a compound, as well as structural isomers. The analog can be a branched or cyclic variant of a linear compound. For example, a linear compound can have an analog that is branched or otherwise substituted to impart certain advantageous properties (e.g., improved hydrophobicity or bioavailability). Exemplary of the analogs used in the provided compositions and methods are TPGS analogs, which can be formed using the methods provided herein and can be used in place of TPGS in the provided compositions.

As used herein, "tocopheryl polyethylene glycol succinate analog" or "TPGS analog" refers to compounds, other than TPGS, that are similar to a parent TPGS compound, but differ slightly in composition, for example, by the variation, addition or removal of an atom, one or more units (e.g., methylene units, —$(CH_2)_n$—), or one or more functional groups. TPGS analogs include vitamin E-derived surfactants, e.g., tocopheryls and tocotrienols, including PEG derivatives of vitamin E, including vitamin E PEG monomers and dimers, such as, but not limited to, tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz), and polyoxyethanyl tocotrienyl sebacate (PTrienS), as well as other PEG derivatives of vitamin E. The compositions provided herein include at least 13%, typically more than 29%, such as 29%-55% or 30%-52%, dimer form in the composition, with the rest of the composition the monomer form or small amounts of other forms and trace contaminants.

Exemplary of TPGS analogs are compounds having the formula shown in Formula I:

5000, 6000, 8000, 10,000, 20,000 Da, or more. Also exemplary of TPGS 1000 analogs are TPGS compounds including PEG analogs, e.g., PEG-NHS, PEG-aldehyde, PEG-SH, PEG-NH$_2$, PEG-CO$_2$H, and branched PEGs. Also exemplary of TPGS 1000 analogs are any TPGS analogs, e.g., vitamin E-derived surfactants, including PEG derivatives of vitamin E, including, but not limited to, tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz) and polyoxyethanyl tocotrienyl sebacate (PTrienS), as well as other PEG derivatives of vitamin E.

As used herein, "homolog" refers to an analog that differs from the parent compound only by the presence or absence of a simple unit, such as a methylene unit, or some multiple of such units, e.g., —$(CH_2)_n$—. Typically, a homolog has similar chemical and physical properties as the parent compound. Exemplary of the homologs used in the provided compositions and methods are TPGS homologs.

As used herein, "TPGS homologs" are analogs of TPGS that differ from a TPGS parent compound only by the presence or absence of a simple unit, such as a methylene unit, or some multiple of such units, e.g., —$(CH_2)_n$—. Typically, suitable TPGS homologs have similar surfactant properties compared to the parent compound (TPGS), for example, similar HLB values, for example, HLB values between 12 or about 12 and 20 or about 20. Exemplary of TPGS homologs are tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz). Exemplary of TPGS homologs are compounds having the formula in Formula I

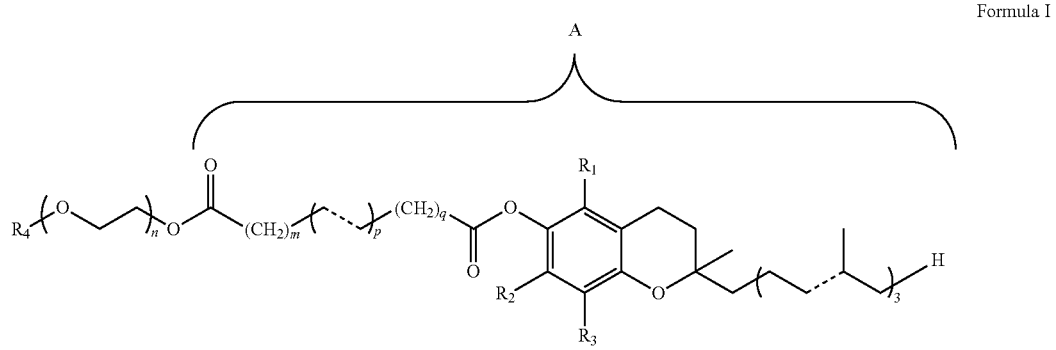

where $R_1$, $R_2$ and $R_3$ each independently is hydrogen (H) or methyl ($CH_3$); $R_4$ is H, $CH_3$ or the portion marked "A"; each dashed line (-----) is independently a single or double bond; n is an integer from 1 to 5000; m and q each independently are 0 or 1; and p is an integer from 1 to 20.

As used herein, "TPGS 1000 analogs" are compounds other than TPGS 1000 that are similar to a parent TPGS 1000 compound due to the addition or removal of an atom, one or more units (e.g., methylene units —$(CH_2)_n$—), or one or more functional groups. TPGS 1000 analogs include, but are not limited to, TPGS compounds having one or more PEG moieties that vary in chain length and molecular weight compared to TPGS 1000, including, for example, TPGS compounds having PEG moieties having a molecular weight between or about between 200 Da to 20,000 Da or about 20,000 Da, for example, PEG moieties having a molecular weight of or about 200, 300, 400, 500, 600, 800, 1000, 3000, Formula I (above), where neither of the dashed lines represent a double bond and where, when m and q both are 0, p is greater than 1.

As used herein, "TPGS 1000 homologs" are analogs of TPGS 1000 that differ from a TPGS 1000 parent compound only by the presence or absence of a simple unit, such as a methylene unit, or some multiple of such units, e.g., —$(CH_2)_n$—. Suitable TPGS 1000 homologs have similar surfactant properties compared to the parent compound (TPGS 1000), for example, similar HLB values, for example, HLB values between 12 or about 12 and 20 or about 20, such as 13-18. TPGS 1000 homologs include TPGS 1000 homologs with slight variations in the length of the PEG chain moiety.

As used herein, a "concentrate," particularly a "pre-emulsion concentrate," is a composition that generally is formulated for dilution, rather than direct ingestion, or for direct ingestion in a small quantity, such as in a capsule. For purposes herein, a "pre-gel concentrate," refers to a composition that is formulated as a composition for dilution, where a single concentrate provides a single dosage or a fractional dosage.

As used herein, "fractional dosage" refers to an amount that is less than a full dosage so that, when provided as a concentrate, a plurality of concentrates will be required to provide a single dosage. Typically, a fractional dosage is at least 20%, 25%, 50% of a full dosage.

As used herein, "colloid" refers to a mixture containing two phases, a dispersed phase and a continuous phase, with the dispersed phase containing particles (droplets) distributed throughout the continuous phase. Colloidal mixtures include aerosols, foams, and dispersions, for example, emulsions, for example, nanoemulsions. A liquid colloid, for example, a nanoemulsion, can have a similar appearance, for example, similar clarity, to a solution in which there is no dispersed phase.

As used herein, "emulsion" refers to a colloidal dispersion of two immiscible liquids, for example, an oil and water (or other aqueous liquid, e.g., a polar solvent), one of which is part of a continuous phase and the other of which is part of a dispersed phase. Emulsions typically are stabilized by one or more surfactants and/or co-surfactants and/or emulsion stabilizers. Surfactants form an interfacial film between the oil and water phase of the emulsion, providing stability. Typically, emulsions contain micelles that contain one or more surfactants surrounding a non-polar compound which is dispersed in the water phase. In general, emulsions (e.g., oil-in-water emulsions) are colloidal dispersions of two immiscible liquids (e.g., oil and an aqueous liquid, such as water) that contain a continuous and a dispersed phase. Emulsions can be used to disperse non-polar compounds in aqueous liquids. In an oil-in-water emulsion, the dispersed phase is an oil phase and the continuous phase is an aqueous (e.g., water) phase.

As used herein, "surfactant" refers to synthetic and naturally occurring amphiphilic molecules that have hydrophobic portion(s) and hydrophilic portion(s). Due to their amphiphilic (amphipathic) nature, surfactants typically can reduce the surface tension between two immiscible liquids, for example, the oil and water phases in an emulsion, stabilizing the emulsion. Surfactants can be characterized based on their relative hydrophobicity and/or hydrophilicity. For example, relatively lipophilic surfactants are more soluble in fats, oils and waxes, and typically have HLB values less than or about 10, while relatively hydrophilic surfactants are more soluble in aqueous compositions, for example, water, and typically have HLB values greater than or about 10. Relatively amphiphilic surfactants are soluble in oil- and water-based liquids and typically have HLB values close to 10 or about 10.

As used herein, "co-surfactant" is used to refer to a surfactant that is used in the provided compositions in combination with the primary surfactant, for example, the water-soluble vitamin E derivative mixtures (compositions) described herein, for example, to improve the emulsification of the provided compositions and/or compounds, for example, to emulsify the ingredients. In one example, the provided compositions can contain at least one surfactant and at least one co-surfactant. Typically, the co-surfactant represents a lower percent, by weight (w/w), of the provided compositions, compared to the surfactant. Thus, the provided compositions typically have a lower concentration of the co-surfactant(s) than of the surfactant.

As used herein, "HLB" refers to a value that is used to index and describe a surfactant according to its relative hydrophobicity/hydrophilicity, relative to other surfactants. A surfactant's HLB value is an indication of the molecular balance of the hydrophobic and hydrophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactants form and the solubility of the surfactant. See, for example, Griffin (1949) J. Soc. Cos. Chem. 1:311. Surfactant HLB values range from 1-45, while the range for non-ionic surfactants typically is from 1-20. The more lipophilic a surfactant is, the lower its HLB value. Conversely, the more hydrophilic a surfactant is, the higher its HLB value.

As used herein, "micelle" refers to aggregates formed by surfactants that typically form when a surfactant is present in an aqueous composition, typically when the surfactant is used at a concentration above the critical micelle concentration (CMC). In micelles, the hydrophilic portions of the surfactant molecules contact the aqueous or the water phase, while the hydrophobic portions form the core of the micelle, which can encapsulate non-polar ingredient(s), for example, the non-polar compounds in the provided concentrates. Typically, the surfactants in the provided concentrates form micelles containing the non-polar ingredient at their center in the aqueous liquid dilution compositions. Typically, the micelles in the provided concentrates have a particle size of about 1000 nm, typically less than or less than about 500 nm, typically less than 300 or less than about 300 nm, for example, less than 250 nm or less than about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm.

As used herein, "shelf life" refers to a time period within which the provided compositions retain desirable organoleptic properties, for example, the ability of the provided compositions to retain desirable organoleptic properties for a period of time, for example, for at least or more than 1, 2, 3, 4, or more weeks, typically at least or more than 1, 2, 3, 4, 5, 6, 7, 8, 9, 10, 11, 12, or more months, or at least or more than 1, 2, 3, 4, or more years. In one example, the compositions retain desirable organoleptic properties if they exhibit one or more of these described characteristics, over time, when kept at a particular temperature. In one example, the compositions retain desirable organoleptic properties at room temperature, for example, 25° C. or about 25° C. In another example, the compositions retain desirable organoleptic properties at between 19° C. and 25° C. In another example, the compositions retain desirable organoleptic properties at refrigerated temperatures, for example, 4° C. or about 4° C., or at frozen temperatures, for example, at −20° C. or about −20° C. In another example, the compositions retain desirable organoleptic properties at elevated temperatures, for example, at 40° C. or at about 40° C.

As used herein, "room temperature" and "ambient temperature" are used to describe a temperature that is common in one or more enclosed spaces in which human beings typically are or reside. Room temperature can vary, but generally refers to temperatures between or between about 19° C. and 25° C. When a composition is stored at room temperature, it should be understood it is generally kept at a temperature within this range or about within this range.

As used herein, "refrigerated temperature" refers to a temperature that is common in a refrigerator, for example, a household or restaurant refrigerator, for example, a temperature that is cooler than room temperature, but typically a few degrees above the freezing point of water. Typically, refrigerated temperatures are between or between about 0° C. and 10° C., for example, at or about 4° C. When a composition is stored at a refrigerated temperature, it should be understood that it is kept at a temperature common to household or industrial refrigerators.

As used herein, "hydrophilic" and "polar" refer synonymously to ingredients and/or compounds having greater solubility in aqueous liquids, for example, water, than in fats, oils and/or organic solvents (e.g., methanol, ethanol, ethyl ether, acetone and benzene).

As used herein, a "solvent" is an ingredient that can be used to dissolve another ingredient. Solvents include polar and non-polar solvents. Non-polar solvents include oils and other non-polar ingredients that dissolve non-polar compounds. Typically, the non-polar solvent is an oil that is included in the concentrates or liquid dilution compositions provided herein in addition to the non-polar ingredient. The non-polar solvent typically is not the non-polar ingredient itself, i.e., is distinct from the non-polar ingredient. More than one non-polar solvent can be used. Certain compounds, for example, flaxseed oil and safflower oil, can be non-polar solvents and non-polar ingredients. Typically, the non-polar solvent contains one or more oils, typically oils other than the non-polar ingredient or oil(s) not contained in the non-polar ingredient. Exemplary non-polar solvents include, but are not limited to, oils (in addition to the non-polar ingredient), for example, vitamin E oil, flaxseed oil, CLA, borage oil, rice bran oil, d-limonene, canola oil, corn oil, MCT oil, and oat oil. Other oils also can be used.

As used herein, "polar solvent" refers to a solvent that is readily miscible with water and other polar solvents. Polar solvents are well-known and can be assessed by measuring any parameter known to those of skill in the art, including dielectric constant, polarity index and dipole moment (see, e.g., Przybitek (1980) "High Purity Solvent Guide," Burdick and Jackson Laboratories, Inc.). For example, polar solvents generally have high dielectric constants, such as greater than or about 15, generally have high polarity indices, typically greater than or about 3, and generally large dipole moments, for example, greater than or about 1.4 Debye. Polar solvents include polar protic solvents and polar aprotic solvents.

As used herein, "non-polar," "lipophilic" and "lipid-soluble" synonymously refer to compounds and/or ingredients, for example, non-polar compounds and non-polar ingredients, which have greater solubility in organic solvents (e.g., ethanol, methanol, ethyl ether, acetone and benzene), fats and oils than in aqueous liquids, for example, water. Non-polar ingredients include drugs, hormones, vitamins, nutrients and other lipophilic compounds. Typically, non-polar compounds and ingredients are poorly water-soluble, for example, water insoluble or compounds having low water solubility. Exemplary non-polar ingredients include compounds that contain one or more non-polar compounds, for example, lipid-soluble drugs, hormones, essential fatty acids, for example, polyunsaturated fatty acids (PUFA), for example, omega-3 and omega-6 fatty acids, vitamins, nutrients, nutraceuticals, minerals and other compounds. Additional exemplary non-polar ingredients are described herein. The provided compositions can be formulated with any non-polar ingredient or compound, for example, any non-polar ingredient that is or contains a non-polar compound.

As used herein, "non-polar ingredient" refers to a component that is or contains one or more non-polar compounds. For example, the non-polar ingredient algae oil contains polyunsaturated fatty acid non-polar compounds, for example, the omega-3 polyunsaturated fatty acid DHA.

As used herein "non-polar compound" refers to a compound that contains an active component or is active such that, when administered to a subject, for example, a human, induces or is proposed to induce a desired response, such as altering body function at the cellular, tissue, organ or other level, and/or altering the cosmetic appearance or other property, or a compound that is ingested in order to achieve a desired effect. Non-polar compounds include any synthetic or natural non-polar ingredient or compound, including a pharmaceutical, drug, therapeutic, nutritional supplement, herb, hormone or other ingredient. Non-polar compounds can include the non-polar compounds listed herein, as well as other pharmaceutically acceptable or food-grade active derivatives of the non-polar compounds, for example, salts, esters, amides, prodrugs, active metabolites, isomers, fragments and analogs. Non-polar compounds can include compounds proven to have a desired effect and also compounds thought to produce such effects, for example, compounds typically ingested for nutritional supplementation purposes. The non-polar compound can be contained in a non-polar ingredient or is the non-polar ingredient.

As used herein, "drying" refers to the process by which the solvent is removed from a liquid composition, e.g., an emulsion, to yield a composition with no or a minimal amount of solvent. A liquid composition can be dried to remove the solvent and form a powder. Processes for producing powders from liquid compositions, e.g., emulsions, include spray drying, freeze drying, evaporation, lyophilization, and absorption plating.

"Spray drying" refers to a process by which a liquid composition is dried to form a spray dried composition, e.g., a powder. Generally, spray drying is used to dry a liquid composition to form a powder.

As used herein, a "sucrose fatty acid ester" is a compound having the formula shown in Scheme II, below.

Scheme II

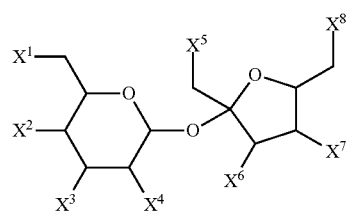

where each of $X^1$, $X^2$, $X^3$, $X^4$, $X^5$, $X^6$, $X^7$ and $X^8$ independently is:

a hydroxyl (—OH) group, or

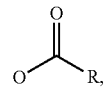

where:
  each R is an alkyl group having 3-27 carbon atoms; and
  when more than one of $X^1, X^2, X^3, X^4, X^5, X^6, X^7$ and $X^8$ is

each R can be a different alkyl group (e.g., having different number of carbon atoms and/or different saturation), or can be the same alkyl group. Sucrose fatty acid ester also refers to sucrose fatty acid ester mixtures, or blends, of sucrose fatty acid esters, which typically include monoesters, and can also include diesters, triesters and polyesters.

As used herein, a "subject" includes an animal, typically a mammal, typically a human.

As used herein, an "additive" includes anything that one can add to a food, beverage, or other human consumable to enhance one or more of its nutritional, pharmaceutical, dietary, health, nutraceutical, health benefit, energy-providing, treating, holistic, or other properties. For example, the additives can be oil-based additives (e.g., non-polar ingredients), such as nutraceuticals; pharmaceuticals; vitamins, for example, oil-soluble vitamins, e.g., vitamin D, vitamin E and vitamin A; minerals; fatty acids, such as essential fatty acids, for example, polyunsaturated fatty acids, e.g., omega-3 fatty acids and omega-6 fatty acids, such as alpha-linolenic acid (ALA), docosahexaenoic acid (DHA), eicosapentaenoic acid (EPA), gamma-linolenic acid (GLA), CLA, saw palmetto extract, flaxseed oil, fish oil and algae oil. phytosterols; coenzymes, such as coenzyme Q10; and any other oil-based additives.

As used herein, "water insoluble" refers to a compound that does not dissolve when the compound is mixed with water, for example, when mixed with water at room temperature, for example, between or between about 25° C. and 50° C.

As used herein, "low water solubility" refers to a compound that has a solubility in water of less than or about 30 mg/mL, for example, when mixed with water at room temperature, such as between or between about 25° C. and 50° C. As used herein, "poorly water-soluble" can be used to refer to compounds, for example, non-polar ingredients, that are water insoluble or have low water solubility.

As used herein, "waxy" is used to describe compositions and materials, typically oil-soluble compositions or materials, that are similar in consistency to one or more waxes or semi-solids. Typically, waxy compositions are of relatively low viscosity a little above their liquefying point. Exemplary of waxes that have waxy consistencies are natural waxes, including waxes of vegetal origin, such as purcellin, shea butter, cocoa butter, Japan wax, esparto grass wax, cork wax, Guaruma wax, rice shoot wax, Ouricury wax, montan wax, sunflower wax, sugar cane wax, carnauba wax, candelilla wax; fruit-derived waxes, such as orange wax, lemon wax, grapefruit wax and bayberry wax, and the like; waxes of animal origin, such as beeswax, lanolin, woolwax, spermateci and bear fat, shellac wax, and the like; mineral waxes such as ceresine and ozokerite waxes; and synthetic waxes, including petroleum-based waxes such as paraffin, petrolatum, micro wax, polyalkylene and polyethyleneglycol waxes, e.g. polyethylene wax; waxes based on chlorinated naphthalenes, such as "Halowax" and synthetic hydrocarbon waxes.

As used herein, "food and beverage product" refers to a product that is suitable for human consumption. For example, "food and beverage product" can refer to a pre-emulsion concentrate that is dissolved in a solvent, typically an aqueous solvent, e.g., water, to form a beverage composition or beverage product. "Food and beverage product" can also refer to the final product that is suitable for human consumption.

As used herein, "fatty acid" refers to straight-chain hydrocarbon molecules with a carboxyl (—COOH) group at one end of the chain.

As used herein, "polyunsaturated fatty acid" and "PUFA" are used synonymously to refer to fatty acids that contain more than one carbon-carbon double bonds in the carbon chain of the fatty acid. PUFAs, particularly essential fatty acids, are useful as dietary supplements.

As used herein, "essential fatty acids" are PUFAs that mammals, including humans, cannot synthesize using any known chemical pathway. Thus, essential fatty acids must be obtained from diet or by supplementation. Exemplary of essential PUFA fatty acids are the omega-3 (ω3; n-3) fatty acids and omega-6 (ω-6; n-6) fatty acids.

As used herein, "omega-3 (ω-3; n-3) fatty acids" and "omega-3 fatty acids" are used synonymously to describe methylene-interrupted polyenes which have two or more cis double bonds separated by a single methylene group, in which the first double bond appears at the third carbon from the last (ω) carbon. Omega-3 fatty acids are used as dietary supplements, for example, for disease treatment and prevention. The provided powders and emulsions and concentrates can contain non-polar ingredients that include at least one omega-3 fatty acid. Exemplary of omega-3 fatty acids are alpha-linolenic acid (α-linolenic acid; ALA) (18:3 ω-3) (a short-chain fatty acid); stearidonic acid (18:4 ω-3) (a short-chain fatty acid); eicosapentaenoic acid (EPA) (20:5 ω-3); docosahexaenoic acid (DHA) (22:6 ω-3); eicosatetraenoic acid (20:4 ω-3); docosapentaenoic acid (DPA, clupanodonic acid) (22:5 ω-3); 16:3 ω-3; 24:5 ω-3 and nisinic acid (24:6 ω-3). Longer chain omega-3 fatty acids can be synthesized from ALA (the short-chain omega-3 fatty acid). Exemplary of non-polar ingredients containing omega-3 fatty acids are non-polar ingredients containing DHA and/or EPA, for example, containing fish oil, krill oil and/or algae oil, for example, microalgae oil, and non-polar ingredients containing alpha-linolenic acid (ALA), for example, containing flaxseed oil.

As used herein, "omega-6 (ω-6; n-6) fatty acids" and "omega-6 fatty acids" are used synonymously to describe methylene-interrupted polyenes which have two or more cis double bonds separated by a single methylene group, in which the first double bond appears at the sixth carbon from the last (w) carbon. The provided concentrates and powder compositions can contain non-polar ingredients that include at least one omega-6 fatty acid. Exemplary of omega-6 fatty acids are linoleic acid (18:2 ω-6) (a short-chain fatty acid); gamma-linolenic acid (GLA) (18:3 ω-6); dihomo gamma linolenic acid (DGLA) (20:3 ω-6); eicosadienoic acid (20:2 ω-6); arachidonic acid (AA) (20:4 ω-6); docosadienoic acid (22:2 ω-6); adrenic acid (22:4 ω-6); and docosapentaenoic acid (22:5 ω-6). Exemplary of non-polar ingredients containing omega-6 fatty acids are ingredients containing GLA, for example, borage oil. Also exemplary of omega-6-containing non-polar ingredients are ingredients containing conjugated fatty acids, for example, conjugated linoleic acid (CLA) and ingredients containing saw palmetto extract.

As used herein, "algae oil" refers to any oil derived from marine dinoflagellates in, for example, microalgae, for example, *Crypthecodinium* sp, particularly, *Cryptheco-dinium cohnii*. Algae oil can be used as a non-polar ingredient, for example, in the provided concentrates and powder compositions. The algae oil typically contains DHA. The algae oil can be a source of EPA.

As used herein, "fish oil" refers to any oil derived from any fish, typically a cold water fish, for example, from fish tissue, such as from frozen fish tissue, for example, from cod liver. Fish oil can be used as a non-polar ingredient, for example, in the provided concentrates and powders. The fish oil typically contains DHA. The fish oil can also contain EPA. For example, the fish oil can contain a mixture of DHA and EPA.

As used herein, "flavor" is any ingredient that changes, typically improves, the taste and/or smell of the provided compositions.

As used herein, "G.R.A.S." and "GRAS" are used synonymously to refer to compounds, compositions and ingredients that are "Generally Regarded as Safe" by the USDA and FDA for use as additives, for example, in foods, beverages and/or other substance for human consumption, such as any substance that meets the criteria of sections 201(s) and 409 of the U.S. Federal Food, Drug and Cosmetic Act. Typically, the concentrates and powders provided herein are GRAS certified.

As used herein, "kosher" is used to refer to substances that conform to Jewish Kosher dietary laws, for example, substances that do not contain ingredients derived from non-kosher animals or do not contain ingredients that were not made following kosher procedures. Typically, the concentrates and powders provided herein are Kosher-certified.

As used herein, "rapid cooling" refers to a process by which a composition is cooled to a desired temperature, for example, between or between about 25° C. and 45° C., in less than or less than about 2 hours, typically less than or less than about 1 hour, for example, less than or less than about 30 minutes, such as 15 minutes.

As used herein, "particle size" and "average particle size" refer synonymously to the average diameter of particles in a provided liquid, for example, the droplet diameter or micelle diameter in an emulsion. Particle size diameter can be expressed in terms of a unit of length, for example, nanometers (nm). Alternatively, information about particles in concentrates and liquid dilution compositions can be expressed in terms of particle density, for example, ppm (parts per million), or percent solids, in the compositions.

As used herein, "visible particles" are particles, for example, in a liquid, such as an emulsion, that are visible when viewing the liquid with the naked eye (i.e., without magnification). For example, the visible particles can be particles that are observed by the artisan formulating the compositions, for example, the concentrates or the aqueous liquid dilution compositions containing the diluted concentrates. In one example, the provided compositions contain no visible particles. In another example, the compositions contain few visible particles, for example, no more visible particles than another liquid, for example, a beverage. The presence of visible particles and the number of visible particles is determined by empirical observation.

As used herein, "turbidity" is a measure of the cloudiness or haziness of a liquid, caused by particles in suspension in the liquid. Turbidity can be measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light passes through a sample with low turbidity with little disturbance. Other methods for measuring turbidity are well known and can be used with the provided methods and compositions. The units of a turbidity value measured with a nephelometer are Nephelometric Turbidity Units (NTU). For purposes herein, the compositions provided herein typically have low turbidity, for example, a turbidity value (NTU) of less than or about 80. For example, the compositions provided herein can have a turbidity value (NTU) of less than or about 30.

As used herein, a "turbid liquid" is one that is thick or opaque with visible particles in suspension, for example, a liquid that is cloudy or muddy in appearance.

As used herein, "clear" can be used to describe the compositions provided herein, for example, the aqueous liquid dilution compositions containing the diluted nanoemulsion concentrates and/or the nanoemulsion concentrates themselves. In one example, a clear liquid is one that does not appear cloudy by empirical observation, such as to the naked eye, and/or does not contain particles or crystals that are visible to the naked eye, or that does not exhibit "ringing." In another example, a clear liquid is one that has a low or relatively low turbidity value, for example an NTU value, that is less than or equal to a desired NTU value. For example, a liquid is described as clear that has an NTU value of less than or about 80. For example, a liquid can be clear and have an NTU value of less than or about 30. In another example, a clear liquid is one that has a small or relatively small average particle size, for example, less than or about 1000 nm. For example, a liquid can be described as clear and have an average particle size of less than or about 200 nm. In another example, clarity is expressed relatively. For example, it can be desired that a particular composition is equally as clear, about as clear, or more clear than another liquid (as measured empirically, or by measuring turbidity value or particle size). For example, clarity can be assessed relative to another aqueous liquid dilution composition, for example, a beverage. In one example, a liquid is clear if it is similar in appearance to another clear liquid, for example, a beverage, for example, water. In another example, it can be desired that a composition has a particle size that is less than or equal to another liquid, for example, a beverage. In another example, it can be desired that a composition has a turbidity value that is less than or equal to another liquid, for example, a beverage. In another example, it can be desired that a composition appears more clear or as clear as another liquid, for example, a beverage, for example, by having no more visible particles, no more crystal formation and/or no more cloudiness than the other liquid. In one example, the provided compositions are clear. In another example, they are relatively clear or as clear as or about as clear as another liquid, for example, a beverage that does not contain the non-polar ingredient or powder or emulsion.

As used herein, "ringing" refers to the formation of a whitish or opaque ring around a container containing a liquid, for example, an aqueous liquid, for example a beverage, for example, a liquid dilution composition containing an emulsion or nanoemulsion. Typically, the ring forms around the perimeter of the container, typically at the surface level of the liquid in the container, for example, at the neck of the container. Ringing can occur over time and, if it occurs over a short period of time, can be a sign of instability. Ringing typically is undesirable, particularly in the case of a liquid for human consumption, for example, a beverage. Typically, the provided concentrates and liquid dilution compositions do not exhibit ringing or are stable, without ringing, for a period of time, for example, days, weeks, months or years.

As used herein, "stability" refers to a desirable property of the provided concentrates, emulsions and powders, for example, the ability of the provided concentrates, emulsions and powders to remain free from one or more changes over a period of time, for example, at least or longer than 1 day, 1 week, 1 month, 1 year, or more. For example, a concentrate, emulsion and powder can be described as stable if it is formulated such that it remains free from oxidation or substantial oxidation over time, remains clear over time, remains safe and/or desirable for human consumption over time, has a lack of precipitates forming over time, has a lack of ringing over time, and/or does not exhibit any visible phase separation over a period of time. For example, the concentrates, emulsions and powders can be described as stable if they exhibit one or more of these described characteristics, over time, when kept at a particular temperature, for example, room temperature, e.g., at or about 25° C., slightly below room temperature, e.g., between or between about 19° C. and 25° C., at refrigerated temperatures, e.g., at or about 4° C., or at frozen temperatures, e.g., at or about −20° C. or lower.

As used herein, "phase separation" refers to the physical separation of a homogenous emulsion, for example, the separation of the oil and water phases of an emulsion, into two separate visible heterogeneous layers.

As used herein, "stabilize" means to increase the stability of one of the provided compositions.

As used herein, a "polar protic solvent" is a polar solvent containing a hydrogen atom attached to an electronegative atom, such that the hydrogen has a proton-like character and/or the bond between the hydrogen and electronegative atom is polarized. Exemplary polar protic solvents include, but are not limited to, water, alcohols, including monohydric, dihydric and trihydric alcohols, including, but not limited to, methanol, ethanol, glycerin and propylene glycol.

As used herein, "monohydric alcohols" are alcohols that contain a single hydroxyl group including, but not limited to, methanol, ethanol, propanol, isopropanol, n-butanol and t-butanol.

As used herein, "dihydric alcohols" are alcohols that contain two hydroxyl groups. Exemplary dihydric alcohols include, but are not limited to, glycols, e.g., propylene glycol, ethylene glycol, tetraethylene glycol, triethylene glycol and trimethylene glycol.

As used herein, "trihydric alcohols" are alcohols that contain three hydroxyl groups. Exemplary trihydric alcohols include, but are not limited to, glycerin, butane-1,2,3-triol, pentane-1,3,5-triol and 2-amino-2-hydroxymethyl-propane-1,3-diol.

As used herein, "preservative" refers to ingredients that can improve the stability of the provided concentrates, emulsions, and powders. Preservatives, particularly food and beverage preservatives, are well known. Any known preservative can be used in the provided concentrates, emulsions, and powders. Exemplary of the preservatives that can be used in the provided concentrates, emulsions, and powders are oil-soluble preservatives, such as benzyl alcohol, benzyl benzoate, methyl paraben, propyl paraben, antioxidants, for example, vitamin E, vitamin A palmitate and beta carotene. Typically, a preservative is selected that is safe for human consumption, for example, in foods and beverages, for example, a GRAS certified and/or Kosher-certified preservative, for example, benzyl alcohol.

As used herein, an "antioxidant" refers to a stabilizer or one component of a stabilizing system that acts as an antioxidant, and that, when added to a beverage composition in combination with the other required components (i.e., acid and/or bicarbonate or carbonate) yields beverage compositions that retain one or more desired organoleptic properties, such as, but not limited to, the taste, smell, odor and/or appearance, of the beverage composition over time. Typically, antioxidants are food-approved, e.g., edible antioxidants, for example, antioxidants that are safe and/or approved for human consumption. Exemplary antioxidants include, but are not limited to, ascorbic acid, vitamin C, ascorbate and coenzyme Q-containing compounds, including, but not limited to, coenzyme Q10.

As used herein, an "acid" or "ingestible acid" refers to a stabilizer or one component of a stabilizing system that, when added to a beverage composition in combination with the other components (i.e., antioxidant and/or bicarbonate or carbonate), yields beverage compositions that retain one or more desired organoleptic properties, such as, but not limited to, the taste, smell, odor and/or appearance of the beverage composition over time. Typically, the acids are food-approved, e.g., edible acids or ingestible acids, for example, acids that are safe and/or approved for human consumption. Exemplary acids include, but are not limited to, citric acid, phosphoric acid, adipic acid, ascorbic acid, lactic acid, malic acid, fumaric acid, gluconic acid, succinic acid, tartaric acid and maleic acid.

As used herein, a "bicarbonate" or "carbonate" refers to a stabilizer or one component of a stabilizing system that, when added to a beverage composition in combination with the other components (i.e., the acid and/or antioxidant) yields beverage compositions that retain one or more desired organoleptic properties, such as, but not limited to, the taste, smell, odor and/or appearance of the beverage composition over time. Typically, bicarbonates or carbonates are food-approved, e.g., edible bicarbonates or carbonates, for example, bicarbonates or carbonates that are safe and/or approved for human consumption. Exemplary bicarbonates include, but are not limited to, potassium bicarbonate and sodium bicarbonate. Exemplary carbonates include, but are not limited to, potassium carbonate, sodium carbonate, calcium carbonate, magnesium carbonate and zinc carbonate.

As used herein, "carbonation" or "carbonated" refers to carbon dioxide dissolved in liquid, such as a beverage base, including water. A liquid, or beverage, can be carbonated by direct addition of carbon dioxide to the liquid or beverage.

As used herein, "emulsion stabilizer" refers to compounds that can be used to stabilize and/or emulsify and/or change the viscosity of the provided concentrates and aqueous compositions containing the diluted concentrates. For example, the emulsion stabilizer can increase the viscosity of the liquid concentrate. One or more emulsion stabilizers can be added, for example, during formulation after evaluation of an initial concentrate, particularly if the oil and water phases of the initial concentrate (or the aqueous liquid dilution composition resulting from dilution of the initial concentrate) appear to be separating. Addition of the emulsion stabilizer can prevent separation of the oil and water phases.

As used herein, a "pH adjuster" is any compound, typically an acid or a base, that is capable of changing the pH of the provided concentrates and liquid dilution compositions, for example, to reduce the pH of the concentrates or liquid dilution composition or to increase the pH of the concentrates or liquid dilution composition, typically without altering other properties of the concentrates and liquid dilution composition, or without substantially altering other properties. pH adjusters are well known. Exemplary of the pH adjusters are acids, for example, citric acid and phosphoric acid, and bases.

As used herein, "vessel" refers to any container, for example, any tank, pot, vial, flask, cylinder or beaker that can be used to contain the ingredients and/or phases of the provided concentrates and liquid dilution compositions during the methods for making the concentrates and liquid dilution compositions. The vessel can be a tank that is used to mix and/or heat one or more ingredients and/or phases of the composition, for example, the water phase tanks and oil phase tanks, such as during the provided scaled-up methods. The oil and the water phases can be mixed and heated in separate tanks before combining the phases to form an emulsion. The tank can be a packaging or holding tank, which holds the provided compositions after forming the compositions, for example, the emulsions. A number of tanks are available for mixing ingredients. Typically, the tanks are cleaned, for example, rinsed, soaped and/or sanitized according to known procedures prior to use and between uses. The tanks can be equipped with one or more mixers, for example, a standard mixer and/or homogenizer, which are used to mix the ingredients added to the tank. The tank can be equipped with a heating and/or cooling device. For example, the tank can be a water-jacketed tank. The temperature of the water-jacketed tank is controlled through the water-jacket, for example, to heat the contents, for example, while mixing.

As used herein, a "water phase vessel" refers to a vessel used to mix and/or heat the water phase ingredients to generate the water phase of the provided compositions. The water phase vessel can be a tank. The tank can be a water-jacketed tank, which is a tank equipped with a water jacket that can be used to heat the contents of the tank.

As used herein, an "oil phase vessel" refers to a vessel used to mix and/or heat the oil phase ingredients to generate the oil phase of the provided compositions. The oil phase vessel can be an oil phase tank. The tank can be a water-jacketed tank.

As used herein, "transfer device" refers to any equipment, combination of equipment and/or system that can be used to transfer liquid, for example, from one tank to another tank, in the provided methods for making the concentrates and liquid dilution compositions. Exemplary of the transfer devices is a transfer pump and appropriate fittings, for example, sanitary fittings, ball valves and transfer hoses, for example, food grade hoses.

As used herein a "mixer" is any piece of equipment or combination of equipment that can be used to mix ingredients in the provided methods for making the concentrates and liquid dilution compositions, for example, standard mixers and homogenizers (shears). For example, mixers can be used to mix the ingredients of the water phase and the oil phase and/or to mix the additional ingredients.

As used herein, "standard mixers" are mixers that are used to combine a group of ingredients, for example, the oil phase ingredients or the water phase ingredients, or to mix one or more ingredients with a liquid, for example, with an emulsion, for example, to mix additional ingredients with the emulsion. Standard mixers can be any mixers that move the material, for example, the ingredients, during heating, for example, to promote dissolving of the ingredients.

As used herein, "homogenizer" and "shear" are used to refer to mixers that typically have high shear, which can be used, for example, to form an emulsion, for example, to emulsify the water phase and the oil phase, in the provided methods. The homogenizers typically are capable of high-shear mixing, which emulsifies the phases.

As used herein, a "cooling apparatus" is any piece of equipment or combination of equipment that can be used with the provided methods to cool the compositions and phases and ingredients thereof, for example, during mixing and/or homogenizing, for example, to chill the mixture while emulsifying the oil and water phases. Exemplary of the cooling apparatuses are coolers (chillers), for example, recirculating coolers which can be attached, for example, to the tanks used in the provided methods, for example, remotely or by a tank mounted in the cooler, to recirculate fluid from the tank, through the chiller and back to the tank, in order to rapidly cool and maintain the temperature of the mixture during mixing. Typically, the cooling apparatus can be used to cool the liquid to between or about between 25° C. and 45° C., for example, to at or about 25, 26, 27, 28, 29, 30, 31, 32, 33, 34, 35, 36, 37, 38, 39, 40, 41, 42, 43, 44 or 45° C.

As used herein, "excipients," refer to any substance needed to formulate the composition to a desired form. For example, suitable excipients include but are not limited to, diluents or fillers, binders or granulating agents or adhesives, disintegrants, lubricants, antiadherants, glidants, wetting agents, dissolution retardants or enhancers, adsorbents, buffers, chelating agents, preservatives, colors, flavors and sweeteners. Typical excipients include, but are not limited to, starch, pregelatinized starch, maltodextrin, monohydrous dextrose, alginic acid, sorbitol and mannitol. In general, the excipient should be selected from non-toxic excipients (IIG, Inactive Ingredient Guide, or GRAS, Generally Regarded as safe, Handbook of Pharmaceutical Excipients).

As used herein, a "binder" is an excipient added to a composition to aid formation of a powder when the composition is dried. Non-limiting examples of suitable binders include, but are not limited to, acacia, dextrin, starch, povidone, carboxymethylcellulose, guar gum, glucose, hydroxypropyl methylcellulose, methylcellulose, polymethacrylates, maltodextrin, hydroxyethyl cellulose, whey, disaccharides, sucrose, lactose, polysaccharides and their derivatives, such as starches, cellulose or modified cellulose, such as microcrystalline cellulose and cellulose ethers, such as hydroxypropyl cellulose, sugar alcohols, such as xylitol, sorbitol or maltitol, protein, gelatins and synthetic polymers, such as polyvinylpyrrolidone (PVP) or polyethylene glycol (PEG).

As used herein, "stabilizers" refer to additives that aid in retaining organoleptic properties. These include, but are not limited to, carbonate, bicarbonate and/or $CO_2$. Additional components, such as ingestible acids and antioxidants, such as, for example, ascorbic acid, ascorbate or a coenzyme Q-containing compound, improve organoleptic properties.

As used herein, "w/w," "by weight," "% by weight," "wt %" and "weight percent" are used synonymously to express the ratio of the mass of one component of a composition compared to the mass of the entire composition. For example, when the amount of a particular ingredient represents 1%, by weight (w/w), of a concentrate, the mass of that ingredient is 1% of the mass of the entire concentrate. Similarly, when the amount of an ingredient is 50% (w/w) of the concentrate, the mass of that ingredient is 50% of the entire mass of the concentrate. Similarly, when a composition and/or a compound contains 10%, by weight, of an ingredient, the mass of the ingredient is 10% of the total mass of the composition or compound. When a composition contains 10 wt % of an ingredient, the mass of that ingredient is 10% of the mass of the entire composition. When only a concentration, amount, or percentage (without units) is listed, it is to be understood that the concentration or percentage is a concentration or percentage by weight.

As used herein "v/v" and "volume percent" are used synonymously to express the ratio of the volume of one component of a composition to the volume of the entire composition.

As used herein, "not more than" and "NMT" refer to a quantity that is less than or equal to the listed quantity. Similarly, "not less than" and "NLT" refer to a quantity that is greater than or equal to the listed quantity.

As used herein, the singular forms "a," "an" and "the" include plural referents unless the context clearly dictates otherwise. Thus, for example, reference to a composition containing "a non-polar ingredient" includes compositions with one or more non-polar ingredients.

As used herein, ranges and amounts can be expressed as "about" a particular value or range. About also includes the exact amount. Hence, "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.72, 8.5 and 11.95 grams.

As used herein, "optional" or "optionally" means that the subsequently described event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

As used herein, "consisting essentially of" means containing the following list of ingredient(s), and not including any additional non-polar ingredient other than those listed.

B. Compositions Containing Non-Polar Compounds

Non-polar compounds and ingredients are poorly water soluble (e.g., have low water solubility or are water-insoluble). Thus, it generally can be difficult to formulate non-polar compounds and ingredients into compositions, such as powders, for example, spray-dried powders, that are free flowing, i.e., not sticky, and water soluble. In order to produce powders, such as spray-dried powders, that are free flowing, i.e., not sticky, a threshold amount of solids, and a minimal moisture content, is necessary. Typical powders, for example, typical spray-dried powders, with high concentrations of non-polar ingredients also have a high oil load, for example, a high concentration of non-polar ingredients and solvents, thus making it very difficult to produce a powder that is both water-soluble and free flowing, i.e., not sticky, due to the high moisture content. Typical powders will separate, rather than dissolve, in water, and are not stable. Provided herein are water-soluble powders that are free flowing, i.e., not sticky, that contain a surfactant, for example, a sugar fatty acid ester, e.g., a sucrose fatty acid ester, that also acts as a binder and/or in combination with a binder, that does not contribute to the oil load, thus allowing the addition of high concentrations of non-polar compounds. The provided water-soluble powders have high concentrations of non-polar ingredients, for example, at least 10%, 20%, 30%, 40%, 50%, or more, and are stable and free-flowing, i.e., not sticky.

Provided herein are water-soluble powder compositions that contain high concentrations of non-polar ingredients that contain non-polar compounds. The powders are formulated so that they contain high concentrations of non-polar ingredients and are free flowing, i.e., not sticky, and water-soluble. The powders contain sugar fatty acid esters, such as sucrose fatty acid esters, that serve as surfactants and binders. The sugar fatty acid esters, such as sucrose fatty acid esters, are present in the water-soluble powders in place of or in combination with binders, and result in powders that are water-soluble and contain high concentrations of non-polar ingredients. Also provided are pre-spray emulsions from which the powders are produced.

Also provided herein are the pre-spray emulsions that contain a sugar fatty acid ester surfactant, such as a sucrose fatty acid ester surfactant, in place of or in combination with a binder, and high concentrations of non-polar ingredients. When dried, the emulsions provided herein are able to form free-flowing powders, i.e., not sticky, when dried, e.g., spray dried, as compared to the same emulsions not containing a sugar fatty acid ester surfactant in place of or in combination with a binder, which instead produce oily, sludge-like compositions with a high moisture content. Methods and compositions for formulating compositions, for example, water-soluble powders, containing non-polar ingredients also are provided herein.

1. Pre-Emulsions Concentrates Containing Non-Polar Compounds

Exemplary of the provided compositions are pre-emulsion concentrates containing one or more non-polar ingredients that are or contain non-polar compounds and a polyalkylene glycol derivative of vitamin E. The concentrates can include a preservative, e.g., benzyl alcohol. The pre-emulsion concentrates can be liquid compositions at room temperature or can be semi-solid compositions, typically having a waxy or creamy consistency, for example, the consistency of a substance such as wax, for example, a lip balm, at room temperature, for example, at 25° C. or about 25° C., and become liquid at higher temperatures, for example, when heated to higher temperatures, such as to 125° F. or about 125° F., or to 50° C. or about 50° C., or to 60° C. or about 60° C.

The pre-emulsion concentrates can be combined with other ingredients in an aqueous media, using the provided methods, to form the provided pre-spray emulsion compositions containing non-polar ingredients. The pre-emulsion concentrates are formulated such that addition of the concentrates, for example, to an aqueous media, yields a pre-spray emulsion composition having one or more desirable properties, for example, an emulsion that is able to be spray dried into a powder, such as a free-flowing, i.e., not sticky, powder, such as the powders provided herein.

The pre-emulsion concentrates can be formulated such that, when added to an aqueous medium (e.g., water), they result in composition that is an emulsion, such as a nanoemulsion, e.g., a pre-spray emulsion, in which the non-polar compound(s) are present in micelles. These micelles, containing the non-polar compound surrounded by the one or more surfactants, facilitate the dispersion of the non-polar compound among the polar solvent(s) of the aqueous medium in the pre-spray emulsion compositions. The pre-emulsion concentrates are formulated such that the micelles in the pre-spray emulsion have a small or relatively small particle size, for example, less than 1000 or about 1000 nm, less than 500 or about 500 nm, typically less than 300 or about 300 nm, typically less than 250 or about 250 nm, typically less than 200 or about 200 nm, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with increased clarity of the pre-spray emulsion compositions that results from diluting the pre-emulsion concentrates. For example, an emulsion with a smaller particle size can be more clear than an emulsion with a larger particle size. Small particle size also can contribute to other desirable properties, for example, stability.

A number of parameters of the pre-emulsion concentrates, including ingredients, their relative concentrations, and methods for making the pre-emulsion concentrates, affect the particle size of the liquid dilution compositions made by diluting the pre-emulsion concentrates. In particular, the nature of the ingredients and the relative concentrations of the ingredients in the pre-emulsion concentrates contribute to small particle size and clarity of the pre-spray emulsions.

Accordingly, properties of the ingredients and their relative concentrations in the pre-emulsion concentrates are important for the ability of the pre-emulsion concentrate to yield desirable pre-spray emulsion compositions which, in turn affect the ability of the pre-spray emulsion compositions to yield desirable water-soluble powders. Determining the appropriate ingredients, and relative concentrations thereof, that yield pre-spray emulsions and water-soluble powders having desirable properties is carried out using the provided methods for formulating the pre-emulsion concentrates.

a. Formulating the Pre-Emulsion Concentrates Containing Non-Polar Compounds

Typically, the pre-emulsion concentrates contain one or more non-polar ingredients, e.g., non-polar ingredients that contain one or more non-polar compounds and a polyethylene glycol derivative of vitamin E, e.g., TPGS. The pre-emulsion concentrates can additionally include a preservative, e.g., benzyl alcohol.

As a first step in formulating the provided pre-gel concentrates, one or more initial pre-gel concentrates are made and evaluated for desired properties. For this step, ingredients are selected, for example, from one or more of the lists of ingredients provided below. A starting concentration (weight percentage) of each selected ingredient is selected from within an appropriate concentration range for that ingredient or category of ingredient. For example, a starting concentration of a polyethylene glycol derivative of vitamin E, e.g., TPGS, is selected from within an appropriate concentration range. In some cases, the initial pre-emulsion concentrate is formulated based on the ingredients, and concentrations thereof, of an existing pre-emulsion concentrate, having one or more desired properties.

The initial pre-emulsion concentrate(s) is then made, using the methods for making the pre-emulsion concentrates provided below, adding each ingredient at its starting concentration at the appropriate step. In one example, more than one initial pre-emulsion concentrate is made. For example, multiple initial pre-emulsion concentrates, each having a different concentration of one or more ingredients, can be made and compared. For example, multiple initial pre-emulsion concentrates can be made in order to test various representative concentrations within an appropriate concentration range for one or more particular ingredient.

Each of the provided pre-emulsion concentrates contains at least one non-polar compound, typically more than one non-polar compound, for example, non-polar ingredients that contain one or more non-polar compounds. Any non-polar ingredient that contains one or more non-polar compounds can be formulated with the provided methods and pre-emulsion concentrates. Several exemplary non-polar ingredients that can be incorporated into the provided concentrates are described herein below. Typically, the non-polar ingredient is or contains a non-polar compound, for example, an oil-based ingredient, for example, a polyunsaturated fatty acid (PUFA), a coenzyme Q, or a vitamin.

The pre-emulsion concentrates provided herein contain high amounts of non-polar compounds, e.g., non-polar ingredients that contain non-polar compounds, for example, between or between about 30 wt % and 99 wt % non-polar ingredient, typically at least 40 wt %, or at least 50 wt %, such as between or between about 55% and 60%, 55% and 65%, 55% and 70%, 55% and 75%, 55% and 80%, 55% and 85%, 55% and 90%, 55% and 95%, 55% and 99%, 60% and 65%, 60% and 70%, 60% and 75%, 60% and 80%, 60% and 85%, 60% and 90%, 60% and 95%, 60% and 99%, 65% and 70%, 65% and 75%, 65% and 80%, 65% and 85%, 65% and 90%, 65% and 95%, 65% and 99%, 70% and 75%, 70% and 80%, 70% and 85%, 70% and 90%, 70% and 95%, 70% and 99%, 75% and 80%, 75% and 85%, 75% and 90%, 75% and 95%, 75% and 99%, 80% and 85%, 80% and 90%, 80% and 95%, 80% and 99%, 85% and 90%, 85% and 95%, 85% and 99%, 90% and 95%, 90% and 99%, and 95% and 99%, by weight of the pre-emulsion concentrate.

In addition to the non-polar compounds, the pre-emulsion concentrates contain a polyethylene glycol derivate of vitamin E, e.g., TPGS. Typically, the polyethylene glycol derivate of vitamin E has an HLB value between 12 or about 12 and 20 or about 20, for example, 12, 13, 14, 15, 16, 17, 18, 19, 20, about 12, about 13, about 14, about 15, about 16, about 17, about 18, about 19 or about 20. Exemplary of suitable polyethylene glycol derivatives of vitamin E described herein, such as tocopherol polyethylene glycol succinate (TPGS), such as the TPGS, TPGS analogs, TPGS homologs and TPGS derivatives described herein. Typically, the polyethylene glycol derivate of vitamin E is GRAS (generally recognized as safe)-certified by the FDA and/or Kosher certified, for example, TPGS.

In the pre-emulsion concentrates provided herein, the concentration of the polyethylene glycol derivative of vitamin E, e.g., TPGS, is less than 65% or about 65%, typically less than 55% or about 55%, typically less than 45% or about 45%, for example, less than 40% or about 40%, for example, a concentration within the concentration range of between 1% or about 1% and 40% or about 40%, typically between 1% or about 1% and 35% or about 35%, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%, by weight, of the pre-emulsion concentrate.

The pre-emulsion concentrates can further contain a preservative. Typically, the preservative is present in an amount sufficient to preserve the composition. The preservative, for example, can contain benzyl alcohol.

A number of parameters of the pre-emulsion concentrates, including ingredients, their relative concentrations, and methods for making the pre-emulsion concentrates, affect the desirable properties of the concentrate, for example, the ability of the concentrate to form a stable pre-spray emulsion when added to water. By extension, these parameters of the pre-emulsion concentrates also affect the desirable properties of the pre-spray emulsions and water-soluble powders, for example, the ability of the pre-spray emulsion to form a free-flowing, i.e., not sticky, powder upon drying. In particular, the nature of the ingredients, and the relative concentrations of the ingredients in the pre-emulsion concentrates, contribute to the desirable properties of the pre-emulsion concentrates, the pre-spray emulsions, and thus, the water-soluble powders provided herein.

Accordingly, properties of the ingredients and their relative concentrations in the pre-emulsion concentrates are important for the ability of the pre-emulsion concentrates to yield desirable water-soluble powders. Determining the appropriate ingredients, and relative concentrations thereof, that will yield water-soluble powders having desirable properties, is carried out using the provided methods for formulating the pre-emulsion concentrates.

b. Polyalkylene Glycol Derivatives of Vitamin E

The pre-emulsion concentrates provided herein contain at least one polyalkylene glycol derivative of vitamin E. Exemplary of the polyalkylene glycol derivatives of vitamin E described herein are polyethylene glycol (PEG) derivatives of vitamin E, for example, PEG derivatives of tocopherols or tocotrienols. Suitable PEG derivatives of vitamin E can contain one or more tocopherol or tocotrienol, attached to one or more PEG moiety via a linker, for example, a dicarboxylic acid linker. Exemplary dicarboxylic acid linkers include succinic acid and succinic anhydride. An exemplary polyethylene glycol derivative of vitamin E is shown schematically below:

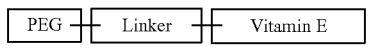

where the line between the PEG and the linker, and the line between the linker and the vitamin E moiety, each independently represent a covalent bond, for example, a covalent bond that forms an ester, ether, amide or thioester.

Typically, the vitamin E-PEG derivatives are made by covalently attaching the PEG moiety, such as by esterification, to a vitamin E-linker conjugate (e.g., a tocopherol-linker conjugate). The vitamin E-linker conjugate can be formed through esterification of the hydroxyl group of the vitamin E moiety with a carboxylic acid group of a linker, such as a dicarboxylic acid linker. In one example, the vitamin E-linker conjugate can be a tocopherol-linker conjugate, such as a tocopherol ester, for example, tocopherol succinate. The esterification reaction can be performed by any of a number of known methods, including those described in U.S. Pat. Nos. 2,680,749; 4,665,204; 3,538,119; and 6,632,443. The resulting vitamin E-linker conjugate can then be attached to a PEG moiety by another esterification reaction, for example, between a carboxylic acid group of the vitamin E-linker conjugate and a hydroxyl group of the PEG moiety, to form a vitamin E-PEG derivative.

PEG derivatives of a tocopherol-linker or tocotrienol-linker compound can be made by any other method known to those of skill in the art. Various methods known in the art for producing PEG derivatives can be used to attach a PEG molecule to tocopherol-linker or tocotrienol-linker compounds. For example, a tocopherol-linker compound can form a covalent bond to the PEG molecule via an amide, ether or thioether bond. For example, a tocopherol-linker conjugate that contains an amine group can be reacted with a PEG-NHS (N-hydroxysuccinimide) derivative to form an amide bond between the tocopherol-linker conjugate and the PEG molecule. A tocopherol-linker conjugate that contains an amine group can be reacted with a PEG-aldehyde derivative to form an amide bond between the tocopherol-linker conjugate and the PEG molecule. In another example, a tocopherol-linker conjugate that contains an carboxylic acid can be activated to the corresponding acid halide and reacted with a PEG-SH derivative to form a thioester bond between the tocopherol-linker conjugate and the PEG molecule.

i. Tocopherols and Tocotrienols

The vitamin E derivative can be any vitamin E derivative, for example, any tocopherol or tocotrienol. The tocopherols used can be any natural or synthetic vitamin E tocopherol, including, but not limited to, alpha-tocopherols, beta-tocopherols, gamma-tocopherols, and delta tocopherols, either in pure forms or in heterogeneous mixtures of more than one form. Exemplary tocopherols are d-α-tocopherols and dl-tocopherols. To make the vitamin E derivative, the tocopherol typically is esterified with a linker, for example, a dicarboxylic acid, to form a tocopherol ester, which then is joined to a PEG moiety.

The tocotrienols used can be any natural or synthetic vitamin E tocotrienol, including, but not limited to, alpha-tocotrienols, beta-tocotrienols, gamma-tocotrienols, and delta-tocotrienols, either in pure forms or in heterogeneous mixtures of more than one form. Mixtures of tocopherols and tocotrienols are contemplated for use in the provided methods and compositions. A tocotrienol can be esterified with a linker, such as a dicarboxylic acid, before joining with a PEG moiety.

ii. Linkers

Typically, the PEG derivatives of vitamin E are diesters or other esters, e.g., triesters. When the PEG derivative is a diester, the linker joining the vitamin E moiety to the PEG typically is a carboxylic acid, typically a dicarboxylic acid, as in, for example, tocopherol polyethylene glycol succinate (TPGS), where the linker is a succinic acid, and the derivative is made by an esterification reaction joining a PEG moiety and a tocopherol ester of the dicarboxylic acid. In another example, the linker is another molecule, for example, an amino acid, such as glycine, alanine, 5-aminopentanoic acid or 8-aminooctanoic acid, or the linker is an amino alcohol, such as ethanolamine.

iii. PEG Moieties

The polyalkylene glycol moiety used in the polyalkylene glycol vitamin E derivative can be any of a plurality of known polyalkylene glycol moieties, such as any known PEG moiety. Exemplary of suitable polyalkylene glycol moieties are for example, PEG moieties, such as PEG moieties having varying chain lengths, and varying molecular weights, for example, PEG 1000, PEG 200, PEG 500, and PEG 20,000. The number following the individual PEG moiety indicates the molecular weight (in daltons (Da) of the PEG moiety. Typically, the PEG moiety of a tocopherol-derived surfactant has a molecular weight of between 200 or about 200 to 20,000 or about 20,000 Da, typically between 200 and 6000 Da, for example, between 600 or about 600 Da and 6000 or about 6000 Da, typically between 200 or about 200 Da and 2000 or about 2000 Da, between 600 or about 600 Da and 1500 or about 1500 Da, such as 200, 300, 400, 500, 600, 800, and 1000 Da. Exemplary of a PEG derivative of a tocopherol ester having a PEG moiety with a molecular weight of 1000 Da is TPGS-1000. Also exemplary of suitable PEG moieties are PEG moieties that are modified, for example, methylated PEG (m-PEG), which is a PEG chain capped with a methyl group. Other known PEG analogs also can be used. The PEG moieties can be selected from among any reactive PEG, including, but not limited to, PEG-OH, PEG-NHS, PEG-aldehyde, PEG-SH, PEG-NH$_2$, PEG-COOH, and branched PEGs.

iv. Tocopheryl Polyalkylene Glycol Derivatives

In its natural water-insoluble state, vitamin E, e.g., tocopherol or tocotrienol, is easily absorbed and used in humans and animals. Processing of foods and feeds by industry for long-term storage can promote accelerated degradation of the effective vitamin E content. To compensate for the loss of natural vitamin E from food sources, nutritional supplements of natural or synthetic fat-soluble vitamin E have been developed. Not all humans and animals can sufficiently absorb the supplements though. To address this problem, water-soluble vitamin E derivatives have been developed that are an excellent source of vitamin E (i.e., maintain a high degree of vitamin E biological activity) in humans with impaired vitamin E absorption, for example, in humans with malabsorption syndromes (Traber et al. (1986) Am. J. Clin. Nutr. 44:914-923). Water-soluble vitamin E derivatives have been developed for this purpose. The water-soluble vitamin E derivative D-α-tocopheryl polyethylene glycol succinate (TPGS) is exemplary of the tocopheryl polyethylene glycol derivatives.

TPGS contains a hydrophilic (i.e., water-soluble) polyethylene glycol (PEG) chain and a lipophilic (i.e., water-insoluble) α-tocopherol head. The amphiphilic structure of TPGS, shown below, renders it much more water-soluble than traditional vitamin E, allowing TPGS to form a micellar solution at low concentrations (0.04-0.06 mmol/L) that can be absorbed by humans and animals in the absence of bile salts.

J. Controlled Release 88:355-368), and fat-soluble vitamins such as vitamin D (Argao et al. (1992) Ped. Res. 31(2):146-150).

Exemplary of a tocopheryl polyalkylene glycol derivative suitable for use in the pre-emulsion concentrates provided herein is D-α-tocopheryl polyethylene glycol succinate (TPGS), such as TPGS-1000, for example, the food grade TPGS sold under the name Eastman Vitamin E TPGS®, food grade, by Eastman Chemical Company, Kingsport, Tenn. Other exemplary tocopheryl polyalkylene glycol derivatives suitable for use in the pre-gel concentrates provided herein are tocopheryl polyalkylene glycol compositions, for example, TPGS compositions, containing a relatively high percentage, such as at least 13%, typically at least 20%, 25%, 29%, 30%, 35%, 40%, 45%, 48%, 49%, 50%, or more, typically up to 60-65%, of the dimer form of TPGS, with the remainder of the TPGS composition containing the monomer form of TPGS and a small percentage, such as less

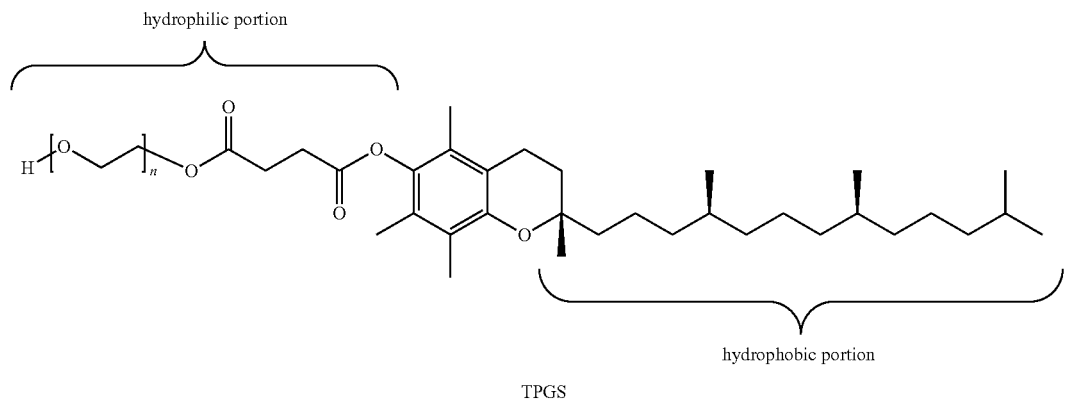

TPGS

TPGS has been approved by the FDA as a water-soluble vitamin E nutritional supplement. It is a GRAS (Generally Regarded As Safe)-listed supplement that can be taken orally at long-term doses of 13.4-16.8 mg/kg/day or up to 100 mg/kg/day for people with impaired uptake. In the body, TPGS undergoes enzymatic cleavage to deliver the lipophilic antioxidant α-tocopherol (vitamin E) to cell membranes. Cellular enzymatic hydrolysis by cytoplasmic esterases liberates free α-tocopherol, which then localizes in the cell membrane, and through free radical quenching, protects the membrane from lipid peroxidation and damage.

TPGS also is used as a non-ionic surfactant and emulsifier that, as reported, has an HLB value of approximately 13. Non-ionic surface-active agents are used in oral formulations to enhance the bioavailability of water-insoluble pharmaceuticals, such as drugs, vitamins, or other biologically active compounds. TPGS is an effective absorption and bioavailability enhancer, and has been approved for use as a drug solubilizer in oral, parenteral, topical, nasal, and rectal/vaginal therapies (see, e.g., Constantinides et al. (2006) Pharm. Res. 23(2):243-255; Varma et al. (2005) Eur. J. Pharm. Sci. 25(4-5):445-453) and as a solubilizer for inhalation drug delivery (Fulzele et al. (2006) 23(9):2094-2106). TPGS improves the bioavailability of such water-insoluble drugs as the HIV protease inhibitor amprenavir (Yu et al. (1999) Pharm. Res. 16:1812-1817; Brouwers et al. (2006) J. Pharm. Sci. 95:372-383), the non-nucleoside reverse transcriptase inhibitor UC 781 (Goddeeris et al. (2008) Eur. J. Pharm. Sci. 35:104-113), cyclosporin (Sokol et al. (1991) Lancet 338:212-215), paclitaxel (Zhao et al. (2010) J. Pharm. Sci. 99(8):3552-3560), estradiol (Sheu et al. (2003)

than 5%, 4%, 3%, 2%, 1% of contaminants, such as higher order polymers and reagents, such as vitamin E and polyethylene glycol. Exemplary of tocopheryl polyalkylene glycol derivatives are those described in U.S. patent application Ser. No. 14/207,310 and International PCT Application No. PCT/US14/25006, now published as US-2014-0271593-A1 and WO 2014/151109, respectively, both of which are incorporated herein by reference in their entirety.

Typically, the polyalkylene glycol derivatives of vitamin E used in the provided methods and compositions have an HLB value of between 12 or about 12 and 20 or about 20, for example, 12, 13, 14, 15, 16, 17, 18, 19, 20, or about 12, about 13, about 14, about 15, about 16, about 17, about 18, about 19 or about 20. Exemplary of suitable polyalkylene glycol derivatives of vitamin E include, but are not limited to, tocopherol and/or tocotrienol-derived surfactants, in which the vitamin E moiety represents the hydrophobic region of the surfactant, and is attached, via a linker, to another moiety, such as a polyethylene glycol (PEG) moiety, that provides the hydrophilic portion of the surfactant. Vitamin-E derived surfactants include, but are not limited to, tocopherol derived surfactants, including polyalkylene glycol derivatives of tocopherol, typically polyethylene glycol (PEG) derivatives of tocopherol, such as tocopherol polyethylene glycol succinate (TPGS), TPGS analogs, TPGS homologs and TPGS derivatives. Alternatively, the surfactants can be other PEG derivatives having similar properties, for example, PEG derivatives of sterols, e.g., a cholesterol or a sitosterol (including, for example, any of the PEG derivatives disclosed in U.S. Pat. No. 6,632,443) or PEG derivatives of other fat-soluble vitamins, for example, some forms of vitamin A (e.g., retinol) or vitamin D (e.g., vitamins D1-D5). Typically, the polyalkylene glycol derivatives of vitamin E is GRAS (generally recognized as safe) by the FDA and/or Kosher certified, for example, TPGS.

(a) Synthesis

Scheme 1 shows the synthesis of an exemplary water-soluble vitamin E derivative, TPGS, but any vitamin E moiety, i.e., any tocopherol or tocotrienol, can be used as the starting material and reacted with any linker, such as those described herein, that is capable of reacting with a polyalkylene glycol moiety to form a monomer form and dimer form of a water-soluble vitamin E derivative. As shown in Scheme 1 below, TPGS can be prepared by reacting vitamin E with succinic anhydride or succinic acid to obtain vitamin E succinate, i.e., D-α-tocopheryl succinate, followed by esterification with a polyethylene glycol molecule, to obtain TPGS (see U.S. Pat. No. 2,680,749). TPGS analogs varying in PEG chain length (e.g., TPGS 200, 238, 400, 600, 2000, 3400, 3500, 4000 and 6000) have been synthesized, but the most widely used form of TPGS is TPGS 1000, which incorporates PEG 1000, a polyethylene glycol molecule with a molecular weight of approximately 1,000 Daltons (Collnot et al. (2006) J. Controlled Release 111:35-40). TPGS 1000 is a pale yellow, waxy solid substance that is amphipathic and hydrophilic, with a molecular weight of approximately 1,513 Daltons.

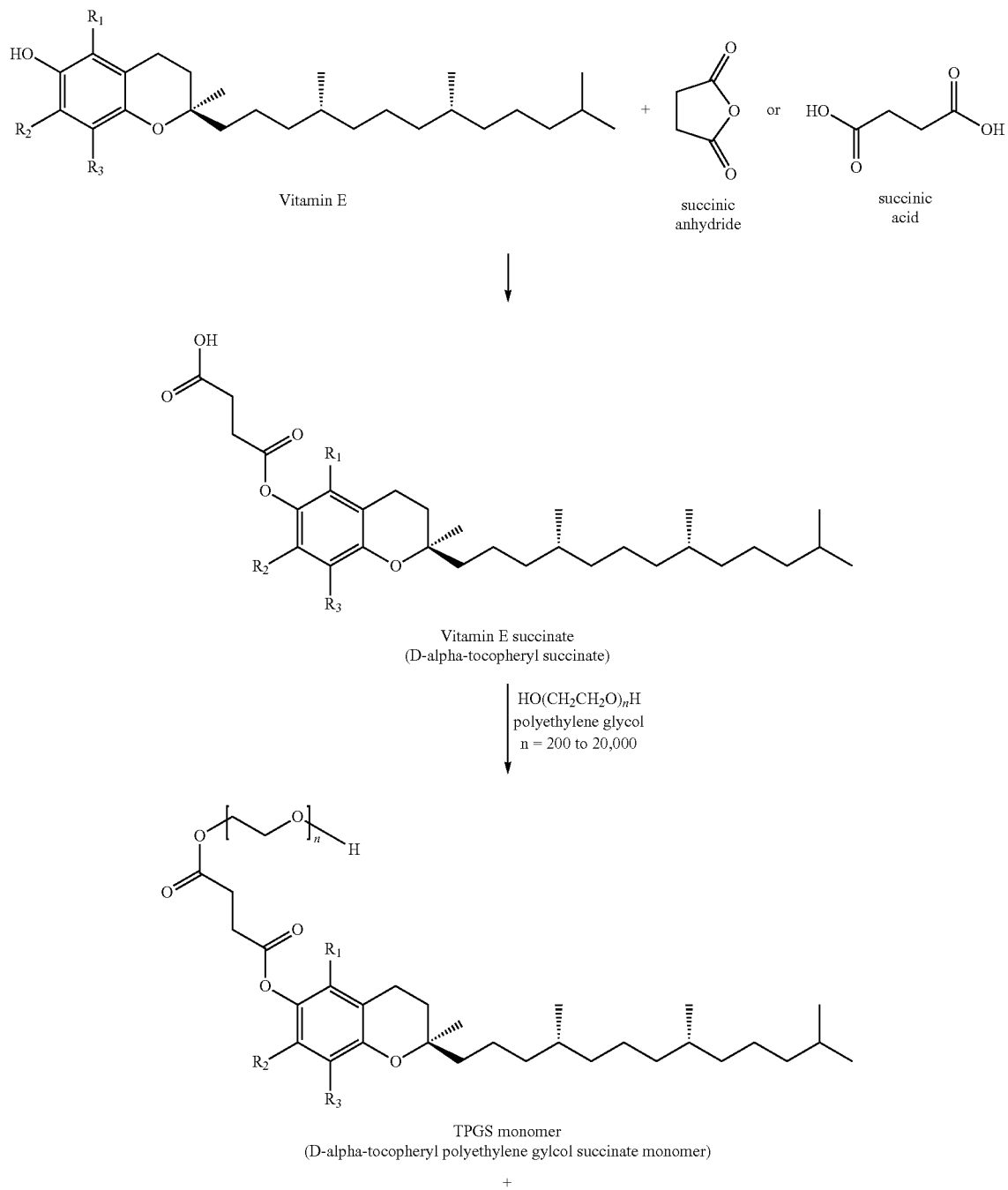

Scheme 1

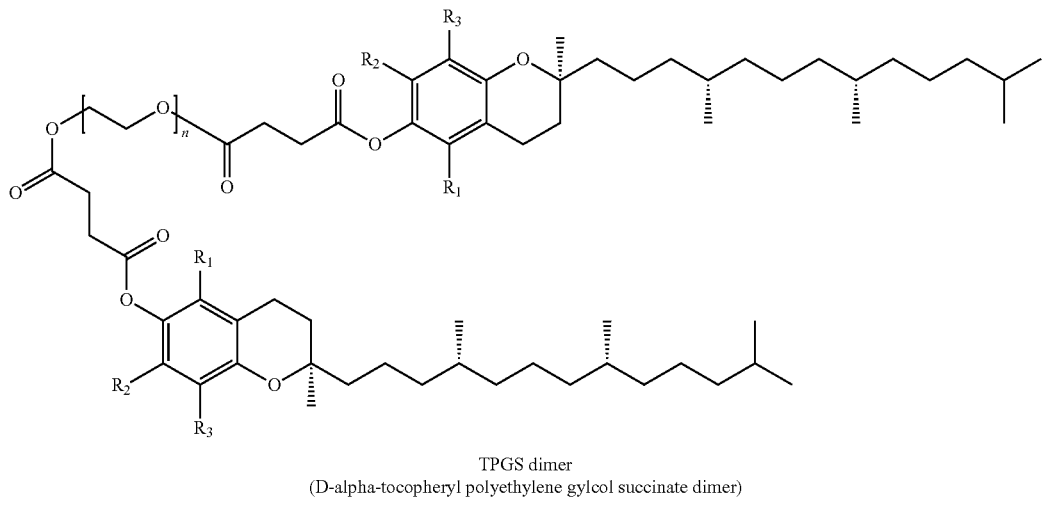

TPGS dimer
(D-alpha-tocopheryl polyethylene gylcol succinate dimer)

TPGS compositions, as generally prepared, such as commercially available TPGS 1000, are mixtures that contain primarily TPGS monomer (between 70% and 87% or more) and a lesser amount of TPGS dimer (less than 12%). The monomer is considered the effective component in TPGS, while the dimer is viewed as a byproduct of the esterification reaction between polyethylene glycol and vitamin E succinate. For example, commercially available TPGS, such as the TPGS 1000 available from Eastman Chemical Company (Kingsport, Tenn.), contains primarily TPGS monomer (~86% or more) and a small amount of TPGS dimer (~11% or less) (Christiansen et al. (2011) J. Pharm. Sci. 100(5): 1773-1782). TPGS synthesized according to standard methods, for example, the method described in U.S. Pat. No. 2,680,749, results in a TPGS composition that is composed primarily of TPGS monomer (70-87%) and a small amount of TPGS dimer (<12%) (US Pharmacopeia 23 (1998) Supp. 9:4712; Scientific Panel of the European Food Safety Authority (2007) EFSA J. 490:1-20). Because the separation of TPGS monomer and TPGS dimer is difficult and because TPGS monomer is considered the effective component of TPGS, TPGS compositions containing primarily TPGS dimer have not been developed (Kong et al. (2011) J. Chromatography A 1218:8664-8671). TPGS dimer, shown below, is usually considered an unwanted byproduct of the esterification reaction between PEG and vitamin E succinate, formed due to the equal reactivity of both terminal hydroxyl groups of the PEG moiety.

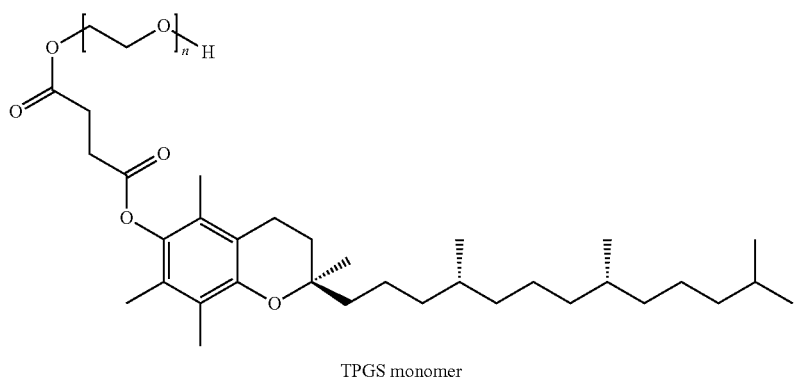

TPGS monomer

-continued

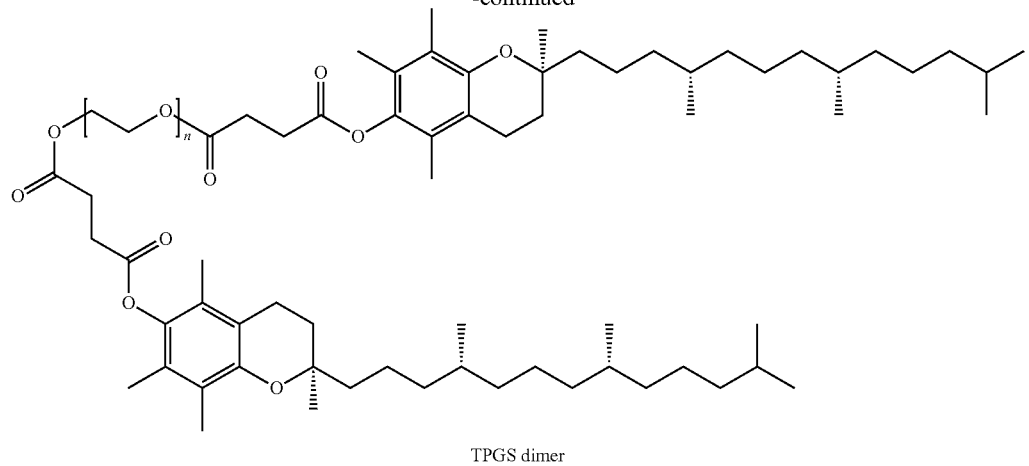

TPGS dimer (b) Water-Soluble Vitamin E Derivative Mixtures (Compositions)

The water-soluble vitamin E derivative mixtures (compositions), for example, TPGS compositions, that can be used in concentrates, emulsions and powders provided herein can contain varying amounts of monomer and dimer, particularly TPGS compositions that contain less monomer than is found in typical, known water-soluble vitamin E derivative mixtures (compositions), for example, less than 70 wt % monomer, and more dimer, i.e., greater than 12 wt % dimer, than in typical, known water-soluble vitamin E derivative mixtures (compositions), for example, known TPGS compositions. For example, the water-soluble vitamin E derivative mixtures (compositions) can contain between or between about 25 wt % and 69 wt % monomer and between or between about 13 wt % and 95 wt % dimer, such as water-soluble vitamin E derivative mixtures (compositions) containing between or about between 40 wt % and 60 wt % monomer and between or about between 25 wt % and 60 wt % dimer, such as 29% to 55%, 35% to 50% or 30% to 45%, dimer. Advantageous properties are exhibited by powders, emulsions and concentrates that contain TPGS compositions with at least these amounts.

In the water-soluble vitamin E derivative mixtures (compositions) that can be used in the powders, emulsions and concentrates described herein, the total amount of monomer as a percentage (%) by weight of the water-soluble vitamin E derivative mixture (composition) (wt %) can be, e.g., between or between about 25 wt % and 69 wt % monomer, inclusive, such as between or between about 25% and 30%, 25% and 35%, 25% and 40%, 25% and 45%, 25% and 50%, 25% and 55%, 25% and 60%, 25% and 65%, 25% and 69%, 30% and 35%, 30% and 40%, 30% and 45%, 30% and 50%, 30% and 55%, 30% and 60%, 30% and 65%, 30% and 69%, 35% and 40%, 35% and 45%, 35% and 50%, 35% and 55%, 35% and 60%, 35% and 65%, 35% and 69%, 40% and 45%, 40% and 50%, 40% and 55%, 40% and 60%, 40% and 65%, 40% and 69%, 45% and 50%, 45% and 55%, 45% and 60%, 45% and 65%, 45% and 69%, 50% and 55%, 50% and 60%, 50% and 65%, 50% and 69%, 55% and 60%, 55% and 65%, 55% and 69%, 60% and 65%, 60% and 69%, and 65% and 69% monomer, by weight of the composition. Generally, the water-soluble vitamin E derivative mixtures (compositions) contain less than 69 wt % monomer. For example, the water-soluble vitamin E derivative mixtures (compositions) described herein contain at least or about at least 25%, 30%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, but less than 69% (wt %), total monomer.

In the water-soluble vitamin E derivative mixtures (compositions) that can be used in the powders, emulsions and concentrates described herein, the total amount of dimer as a percentage (%) by weight of the water-soluble vitamin E derivative mixture (composition) (wt %) can be, e.g., between or between about 13 wt % and 95 wt % dimer, inclusive, such as between or between about 13% and 20%, 13% and 25%, 13% and 30%, 13% and 35%, 13% and 40%, 13% and 45%, 13% and 50%, 13% and 55%, 13% and 60%, 13% and 65%, 13% and 70%, 13% and 75%, 13% and 80%, 13% and 85%, 13% and 90%, 13% and 95%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 20% and 80%, 20% and 85%, 20% and 90%, 20% and 95%, 25% and 30%, 25% and 35%, 25% and 40%, 25% and 45%, 25% and 50%, 25% and 55%, 25% and 60%, 25% and 65%, 25% and 70%, 25% and 75%, 25% and 80%, 25% and 85%, 25% and 90%, 25% and 95%, 30% and 35%, 30% and 40%, 30% and 45%, 30% and 50%, 30% and 55%, 30% and 60%, 30% and 65%, 30% and 70%, 30% and 75%, 30% and 80%, 30% and 85%, 30% and 90%, 30% and 95%, 35% and 40%, 35% and 45%, 35% and 50%, 35% and 55%, 35% and 60%, 35% and 65%, 35% and 70%, 35% and 75%, 35% and 80%, 35% and 85%, 35% and 90%, 35% and 95%, 40% and 45%, 40% and 50%, 40% and 55%, 40% and 60%, 40% and 65%, 40% and 70%, 40% and 75%, 40% and 80%, 40% and 85%, 40% and 90%, 40% and 95%, 45% and 50%, 45% and 55%, 45% and 60%, 45% and 65%, 45% and 70%, 45% and 75%, 45% and 80%, 45% and 85%, 45% and 90%, 45% and 95%, 50% and 55%, 50% and 60%, 50% and 65%, 50% and 70%, 50% and 75%, 50% and 80%, 50% and 85%, 50% and 90%, 50% and 95%, 55% and 60%, 55% and 65%, 55% and 70%, 55% and 75%, 55% and 80%, 55% and 85%, 55% and 90%, 55% and 95%, 60% and 65%, 60% and 70%, 60% and 75%, 60% and 80%, 60% and 85%, 60% and 90%, 60% and 95%, 65% and 70%, 65% and 75%, 65% and 80%, 65% and 85%, 65% and 90%, 65% and 95%, 70% to 75%, 70% and 80%, 70% and 85%, 70% and 90%, 70% and 95%, 75% and 80%, 75% and 85%, 75% and 90%, 75% and 95%, 80% and 85%, 80% and 90%, 80% and 95%, 85% and 90%, 85% and 95% and 90% and 95% dimer, by weight of the water-soluble vitamin E derivative mixture (composition). Generally, the water-soluble vitamin E derivative mixtures (compositions) contain less than 95 wt % dimer. For example, the water-soluble vitamin E derivative mixtures (compositions) described herein contain at least or about at least 13%, 15%, 20%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, but less than 95% (wt %) total dimer.

The water-soluble vitamin E derivative mixtures (compositions) that can be used in the powders, emulsions and concentrates described herein that contain less than 70 wt % monomer and greater than 12 wt % dimer exhibit decreased turbidity values when dissolved in an aqueous solution, for example, when dissolved in water, as compared to typical, known water-soluble vitamin E derivative mixtures (compositions), i.e., water-soluble vitamin E derivative mixtures (compositions) that contain more than 70 wt % monomer and less than 12 wt % dimer. The compositions containing less than 70 wt % monomer and greater than 12 wt % dimer allow for the addition of a higher concentration of non-polar compounds when used in aqueous food and beverage products as compared to available aqueous food and beverage products, while maintaining clarity and stability, for example, exhibiting decreased turbidity values.

Exemplary of the compositions are TPGS compositions containing less than 70 wt % TPGS monomer and more than 12 wt % TPGS dimer, such as compositions containing between or about between 25 wt % and 69 wt % TPGS monomer and between or about between 13 wt % and 95 wt % TPGS dimer, such as TPGS compositions containing between or about between 40 wt % and 60 wt % TPGS monomer and between or about between 25 wt % and 60 wt % TPGS dimer, are described herein. The compositions containing less than 70 wt % TPGS monomer and greater than 12 wt % TPGS dimer exhibit decreased turbidity values when dissolved, for example, when dissolved in water, as compared to typical, known TPGS compositions, i.e., TPGS compositions that contain more than 70 wt % TPGS monomer and less than 12 wt % TPGS dimer. The TPGS compositions allow for the addition of a higher concentration of non-polar compounds when used in aqueous food and beverage products as compared to available aqueous food and beverage products, while maintaining clarity and stability, for example, exhibiting decreased turbidity values.

The water-soluble vitamin E derivative mixtures (compositions), e.g., TPGS compositions, that can be used in the powders, emulsions and concentrates described herein contain a mixture of monomer and dimer, e.g., a mixture of TPGS monomer and TPGS dimer. The monomer, for example, a TPGS monomer, can be present in an amount that is less than what is typically found in known water-soluble vitamin E derivative mixtures (compositions), e.g., known TPGS compositions, i.e., less than 70 wt % monomer. The dimer, for example, a TPGS dimer, can be present in an amount that is greater than what is typically found in known water-soluble vitamin E derivative mixtures (compositions), e.g., known TPGS compositions, i.e., greater than 12 wt % dimer. The water-soluble vitamin E derivative mixtures (compositions), such as the TPGS compositions, can also contain other components, such as, for example, unreacted PEG, unreacted vitamin E, e.g., D-α-tocopheryl succinate, and one or more catalysts.

Methods for preparing the water-soluble vitamin E derivative mixtures (compositions), such as the TPGS compositions described herein, are described herein, for example, methods of preparing water-soluble vitamin E derivative compositions, such as TPGS compositions, that contain less than 70 wt % TPGS monomer and more than 12 wt % TPGS dimer. Existing methods for preparing derivatives of vitamin E can be employed, except that the methods are modified to produce higher concentrations of the dimer form by modifying reaction conditions. Such modifications can be determined empirically if needed, such as by varying reaction parameters, such as time, temperature and reactant concentrations, to identify conditions that favor higher levels of dimer production.

The water-soluble vitamin E derivative mixtures e.g., TPGS monomer-dimer mixtures, prepared according to the methods, can contain between or about between 25 wt % and 69 wt % monomer, for example, at or about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 or 69 wt % monomer and between or about between 13 wt % and 95 wt % dimer, for example, at or about 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 89, 80, 81, 82, 83, 84, 85, 86, 87, 88, 89, 90, 91, 92, 93, 94 or 95 wt % dimer.

Exemplary of the water-soluble vitamin E derivative mixtures (compositions) that can be used in the powders, emulsions and concentrates described herein that contain a mixture of monomer and dimer, for example, TPGS compositions that contain a mixture of TPGS monomer and TPGS dimer, are compositions that contain between or about between 25 wt % and 69 wt % monomer and between or about between 13 wt % and 95 wt %, such as 29% to 55%, dimer. Thus, described herein are water-soluble vitamin E derivative mixtures (compositions), such as TPGS compositions, that contain less monomer, i.e., less than 70 wt % monomer, such as between 25 wt % and 69 wt % monomer, and more dimer, i.e., more than 12 wt % dimer, such as between 13 wt % and 95% dimer, than typical commercial TPGS compositions.

v. Methods for Making Water-Soluble Vitamin E Derivatives

The water-soluble vitamin E derivative mixtures (compositions) with higher amounts of dimer can be prepared by modification of methods that compositions with higher amounts of monomer and lower amounts of dimer are prepared by, appropriately varying reaction conditions to favor increased dimer formation. Alternatively, standard known methods can be employed and the dimers purified or partially purified and added to compositions to increase the percentage of dimer to a desired level.

For example, for production of compositions with higher amounts of TPGS dimer, the methods employ the use of vitamin E succinate, e.g., D-α-tocopheryl succinate, as a starting material. Methods that use vitamin E, e.g., tocopherol or tocotrienol, and succinic acid or succinic anhydride as the starting materials (to synthesize vitamin E succinate) also can be used to prepare the water-soluble vitamin E derivative mixtures (compositions) described herein. The methods can be adapted for production of any desired water-soluble vitamin E derivative composition that contains the higher amounts of dimer.

As noted, these water-soluble vitamin E derivative mixtures (compositions) exhibit decreased turbidity values as compared to known water-soluble vitamin E derivative mixtures (compositions), such as known TPGS compositions, when dissolved, such as, for example, when dissolved in water or other aqueous beverages. Thus, the described methods are advantageous over existing prior art methods of preparing TPGS compositions that exhibit high turbidity values, e.g., higher than 80 NTUs, when dissolved, such as when dissolved in water.

Water-soluble vitamin E derivatives, such as TPGS, can be prepared by esterifying vitamin E succinate, for example, D-α-tocopheryl acid succinate, with polyethylene glycol. The resulting vitamin E TPGS has a chemical formula of $C_{33}O_5H_{54}(CH_2CH_2O)_n$, where "n" represents the number of polyethylene oxide moieties attached to the acid group of the vitamin E succinate. In an exemplary embodiment, the method includes preparing a crude water-soluble vitamin E, e.g., TPGS, composition by first preparing a reaction mixture containing vitamin E succinate, a polyethylene glycol (PEG), and optionally, a catalyst, in a solvent, and heating the reaction mixture to an elevated temperature to produce a crude water-soluble vitamin E, e.g., TPGS, composition containing less TPGS monomer and more TPGS dimer than what is typically found in known TPGS compositions, i.e., less than 70 wt % TPGS monomer and more than 12 wt % TPGS dimer. The crude water-soluble vitamin E, e.g., TPGS, composition then can be purified and concentrated to obtain a purified water-soluble vitamin E, e.g., TPGS, composition containing less TPGS monomer and more TPGS dimer than what is typically found in known TPGS compositions, i.e., less than 70 wt % TPGS monomer and more than 12 wt % TPGS dimer. Any purification process known in the art can be used to purify the reaction product.

(a) Reaction Mixture

The water-soluble vitamin E derivative mixtures can be prepared by first preparing a crude water-soluble vitamin E derivative mixture, such as a crude TPGS composition, by esterifying vitamin E succinate with polyethylene glycol in a solvent. The esterification procedure can be promoted by a catalyst, for example, an esterification catalyst. The crude composition can be prepared from a reaction mixture containing vitamin E succinate, a polyethylene glycol (PEG), a solvent, and optionally, a catalyst. The components of the reaction mixture can be added in any order. In an exemplary embodiment, the polyethylene glycol is dissolved in the solvent before the addition of vitamin E succinate and the catalyst.

A crude water-soluble vitamin E derivative mixture, such as a crude TPGS composition, that contains less TPGS monomer and more TPGS dimer than what is typically found in known TPGS compositions, i.e., less than 70 wt % TPGS monomer and more than 12 wt % TPGS dimer can be produced. In some instances, the crude TPGS composition contains between or about between 25 wt % and 69 wt % TPGS monomer and between or about between 13 wt % and 95 wt % TPGS dimer, such as between or about between 40 wt % and 60 wt % TPGS monomer and between or about between 25 wt % and 60 wt % TPGS dimer.

(i) Vitamin E Succinate

The reaction mixtures can contain vitamin E succinate, for example, D-α-tocopheryl succinate. Vitamin E succinate can be purchased from suppliers such as Sigma-Aldrich (St. Louis, Mo.), Parchem (New Rochelle, N.Y.), Fisher Scientific (Fair Lawn, N.J.), and VWR International (Radnor, Pa.), or can be synthesized according to methods known to those of skill in the art. Typically, vitamin E succinate can be synthesized by reacting vitamin E (i.e., D-α-tocopherol) with succinic anhydride in a solvent (e.g., toluene) in the presence of a base (e.g., triethylamine) (see, for example, U.S. Patent Pub. Nos. 2011/0130562 and 2011/0184194; Lipshutz et al. (2011) J. Org. Chem. 76(11):4379-4391; Gelo-Pujic et al. (2008) Int. J. Cosmet. Sci. 30(3):195-204; and Vraka et al. (2006) Bioorg. Med. Chem. 14(8):2684-2696).

The total amount of vitamin E succinate in the reaction mixture as a percentage (%) by weight of the reaction mixture (wt %) can be, e.g., from at or about 0.1% to at or about 15%, such as 0.1% to 1%, 0.1% to 3%, 0.1% to 5%, 0.1% to 10%, 0.1% to 15%, 0.5% to 1%, 0.5% to 3%, 0.5% to 5%, 0.5% to 10%, 0.5% to 15%, 1% to 3%, 1% to 5%, 1% to 10%, 1% to 15%, 3% to 5%, 3% to 10%, 3% to 15%, 5% to 10%, 5% to 15%, or 10% to 15% by weight of the reaction mixture. Generally, the reaction mixtures contain less than 15 wt % vitamin E succinate. For example, the reaction mixtures described herein contain up to at or about 1%, 2%, 3%, 4%, 5%, 6%, 7%, 8%, 9%, 10%, 11%, 12%, 13%, 14% or 15% vitamin E succinate. Generally, the reaction mixtures described herein contain less than 15% (wt %) total vitamin E succinate.

(ii) Polyethylene Glycol

The reaction mixtures include any polyethylene glycol that can react with the acid moiety of vitamin E succinate to form an ester. The polyethylene glycol can include, for example, any polyethylene glycol that gives the desired molecular weight of the water-soluble vitamin E compound, the desired polyethylene glycol chain length of the water-soluble vitamin E compound or the desired amount of water-soluble vitamin E water-solubility. The polyethylene glycol in the reaction mixtures can include, for example, any polyethylene glycol that is capable of forming an ester when reacted with vitamin E succinate to produce a vitamin E derivative that is water-soluble. For example, the polyethylene glycol can include PEG-OH, PEG-SH, PEG-NH$_2$ and branched PEGs. Typically, the polyethylene glycol is PEG-OH. The resulting water-soluble vitamin E product, for example, TPGS, formed by the reaction between vitamin E succinate and a polyethylene glycol contains at least polyethylene glycol esters of vitamin E succinate. The esters can be a mixture of esters, such as a mixture of TPGS monomer and TPGS dimer.

The polyethylene glycols in the reaction mixtures can be any molecular weight, for example, any molecular weight that renders vitamin E succinate water-soluble after esterification with the polyethylene glycol (i.e., the resulting TPGS is water-soluble). Such polyethylene glycols are known in the art and can be purchased from suppliers such as Sigma-Aldrich (St. Louis, Mo.), Fisher Scientific (Fair Lawn, N.J.), and VWR International (Radnor, Pa.). The polyethylene glycol can be added to the reaction mixture by any method suitable for transferring the PEG to the reaction mixture. For example, the PEG can be transferred to the reaction mixture in molten form.

Suitable polyethylene glycols include polyethylene glycols having an average molecular weight ranging from between or about between 100 Daltons (Da) and 20,000 Da. For example, the average molecular weight can be between or about between 200 Da and 10,000 Da, or 400 Da and 5,000 Da, or 500 Da and 1500 Da, or 750 Da and 1200 Da, or 1000 Da and 2,500 Da. Generally, the molecular weight of the polyethylene glycol is less than 20,000 Da. For example, the average molecular weight of the polyethylene glycol used in the reaction mixtures can be or can be about 100, 200, 238, 300, 400, 500, 600, 750, 800, 1000, 1200, 1500, 2000, 2500, 3000, 3400, 3500, 4000, 6000, 8000, 10,000, or 12,000 Da, but less than 20,000 Da.

Exemplary polyethylene glycols include PEG 100 (where 100 represents the PEG chain molecular weight), PEG 200, PEG 238, PEG 300, PEG 400, PEG 500, PEG 600, PEG 750, PEG 800, PEG 1000, PEG 1200, PEG 1500, PEG 2000, PEG 2500, PEG 3000, PEG 3400, PEG 3500, PEG 4000, PEG 6000, PEG 8000, PEG 10,000, PEG 12,000 or PEG 20,000. Any other suitable polyethylene glycol known to those of skill in the art also can be used in the methods. In some embodiments described herein, the polyethylene glycol is PEG 1000.

The total amount of PEG in the reaction mixture as a percentage (%) by weight of the reaction mixture (wt %) can be, e.g., from at or about 1% to at or about 50%, such as 1% to 5%, 5% to 10%, 5% to 15%, 5% to 20%, 5% to 25%, 5% to 30%, 5% to 35%, 5% to 40%, 5% to 45%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 40%, 20% to 50%, 25% to 50%, or 30% to 50% by weight of the reaction mixture. Generally, the reaction mixtures contain less than 50 wt % PEG For example, the reaction mixtures described herein contain at least or about at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, but less than 50% (wt %) total PEG (iii) Catalyst The reaction mixtures can optionally contain a catalyst. Suitable catalysts include those catalysts that can be used to promote the esterification reaction between the PEG and the acid moiety of vitamin E succinate. Exemplary catalysts include acidic catalysts, such as p-toluenesulfonic acid, oxalic acid, hydrochloric acid, trichloroacetic acid, and any other known catalyst that can promote esterification.

In the reaction mixtures, the total amount of catalyst, as a percentage (%) by weight of the reaction mixture (wt %) can be, e.g., from at or about 0% to at or about 15%, such as 0.01% to 0.05%, 0.01% to 0.1%, 0.01% to 0.5%, 0.01% to 0.75%, 0.01% to 1%, 0.01% to 3%, 0.01% to 5%, 0.01% to 10%, 0.01% to 15%, 0.01% to 0.5%, 0.01% to 0.75%, 0.01% to 1%, 0.01% to 3%, 0.01% to 5%, 0.01% to 10%, 0.01% to 15%, 0.05% to 0.1%, 0.05% to 0.5%, 0.05% to 0.75%, 0.05% to 1%, 0.05% to 3%, 0.05% to 5%, 0.05% to 10%, 0.05% to 15%, 0.05% to 0.5%, 0.05% to 0.75%, 0.05% to 1%, 0.05% to 3%, 0.05% to 5%, 0.05% to 10%, 0.05% to 15%, 0.1% to 0.5%, 0.1% to 0.75%, 0.1% to 1%, 0.1% to 3%, 0.1% to 5%, 0.1% to 10%, 0.1% to 15%, 0.5% to 0.75%, 0.5% to 1%, 0.5% to 3%, 0.5% to 5%, 0.5% to 10%, 0.5% to 15%, 1% to 3%, 1% to 5%, 1% to 10%, 1% to 15%, 3% to 5%, 3% to 10%, 3% to 15%, 5% to 10%, 5% to 15%, 10% to 15% by weight of the reaction mixture. Generally, the reaction mixtures contain less than 15 wt % catalyst. For example, the reaction mixtures described herein can contain up to at or about 1%, 2%, 3%, 4%, 5%, 6%, 7%, 8%, 9%, 10%, 11%, 12%, 13%, 14% or 15% catalyst, based on the weight of the reaction mixture.

(iv) Solvent

The reaction mixtures include a solvent or combination of solvents. Suitable solvents include those that do not prevent the esterification reaction between the PEG and acid moiety of vitamin E succinate from taking place. For example, the solvent or combination of solvents can be aprotic solvents.

Suitable solvents include solvents that are inert to the reaction and are aprotic, for example, solvents that lack an acidic hydrogen, such as toluene, xylenes, ethers such as tetrahydrofuran (THF), diethyl ether and dioxane, ethyl acetate, acetone, dimethylformamide (DMF), N,N-dimethylacetamide, acetonitrile, methyl ethyl ketone (MEK), methyl isobutyl ketone (MIBK), dimethyl sulfoxide (DMSO), ethyleneglycol dimethylether, hexanes, cyclohexane, pentane, cyclopentane and any combination thereof. An exemplary solvent used in the reaction mixtures is toluene.

In the reaction mixtures, the total amount of solvent as a percentage (%) by weight of the reaction mixture (wt %) can be, e.g., from at or about 60% to at or about 95%, such as 60% to 65%, 60% to 70%, 60% to 75%, 60% to 80%, 60% to 85%, 60% to 90%, 60% to 95%, 65% to 70%, 65% to 75%, 65% to 80%, 65% to 85%, 65% to 90%, 65% to 95%, 70% to 75%, 70% to 80%, 70% to 85%, 70% to 90%, 70% to 95%, 75% to 80%, 75% to 85%, 75% to 90%, 75% to 95%, 80% to 85%, 80% to 90%, 80% to 95%, 85% to 90%, 85% to 95% and 90% to 95%, by weight of the reaction mixture. Generally, the reaction mixtures contain less than 95 wt % solvent. For example, the reaction mixtures can contain at least or about at least 60%, 65%, 70%, 75%, 80%, 85%, 90%, but less than 95% (wt %) total solvent.

(v) Exemplary Reaction Mixtures

Exemplary reaction mixtures that can be used to ultimately produce a water-soluble vitamin E derivative mixture, for example, a TPGS composition, that contains less TPGS monomer and more TPGS dimer than what is typically manufactured, i.e., less than 70 wt % TPGS monomer and more than 12 wt % TPGS dimer, are described. They are exemplified with TPGS, but similar reaction mixtures can be prepared and reactions performed to produce tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol and tocopherol phthalate polyethylene glycol, TPGS analogs and TPGS homologs.

The reaction mixtures exemplified herein include vitamin E succinate, a polyethylene glycol, a solvent, and optionally, a catalyst. Exemplary of such reaction mixtures contain from at or about 0.1 wt % to at or about 15 wt % of vitamin E succinate; a polyethylene glycol, in an amount from at or about 1 wt % to at or about 50 wt %; a catalyst, in an amount from at or about 0.01 wt % to at or about 15 wt %; and from at or about 60% to at or about 95% of a solvent.

In some embodiments, the polyethylene glycol can be a polyethylene glycol with a molecular weight of around 1000 Da, for example, PEG 1000. For example, the exemplary reaction mixtures described herein can contain from at or about 0.1 wt % to at or about 15 wt % of vitamin E succinate; from at or about 1 wt % to at or about 50 wt % of a polyethylene glycol, for example, PEG 1000; from at or about 0.01 wt % to at or about 15 wt % of a catalyst, for example, p-toluenesulfonic acid; and from at or about 60% to at or about 95% of a solvent, for example, toluene.

(b) Exemplary Methods

The methods include preparing a reaction mixture containing vitamin E succinate, a polyethylene glycol and optionally, a catalyst, in a solvent; heating the reaction mixture to a temperature equal to or higher than the boiling point of the solvent to form a crude water-soluble vitamin E derivative mixture; processing the reaction mixture to obtain the crude water-soluble vitamin E derivative mixture; and purifying the crude water-soluble vitamin E derivative mixture to obtain a purified water-soluble vitamin E derivative mixture. In particular, the methods use the exemplary reaction mixtures described above. The methods to synthesize water-soluble vitamin E derivative mixtures described herein result in water-soluble vitamin E derivative mixtures, such as TPGS compositions, that are less turbid than known water-soluble vitamin E derivative mixtures, i.e., known compositions that contain more than 70% TPGS monomer and less than 12% TPGS dimer, when diluted in an aqueous medium, e.g., water.

The following methods are exemplary only and provide a platform from which adjustments can be made. It is understood that changes can be made to the steps of the method and to the reaction components while retaining some if not all of the desirable properties of the method. Further changes can be made by adding or altering steps or components of each step. For example, the order in which the steps are performed can be changed.

(i) Preparation of a Crude Water-Soluble Vitamin E Derivative Mixture

An exemplary method of preparing a high dimer-containing mixture of TPGS is described. The method can be employed to produce high dimer-containing mixtures of any vitamin E derivative, including PEG derivatives of vitamin E. Exemplary is a method of preparing a crude water-soluble vitamin E derivative mixture, for example, a crude TPGS composition, by providing a reaction mixture containing vitamin E succinate, e.g. D-α-tocopheryl succinate, a polyethylene glycol, e.g., PEG 1000, a catalyst, e.g., p-toluenesulfonic acid, and a solvent, e.g., toluene, heating the reaction mixture to a temperature of at least or about at least 110° C. and maintaining the elevated temperature for a period of up to at or about 6.5 hours before cooling, for example, to room temperature, i.e., at or about 20° C., and washing the reaction mixture with an aqueous solution of a weak base, e.g., a 10% aqueous solution of sodium bicarbonate.

A crude water-soluble vitamin E derivative mixture is prepared by providing a reaction mixture containing vitamin E succinate, a polyethylene glycol and optionally, a catalyst, in a solvent and heating the reaction mixture from room temperature, i.e., at or about 20° C., to an elevated temperature, and maintaining the elevated temperature for a period of time until a crude water-soluble vitamin E derivative mixture, for example, a crude TPGS composition, is formed that contains the desired amounts of TPGS monomer and TPGS dimer. The elevated temperature can be any temperature in the range of from 30° C. to about 300° C., generally between 80° C. and 250° C., such as between 100° C. and 200° C. The elevated temperature can be, for example, the boiling point of the solvent in the reaction mixture. A typical heating schedule can be heating the reaction mixture to a temperature of at least or about at least 110° C. with stirring, and once achieved, the elevated temperature, e.g., at least or about at least 110° C., is maintained for a total time of up to at or about 6.5 hours with stirring. Other heating temperatures and times can be used depending on the substrates, solvent and formation of the desired crude water-soluble vitamin E derivative mixture. For example, the total time the elevated temperature is maintained can be at least at or about 1 hour, at least at or about 1.5 hours, at least at or about 2 hours, at least at or about 2.5 hours, at least at or about 3 hours, at least at or about 3.5 hours, at least at or about 4 hours, at least at or about 4.5 hours, at least at or about 5 hours, at least at or about 5.5 hours, at least at or about 6 hours, or at least at or about 6.5 hours, or longer, before cooling.

After the elevated temperature has been maintained for the desired amount of time, e.g., the amount of time required to produce the desired amounts of TPGS monomer and TPGS dimer, the reaction mixture can be cooled to a temperature lower than the elevated temperature. For example, the reaction mixture can be cooled to room temperature, i.e., at or about 20° C., after heating at an elevated temperature for the desired amount of time. The reaction mixture can be heated to at least or about at least 110° C. for a total time of about 6.5 hours before cooling, e.g., to room temperature (i.e., at or about 20° C.), depending on the substrates, solvent and formation of the crude water-soluble vitamin E derivative mixture, for example, a crude TPGS composition, resulting in the desired amounts of TPGS monomer and TPGS dimer. One of skill in the art can perform the methods and, if necessary, empirically determine the appropriate reaction duration to produce the desired ratio of dimer to monomer, based on the formation of the desired amounts of TPGS monomer and TPGS dimer.

In the exemplary method, the reaction mixture can be heated from room temperature (i.e., at or about 20° C.) to an elevated temperature of at least at or about 30° C., 40° C., 50° C., 60° C., 70° C., 80° C., 90° C., 100° C., 105° C., 110° C., 115° C., 120° C., 125° C., 130° C., 140° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., or higher. The reaction mixture can be maintained at a temperature elevated from room temperature for at least at or about 1 hour, 1.5 hours, 2 hours, 2.5 hours, 3 hours, 3.5 hours, 4 hours, 4.5 hours, 5 hours, 5.5 hours, 6 hours, 6.5 hours, or longer before cooling. In an exemplary method, the reaction mixture can be maintained at an elevated temperature for up to at or about 6.5 hours before cooling, e.g., to room temperature, i.e., at or about 20° C. The particular conditions depend upon the particular vitamin E derivative and the amount of monomer and dimer desired.

The amount of time that the reaction mixture is maintained at the temperature elevated from room temperature, for example, between or about between 30° C. and 300° C., such as the boiling point of the solvent in the reaction mixture, can be determined by monitoring the progress of reaction during heating. For example, the reaction mixture can be monitored during heating to determine the amounts of TPGS monomer and TPGS dimer present in the reaction mixture. The heating can then be terminated when the desired amounts of TPGS monomer and TPGS dimer are formed. The monitoring can be done by any method of monitoring a reaction known to those of skill in the art, such as by chromatography, spectroscopy or spectrometry. For example, the reaction can be monitored by thin layer chromatography (TLC), high performance liquid chromatography (HPLC), infrared spectroscopy (IR), Fourier transform infrared spectroscopy (FTIR), mass spectrometry (MS), nuclear magnetic resonance (NMR) spectroscopy, or any combination thereof. In some embodiments of the methods, the reaction progress is monitored by TLC. In other embodiments, the reaction progress is monitored by HPLC. In yet other embodiments, the reaction progress is monitored by both TLC and HPLC. One of skill in the art, if necessary, can determine particular parameters empirically, such as appropriate reaction duration, based on monitoring the formation of the desired amounts of vitamin E derivative monomer and dimer, such as TPGS monomer and TPGS dimer.

The reaction mixture can be heated to an elevated temperature under an inert gas atmosphere, such as a nitrogen gas or argon gas atmosphere, or under air. The reaction mixture can be heated to an elevated temperature at atmospheric pressure or at an elevated pressure, i.e., a pressure higher than atmospheric pressure. The elevated pressure can be achieved, e.g., by performing the reaction in a closed vessel or in a vented vessel.

The progress of the reaction can be terminated after heating for the desired amount of time, for example, up to at or about 6.5 hours, by cooling the reaction mixture, for example, to room temperature, i.e., at or about 20° C. After cooling, such as cooling to room temperature, i.e., at or about 20° C., the reaction mixture can be washed with an aqueous solution. The aqueous solution can be an aqueous solution of base, such as a weak base, i.e., bases that do not fully ionize in an aqueous solution. Suitable weak bases include, for example, carbonates or bicarbonates, e.g., sodium carbonate, sodium bicarbonate, potassium carbonate and potassium bicarbonate; amines, ammonias or ammoniums, e.g., methyl amine, methyl ethyl amine, dimethyl amine, aniline, ammonia, trimethyl ammonia and ammonium hydroxide; and pyridine. For example, the aqueous solution of base can be an aqueous solution of sodium bicarbonate. Suitable aqueous solutions of the weak base include solutions that contain, e.g., 1% to 20% weak base, such as at least or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, or more, weak base. For example, the aqueous solution can be an aqueous solution containing at or about 10% sodium bicarbonate. After the aqueous solution of a weak base has been added to the reaction mixture, the aqueous solution can be separated from the reaction mixture, such as by allowing the reaction mixture and aqueous solution of weak base to separate into layers, and removed. In some embodiments, the reaction mixture and aqueous solution of weak base can be stirred for a period of time before separating. For example, the reaction mixture and aqueous solution can be stirred for 1 minute, 2 minutes, 3 minutes, 4 minutes, 5 minutes, 6 minutes, 7 minutes, 8 minutes, 9 minutes, 10 minutes, 15 minutes, 20 minutes, or more, before allowing the reaction mixture and aqueous solution of weak base to separate into layers.

(ii) Processing the Reaction Mixture to Obtain a Crude Water-Soluble Vitamin E Derivative Mixture After preparing the reaction mixture, the reaction mixture can be further processed in order to obtain a crude water-soluble vitamin E mixture, for example, a crude TPGS composition that contains less TPGS monomer, i.e., less than 70 wt %, and more TPGS dimer, i.e., more than 12 wt %, than known water-soluble vitamin E derivative mixtures. The further processing can be performed to remove impurities from the reaction mixture before obtaining the crude water-soluble vitamin E derivative mixture. The further processing can be performed in order to isolate the crude water-soluble vitamin E derivative mixture from the reaction mixture. For example, the reaction mixture can be further processed by treating the reaction mixture with an adsorbent, such as activated charcoal (i.e., activated carbon). Activated charcoal can be used as a decolorizer and to remove impurities by chemical adsorption. Any activated charcoal known to those of skill in the art can be used to treat the reaction mixture. Such activated charcoal is available from commercial sources under such trade names as Calgon-Type CPG®, Type PCB®, Type SGL®, Type CAL®, and Type OL®).

Further processing of the reaction mixture, for example, treating the reaction mixture with activated charcoal, can take place for a period of time of from at or about 0.5 hours to at or about 5 hours, or longer if required. For example, treating the reaction mixture with activated charcoal can take place for at least or about at least 0.5 hours, 1 hour, 1.5 hours, 2 hours, 3 hours, 4 hours, 5 hours, or longer. The further processing, for example, treating the reaction mixture with activated charcoal, can be done at any temperature of from at or about room temperature, i.e., at or about 20° C., to a temperature elevated from room temperature. For example, the temperature of the process, e.g., activated charcoal treatment, can be at or about 20° C., 30° C., 40° C., 50° C., 55° C., 60° C., 70° C., 80° C., 90° C., or 100° C., or any temperature between 20° C. and 100° C., such as between or about between 55° C. and 60° C. The treatment temperatures and times can be varied depending on the reaction mixture, the solvent, and the impurities present in the reaction mixture. In an exemplary process, such as an activated charcoal treatment process, the reaction mixture can be treated, e.g., with activate charcoal, for at least or about at least 1 hour at a temperature of between or about between 55° C. and 60° C., before cooling.

The reaction mixture can be filtered and washed after cooling, such as cooling to room temperature, i.e., at or about 20° C., after further processing, such as after treating the reaction mixture with activated charcoal. The reaction mixture can be filtered and washed, for example, to remove the activated charcoal from the reaction mixture. For example, the reaction mixture can be filtered through a filter aid, such as diatomaceous earth. Suitable filter aids for use in the methods include, for example, those sold under the trademark Celite®, such as those sold under the trademark Hyflo®. After filtering through a filter aid, such as diatomaceous earth, the reaction mixture can be washed, for example, with the same solvent used in the reaction mixture. In an exemplary embodiment, after further processing, e.g., treatment with activated charcoal, and cooling, e.g., to room temperature, i.e., at or about 20° C., the reaction mixture is filtered through diatomaceous earth, e.g., Hyflo® filter aid, and washed with solvent, e.g., toluene.

The reaction mixture can be further processed in order to isolate the crude water-soluble vitamin E derivative mixture from the reaction mixture. For example, the reaction mixture can be further processed by removing the solvent from the reaction mixture, i.e., concentrating the reaction mixture, in order to obtain a crude water-soluble vitamin E derivative mixture. Any method of removing a solvent from a reaction mixture known to those of skill in the art can be used, including, for example, vacuum distillation, rotary evaporation and filtration. Removing the solvent from the reaction mixture can be done at any temperature, for example at room temperature, i.e., 20° C., or at a temperature elevated from room temperature. For example, the solvent can be removed at a temperature of at or about 20° C., 30° C., 40° C., 50° C., 55° C., 60° C., 70° C., 80° C., or 90° C., but below or about below 100° C., such as below or about below 60° C. In an exemplary embodiment, the solvent can be removed from the reaction mixture by distillation, e.g., vacuum distillation, at a temperature elevated from room temperature, i.e., at or about 20° C., but below or about below 60° C.

Further processing of the reaction mixture of the methods can include further processing by treating the reaction mixture to remove impurities from the reaction mixture, such as by treating the reaction mixture with activated charcoal. Further processing of the reaction mixture of the methods can include further processing by removing the solvent from the reaction mixture, such as by removing the solvent by vacuum distillation. The further processing can include treating the reaction mixture with activated charcoal or removing the solvent from the reaction mixture or both. In an exemplary method, the further processing of the reaction mixture includes removing the impurities from the reaction mixture, e.g., treating the reaction mixture with activated charcoal, and removing the solvent from the reaction mixture, e.g., removing the solvent by vacuum distillation, in order to obtain a crude water-soluble vitamin E derivative mixture, for example, a crude TPGS composition, containing less TPGS monomer, i.e., less than 70 wt %, and more TPGS dimer, i.e., more than 12 wt %, than in known TPGS compositions.

(iii) Purification of the Crude Water-Soluble Vitamin E Derivative Mixture to Obtain a Purified High Dimer-Containing Water-Soluble Vitamin E Derivative Mixture The crude water-soluble vitamin E derivative mixture obtained after further processing can be further purified in order to obtain a purified high dimer-containing water-soluble vitamin E derivative mixture. For example, the purified water-soluble vitamin E derivative mixture can be a PEG derivative of vitamin E, such as TPGS, PTS, PTD and other TPGS analogs and PEG derivatives of vitamin E, mixture. The mixture contains less TPGS monomer, i.e., less than 70 wt %, and more TPGS dimer, i.e., more than 12, 19, 24, 29 wt % dimer. The purification process removes impurities from the crude water-soluble vitamin E derivative mixture, such as impurities that were not removed by further processing of the reaction mixture. For example, the crude water-soluble vitamin E derivative mixture can be purified by performing one or more wash, i.e., extraction, steps. The wash can be performed using more than one solvent, such as more than one organic solvent, for example, two organic solvents that are not miscible with each other. For example, in the methods, the crude water-soluble vitamin E derivative mixture can be dissolved in a first solvent, for example, a polar solvent, such as an alcohol, and can be washed with a second solvent, for example, a non-polar solvent, such as a hydrocarbon solvent that is not miscible with the first solvent. The purification process, e.g., the wash, can be performed one time, two times, three times, four times, or more, depending on the desired purity level of the water-soluble vitamin E derivative mixture and the amount of impurities present. For example, the purification process, e.g., the wash, can be performed one or more times on the crude water-soluble vitamin E derivative mixture, e.g., after the crude water-soluble vitamin E derivative mixture is obtained after processing. In an exemplary method, the purification process can be performed three or more times on the crude water-soluble vitamin E derivative mixture after the further processing is complete.

The purification process, i.e., the wash, can be performed by dissolving the crude water-soluble vitamin E derivative mixture in a first solvent, for example, an organic solvent, such as a polar organic solvent. The polar organic solvent can be any solvent that can dissolve the crude water-soluble vitamin E derivative mixture, such as a polar protic solvent, for example, an alcohol, e.g., methanol, ethanol, propanol or butanol. In the methods, the amount of first solvent, e.g., polar organic solvent, used to dissolve the crude water-soluble vitamin E derivative mixture can be based on the ratio of the volume of the first solvent to the volume of the crude water-soluble vitamin E derivative mixture. The ratio of the volume of the first solvent to the volume of the crude water-soluble vitamin E derivative mixture can range from 0.1:1 to 10:1. In some embodiments, the ratio of the volume of the first solvent to the volume of the crude TPGS composition is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the volume of the first solvent to the volume of the crude water-soluble vitamin E derivative mixture can be 2:1.

The wash can be performed using a second solvent, for example, an organic solvent, that is not miscible with the first solvent, i.e., the solvent used to dissolve the crude water-soluble vitamin E derivative mixture. The second solvent can be any solvent that is not miscible with the first solvent, for example, any solvent that is not miscible with a polar protic solvent such as an alcohol. Suitable organic solvents that can be used as a second solvent include non-polar organic solvents, such as hydrocarbons, e.g., alkanes and cycloalkanes, such as hexane and cyclohexane; halogenated hydrocarbons, e.g., chloroform and dichloromethane; ethers, e.g., diethyl ether; and aromatics, e.g., benzene and toluene. In the methods, the amount of second solvent, e.g., a non-polar organic solvent immiscible with the first solvent, used to wash the crude water-soluble vitamin E derivative mixture dissolved in the first solvent can be based on the ratio of the volume of the second solvent to the volume of the crude water-soluble vitamin E derivative mixture. The ratio of the volume of the second solvent to the volume of the crude water-soluble vitamin E derivative mixture can range from 0.1:1 to 10:1. In some embodiments, the ratio of the volume of second solvent to the volume of crude water-soluble vitamin E derivative mixture is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the volume of the second solvent to the volume of the crude water-soluble vitamin E derivative mixture can be 3:1.

The purification process, for example, a wash with organic solvent, can be performed one or more times on the crude water-soluble vitamin E derivative mixture, for example, two times, three times, four times, or more. The wash can be performed while stirring. In an exemplary method, the crude water-soluble vitamin E derivative mixture can be dissolved in a first solvent, for example, a protic polar organic solvent, e.g., an alcohol, and washed three or more times with a second solvent, for example, a non-polar organic solvent not miscible in the first solvent, e.g., a hydrocarbon.

Exemplary is a method of purifying a crude water-soluble vitamin E derivative mixture by performing a purification process, such as a wash with an organic solvent, e.g., by dissolving the crude water-soluble vitamin E derivative mixture in methanol and washing with cyclohexane, and repeating the wash with the cyclohexane three or more times.

The crude water-soluble vitamin E derivative mixture can be further purified in order to obtain a purified water-soluble vitamin E derivative mixture, for example, a purified TPGS composition. The purified water-soluble vitamin E derivative mixture can be a purified TPGS composition that contains less TPGS monomer, i.e., less than 70 wt %, and more TPGS dimer, i.e., more than 12 wt %, than known TPGS compositions. The further purification can be performed to remove impurities from the crude water-soluble vitamin E derivative mixture. The further purification can be performed in order to isolate the purified water-soluble vitamin E derivative mixture from the first solvent. For example, the crude water-soluble vitamin E derivative mixture can be further purified by treating the crude water-soluble vitamin E derivative mixture with an adsorbent, such as activated charcoal (i.e., activated carbon). Activated charcoal can be used as a decolorizer and to remove impurities by chemical adsorption. Any activated charcoal known to those of skill in the art can be used to treat the crude water-soluble vitamin E derivative mixture. Such activated charcoal is available from commercial sources under such trade names as Calgon-Type CPG®, Type PCB®, Type SGL®, Type CAL®, and Type OL®).

Further purification of the crude water-soluble vitamin E derivative mixture, for example, treating the crude water-soluble vitamin E derivative mixture with activated charcoal, can take place for a period of time of from at or about 0.5 hours to at or about 5 hours, or longer if required. The crude water-soluble vitamin E derivative mixture to be treated can be dissolved in a solvent, for example, the first solvent used in the wash described above. Additional solvent can be added, for example, the same solvent used to dissolve the crude water-soluble vitamin E derivative mixture during the wash, e.g., a polar protic organic solvent. In the methods, the amount of additional solvent, e.g., polar protic organic solvent, added to the crude water-soluble vitamin E derivative mixture can be based on the ratio of the total volume of the solvent, e.g., the first solvent, such as a polar protic organic solvent, plus the additional solvent, to the volume of the crude water-soluble vitamin E derivative mixture. The ratio of the total volume of the first solvent plus the additional solvent to the volume of the crude TPGS composition can range from 0.1:1 to 10:1. In some embodiments, the ratio of the volume of total solvent to the volume of crude water-soluble vitamin E derivative mixture is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the total volume of the first solvent plus additional solvent to the volume of the crude water-soluble vitamin E derivative mixture can be 5:1.

Further purification, such as treating the reaction mixture with, for example, activated charcoal, can take place for at least or about at least 0.5 hours, 1 hour, 1.5 hours, 2 hours, 3 hours, 4 hours, 5 hours, or longer. The further purification, for example, treating the reaction mixture with activated charcoal, can be done at any temperature of from at or about room temperature, i.e., at or about 20° C., to a temperature elevated from room temperature. For example, the temperature of the purification process, e.g., activated charcoal treatment, can be at or about 20° C., 30° C., 40° C., 50° C., 55° C., 60° C., 70° C., 80° C., 90° C., or 100° C., or any temperature between 20° C. and 100° C., such as between or about between 55° C. and 60° C. The treatment temperatures and times can be varied depending on the nature of the crude water-soluble vitamin E derivative mixture, the solvent, and the impurities present in the crude water-soluble vitamin E derivative mixture. In an exemplary purification process, such as an activated charcoal treatment process, the crude water-soluble vitamin E derivative mixture can be treated, e.g., with activate charcoal, for at least or about at least 1 hour at a temperature of between or about between 55° C. and 60° C., before cooling.

The crude water-soluble vitamin E derivative mixture can be filtered and washed after cooling, such as cooling to room temperature, i.e., at or about 20° C., after further purification, such as after treating the crude water-soluble vitamin E derivative mixture with activated charcoal. The crude water-soluble vitamin E derivative mixture, for example, the crude water-soluble vitamin E derivative mixture dissolved in a solvent, can be filtered and washed, for example, to remove the activated charcoal from the crude water-soluble vitamin E derivative mixture. For example, the crude water-soluble vitamin E derivative mixture, for example, the crude water-soluble vitamin E derivative mixture dissolved in a solvent, can be filtered through a filter aid, such as diatomaceous earth. Suitable filter aids for use in the methods include, for example, those sold under the trademarks Celite® and Hyflo®. After filtering through a filter aid, such as diatomaceous earth, the crude TPGS composition can be washed, for example, with the same solvent used to dissolve the crude water-soluble vitamin E derivative mixture, e.g., the first solvent. In an exemplary embodiment, after further purification, e.g., treatment with activated charcoal, and cooling, e.g., to room temperature, i.e., at or about 20° C., the crude water-soluble vitamin E derivative mixture is filtered through diatomaceous earth, e.g., Hyflo® filter aid and washed with solvent, e.g., methanol.

The crude water-soluble vitamin E derivative mixture can be further purified in order to isolate the purified water-soluble vitamin E derivative mixture from the solvent, e.g., the first solvent. For example, the crude water-soluble vitamin E derivative mixture can be further purified by removing the solvent from the water-soluble vitamin E derivative mixture dissolved in solvent, i.e., concentrating the crude water-soluble vitamin E derivative mixture, in order to obtain a purified water-soluble vitamin E derivative mixture. Any method of removing a solvent from a composition known to those of skill in the art can be used, including, for example, vacuum distillation, rotary evaporation and filtration. Removing the solvent from the water-soluble vitamin E derivative mixture can be done at any temperature, for example at room temperature, i.e., 20° C., or at a temperature elevated from room temperature. For example, the solvent can be removed at a temperature of at or about 20° C., 30° C., 40° C., 50° C., 55° C., 60° C., 70° C., 80° C., or 90° C., but below or about below 100° C., such as below or about below 60° C. In an exemplary embodiment, the solvent can be removed from the crude water-soluble vitamin E derivative mixture by distillation, e.g., vacuum distillation, at a temperature elevated from room temperature, i.e., at or about 20° C., but below or about below 60° C. After removing the solvent, the purified water-soluble vitamin E derivative mixture can be dried by any method of drying known to those of skill in the art. Suitable methods of drying include drying under an inert gas, for example, nitrogen or argon, or drying under vacuum, or any combination thereof.

Further purification of the crude water-soluble vitamin E derivative mixture produced by the exemplified method can include further purification by treating the crude water-soluble vitamin E derivative mixture to remove impurities from the reaction mixture, such as by treating the crude water-soluble vitamin E derivative mixture with activated charcoal. Further purification of the crude water-soluble vitamin E derivative mixture produced by the exemplified method can include further purification by removing the solvent from the crude water-soluble vitamin E derivative mixture, for example, a crude water-soluble vitamin E derivative mixture dissolved in a solvent, such as by removing the solvent by vacuum distillation. The further purification can include treating the crude water-soluble vitamin E derivative mixture with activated charcoal or removing the solvent from the crude water-soluble vitamin E derivative mixture or both. In an exemplary method, the further purification of the crude water-soluble vitamin E derivative mixture includes removing the impurities from the crude water-soluble vitamin E derivative mixture, e.g., treating the crude water-soluble vitamin E derivative mixture with activated charcoal, and removing the solvent from the crude water-soluble vitamin E derivative mixture, e.g., removing the solvent by vacuum distillation, in order to obtain a purified water-soluble vitamin E derivative mixture, for example, a purified TPGS composition. The purified TPGS composition can contain less TPGS monomer, i.e., less than 70 wt %, and more TPGS dimer, i.e., more than 12 wt %, than in known TPGS compositions.

The exemplified methods yield a purified water-soluble vitamin E derivative mixture, such as a purified TPGS composition, with the desired amount of dimer (greater than 12%) that can be used in any application where water-soluble vitamin E derivative mixtures are used, such as in food, beverage, pharmaceutical or nutraceutical products for human consumption, and particularly to prepare concentrates that contain the water-soluble vitamin E derivative composition and a non-polar ingredient(s) and other optional ingredients. For example, a purified water-soluble vitamin E derivative mixture, such as a purified TPGS composition, for example, a TPGS composition that contains less TPGS monomer, i.e., less than 70 wt %, and more TPGS dimer, i.e., more than 12 wt %, than in known TPGS compositions, that can be used in products for human consumption, for example, food and beverage products, particularly aqueous food and beverage products, and any other application in which a water-soluble vitamin E derivative mixture can be added, is produced. Exemplary purified water-soluble vitamin E derivative mixtures (compositions) that can be prepared following the exemplified methods are those that contain less than 70 wt % monomer and more than 12 wt % dimer, such as such as compositions containing between or about between 25 wt % and 69 wt % monomer and between or about between 13 wt % and 95 wt % dimer, such as compositions containing between or about between 40 wt % and 60 wt % monomer and between or about between 25 wt % to 60 wt % dimer. For example, the methods can be followed to obtain water-soluble vitamin E derivative mixtures (compositions) that contain between or about between 25 wt % and 69 wt % monomer, for example, at or about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 or 69 wt % monomer and between or about between 13 wt % and 95 wt % dimer, for example, at or about 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 wt % dimer.

These methods are described with reference to TPGS and can be adapted to produce any higher dimer-containing water-soluble vitamin E derivative composition. Other methods to produce compositions with the desired dimer or dimer and monomer concentrations can be employed, including purifying dimer from standard preparations and adding the dimer back to a standard preparation to increase its concentration. The resulting compositions can be employed in the powders, emulsions and concentrates described herein.

c. Non-Polar Compounds

The pre-emulsion concentrates provided herein contain one or more non-polar ingredients, where the ingredient is a non-polar compound or contains one or more non-polar compounds. Exemplary of non-polar ingredients, is a fish oil which contains a plurality of different non-polar compounds, including compounds that have desirable activity, such as omega-3 fatty acids. Non-polar ingredients include any lipophilic or lipid-soluble compound that has greater solubility in organic solvents (e.g., ethanol, methanol, ethyl ether, acetone, and benzene) and in fats and oils, than in polar solvents, for example, water. Typically, the non-polar ingredients are poorly water-soluble, for example, water insoluble, or are compounds that have low water solubility. The non-polar ingredients include, but are not limited to, drugs, hormones, vitamins, nutrients and other lipophilic compounds. Exemplary non-polar ingredients include, but are not limited to, omega-3 EPA and DHA, resveratrol, sesamin, curcumin, *Boswellia* (Boswellic acids), lipoic acid, such as alpha lipoic acids, capsaicinoids, PQQ, carotenoids, such as astaxanthin, zeaxanthin, lutein, beta-carotene, and lycopene, and vitamins, such as vitamin A, vitamin D, and vitamin E complexes, vitamin K1 and vitamin K as MK7. Exemplary non-polar ingredients are listed herein below. The provided methods and compositions can be used to dilute (e.g., dissolve/disperse) any non-polar ingredient in aqueous medium, such as water. The non-polar ingredient can differ from the surfactant, polyalkylene glycol derivative of vitamin E, for example, the non-polar ingredient is not a polyalkylene glycol vitamin E derivative. Exemplary of non-polar ingredients that can be used in the provided pre-emulsion concentrates are:

non-polar ingredients containing essential fatty acids, such as polyunsaturated fatty acids (PUFAs), for example, gamma-linolenic acid (GLA), e.g., borage oil and evening primrose (*Oenothera biennis*) oil, blackcurrant seed oil, hemp seed oil and *spirulina* extract; compounds containing omega-3 fatty acids, such as natural and synthetic omega-3 fatty acids, for example, compounds containing omega-3 polyunsaturated long-chain fatty acids, including eicosapentaenoic acid (EPA) (20:5ω3); docosahexaenoic acid (DHA) (22:6ω3); eicosatetraenoic acid (20:4 ω-3); docosapentaenoic acid (DPA, clupanodonic acid) (22:5ω3); 16:3 ω3; 24:5 ω3 and/or nisinic acid (24:6ω3), e.g., fish oil, algae oil, krill oil, canola oil, flaxseed oil, soybean oil and walnut oil; compounds containing short-chain omega-3 fatty acids, for example, alpha-linolenic acid (α-linolenic acid; ALA; 18:3ω3) and stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), e.g., highly purified fish oil concentrates, *perilla* oil, krill oil, and algae oil, e.g., microalgae oil; compounds containing omega-6 fatty acids, such as compounds containing linoleic acid (18:20ω6) (a short-chain fatty acid); gamma-linolenic acid (GLA; 18:30ω6); dihomo gamma linolenic acid (DGLA; 20:3ω6); eicosadienoic acid (20:2ω6); arachidonic acid (AA; 20:4ω6); docosadienoic acid (22:2ω6); adrenic acid (22:4ω6); and/or docosapentaenoic acid (22:5ω6), for example, borage oil, corn oil, cottonseed oil, grapeseed oil, peanut oil, primrose oil, e.g., evening primrose (*Oenothera biennis*) oil, blackcurrant seed oil, hemp seed oil, *spirulina* extract, safflower oil, sesame oil, coconut oil and soybean oil;

other fatty acids, such as triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; ethyl linoleate; herb oils, for example, garlic oils and scordinin; short-chain saturated fatty acids (4:0-10:0), lauric acid (12:0), myristic acid (14:0), pentadecanoic acid (15:0), palmitic acid (16:0), palmitoleic acid (16:1 ω7), heptadecanoic acid (17:0), stearic acid (18:0), oleic acid (18:1 ω9), and arachidic acid (20:0);

micronutrients, such as vitamins, minerals, co-factors, for example, coenzyme Q10 (coQ10, also called ubiquinone), ubiquinol, turmeric extract (curcuminoids), saw palmetto lipid extract (saw palmetto oil), *echinacea* extract, hawthorn berry extract, *ginseng* extract, lipoic acid (thioctic acid), e.g., alpha-lipoic acid, ascorbyl palmitate, kava extract, St. John's Wort (hypericum, Klamath weed, goat weed), extract of quercitin, dihydroepiandrosterone, and indol-3-carbinol;

carotenoids, including hydrocarbons and oxygenated, alcoholic derivatives of hydrocarbons, for example, beta carotene, mixed carotenoid complex, lutein, lycopene, zeaxanthin, cryptoxanthin, for example, beta-crytoxanthin, beta carotene, astaxanthin, bixin, canthaxanthin, capsanthin, capsorubin, apo-carotenal, beta-12'-apo-carotenal, "Carotene" (mixture of alpha- and beta-carotene), gamma carotene, ciolerythrin, and esters of hydroxyl- or carboxyl-containing members thereof;

fat-soluble vitamins, for example, vitamins A, D, E and K, and corresponding pro-vitamins and vitamin derivatives, such as esters, with an action resembling that of vitamin A, D, E or K, for example; retinol (vitamin A) and pharmaceutically acceptable derivatives thereof, such as palmitate ester of retinol and other esters of retinol, calciferol (vitamin D) and its pharmaceutically acceptable derivatives thereof and precursors of vitamin D, d-alpha tocopherol (vitamin E) and derivatives thereof, including pharmaceutical derivatives thereof, for example, tocotrienols, d-alpha tocopherol acetate and other esters of d-alpha tocopherol, and ascorbyl palmitate, a fat-soluble version of vitamin C;

phytochemicals, including phytoestrogens, for example, genistein and daidzein, such as isoflavones, e.g., soy isoflavones, flavonoids, phytoalexins, for example, resveratrol (3,5,4'-trihydroxystilbene), red clover extract, and phytosterols;

lipid-soluble drugs, including natural and synthetic forms of immunosuppressive drugs, such as cyclosporin, protease inhibitors such as ritonavir, macrolide antibiotics and oil soluble anesthetics such as propofol, natural and synthetic forms of steroidal hormones, for example, estrogens, estradiols, progesterone, testosterone, cortisone, phytoestrogens, dehydroepiandrosterone (DHEA), growth hormones and other hormones; and oil-soluble acids and alcohols, for example, tartaric acid, lactylic acid, butylated hydroxyanisole, butylated hydroxytoluene, lignin, sterols, polyphenolic compounds, oryzanol, cholesterol, phytosterols, flavonoids, such as quercetin and resveratrol, and diallyl disulfides;

cannabinoids, including natural, synthetic, and semi-synthetic compounds, for example, phytocannabinoids, endocannabinoids, and synthetic cannabinoids; and hops-containing compounds, including compounds isolated or derived from hops (*Humulus lupulus* L.), such as extracts of hops cones, for example, hops oils, hops resins or hops resin derivatives, hops acids or hops acid derivatives, or mixtures thereof.

i. Polyunsaturated Fatty Acid (PUFA)-Containing Non-Polar Compounds

Exemplary of the non-polar ingredients contained in the pre-emulsion concentrates are compounds containing fatty acids, for example, non-polar ingredients containing the non-polar compounds polyunsaturated fatty acids (PUFAs). Fatty acids are straight-chain hydrocarbon molecules with a carboxyl (COOH) group at one end of the chain. PUFAs are fatty acids that contain more than one carbon-carbon double bond in the carbon chain of the fatty acid. PUFAs, particularly essential fatty acids, are useful as dietary supplements.

Different nomenclature is used to describe fatty acid molecules. Lipid nomenclature, for example, 18:3 ω-3, indicates the carbon chain length, number of double bonds and the position along the carbon chain of the first carbon-carbon double bond in a fatty acid. Using this nomenclature, each carbon along the chain is labeled according to its position relative to one end of the chain. For example, the first carbon away from the carboxylate end is named α, the second is named β, and so forth. The last carbon in the molecule (furthest from the carboxy group) always is labeled w (or omega, or n). The number of carbons and the number of double bonds are listed first in the lipid name of a fatty acid, separated by a colon. For example, the name "18:3" indicates that the molecule has eighteen (18) carbons and three (3) double bonds. Following these numbers, the position at which the first double bond appears, relative to the last (ω) carbon, is listed. For example, the nomenclature, 18:3 ω-3 (or 18:3 omega-3; or 18:3 n-3), describes a fatty acid with eighteen (18) carbons and three (3) double bonds, the first of which occurs at the third carbon away from the omega carbon.

Alternatively, chemical nomenclature can be used. The chemical name of a fatty acid describes the position of each double bond. In the chemical naming, the carbons are numbered, beginning with 1, starting with the carbon that is part of the carboxy (COOH) group. Thus, with this numbering system, the a carbon is labeled "2." The chemical name of the fatty acid lists the first carbon (from the COOH end) to participate in each double bond.

Certain PUFAs are called essential fatty acids because they are required for biological processes and mammals, including humans, cannot synthesize them using any known chemical pathway, and therefore must obtain them from diet or by supplementation (U.S. Pat. No. 6,870,077; Covington (2004) Am. Fam. Phys. 70(1):133-140). The essential PUFAs are the omega-3 (ω3; n-3) fatty acids and the omega-6 (ω-6; n-6) fatty acids. Omega-3 and omega-6 fatty acids are methylene interrupted polyenes which have two or more cis double bonds separated by a single methylene group. Exemplary of omega-3 fatty acids are alpha-linolenic acid (α-linolenic acid; ALA; 18:3ω3) (a short-chain fatty acid); stearidonic acid (18:4ω3) (a short-chain fatty acid); eicosapentaenoic acid (EPA; 20:5ω3); docosahexaenoic acid (DHA; 22:6ω3); eicosatetraenoic acid (20:4 ω-3); docosapentaenoic acid (DPA; clupanodonic acid; 22:5ω3); 16:3 ω3; 24:5 ω3 and nisinic acid (24:6ω3). Longer chain omega-3 fatty acids can be synthesized from ALA (the short-chain omega-3 fatty acid). Exemplary of omega-6 fatty acids are linoleic acid (18:2ω6) (a short-chain fatty acid); gamma-linolenic acid (GLA; 18:3ω6); dihomo gamma linolenic acid (DGLA; 20:3ω6); eicosadienoic acid (20:2ω6); arachidonic acid (AA; 20:4ω6); docosadienoic acid (22:2ω6); adrenic acid (22:4ω6); and docosapentaenoic acid (22:5ω6).

While the longer chain omega-3 and omega-6 essential fatty acids can be synthesized from ALA (the short-chain omega-3 fatty acid) and linolenic acid (LA), respectively, evidence suggests that conversion of these short chain fatty acids in humans is slow. Thus, a major source of long chain essential PUFAs is dietary (see, e.g., Ross et al. (2007) Lipids Health Dis. 6:21; Lands (1992) FASEB J. 6(8):2530). Dietary supplements containing PUFAs, particularly essential PUFAs, are desirable for protection against cardiovascular disease, inflammation and mental illnesses (see, e.g., Ross et al. (2007) Lipids Health Dis. 6:21; Lands (1992) FASEB J. 6(8):2530; and U.S. Pat. No. 6,870,077). Evidence suggests that essential fatty acids, particularly EPA and DHA, in the form of food and nutritional supplements, play a role in preventing a number of disease states, including cardiovascular diseases, inflammation, mental health and behavioral diseases and disorders (see, e.g., Ross et al. (2007) Lipids Health Dis. 6:21; Lands (1992) FASEB J. 6(8):2530; U.S. Pat. No. 6,870,077; and Covington (2004) Am. Fam. Phys. 70(1):133-140).

Omega-9 fatty acids are non-essential PUFAs. Exemplary of omega-9 fatty acids are oleic acid (which is monounsaturated) (18:1 ω9); eicosenoic acid (20:1 ω9); mead acid (20:3 ω9); erucic acid (22:1 ω9); and nervonic acid (24:1 ω9).

Conjugated fatty acids are PUFAs with two or more conjugated double bonds. Conjugated fatty acids can be used as nutritional supplements. Exemplary of conjugated fatty acids are conjugated linoleic acid (CLA), for example, 18:2 ω7, 18:2 ω6; conjugated linolenic acid, for example, 18:3ω6, 18:3ω5; and other conjugated fatty acids, for example, 18:3 ω3, 18:4 ω3, and 20:5 ω6.

(a) Omega-3 Fatty Acid Compounds

Exemplary of the PUFA-containing non-polar ingredients that can be used in the provided pre-emulsion concentrates are non-polar ingredients that contain one or more of the non-polar compound omega-3 (ω3; n-3) fatty acids, for example, compounds containing DHA and/or EPA fatty acids, for example, marine oils, e.g., fish oil, krill oil and algae oil; and compounds containing ALA fatty acids, for example, flaxseed oil.

Typically, oils and aqueous compositions containing long-chain polyunsaturated fatty acids (PUFAs) are susceptible to oxidation, making them unstable and giving them an unpleasant taste. The ingredients and relative concentrations thereof, as well as the methods for making the concentrates, contribute to desirable properties of DHA/EPA-containing concentrates. For example, the ingredients and methods used to make the concentrates provided herein minimize the "fishy" odor and/or taste of DHA/EPA compositions and increase their stability over time. For example, the compounds in the concentrates can have low oxidation, contributing to these desirable properties.

(1) DHA/EPA

Exemplary of non-polar ingredients that contain one or more omega-3 fatty acids which can be used in the provided pre-emulsion concentrates are compounds containing DHA and/or EPA, for example, marine oil, e.g., fish oil, krill oil and algae oil. Any oil containing DHA and/or EPA can be used. Exemplary non-polar ingredients that can be used in the pre-emulsion concentrates provided herein include non-polar ingredients that contain only DHA, for example, non-polar ingredients that contain between 10% or about 10% and 40% or about 40% DHA, between 25% or about 25% and 45% or about 45% DHA, or between 60% or about 60% and 90% or about 90% DHA, for example, at least 35% or about 35%, at least 50% or about 50%, at least 65% or about 65%, at least 80% or about 80%, at least 85% or about 85%, or at least 90% or about 90%, by weight (wt %), DHA. Exemplary non-polar ingredients that can be used in the pre-emulsion concentrates provided herein include non-polar ingredients that contain only EPA, for example, non-polar ingredients that contain between 5% or about 5% and 15% or about 15% EPA, or non-polar ingredients that contain not more than 10% or about 10% EPA. Exemplary non-polar ingredients that contain a mixture of DHA and EPA are suitable for use in the pre-emulsion concentrates provided herein, for example, compositions containing at least 20% or about 20% DHA and not more than 13% or about 13% EPA, by weight, of the non-polar ingredient; at least 35% or about 35% DHA and not more than 13% or about 13% EPA; at least 70% or about 70% DHA and not more than 13% or about 13% EPA; or the total amount of DHA and EPA represents at least 30% or about 30% of the non-polar ingredient, or at least 50% or about 50% of the non-polar ingredient, or at least 61% or about 61% of the non-polar ingredient.

(i) Fish Oils

Exemplary of the PUFA-containing non-polar ingredients that can be used in the provided pre-emulsion concentrates are oils derived from fish which contain DHA, EPA or both DHA and EPA. Particularly, cold water marine fish are a known source of omega-3 fatty acids (U.S. Pat. No. 4,670,285). Suitable fish oils containing DHA, EPA or both DHA and EPA can be obtained from any of a number of commercial sources, for example, fish oils available from Jedwards International, Inc., any of which can be used with the provided compositions.

Fish oils typically are extracted from fish tissue, for example, frozen fish tissue. For example, the fish oil can be a tasteless fish oil, for example, a cod liver oil, which has been isolated from fish, for example, from cod liver, and then refined and deodorized, or in some other way treated so its taste becomes neutral, such as described in International Patent Publication Nos. WO 00/23545 and WO 2004/098311. In one example, these fish oils are isolated from frozen fish tissue by a process that minimizes oxidation. Exemplary of such a tasteless fish oil is a fish oil sold under the trademark Denomega™ 100 (Borregaard Ingredients, Sarpsborg, Norway; distributed by Denomega Nutritional Oils AS, Boulder, Colo.). Typically, the tasteless fish oil, for example, cod liver oil, contains between or between about 25% and 35% omega-3 fatty acids, for example, 34% omega-3 fatty acids. In one example, the fish oil, for example, the Denomega™ 100 oil, contains 13% or about 13% DHA and 13% or about 13% EPA.

Also exemplary of the fish oils that can be included in the provided pre-emulsion concentrates are fish oils containing high amounts of omega-3 fatty acids, for example, high amounts of DHA. One example of such a fish oil contains at least or about at least 85% DHA, typically greater than 85% DHA, and at least or about at least 90% omega-3 fatty acids, typically greater than 90% omega-3 fatty acids. In another example, the fish oil can contain 98% PUFA, 89% omega-3 fatty acids, about 70% DHA, about 10% EPA, 8.9% omega-6 fatty acids and 0.7% omega-9 fatty acids.

Exemplary of a fish oil containing high amounts of omega-3 fatty acids that can be used as the non-polar ingredient in the provided concentrates is an omega-3 fish oil EE (O3C Nutraceuticals; supplied by Jedwards International Inc., Quincy, Mass.), which contains a total of 98% polyunsaturated fatty acids (PUFAs), including 89% omega-3 fatty acids, 8.9% omega-6 fatty acids, and 0.7% omega-9 fatty acids, made up of 0.1% saturated fatty acids, 1.0% monounsaturated fatty acids, 74.5% docosahexanoic (DHA) fatty acids, and 9.3% eicosapentaenoic (EPA) fatty acids. This fish oil also contains 0.1% (16:0) palmitic acid, 0.1% (16:1 ω-7) palmitoleic acid, 0.1% (18:0) stearic acid, 0.6% (18:1 ω-9) oleic acid, 0.1% (18:1 ω-7) oleic acid, 0.3% (18:2 ω-6) linoleic acid, 0.2% (18:3 ω-3) linolenic acid, 0.2% (18:4 ω-3) octadecatetraenoic acid, 0.1% (20:1 ω-9) eicosanoic acid, 0.1% (20:2 ω-6) eicosadienoic acid, 0.2% (20:3 ω-6) eicosatrienoic acid, 2.4% (20:4 ω-6) arachidonic acid, 0.6% (20:4 ω-3) arachidonic acid, 0.1% (22:1 ω-11) erucic acid, 0.6% (21:5 ω-3) uncosapentaenoic acid, 0.5% (22:4 ω-6) docosatetraenoic acid, 5.4% (22:5 ω-6) docosapentaenoic acid, 3.6% (22:5 ω-3) docosapentaenoic acid and 0.9% other fatty acids.

Also exemplary of a fish oil containing high amounts of omega-3 fatty acids that can be used in the provided concentrates is Omega Concentrate 85 DHA TG Ultra (O3C Nutraceuticals AS, Oslo, Norway), which contains greater than 85% DHA (C22:6n-3) and greater than 90% total omega-3 fatty acids and is isolated from fatty fish species in the Engraulidae, Clupeidae and Scombridae families. This fish oil is produced by purifying and concentrating the oils from these fish with gentle technologies to increase the concentration of omega-3 fatty acid DHA. Also exemplary of the fish oils are other fish oils made by O3C Nutraceuticals, AS and other fish oils supplied by Jedwards International, Inc.

Any fish oil containing DHA and/or EPA can be used as the non-polar ingredient in the provided concentrates. Exemplary of a fish oil that can be included in the provided pre-emulsion concentrates is Eterna™ Omegasource™ Oil (supplied by Hormel Foods Specialty Products Division, Austin, Minn.), which contains at least 30% omega-3 fatty acids (DHA, EPA and ALA), is odorless, virtually free of cholesterol, and bland in flavor. This fish oil contains about 28% DHA and EPA, typically 17% EPA and 11% DHA, and additionally contains 4.5% omega-6 fatty acids. Also exemplary of the fish oils that can be included in the provided compositions are Omega 30 TG Food Grade (Non-GMO) MEG-3™ Fish Oil (supplied by Ocean Nutrition Canada, Dartmouth, Nova Scotia, Canada), a kosher fish oil which contains about 30% DHA/EPA and Marinol C-38 (supplied by Lipid Nutrition B.V., Channahon, Ill.), which contains about 52% omega-3 fatty acids, including at least 38% DHA/EPA, more specifically includes about 22% EPA and 14% DHA. Also exemplary of fish oils are Marinol D-40 (supplied by Lipid Nutrition B.V., Channahon, Ill.), which contains about 40% DHA and 7% EPA; VivoMega 3322 TG fish oil that contains 50% of the non-polar ingredients DHA/EPA (GC Rieber Oils, Kristiansund, Norway); an omega-3 fish oil 70TG that is 61% by weight DHA/EPA; fish oils sold by GC Rieber Oils (Kristiansund, Norway) that contain 30% or 65% DHA; ONC TG fish oil sold by Ocean Nutrition Canada (Dartmouth, Nova Scotia); Omevital™ 30% MP Gold, a fish oil that contains 30% DHA/EPA (Cognis, Monheim am Rhein, North Rhine-Westphalia, Germany); and a fish oil containing 60% DHA (sold by FINA LLC, Cincinnati, Ohio). Also exemplary of the fish oils are krill oils, such as those made according to International Patent Publication No. WO 2007/080515.

(ii) Algae Oil

Also exemplary of non-polar ingredients containing omega-3 PUFAs, particularly DHA (and optionally EPA), that can be used as the non-polar ingredient in the provided pre-emulsion concentrates are oils derived from microorganisms, for example, oils derived from marine dinoflagellates, such as microalgae, e.g., *Crypthecodinium* sp., particularly *Crypthecodinium cohnii*. Microalgae oils, like fish oils, are an excellent source of omega-3 fatty acids, particularly DHA (U.S. Pat. Nos. 5,397,591; 5,407,957; 5,492,938; and 5,711,983). Exemplary of oils derived from microalgae are the oils disclosed in (and oils made according to the methods described in) U.S. Pat. Nos. 5,397,591; 5,407,957; 5,492,938; and 5,711,983 and U.S. Patent Publication No. 2007/0166411, including DHASCO® and DHASCO-S® (Martek Biosciences Corporation).

For example, U.S. Pat. No. 5,397,591 describes, inter alia, single-cell edible oils (algae oils) (and methods for making the oils), which contain at least 70% triglycerides, which contain about 20-35% DHA and lack EPA, isolated from *Crypthecodinium cohnii*, preferably containing more than 70% triglycerides, having 15-20% myristic acid; 20-25% palmitic acid; 10-15% oleic acid; 30-40% DHA; and 0-10% other triglycerides. U.S. Pat. No. 5,407,957 describes, inter alia, algae oils (and methods for making the oils) derived from *Crypthecodinium cohnii*, preferably containing greater than about 90% triglycerides, at least 35% DHA by weight (w/w), in one example, having 15-20% myristic acid; 20-25% palmitic acid; 10-15% oleic acid; 40-45% DHA; and 0-5% other oils. U.S. Pat. No. 5,492,938 describes, inter alia, single cell edible oils (and methods for making the oils) containing at least 70% triglycerides, which contain about 20-35% DHA and lack EPA, isolated from *Crypthecodinium cohnii*, in one example containing more than 70% triglycerides, having 15-20% myristic acid; 20-25% palmitic acid; 10-15% oleic acid; 30-40% DHA; and 0-10% other triglycerides. U.S. Pat. No. 5,711,983 describes, inter alia, single cell edible oils (and methods for making the oils) containing at least 70% triglycerides, which contain about 20-35% DHA and lack EPA, isolated from *Crypthecodinium cohnii*, in one example, containing more than 70% triglycerides, having 15-20% myristic acid; 20-25% palmitic acid; 10-15% oleic acid; 30-40% DHA; and 0-10% other triglycerides.

Exemplary of suitable algal oils for use in the pre-emulsion concentrates provided herein are an algal oil that contains 40% of the non-polar ingredient DHA (sold by GC Rieber Oils, Kristiansund, Norway) and an algal oil that contains 35% of the non-polar ingredient DHA and contains 350 mg DHA/g oil (life'sDHA™ S35-O300, sold by DSM Nutritional Products Inc., Kaiseraugst, Switzerland).

Also exemplary of suitable microalgae oils are those disclosed, for example, in U.S. Pat. No. 6,977,166 and U.S. Patent Publication No. US 2004/0072330. Any oil derived from dinoflagellate, for example, microalgae, which contains DHA, and optionally EPA, is suitable as an algae oil for use with the provided compositions, for example, V-Pure algae oil (Water4Life, Switzerland), which contains EPA and DHA, and Martek DHA™-S (supplied by Martek Biosciences Corporation, Columbia, Md.), derived from the marine alga *Schizochytrium* sp., containing not less than 35% DHA and 16.1% (22:5 ω-6) docosapentaenoic acid, 1.3% (20:5 ω-3) eicosapentaenoic acid, 0.6% (20:4 ω-6) arachidonic acid, 1.6% (18:2 ω-6) linoleic acid, 16.9% (18:1 ω-9) oleic acid, and 19.8% other fatty acids.

(2) Flaxseed Oil—Omega 3 (ALA)

Also exemplary of the omega-3-containing non-polar ingredient used in the provided pre-emulsion concentrates is flaxseed oil (linseed oil). Flaxseed oils, which are good sources of omega-3 fatty acids, particularly alpha-linolenic acid (ALA), have been used as nutritional supplements. Flaxseed oils are produced by pressing the flax seed and refining the oil from the flax seeds. Exemplary of flaxseed oil that can be used as the non-polar ingredient in the provided compositions is flaxseed oil derived from *Linum usitatissimum* L. Exemplary of flaxseed oils suitable for use in the concentrates provided herein include flaxseed oil supplied by Sanmark LLC (Greensboro, N.C.; Sanmark Limited, Dalian, Liaoning Province, China), which contains not less than (NLT) 50% C18:3 alpha-linolenic acid, and further contains other fatty acids, for example, 3-8% C16:0 palmitic acid, 2-8% C18:0 stearic acid, 11-24% C18:1 oleic acid, 11-24% C18:2 linoleic acid and 0-3% other fatty acids. Also exemplary of suitable flaxseed oil is a flaxseed oil containing 6% palmitic acid, 2.5% stearic acid, 0.5% arachidic acid, 19% oleic acid, 24.1% linoleic acid, 47.4% linolenic acid, and 0.5% other fatty acids. The fatty acid composition of flaxseed oil can vary. Any flaxseed oil can be used as the non-polar ingredient in the provided compositions. For example, the flaxseed oil can contain at least or about at least 50%, at least or about at least 65%, or at least or about at least 70% ALA. Exemplary of a flaxseed oil containing greater than 65% alpha-linolenic acid content (of total fatty acid content), for example, 70-80% or 70-75%, is the flaxseed oil described in U.S. Pat. No. 6,870,077.

(b) Omega-6 Compounds

Also exemplary of the non-polar ingredients used in the provided pre-emulsion concentrates are compounds containing omega-6 PUFAs, for example, gamma-linolenic acid (GLA), for example, borage oil and evening primrose (*Oenothera biennis*) oil, blackcurrant seed oil, hemp seed oil, fungal oil and *spirulina* extract. Any oil containing omega-6 fatty acids can be used in the provided compositions.

Exemplary of the omega-6-containing non-polar ingredients are compounds containing GLA, for example, borage oil. GLA is an omega-6 PUFA, which primarily is derived from vegetable oils, for example, evening primrose (*Oenothera biennis*) oil, blackcurrant seed oil, hemp seed oil, and *spirulina* extract. GLA has been used as a nutritional supplement. It has been proposed that GLA has a role in treating various chronic diseases and in particular that it has anti-inflammatory effects (Fan and Chapkin (1998) J. Nutr. 128(9):1411-1414). In one example, the non-polar ingredient contains at least or about at least 22 wt % of GLA, for example, 22, 23, 24, 25, 26, 27, 28, 29, 30, 31, 32, 33, 34, 35, 36, 37, 38, 39, 40, 50, 60 wt % or more, by weight of GLA.

Borage (*Borago officinalis*), also known as "starflower," is an herb with seeds containing high amounts of GLA. Exemplary of borage oils that can be used as a non-polar ingredient in the provided compositions are borage oils supplied by Sanmark LLC (Greensboro, N.C.; Sanmark Limited, Dalian, Liaoning Province, China), derived by pressing and isolating oil from the seeds of *Borago officinalis* L. This oil contains not less than (NLT) 22% C18:3 gamma-linolenic acid (GLA), between 9 and 12% C16:0 palmitic acid, between 3% and 5% C18:0 stearic acid, between 15% and 20% C18:1 oleic acid, between 35% and 42% C18:2 linoleic acid, between 3% and 5% C20:1 ocosenoic acid, between 1% and 4% C22:1 docosenoic acid and between 0% and 4% other fatty acids. Other borage oils can be used. Other GLA-containing oils also can be used as the non-polar ingredient.

(c) Saw Palmetto Extract

Also exemplary of the non-polar ingredients used in the provided pre-emulsion concentrates is saw palmetto extract, a lipophilic extract of the ripe berries of the American dwarf palm (also called *Serenoa repens* or *Sabal serrulata*), which has been used to treat genitourinary and other diseases and to enhance sperm production, breast size and libido, as a mild diuretic, a nerve sedative, an expectorant and a digestive tract tonic, and particularly to treat benign prostate hyperplasia (BHP) (Ernst (2002) Acad. Clin. 136:42-53; Gordon and Shaughnessy (2003) Comp. Alt. Med. 76(6): 1281-1283). Saw palmetto extract is commercially available from a number of sources. Any saw palmetto lipid extract can be used in the provided concentrates. Exemplary of a saw palmetto extract that can be used in the provided concentrates is Saw Palmetto, Lipophilic Extract, commercially available from Natural Medicinals, Inc. (Felda, Fla.). This saw palmetto lipophilic extract is carbon dioxide extracted and, in one example, contains 85.9% total fatty acids, including 0.8% caproic acid, 2% caprylic acid, 2.4% capric acid, 27.% lauric acid, 10.3% myristic acid, 8.1% palmitic acid, 0.2% palmitoleic acid, 2% stearic acid, 26.7% oleic acid, 4.9% linoleic acid, 0.7% linolenic acid, 0.42% phytosterols, including 0.42% beta sitosterol, 0.09% campesterol, 0.03% stigmasterol, and 0.2% moisture. Other sources of saw palmetto extract can be used.

(d) Conjugated Linoleic Acid (CLA)

Also exemplary of the PUFA-containing non-polar ingredients that can be used in the provided pre-emulsion concentrates are non-polar ingredients containing conjugated fatty acids. Conjugated fatty acids are PUFAs with two or more conjugated double bonds. Conjugated fatty acids can be used as nutritional supplements. Exemplary of the ingredients containing conjugated fatty acids are compounds containing conjugated linoleic acid (CLA), for example, 18:2 ω-7 and 18:2 ω-6; conjugated linolenic acid, for example, 18:3ω3-6 and 18:3ω3-5; and other conjugated fatty acids, for example, 18:3 ω-3, 18:4 ω-3 and 20:5 ω-6. CLA refers to a family of linoleic acid isomers found primarily in meat and dairy products of ruminants. Typically, the CLA compounds contain a mixture of different CLA isomers, for example, C18:2 CLA, c9, t11 CLA, t10, c12 CLA, and other CLA isomers. Exemplary of a CLA that can be used as a non-polar ingredient in the provided compositions is the CLA oil (70% CLA) commercially available from Sanmark, LTD (Dalian, Liaoning Province, China; product code 01057-A80). This CLA oil is a clear white to pale yellow oil that has a fatty acid composition of NMT (not more than) 9.0% C16:0 palmitic acid, NMT 4.0% stearic acid, NMT 15.0% C18:1 oleic acid, NMT 3.0% C18:2 linoleic acid, NLT (not less than) 80% C18:2 CLA (including the following isomers: NLT 37.5% C18:2 c9, t11 CLA, 37.5% C18:2 t10, c12 CLA, and NMT 5.0% other CLA isomers); and NMT 5.0% other fatty acids. Other exemplary CLA compounds are a CLA compound that contains 74.5% CLA (Clarinol® CLA) and a CLA compound that contains 79.6% CLA (Clarinol® G-80), both sold by Stepan Lipid Nutrition, Maywood, N.J. Other CLA-containing compounds can be used.

ii. Phytochemical-Containing Non-Polar Compounds

Exemplary of the non-polar ingredients that contain non-polar compounds that can be used in the provided pre-emulsion concentrates are phytochemical-containing compounds, for example, phytosterols (plant sterols), phytoestrogens, for example, genistein and daidzein, flavonoids, for example, quercetin, isoflavones, for example, soy isoflavones, phytoalexins, for example, resveratrol (trans-3,5,4'-trihydroxystilbene), and red clover extract.

(a) Phytosterols

Exemplary of the phytochemical-containing compounds that contain non-polar ingredients that can be used in the provided concentrates are phytosterols (plant sterols). Plant sterols are structurally similar to cholesterol and have been found to reduce the absorption of dietary cholesterol, which can affect the levels of serum cholesterol. According to the U.S. Food and Drug Administration (FDA), two servings per day, each containing 0.4 grams of plant sterols, for a total daily intake of at least 0.8 grams, as part of a diet low in saturated fat and cholesterol, is reported to reduce the risk of heart disease. Thus, plant sterols are used in nutritional supplements.

Any phytosterol-containing compound can be used as a non-polar ingredient in the provided compositions. Exemplary of the phytosterol-containing compounds that can be used as non-polar ingredients in the provided compositions are compounds containing plant sterols, for example, the compound sold under the name CardioAid™, distributed by B&D Nutrition and manufactured by ADM Natural Health and Nutrition (Decatur, Ill.). This compound contains kosher, pareve, and halal plant sterols that are produced under current food good manufacturing practices (GMPs). The sterols are PCR negative and the material is derived from genetically modified organisms (GMOs). This phytosterol compound contains a minimum of 95% plant sterols, which can include up to 5 plant sterols. The compound can contain, for example, 40-58% beta sitosterol, 20-30% campesterol, 14-22% stigmasterol, 0-6% brassicasterol and 0-5% sitostanol. The compound further can contain tocopherols, for example, 0-15 mg/g tocopherols. The compound is tested and is negative for microorganisms, such as *Salmonella, E. coli* and *Staphylococcus aureus*.

(b) Flavonoids

Exemplary of the phytochemical-containing compounds that can be used as in the provided concentrates are flavonoids. Flavonoids are a class of plant secondary metabolites that have a general structure of a 15-carbon skeleton, which consists of two phenyl rings and a heterocyclic ring, that can be abbreviated C6-C3-C6. Exemplary flavonoid compounds include bioflavonoids, isoflavonoids, and neoflavonoids.

Exemplary of a flavonoid is resveratrol, or trans-resveratrol (trans-3,5,4'-trihydroxystilbene), a phytoalexin that is naturally produced by several plants, such as the Japanese knotweed, and also is found in the skin and seeds of grapes, numerous berries, including mulberries, blueberries, bilberries and cranberries, and in peanuts. This polyphenolic compound can act as an antioxidant and additionally, can aid in cancer prevention and reduction of cardiovascular disease.

Any resveratrol-containing compound can be used as a non-polar ingredient in the provided compositions. Exemplary of resveratrol-containing compounds that can be used as non-polar ingredients in the provided compositions are compounds containing trans-resveratrol, for example the compound sold under the name ReserveNature™, sold by Jiaherb, Shaanxi, China. This compound contains trans-resveratrol from the botanical source *Polygonum cuspidatum* (Japanese knotweed). This resveratrol compound contains a minimum of 98.5% trans resveratrol and does not contain emodin. The compound is tested and is negative for microorganisms, such as *Salmonella, E. coli*, yeast and mold. Another exemplary resveratrol compound is the resveratrol sold by Maxsun Industries (Walnut, Calif.).

An exemplary flavonoid that can be used in the pre-emulsion concentrates provided herein is quercetin. Quercetin is a plant pigment that is found in fruits, vegetables, leaves, and grains. Quercetin can act as an antiviral agent, reduce asthma symptoms, minimize eczema, and may have anti-inflammatory properties. An exemplary quercetin compound is the quercetin sold by Pure Assay Ingredients (Walnut, Calif.).

iii. Micronutrient-Containing Compounds

Exemplary of the non-polar ingredients that are or contain non-polar compounds in the provided compositions are micronutrient-containing compounds, for example, vitamins, including vitamins A, B, C, D, E, and K, and corresponding provitamins and vitamin derivatives with an action resembling that of vitamin A, B, C, D, E, or K, and yerba mate, *ginseng* and *ginkgo biloba*.

(a) Vitamins

Exemplary of the vitamins included in the provided pre-emulsion concentrates are fat-soluble vitamins, for example, vitamins A, B, C, D, E and K, and corresponding provitamins and vitamin derivatives, such as esters, with an action resembling that of vitamin A, B, C, D, E or K. Exemplary vitamins include retinol (vitamin A) and pharmaceutically acceptable derivatives thereof, for example, palmitate ester of retinol and other esters of retinol, for example, vitamin A palmitate; B vitamins, for example, thiamin (vitamin B1), riboflavin (vitamin B2), niacin (vitamin B3), pantothenic acid (vitamin B5), pyridoxine (vitamin B6), biotin (vitamin B7), folic acid or folate (vitamin B9), and cyanocobalamin, cobalamin, or reduced forms of cobalamin (vitamin B12); calciferol (vitamin D) and its pharmaceutically acceptable derivatives thereof, for example, for example, cholecalciferol (vitamin D3), and precursors of vitamin D; d-alpha tocopherol (vitamin E) and derivatives thereof, including pharmaceutical derivatives thereof, for example, tocotrienols, d-alpha tocopherol acetate and other esters of d-alpha tocopherol; K vitamins, for examples, phylloquinone or phytonadione (vitamin K1) and menaquinone (vitamin K2), including the MK-4, MK-7, MK-8, and MK-9 forms; and ascorbyl palmitate, a fat-soluble version of vitamin C.

Any vitamin can be used as a non-polar ingredient in the provided pre-emulsion concentrates. Exemplary of the vitamins that can be used in the provided pre-emulsion concentrates are vitamin A palmitate, for example, vitamin A palmitate containing 1.7 mIU/g, produced by DSM Nutritional Products, Inc., Belvidere, N.J., and distributed through Stauber Performance Ingredients, Inc., Fullerton, Calif.; vitamin D3, for example, vitamin D3 in corn oil, containing about 1 mIU/g, produced by DSM Nutritional Products, Inc., Parsippany, N.J.; vitamin K2, for example, vitamin K2 (as MK-7), such as MenaQ7® sold by NattoPharma®, Metuchen, N.J.; vitamin E (d-alpha-tocopherol), for example vitamin E oil containing 1000 IU/g vitamin E, sold as Novatol™ 5-67 by ADM Natural health and Nutrition, Decatur, Ill.; vitamin E acetate, for example, a vitamin E acetate compound that includes 1360 IU tocopheryl/g vitamin E oil (sold by DSM Nutritional Products Inc., Kaiseraugst, Switzerland); vitamin B12; vitamin B1; vitamin B3; vitamin B5; and vitamin B6. Vitamin non-polar ingredients are typically added to the pre-emulsion concentrates in amounts such that one serving of the water-soluble powder provides an amount of the vitamin that corresponds to the dietary reference intakes.

iv. Alkaloids

Exemplary of non-polar ingredients used in the provided pre-emulsion concentrates are non-polar ingredients containing an alkaloid, for example, any edible or food-approved alkaloid or any synthetic or semi-synthetic alkaloid. Exemplary of suitable alkaloids include caffeine, synephrine, γ-aminobutyric acid (GABA) derivatives, e.g., 4-amino-3-phenylbutyric acid (i.e., phenibut), and vinpocetine. Vinpocetine is a semi-synthetic derivative of the vinca alkaloid vincamine, an extract from the lesser periwinkle plant. Vinpocetine is reported to have cerebral blood-flow enhancing and neuroprotective effects. An exemplary vinpocetine compound is the vinpocetine sold by Cyvex Nutrition (Irvine, Calif.). Suitable alkaloids for inclusion in the provided pre-emulsion concentrates are a matter of design choice and well within the skill of the skilled artisan. The alkaloid-containing non-polar ingredients include caffeine that is added in the form of caffeine anhydrous, such as the Caffeine Anhydrous powder, a white crystalline powder sold by Pacific Rainbow International, Inc. (City of Industry, Calif.). Other exemplary non-polar ingredients containing alkaloids include herbal extracts, medicinal extracts and compounds from plants and drugs.

v. Cannabinoids

Cannabinoids and cannabinoid-containing compounds are exemplary of non-polar ingredients suitable for use in the pre-emulsion concentrates provided herein. Cannabinoids include phytocannabinoids (found in the *Cannabis sativa* plant and some other plants), endocannabinoids (produced naturally in the body by humans and animals), and synthetic cannabinoids. Cannabinoids that can be included in the pre-emulsion concentrates provided herein can be natural cannabinoids, synthetic cannabinoids, semi-synthetic cannabinoids, or mixtures thereof. Actual or potential therapeutic applications for cannabinoids include the treatment of multiple sclerosis and other forms of muscular spasm, migraine headache, glaucoma, asthma, inflammation, insomnia, high blood pressure, nausea and vomiting, and the stimulation of appetite. Other potential therapeutic applications include the use of cannabinoids as oxytoxic, anxiolytic, anti-convulsive, anti-depressive, anti-psychotic, and anti-cancer agents.

Exemplary phytocannabinoids derived from the *Cannabis sativa* plant (commonly known as marijuana) are the terpenophenolic compounds $\Delta^9$-tetrahydrocannabinol (THC), $\Delta^8$-tetrahydrocannabinol ($\Delta$8-THC) and other compounds structurally related to THC, cannabidiol (CBD), cannabigerol (CBG), cannabichromene (CBC), cannabinol (CBN), cannabicyclo (CBL), cannabivarin (CBV), tetrahydrocannabivarin (THCV), cannabidivarin (CBDV), cannabielsoin (CBE), cannabicitran (CBT), cannabinodiol (CBDL), cannabichromevarin (CBCV), cannabigerovarin (CBGV), cannabigerol monoethyl ether (CBGM), and mixtures and derivatives thereof, for example, nabiximols (Sativex®), a mixture of THC and CBD. Suitable phytocannabinoids also include those derived from plants other than *Cannabis sativa*, such as, for example, lipophilic alkamides (alkylamides) derived from *Echinacea* plants, and other cannabinoids derived from plants including, but not limited to, *Echinacea purpurea, Echinacea angustifolia, Echinacea pallida, Acmela oleracea, Helichrysum umbraculigerum,* and *Radula marginata* plants.

Endogenous cannabinoids are lipid-like substances produced in the brain and peripheral tissues that bind to and activate cannabinoid receptors present in the cell membrane, including, but not limited to, arachidonate acid-based lipids such as anandamide (N-arachidonoylethanolamide, AEA), 2-arachidonoylglycerol (2-AG), noladin ether (2-arachidonyl glyceryl ether), N-arachidonoyl dopamine (NADA), and virodhamine (OAE).

Also suitable for use in the pre-emulsion concentrates provided herein are synthetic cannabinoids. Synthetic cannabinoids include any compound having a cannabinoid-like structure or that produces effects similar to those of cannabinoids that is manufactured using chemical means, including, for example, synthetic $\Delta^9$-THC; dronabinol (Marinol®; (6aR-trans)-6a,7,8,10a-tetrahydro-6,6,9-trimethyl-3-pentyl-6H-dibenzo[b,d]pyran-1-ol); nabilone (Cesamet™; (±)-trans-3-(1,1-dimethylheptyl)-6,6a,7,8,10,10a-hexahydro-1-hydroxy-6-6-dimethyl-9H-dibenzo[b,d]pyran-9-one); dexanabinol (((6aS,10aS)-9-(hydroxymethyl)-6,6-dimethyl-3-(2-methyloctan-2-yl)-6a,7,10,10a-tetrahydrobenzo[c]chromen-1-ol); ajulemic acid (Resunab™; (6aR,10aR)-3-(1,1-dimethylheptyl)-6a,7,10,10a-tetrahydro-1-hydroxy-6,6-dimethyl-6H-dibenzo(b,d)pyran-9-carboxylic acid); cannabinor ((E)-4-(2-((1R,2R,5R)-6,6-dimethyl-4-oxobicyclo[3.1.1]heptan-2-yl)-3-hydroxy-5-(2-methyloctan-2-yl)phenoxy)-4-oxobut-2-enoic acid); HU 308 ([(1R,2R,5R)-2-[2,6-dimethoxy-4-(2-methyl-octan-2-yl)phenyl]-7,7-dimethyl-4-bicyclo[3.1.1]hept-3-enyl]methanol); rimonabant (Acomplia™; 5-(4-chlorophenyl)-1-(2,4-dichloro-phenyl)-4-methyl-N-(piperidin-1-yl)-1H-pyrazole-3-carboxamide); taranabant (MK-0364; N-[(2S,3S)-4-(4-chlorophenyl)-3-(3-cyanophenyl)-2-butanyl]-2-methyl-2-{[5-(trifluoromethyl)-2-pyridinyl]oxy}propanamide); levonantradol ([(6S,6aR,9R,10aR)-9-hydroxy-6-methyl-3-[(2R)-5-phenylpentan-2-yl]oxy-5,6,6a,7,8,9,10,10a-octahydrophenanthridin-1-yl]acetate); WIN55212-2 ((R)-(+)-[2,3-dihydro-5-methyl-3-(4-morpholinylmethyl) pyrrolo[1,2,3-de]-1,4-benzoxazin-6-yl]-1-napthalenylmethanone); HU 331 (3-hydroxy-2-[(1R)-6-isopropenyl-3-methyl-cyclohex-2-en-1-yl]-5-pentyl-1,4-benzoquinone); and any other compound having a cannabinoid-based structure or that produces effects similar to those of cannabinoids that is manufactured using chemical means.

vi. Hops-Containing Compounds

Exemplary of non-polar ingredients that can be used in the provided pre-emulsion concentrates are compounds that contain hops (*Humulus lupulus* L.), including compounds isolated or derived from hops, such as extracts of hops cones, for example, hops oils, hops resins or hops resin derivatives, hops acids or hops acid derivatives, or mixtures thereof. Hops oils include, but are not limited to, humulene, beta-caryophyllene, mycrene, farnescene, gamma-cadinene, alpha-selinene, and alpha-cadinene. Hops contain alpha-acids, such as humulone ($\alpha$-lupulic acid), cohumulone, adhumulone, hulupone, and isoprehumulone, and beta-acids, such as lupulone, colupulone, adlupulone, tetrahydroisohumulone, and hexahydrocolupulone. Both alpha- and beta-acids have demonstrated antibacterial, antioxidant, and antiinflammatory properties. An exemplary non-polar ingredient containing hops is Perluxan™, a compound containing a supercritical extract of hops cones that includes a minimum of 30% alpha-acids (including humulone, cohumulone, adhumulone, iso-cohumulone and iso-adhumulone) and 10% beta-acids (including lupulone and colupulone), such as sold by Pharmachem Laboratories, Kearny, N.J.

vii. Antioxidants

Exemplary of non-polar ingredients that can be included in the pre-emulsion concentrates provided herein are compounds that contain an antioxidant or have antioxidant properties, for example, a molecule that is capable of inhibiting the oxidation of other molecules. Antioxidants include molecules that scavenge free radicals. Suitable antioxidants include those that are used as ingredients in dietary supplements. The antioxidant can be a natural antioxidant or a synthetic antioxidant.

Examples of antioxidants include, but are not limited to, hormones, carotenoids, carotenoid terpenoids, non-carotenoid terpenoids, flavonoids, flavonoid polyphenolics (e.g., bioflavonoids), flavonols, flavones, lignans, such as sesamin, phenols, polyphenols, esters of phenols, esters of polyphenols, nonflavonoid phenolics, isothiocyanates, vitamins and vitamin cofactors, such as vitamin A, vitamin C, vitamin E, vitamin E phosphate and ubiquinone (ubidecarenone, coenzyme Q, coenzyme Q10), ubiquinol, pyrroloquinoline quinone (PQQ), ascorbic acid, citric acid, rosemary oil, minerals, such as mineral selenium and manganese, melatonin, α-carotene, β-carotene, lycopene, lutein, zeanthin, crypoxanthin, resveratrol, eugenol, quercetin, catechin, gossypol, hesperetin, curcumin, turmeric, turmeric/curcumin blend, ferulic acid, thymol, hydroxytyrosol, thyme, olive oil, lipoic acid, including alpha-lipoic acid, glutathione, oxalic acid, tocopherol, tocopherol-derived compounds, di-alpha-tocopheryl phosphate, tocotrienols, butylated hydroxyanisole, butylated hydroxytoluene, ethylenediaminetetraacetic acid, tert-butylhydroquinone, acetic acid, pectin, zeaxanthin, astaxanthin, canthaxanthin, saponins, limonoids, kaempferol, myricetin, isorhamnetin, proanthocyanidins, quercetin, rutin, luteolin, apigenin, tangeritin, naringenin, eriodictyol, flavan-3-ols (e.g., anthocyanadins), gallocatechins, epicatechin and its gallate forms, epigallocatechin and its gallate forms, theaflavin and its gallate forms, thearubigins, isoflavone phytoestrogens, genistein, daidzein, glycitein, anythocyanins, delphinidin, malvidin, pelargonidin, peonidin, and hops (*Humulus lupulus* L.)-containing compounds. In one example, the antioxidant includes ubiquinol. In another example, the antioxidant includes alpha-lipoic acid. In another example, the antioxidant includes pyrroloquinoline quinone (PQQ). In yet another example, the antioxidant includes a turmeric/curcumin composition.

Any non-polar ingredient that is an antioxidant or has antioxidant properties can be included in the provided pre-emulsion concentrates. Exemplary of an antioxidant that can be used in the provided pre-emulsion concentrates is alpha-lipoic acid, for example, the alpha-lipoic acids sold by NutriChem Resources Company (Walnut, Calif.), Zhejiang Medicines & Health Products Import & Export Co., Ltd (Hangzhou, China), Pure Assay Ingredients (Walnut, Calif.), and any other alpha-lipoic acid. Another exemplary antioxidant that can be used in the provided pre-emulsion concentrates is pyrroloquinoline quinone (PQQ), such as PureQQ, sold by Nascent Health Science (Allentown, N.J.). Exemplary of a non-polar ingredient that contains antioxidants that can be included in the provided pre-emulsion concentrates is a turmeric/curcumin composition, for example, the turmeric/curcumin composition that is 95% curcumin, sold by Siddharth International, Mumbai, India. Another exemplary antioxidant that can be used in the provided pre-emulsion concentrates is sesamin, such as the sesamin sold by KEB Nutraceutical USA, Inc. (Minneapolis, Minn.).

viii. Coenzyme Q Compounds

Exemplary of the non-polar ingredients that can be included in the pre-emulsion concentrates provided herein are compounds containing the non-polar ingredient coenzyme Q, for example, coenzyme Q10 (also called coQ10, ubiquinone, ubidecarenone, ubiquinol and vitamin Q10). Coenzyme Q compounds are benzoquinone compounds containing isoprenoid units. The number of isoprenoid units in each of the different CoQ species is indicated with a number following CoQ. For example, coQ10 contains 10 isoprenoid units. Coenzyme Q10 is a predominant coenzyme Q species. CoQ10 has electron-transfer ability and is present in cellular membranes, such as those of the endoplasmic reticulum, peroxisomes, lysosomes, vesicles and the mitochondria. A decrease in natural coQ10 synthesis has been observed in sick and elderly people. Because of this observation and its potent antioxidant properties, coQ10 is used as a dietary supplement and a treatment for diseases such as cancer and heart disease. CoQ10, however, exhibits relatively poor bioavailability.

Coenzyme Q can exist in two different forms: an oxidized form and a reduced form. When the oxidized form of a coenzyme Q species is reduced by one equivalent, i.e., partially reduced, it becomes a ubisemiquinone (semiquinone), denoted QH, which contains a free radical on one of the oxygens in the benzene ring of the benzoquinone. Further oxidation of QH results in ubiquinol, the fully reduced, active form of coQ10. Both oxidized and reduced coenzyme Q-containing compounds can be used as non-polar ingredients in the provided pre-emulsion concentrates. CoQ10 typically refers to the oxidized form of coQ10, which also is referred to as ubidecarenone, as opposed to the partially reduced form of coQ10, referred to as ubisemiquinone, and the fully reduced form of coQ10, referred to as ubiquinol. Both the reduced (i.e., coQ10, ubiquinone, ubidecarenone) and oxidized forms (i.e., ubisemiquinone and ubiquinol) of coQ10 are exemplary of the coenzyme Q species that can be used as non-polar ingredients in the provided pre-emulsion concentrates.

CoQ10-containing compounds are available commercially. Any coQ10 compound or oxidized coQ10 compound can be used with the provided pre-emulsion concentrates. Exemplary of the coQ10 compounds that can be used are coenzyme Q10 compounds containing greater than 98% or greater than about 98% ubidecarenone, for example, the compound sold under the name Kaneka Q10™ (USP Ubidecarenone) by Kaneka Nutrients, L.P. (Pasadena, Tex.). The compound sold under the name Kaneka Q10™ is fermented entirely from yeast and is identical to the body's own coQ10 and free from the cis isomer found in some synthetically produced coQ10 compounds. Another exemplary compound includes non-polar ingredients containing the reduced form of coQ10, ubiquinol, for example, the compound Kaneka Ubiquinol® sold by Kaneka Nutrients (Pasadena, Tex.). Any coQ10 compound containing the reduced or oxidized form of coQ10 can be used in the provided pre-emulsion concentrates provided herein.

ix. Carotenoid-Containing Compounds

Exemplary of the non-polar ingredients used in the provided pre-emulsion concentrates are carotenoid-containing compounds, for example, carotenoids, including hydrocarbons (carotenes) and oxygenated, alcoholic derivatives of hydrocarbons (xanthophylls), for example, beta-carotene, mixed carotenoids complex, lutein, zeaxanthin, cryptoxanthin, for example, beta-crytoxanthin, lycopene, astaxanthin, bixin, canthaxanthin, capsanthin, capsorubin, apo-carotenal, beta-12'-apo-carotenal, "carotene" (mixture of alpha- and beta-carotene), gamma-carotene, ciolerythrin and esters of hydroxyl- or carboxyl-containing members thereof. Carotenoids are efficient free-radical scavengers, or anti-oxidants, and are capable of enhancing the vertebrate immune system.

(a) Carotenes

Exemplary of the carotenoid-containing compounds used as non-polar ingredients containing non-polar compounds in the provided pre-emulsion concentrates are carotenes, for example, alpha-carotene, beta-carotene, lycopene, and mixtures thereof. Any carotene-containing compound can be used as a non-polar ingredient in the provided compositions. Exemplary of a carotene-containing compound that can be used in the provided pre-emulsion concentrates is lycopene, sold by Zhejiang Medicine CO., LTD (Xinchang Pharmaceutical Factory, Xinchang, China), a purple or red crystalline powder containing not less than 70% all E-lycopene, not more than 23% 5-Z-lycopene and not more than 9% related substances.

(b) Xanthophylls

Exemplary of the carotenoid-containing compounds used as non-polar ingredients containing non-polar compounds in the provided pre-emulsion concentrates are xanthophylls, for example, astaxanthin, neoxanthin, violaxanthin, α- and β-cryptoxanthins, lutein and zeaxanthin. Xanthophylls, or phylloxanthins, are oxygen-containing carotenoids that are typically yellow pigments. Any xanthophyll can be used as a non-polar ingredient in the provided pre-emulsion concentrates. An exemplary xanthophyll included in the pre-emulsion concentrates provided herein is astaxanthin, for example, the astaxanthins AstaREAL® (sold by Fuji Health Science, Burlington, N.J.), AstaPure® (sold by Alga Technologies, Hevel Eilot, Israel), and BioAstin® (sold by Cyanotech, Kailua-Kona, Hi.). Unlike other carotenoids, astaxanthin is not converted to vitamin A (retinol) in the human body, but has potent antioxidant activity and can be beneficial in cardiovascular, immune, inflammatory and neurodegenerative diseases. Other exemplary xanthophyll compounds that can be included in the provided pre-emulsion concentrates are lutein and zeaxanthin, sold under the name Xanmax®-80 (Lutein crystals), by Katra Phytochem (India) Private Limited, Bangalore, India, containing 80% lutein and 4.5% zeaxanthin.

x. *Boswellia* Extracts

Exemplary of non-polar ingredients used in the provided pre-emulsion concentrates are non-polar ingredients containing extracts of a *Boswellia* plant or a boswellic acid or derivative thereof. Extracts of the *Boswellia* family of plants, including, for example, *Boswellia serrata*, exhibit anti-inflammatory, anti-arthritic and anti-ulcerogenic activity (see, e.g., U.S. Pat. No. 6,589,516). Extracts derived from *Boswellia* plants and suitable for use in the pre-gel concentrates provided herein include extracts derived from *Boswellia cartenii*, *Boswellia frereana*, *Boswellia bhaudajaina*, *Boswellia serrata*, and *Boswellia thurifera*. The extracts derived from *Boswellia* plants can be gums, oleogums, resins, essential oils and residues, or mixtures thereof. A typical extract of a *Boswellia* plant suitable for use herein includes at least one boswellic acid, for example, acetyl-11-keto-β-boswellic acid (AKBA). Exemplary of a *Boswellia* extract-containing compound that can be used as the non-polar ingredient in the provided pre-gel concentrates is ApresFLEX®, a compound that includes a *Boswellia serrata* extract that contains acetyl-11-keto-β-boswellic acid (AKBA), sold by PLT Health Solutions, Morristown, N.J.

xi. Phospholipids

Exemplary of the non-polar ingredients that can be used in the provided pre-emulsion concentrates are phospholipids. Phospholipids are amphipathic lipid-like molecules, typically containing a hydrophobic portion at one end of the molecule and a hydrophilic portion at the other end of the molecule. A number of phospholipids can be used as ingredients in the provided pre-emulsion concentrates, for example, lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Exemplary of the phospholipids that can be used in the provided compositions are the phospholipids sold by Lipoid, LLC (Newark, N.J.), for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids, Synthetic Phospholipids, PEG-ylated Phospholipids and phospholipid blends. Exemplary of a phosphatidylserine that can be used in the provided pre-emulsion concentrates is a phosphatidylserine (PS) composition that contains 40% phosphatidylserine and lesser amounts of phosphatidylinositol, phosphatidylethanolamine and phosphatidylserine (sold by Doosan Corporation and distributed by Perrimondo LLC).

d. Preservatives and Sterilizers

The pre-emulsion concentrates provided herein can further contain one or more preservatives (or preservativers) and/or sterilizers. The preservative or sterilizer can be included to improve the stability of the concentrate and the compositions made by diluting the concentrate, over time. Preservatives can be added to preserve the ingredients, for example, in order to prevent oxidation of the ingredients, for example, the non-polar ingredients, for example, the omega-3 containing compounds, for example, the DHA. Preservatives, particularly food and beverage preservatives, are well known. Any known preservative can be used in the provided concentrates. Exemplary of the preservatives that can be used in the provided concentrates are oil soluble preservatives, for example, benzyl alcohol, benzyl benzoate, methyl paraben, propyl paraben, and antioxidants, for example, vitamin E, vitamin A palmitate and beta carotene. Typically, a preservative is selected that is safe for human consumption, for example, in foods and beverages, for example, a GRAS certified and/or Kosher-certified preservative, for example, benzyl alcohol.

The preservative typically represents less than 1%, less than about 1%, 1% or about 1%, by weight (w/w), of the pre-emulsion concentrate or liquid concentrate or between 0.1% or about 0.1% and 1% or about 1%, by weight (w/w), of the concentrate, for example, 0.1%, 0.2%, 0.3%, 0.4%, 0.5%, 0.6%, 0.7%, 0.725%, 0.75%, 0.8%, 0.9%, 1%, about 0.1%, about 0.2%, about 0.3%, about 0.4%, about 0.5%, about 0.6%, about 0.7%, about 0.8%, about 0.9%, about 1%, by weight (w/w), of the concentrate.

2. Pre-Spray Emulsions Containing Non-Polar Compounds

Provided herein are pre-spray emulsions that contain the pre-emulsion concentrates containing non-polar ingredients dispersed in aqueous liquid and have desirable properties, including improved clarity, stability, smell and taste. The provided emulsions (and methods for making the emulsions) can be used to formulate any non-polar ingredient in aqueous compositions, including the non-polar ingredients (e.g., non-polar compounds) described herein and other known non-polar compounds.

In general, emulsions (e.g., oil-in-water emulsions) are colloidal dispersions of two immiscible liquids (e.g., oil and water or other aqueous liquid), containing a continuous and a dispersed phase. Emulsions can be used to disperse non-polar ingredients in aqueous liquids. In an oil-in-water emulsion, the dispersed phase is an oil phase and the continuous phase is an aqueous (water) phase. There is a need for emulsions (e.g., oil-in-water emulsions) containing non-polar ingredients in aqueous liquids and methods and compositions for generating products, such as the water-soluble powders, that are free-flowing, i.e., not sticky. In particular, emulsions are needed that are more suitable and desirable for human consumption of the non-polar ingredients, for example, beverages. For example, emulsions having improved clarity (e.g., small particle size, low turbidity), stability (e.g., lack of separation), taste and smell, that can form powders that are free-flowing, i.e., not sticky, and water-soluble are provided herein.

Typically, the provided emulsions containing the concentrates containing non-polar ingredients are nanoemulsions, which are emulsions having dispersed droplets (particles) with diameters less than 1000 nm or less than about 1000 nm, typically, less than 500 nm or less than about 500 nm, typically less than 300 nm or about 300 nm, typically less than 250 or less than about 250 nm, typically less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Typically, the provided nanoemulsion compositions are oil-in-water nanoemulsions, containing the non-polar ingredients dispersed in aqueous liquid.

The provided emulsion compositions are stabilized by one or more surfactants and/or co-surfactants and/or emulsion stabilizers. Surfactants form an interfacial film in the emulsion, between the oil and water phase, providing stability. Typically, the nanoemulsions of the provided compositions contain micelles, in which one or more surfactant surrounds the non-polar compound. The micelles are dispersed in the water phase.

The provided pre-spray emulsions contain the pre-emulsion concentrates containing non-polar ingredients, which can be spray-dried to provide non-polar compounds in a powder, such as free-flowing, water-soluble powder. The pre-spray emulsions can be made using any concentrate containing non-polar ingredients, a sugar fatty acid ester, and a polyalkylene glycol derivative of vitamin, such as the pre-emulsion concentrates provided herein.

a. Formulating the Pre-Spray Emulsions

In the provided methods, the pre-spray emulsions are formulated by selecting ingredients and concentration ratios of the ingredients that yield compositions having one or more desired properties. The ingredients typically include a concentrate that contains non-polar ingredients and a polyalkylene glycol vitamin E derivative, e.g., TPGS, such as the pre-emulsion concentrates provided herein; a surfactant, such as a sugar fatty acid ester, e.g., sucrose fatty acid ester; and a polar solvent, e.g., water. In some examples, the pre-spray emulsions further include one or more of a stabilizer, a binder, e.g., maltodextrin, a co-surfactant, an emulsion stabilizer, and a pH adjuster. In the provided emulsions, a surfactant, such as a sugar fatty acid ester, e.g., sucrose fatty acid ester, is present in place of or in combination with a binder, e.g., maltodextrin. For example, the pre-spray emulsions provided herein can contain a surfactant, such as such as a sugar fatty acid ester, e.g., sucrose fatty acid ester, and not contain a binder, e.g., maltodextrin. In other examples, the pre-spray emulsions provided herein contain a mixture of surfactant, such as a sugar fatty acid ester, e.g., sucrose fatty acid ester, and binder, e.g., maltodextrin.

The pre-spray emulsions provided herein contain high concentrations of non-polar ingredients, for example, at least 5%, 7%, 10%, 12%, 15%, 20%, 25%, or more, such as 30%, non-polar ingredients. The emulsions are formulated such that drying the emulsion yields a powder composition that contains high concentrations of non-polar ingredient, yet is free-flowing, i.e., not sticky, and water-soluble. A number of parameters of the emulsion, including ingredients, relative concentrations of ingredients, and methods for making the emulsions, affect the ability of emulsion to form a free-flowing, i.e., not sticky, powder when a high concentration of non-polar compound is present. Thus, the parameters of the emulsions affect the advantageous properties of the powders, for example, the solubility of the powder, for example, in an aqueous solution.

b. Exemplary Ingredients and Typical Concentration Ranges i. Pre-Emulsion Concentrates Each pre-spray emulsion provided herein contains a pre-emulsion concentrate, such as the pre-emulsion concentrates provided herein, that contain non-polar ingredients containing non-polar compounds and a polyalkylene glycol derivative of vitamin E, for example, a polyethylene glycol derivative of vitamin, e.g., TPGS. In some examples, the pre-emulsion concentrate contains a preservative, for example, benzyl alcohol.

The pre-emulsion concentrates used in formulating the pre-spray emulsions contain between or between about 30 wt % and 99 wt % non-polar ingredient, typically at least 40 wt %, or at least 50 wt %, or more, such as at least 55%, 60%, 65%, 70%, 75%, 80%, 85%, 90%, 95%, or 99% non-polar ingredient, by weight, of the pre-emulsion concentrate. When formulating the pre-spray emulsions provided herein that contain the pre-emulsion concentrates containing between or between about 30 wt % and 99 wt % non-polar ingredient, the emulsions will contain, for example, between or between about 1 wt % and 40 wt % concentrate, such as between or between about 1% and 5%, 1% and 10%, 1% and 15%, 1% and 20%, 1% and 25%, 1% and 30%, 1% and 35%, 1% and 40%, 5% and 10%, 5% and 15%, 5% and 20%, 5% and 25%, 5% and 30%, 5% and 35%, 5% and 40%, 10% and 15%, 10% and 20%, 10% and 25%, 10% and 30%, 10% and 35%, 10% and 40%, 15% and 20%, 15% and 25%, 15% and 30%, 15% and 35%, 15% and 40%, 20% and 25%, 20% and 30%, 20% and 35%, 20% and 40%, 25% and 30%, 25% and 35%, 25% and 40%, 30% and 35%, 30% and 40%, and 35% and 40% concentrate containing non-polar ingredients, by weight, of the emulsion. Exemplary concentrations of the total amount of concentrate containing non-polar ingredients in the emulsions are at or about 5%, 7%, 10%, 12%, 15%, 17%, and 20% (wt %) of the emulsion. By extension, the amount of non-polar ingredient present in the pre-spray emulsions is typically between or between about 5 wt % and 30 wt % of the emulsion, for example, between or between about 5% and 10%, 5% and 15%, 5% and 20%, 5% and 25%, 5% and 30%, 10% and 15%, 10% and 20%, 10% and 25%, 10% and 30%, 15% and 20%, 15% and 25%, 15% and 30%, 20% and 25%, 20% and 30%, and 25% and 30% non-polar ingredient, by weight of the pre-spray emulsion.

ii. Surfactants

The provided pre-spray emulsions contain surfactants. For example, in addition to the pre-emulsion concentrate containing non-polar ingredients, the emulsions contain one or more surfactants. In the provided methods for producing the emulsions, the surfactant is added to the water phase, the oil phase, or to the water and the oil phase. The emulsions further can contain one or more co-surfactants or emulsifiers. Typically, the surfactants are natural surfactants, for example, a surfactant that is G.R.A.S. (generally recognized as safe) by the FDA and/or Kosher certified. In an exemplary embodiment, the surfactant is a sugar-derived surfactant, for example, a sugar fatty acid ester, e.g., sucrose fatty acid ester.

The surfactants aggregate in aqueous liquids, such as in the provided emulsions to form micelles, which contain the non-polar compounds. The hydrophilic portions of the surfactant molecules are oriented toward the outside of the micelle, in contact with the aqueous medium, while the hydrophobic portions of the surfactant molecules are oriented toward the center of the micelle, in contact with the non-polar compounds, which are contained in the center of the micelle. The micelles can contain more than one surfactant and/or co-surfactant. Properties of the provided compositions, for example, the particle size of the composition and desirable properties related to the particle size, are influenced by the choice of surfactant and the relative amount (concentration) of surfactant. For example, the HLB of the surfactant can affect particle size, clarity, taste, smell, crystal formation and other properties of the provided compositions, for example, the ability of a pre-spray emulsion to form a free-flowing, i.e., not sticky, powder after spray-drying the emulsion. Similarly, the concentration of the surfactant compared with the concentrations of other ingredients, particularly compared with the concentration of the polyalkylene derivative of vitamin E and the concentration of the non-polar compounds, can affect various desirable properties, for example, the ability to form a free-flowing, i.e., not sticky, powder after spray-drying the emulsion.

Surfactants (and co-surfactants) are molecules that contain hydrophobic and hydrophilic portions. In one example, the hydrophobic portion is a hydrophobic tail and the hydrophilic portion is a hydrophilic head of the surfactant molecule.

The HLB value of a surfactant is derived from a semi-empirical formula; HLB values are used to index surfactants according to their relative hydrophobicity and hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin, W. C. J. Soc. Cos. Chem. 1:311 (1949).

Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous liquids. In general, surfactants with HLB values greater than 10 or greater than about 10 are called "hydrophilic surfactants," while surfactants having HLB values less than 10 or less than about 10 are referred to as "hydrophobic surfactants." HLB values are known for a number of surfactants.

Exemplary of surfactants that can be used in the provided methods and compositions are surfactants having an HLB value of between 12 or about 12 and 20 or about 20, for example, 12, 13, 14, 15, 16, 17, 18, 19, 20, about 12, about 13, about 14, about 15, about 16, about 17, about 18, about 19 or about 20.

The surfactants typically are, and typically have an HLB value between at or about 12 and at or about 20. Particular examples of suitable surfactants for use in the provided compositions include non-ionic surfactants, such as sugar derived surfactants, including fatty acid esters of sugars and sugar derivatives. For example, sugar fatty acid esters include fatty acid esters of sucrose, glucose, maltose and other sugars, esterified to fatty acids of varying lengths (e.g., varying numbers of carbons). The fatty acids typically have carbon chains between 8 and 28 carbons in length, and typically between 8 and 20, or between 8 and 18 or between 12 and 18, such as, but not limited to, stearic acid (18 carbons), oleic acid (18 carbons), palmitic acid (16 carbons), myristic acid (14 carbons) and lauric acid (12 carbons). Typically, the sugar ester surfactants are sucrose ester surfactants, typically sucrose fatty acid ester surfactants.

The pre-spray emulsions provided herein contain a surfactant, such as a sugar fatty acid ester, e.g., sucrose fatty acid ester, where the total amount of surfactant, e.g., sucrose fatty acid ester, is typically present in an amount as a percentage (%) by weight of the emulsion (wt %), e.g., from at or about 1 wt % to at or about 20 wt %, such as between or between about 1% and 3%, 1% and 5%, 1% and 7%, 1% and 10%, 1% and 12%, 1% and 15%, 1% and 17%, 1% and 20%, 3% and 5%, 3% and 7%, 3% and 10%, 3% and 12%, 3% and 15%, 3% and 17%, 3% and 20%, 5% and 7%, 5% and 10%, 5% and 12%, 5% and 15%, 5% and 17%, 5% and 20%, 7% and 10%, 7% and 12%, 7% and 15%, 7% and 17%, 7% and 20%, 10% and 12%, 10% and 15%, 10% and 17%, 10% and 20%, 12% and 15%, 12% and 17%, 12% and 20%, 15% and 17%, 15% and 20%, and 17% and 20%, sugar fatty acid ester, e.g., sucrose fatty acid ester, by weight of the powder compositions. Exemplary concentrations of the total amount of sugar fatty acid ester, e.g., sucrose fatty acid ester in the pre-spray emulsions are at or about 1%, 3%, 5%, 7%, 10%, 12%, 15%, 17%, and 20% (wt %) of the pre-spray emulsions.

(a) Sucrose Fatty Acid Ester Surfactants

Sucrose fatty acid ester surfactants contain one or more sucrose fatty acid esters, which are non-ionic surfactants that contain sucrose in the hydrophilic portions and fatty acids in the hydrophobic portions. The sucrose fatty acid esters can be made by well-known methods (see, for example, U.S. Pat. Nos. 3,480,616, 3,644,333, 3,714,144, 4,710,567, 4,898,935, 4,996,309, 4,995,911, 5,011,922 and 5,017,697 and International Patent Application Publication No. WO 2007/082149), typically in an esterification reaction as described below.

Because sucrose contains eight hydroxy (—OH) groups, the esterification reaction can join the sucrose molecule to one fatty acid molecule, or can join it to a plurality of, fatty acid molecules, producing different degrees of esterification, e.g., mono-, di-, tri- and poly- (up to octa-) fatty acid esters, but primarily mono-, di-, and/or tri-esters. The degree of esterification can depend on conditions of esterification. The esterification reaction can be carried out with a single type of fatty acid, or a plurality of fatty acids, such as fatty acids with varying carbon chain lengths, branched and linear fatty acids, and/or saturated or unsaturated fatty acids. The esterification reaction with a single fatty acid can produce a single ester, and typically forms more than one ester, such as mono- di-, tri- and/or poly-esters, formed from one reaction. The relative amounts of mono- di- tri- and/or poly-esters can depend on reaction conditions.

The fatty acid in the sucrose fatty acid ester can be any fatty acid, and can contain between 4 and 28 carbon atoms, typically between 8 and 28 carbon atoms, and typically between 8 and 25 carbon atoms, such as between 8 and 18 carbon atoms, such as 8, 9, 10, 11, 12, 13, 14, 15, 16, 17 and 18 carbon atoms. The fatty acid can be synthetic or naturally occurring, and include linear and branched fatty acids. The fatty acids include, but are not limited to, myristic acid, palmitic acid, stearic acid, oleic acid, caproic acid, capric acid, myristic acid, decanoic acid and pelargonic acid.

Thus, the sucrose fatty acid ester surfactants include sucrose monoesters, diesters, triesters and polyesters, and mixtures thereof, and typically contain sucrose monoesters. The sucrose fatty acid ester surfactants include single fatty acid esters and also include homogeneous mixtures of sucrose esters, containing members with different lengths of fatty acid carbon chain and/or members with different degrees of esterification. For example, the sucrose fatty acid ester surfactants include mixtures of monoesters, diesters, triesters, and/or polyesters. The sugar ester surfactants further include sucrose fatty acid ester analogs and homologs and mixtures thereof.

Sucrose fatty acid esters are compounds having the following formula shown below:

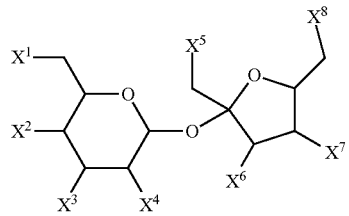

where each of $X^1$, $X^2$, $X^3$, $X^4$, $X^5$, $X^6$, $X^7$ and $X^8$ independently is:
a hydroxyl (—OH) group, or

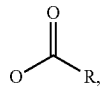

where:
each R is an alkyl group having 3-27 carbon atoms; and
when more than one of $X^1$, $X^2$, $X^3$, $X^4$, $X^5$, $X^6$, $X^7$ and $X^8$ is

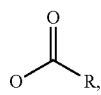

each R can be a different alkyl group (e.g., having different number of carbon atoms and/or different saturation), or can be the same alkyl group.

Typically, in the provided sucrose fatty acid ester surfactants, each R has between 7 and 27 carbon atoms, and typically between 7 and 19 atoms, such as 7, 8, 9, 10, 11, 12, 13, 14, 15, 16, 17, 18, or 19 carbon atoms or between 7 and 17 carbon atoms.

An alkyl group can be a straight chain or branched alkyl group, can be substituted or unsubstituted, and can be a saturated "saturated alkyl group," meaning that it does not contain any alkene or alkyne groups; or an "unsaturated alkyl group," meaning that it contains at least one alkene or alkyne group. An alkyl group that includes at least one carbon-carbon double bond (C=C) also is referred to by the term "alkenyl," and alkenyl groups optionally can be substituted. An alkyl group that includes at least one carbon-carbon triple bond (C≡C) also is referred to by the term "alkynyl," and alkynyl groups optionally can be substituted.

Typically, the sucrose fatty acid ester surfactants contain sucrose fatty acid monoesters, having the structure set forth below, where one of $X^1$, $X^2$, $X^3$, $X^4$, $X^5$, $X^6$, $X^7$ and $X^8$ (typically $X^1$) is

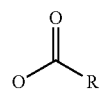

and the other seven of $X^1$, $X^2$, $X^3$, $X^4$, $X^5$, $X^6$, $X^7$ and $X^8$ are each, independently, —OH. An exemplary monoester has the following structure:

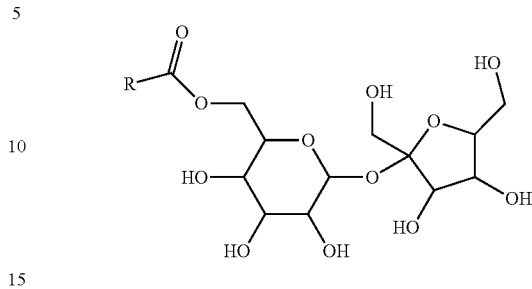

where R is an alkyl group having 3-27 carbons, and typically 7-27 carbons.

The sucrose fatty acid esters include blends of sucrose fatty acid esters, which typically include monoesters, and can also include diesters, triesters and polyesters, which have structures according to Scheme V, above, where two (diesters), three (triesters) or more (polyesters) of $X^1$, $X^2$, $X^3$, $X^4$, $X^5$, $X^6$, $X^7$ and $X^8$, (and typically $X^1$ and $X^8$) independently, are

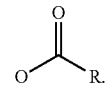

In general, sucrose fatty acid esters, including mixtures of sucrose fatty acid esters, can have varying HLB values, such as HLB values ranging from at or about 1 to at or about 20. The HLB value of the sucrose fatty acid ester generally depends on the degree of esterification (e.g., the average degree of esterification in a mixture of different esters). Typically, the lower the degree of esterification (e.g., average degree), the higher the HLB value of the sucrose fatty acid ester or mixture thereof. Exemplary sucrose esters include sucrose distearate (HLB=3), sucrose distearate/monostearate (HLB 12), sucrose dipalmitate (HLB=7.4); sucrose monostearate (HLB=15), sucrose monopalmitate (HLB>10); Sucrose monolaurate (HLB 15). Typically, the sucrose fatty acid ester surfactants in the provided compositions have an HLB value of between at or about 14 and at or about 20, such as at or about 14, 15, 16, 17, 18, 19, or 20, and typically between at or about 14 and at or about 18, such as, but not limited to, HLB values of at or about 15, 16 and 17, such as, for example, sucrose ester surfactants including sucrose monopalmitate, sucrose monolaurate and sucrose monostearate.

The sugar ester surfactants include sucrose ester blends, for example, sucrose ester mixtures containing a specified amount (e.g., percent, by weight) of sucrose monoesters. Exemplary surfactants include sucrose ester mixtures having at least at or about 50%, by weight (w/w), monoester, such as at or about or at least at or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, by weight (w/w), sucrose monoesters, and typically at least at or about 60%, by weight or at least at or about 70%, by weight (w/w), monoesters. The surfactants include mixtures of sucrose esters containing at least at or about 50% sucrose monoesters, mixtures of sucrose esters containing at least at or about 60% sucrose monoesters, mixtures of sucrose esters containing at least at or about 70% sucrose monoesters, mixtures of sucrose esters containing at least at or about 80% sucrose monoesters, and mixtures of sucrose esters containing at least at or about 90% sucrose monoesters, for example, mixtures containing at or about 72% sucrose monoesters, at or about 61% sucrose monoesters, or at or about 90% sucrose monoesters.

The sucrose fatty acid ester surfactants include sucrose fatty acid monoesters, such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanoate, sucrose monopentadecanoate and sucrose monoheptadecanoate. The sucrose fatty acid esters further include mixtures containing varying percentages of monoesters, diesters, triesters and polyesters, such as, but not limited to, a mixture having at or about 72% monoesters, 23% diesters, 5% triesters and 0% polyesters; a mixture having at or about 61% monoesters, 30% diesters, 7% triesters, and 2% polyesters; and a mixtures having at or about 52% monoesters, 36% diesters, 10% triesters and 2% polyesters.

The sucrose fatty acid ester surfactants include sucrose fatty acid esters sold under the trade name DK Ester®, produced by Dai-Ichi Kogyo Seiyaku Co., Ltd of Japan (which, in some examples, can be produced according to the methods described in U.S. Pat. Nos. 4,898,935, 4,996,309, 4,995,911, 5,011,922 and 5,017,697, and distributed through Montello Inc., Tulsa, Okla., such as the F-160 and F-140 grade esters sold under the trade name DK Ester®, and sucrose esters sold under the trade name SURFHOPE® SE PHARMA, by Mitsubishi-Kagaku Foods Corporation, distributed by Mitsubishi Chemical Performance Polymers, Inc. These sucrose fatty acid esters are mixtures of esters with different degrees of esterification. The sucrose fatty acid esters further include Ryoto sugar esters, which are food-grade esters sold by Mitsubishi-Kagaku Foods Corporation, distributed by Mitsubishi Chemical Performance Polymers, Inc. Exemplary sucrose fatty acid esters sold under the trade name DK Ester®, and those sold under the trade name SURFHOPE® SE PHARMA and Ryoto sugar esters, are listed in the table below. The table lists the average degree of esterification or the fatty acid composition within the mixture, and the HLB of the sucrose fatty acid ester surfactant. Any of the surfactants in the table below can be used. Typically, the surfactant (e.g., a surfactant listed in the table below), has an HLB value between at or about 12 and at or about 20, typically between at or about 15 and at or about 18, e.g., but not limited to, those surfactants in the table having an HLB of 15 or 16, such as the sucrose fatty acid ester surfactant sold under the name DK ESTER® F-160, produced by Dai-Ichi Kogyo Seiyaku Co., Ltd of Japan, and distributed through Montello Inc., Tulsa, Okla. Other exemplary sucrose fatty acid ester surfactants are described in Youan et al., AAPS PharmaSci 2003; 5(2) Article 22; 1-9 and in Okamoto et al., Biol. Pharm. Bull. 28(9): 1689-1694 (2005).

Exemplary Sucrose Fatty Acid Ester (SFAE) Surfactants

| Sucrose Fatty Acid Ester | Average Degree of Esterification | Fatty acid composition | H.L.B. | Distribution (by weight) of Ester Mono:Di:Tri:Poly |
|---|---|---|---|---|
| DK Ester® F-160 | 1.23 | | 16 | 72% monoester; 23% diester; 5% triester |
| DK Ester® F-140 | 1.35 | | 13 | 61% monoester; 30% diester; 7% triester; 2% polyester |
| DK Ester® F-110 | 1.48 | | 11 | 52% monoester; 36% diester; 10% triester; 2% polyester |
| DK Ester® F-90 | 1.53 | | 9.5 | 45% monoester; 39% diester; 12% triester; 4% polyester |
| DK Ester® F-70 | 1.60 | | 8 | 39% monoester; 45% diester; 12% triester; 4% polyester |
| DK Ester® F-50 | 1.69 | | 6 | 34% monoester; 46% diester; 17% triester; 3% polyester |
| DK Ester® F-20W | 3.11 | | 2 | 11% monoester; 21% diester; 14% triester; 54% polyester |
| DK Ester® F-10 | 4.85 | | 1 | 0% monoester; 5% diester; 11% triester; 84% polyester |
| SURFHOPE® SE PHARMA J-1205 | | C12 (100%) | 5 | 32% monoester; 68% di-/tri-/poly-esters |
| SURFHOPE® SE PHARMA J-1216 | | C12 (100%) | 16 | 81% monoester; 19% di-/tri-/poly-esters |
| SURFHOPE® SE PHARMA J-1616 | | C16 (80%); C18 (20%) | 16 | 79% monoester; 21% di-/tri-/poly-esters |
| SURFHOPE® SE PHARMA J-1805 | | C16 (70%); C18 (30%) | 5 | 30% monoester; 70% di-/tri-/poly-esters |
| SURFHOPE® SE PHARMA J-1807 | | C16 (70%); C18 (30%) | 7 | 41% monoester; 59% di-/tri-/poly-esters |
| SURFHOPE® SE PHARMA J-1816 | | C16 (70%); C18 (30%) | 16 | 75% monoester; 25% di-/tri-/poly-esters |
| SURFHOPE® SE PHARMA D-1803 | | Sucrose stearate (approximately 70% stearate) | 3 | Approximately 20% monoester; approximately 80% di-/tri-/poly-esters |
| SURFHOPE® SE PHARMA D-1803F | | Sucrose stearate (70% stearate) | 3 | 20% monoester; 80% di-/tri-/poly-esters |
| SURFHOPE® SE PHARMA D-1805 | | Sucrose stearate (70% stearate) | 5 | 30% monoester; 70% di-/tri-/poly-esters |
| SURFHOPE® SE PHARMA D-1807 | | Sucrose stearate (70% stearate) | 7 | 40% monoester; 60% di-/tri-/poly-esters |
| SURFHOPE® SE PHARMA D-1809 | | Sucrose stearate (70% stearate) | 9 | 50% monoester; 50% di-/tri-/poly-esters |
| SURFHOPE® SE PHARMA D-1811 | | Sucrose stearate (70% stearate) | 11 | 55% monoester; 45% di-/tri-/poly-esters |
| SURFHOPE® SE PHARMA D-1811F | | Sucrose stearate (70% stearate) | 11 | 55% monoester; 45% di-/tri-/poly-esters |
| SURFHOPE® SE PHARMA D-1815 | | Sucrose stearate (70% stearate) | 15 | 70% monoester; 30% di-/tri-/poly-esters |

-continued

| Sucrose Fatty Acid Ester | Average Degree of Esteri- fication | Fatty acid composition | H.L.B. | Distribution (by weight) of Ester Mono:Di:Tri:Poly |
|---|---|---|---|---|
| SURFHOPE® SE PHARMA D-1816 | | Sucrose stearate (70% stearate) | 16 | 75% monoester; 25% di-/tri-/poly-esters |
| SURFHOPE® SE PHARMA D-1615 | | Sucrose palmitate (80% palmitate) | 15 | 70% monoester; 30% di-/tri-/poly-esters |
| SURFHOPE® SE PHARMA D-1616 | | Sucrose palmitate (80% palmitate) | 16 | 80% monoester; 20% di-/tri-/poly-esters |
| SURFHOPE® SE PHARMA D-1216 | | Sucrose laurate (95% laurate) | 16 | 80% monoester; 20% di-/tri-/poly-esters |
| Ryoto S-970 | | Sucrose stearate | 9 | 50% monoester |
| Ryoto S-1170 | | Sucrose stearate | 11 | 55% monoester |
| Ryoto S-1570 | | Sucrose stearate | 15 | 70% monoester |
| Ryoto S-1670 | | Sucrose stearate | 16 | 75% monoester |
| Ryoto P-1570 | | Sucrose palmitate | 15 | 70% monoester |
| Ryoto P-1670 | | Sucrose palmitate | 16 | 80% monoester |
| Ryoto LWA-1570 | | Sucrose laurate | 15 | 70% monoester |
| Ryoto L-1695 | | Sucrose laurate | 16 | 80% monoester |
| Ryoto OWA-1570 | | Sucrose oleate | 15 | 70% monoester |

(b) Production of Sucrose Esters

As noted above, methods for producing sucrose esters are well known (see, for example, U.S. Pat. Nos. 3,480,616, 3,644,333, 3,714,144, 4,710,567, 4,898,935, 4,996,309, 4,995,911, 5,011,922 and 5,017,697 and International Patent Application, Publication No. WO 2007/082149). The sucrose fatty acid surfactants can be produced by any well-known method, and typically in an esterification reaction, for example, by reacting sucrose with a methyl ester of the desired fatty acid, such as a solvent process, where sucrose is reacted with a methyl ester of a fatty acid in the presence of a catalyst (e.g., potassium carbonate) and an organic solvent (e.g., dimethyl formamide (DMF) or dimethyl sulfoxide (DMSO)), followed by purification, or in an aqueous medium process, where sucrose is mixed in a molten mixture with fatty acid salt using water without an organic solvent and then reacted with a higher fatty acid methyl ester in the presence of a catalyst, followed by purification, and such as by any of the methods described in International Patent Application Publication No. WO 2007/082149, whereby a sucrose molecule (which is a disaccharide containing one six-carbon aldo-sugar glucose linked to a five-carbon keto-sugar fructose, having the formula: C12H22O11) is joined to one or more fatty acids.

For example, the sucrose fatty acid ester can be produced by esterification using dimethyl formamide (DMF) as a solvent, by producing a methyl ester of the fatty acid and then reacting the methyl ester with sucrose in DMF in the presence of a catalyst (e.g., potassium carbonate), for example, for 4-6 hours at 83-95° C., for example, using 30 to 127 parts sucrose to 30 parts methyl ester of the fatty acid (e.g., methyl stearate), 2 parts potassium carbonate and 300 parts solvent; by a similar method, but using dimethyl sulfoxide (DMSO) as the solvent, for example, as described in U.S. Pat. No. 3,480,616; or, as described in U.S. Pat. No. 3,644,333, by mixing sucrose with methyl fatty acid and sodium fatty acid and previously prepared sucrose ester, using potassium carbonate as a catalyst and water as a solvent; or, as described in U.S. Pat. No. 3,714,144, where sodium, potassium or lithium soap of the fatty acid is reacted in a molten sugar solution for two to twenty minutes under vacuum at 170-190° C., and purified, for example, as described in U.S. Pat. No. 4,710,567, by adding aqueous salt solution followed by three-phase separation. In one example, the sucrose fatty acid esters are prepared and purified as described in U.S. Pat. Nos. 4,898,935, 4,996,309, 4,995,911, 5,011,922 and 5,017,697, by producing the esters by chemical catalysis, such as with the solvent process, e.g., using a DMSO solvent and potassium carbonate catalyst, or aqueous solution method, followed by extraction and purification of the sucrose fatty acid esters, e.g., by adjusting pH, precipitation, separation and neutralization and filtration.

In another example, the sucrose fatty acid esters can be produced, as described in International Patent Application Publication No. WO 2007/082149, by mixing and reacting sucrose and vinyl esters of the fatty acids which can produce sucrose fatty acid ester mixtures with a monoester content of at or about 90%, and/or an acid value of less than 1. Briefly, this process can be carried out by dissolving sucrose in a solvent (e.g., DMSO), at a reaction temperature of between at or about 30° C. and at or about 60° C., such as between about 40° C. and 60° C. (e.g., at 60° C.), and a catalyst added and the mixture stirred, such as for 30 minutes, followed by removal of undissolved catalyst by decanting or filtration, followed by addition of vinyl fatty acid, and reaction, such as for at or about 15 minutes, with monitoring to measure amount of vinyl fatty acid ester, for example, until the amount of vinyl fatty acid ester reaches no more than at or about 10%, by weight (w/w), of the starting amount. The amount of sucrose and vinyl ester can vary. In one example, the ratio of sucrose to vinyl ester is between at or about 2:1 and at or about 8:1. In one example, the sucrose is added at a concentration of at or about 400 nM and the vinyl ester added at a concentration of at or about 100 nM. The catalyst can be catalyzed by a base, such as metal oxides, metal hydroxides and metal carbonates, such as potassium hydroxide, sodium hydroxide, potassium carbonate, sodium carbonate and lithium carbonate, which can be added at a concentration of between at or about 1.5 grams/L and at or about 6 g/L of reaction volume. In one example, the vinyl ester is vinyl stearate and the catalyst is potassium carbonate. The resulting mixture can then be purified, such as by vacuum distillation and addition of sodium chloride to effect emulsification and purification methods described in International Patent Application Publication No. WO 2007/082149.

iii. Stabilizers

The pre-spray emulsions provided herein can contain a stabilizer or a stabilizing system. Stabilizers include any compound used to stabilize the non-polar ingredients in the emulsions. The stabilizer or stabilizing system can aid in retaining one or more desirable properties of the compositions, for example the appearance, taste or odor. The compositions provided herein, including the pre-spray emulsions and spray-dried powders, containing non-polar ingredients and a stabilizer or stabilizing system can retain one or more desirable properties of the composition for a period of time after formulation, such as at or about 1, 2, 3, 4, 5, 6, or 7 days, at or about 1, 2, 3, 4, 5, 6, 8, 12, 18, 24, or 36 weeks, at or about 1, 2, 3, 4, 5, 6, 8, 12, 18, 24, or 36 months, or at or about 1, 2, 3, or 4 years. The stabilizers include, but are not limited to, carbonates and bicarbonates, acids, antioxidants, and any combination thereof. Typically the stabilizer or stabilizing system are food-approved, i.e., edible or ingestible, stabilizers, for example, stabilizers that are safe and/or approved for human consumption.

Typically, when present, the total amount of stabilizers included in the provided emulsions is less than 20% or about 20%, typically less than 10% or about 10%, for example, less than 20%, 15%, 10%, 5%, 4.5%, 4%, 3.5%, 3%, 2.5%, 2%, 1.5%, 1%, 0.5% or 0.1%, by weight, of the emulsion.

(a) Bicarbonates or Carbonates

Exemplary of a stabilizer used in the provided pre-spray emulsions is a bicarbonate or carbonate, for example, any edible or food-approved bicarbonate or carbonate. Examples of suitable bicarbonates and carbonates include sodium bicarbonate, potassium bicarbonate, sodium carbonate, potassium carbonate, calcium carbonate, magnesium carbonate, zinc carbonate, and any combination thereof. In some examples, the carbonate or bicarbonate is a carbonated beverage, such as a soda, flavored soda, carbonated water or carbonated juice. Alternatively, the beverage can be carbonated by the addition of carbon dioxide. Selection of suitable bicarbonates and carbonates for use in the provided beverage compositions is within the skill of the skilled artisan.

(b) Acids

In one example, the stabilizer used in the pre-spray emulsions contains one or more acids, for example, any compound added to the emulsion that can lower the pH of the emulsion. The acid can be, for example, an edible, ingestible or food-approved acid. Exemplary of suitable acids for use in the provided pre-spray emulsions are citric acid, phosphoric acid, adipic acid, ascorbic acid, lactic acid, malic acid, fumaric acid, gluconic acid, succinic acid, tartaric acid, maleic acid, and any combination thereof. In one example, the acid is citric acid.

(c) Antioxidants

In one example, the stabilizer used in the pre-spray emulsion contains an antioxidant, for example, a molecule that is capable of inhibiting the oxidation of other molecules. Antioxidants include molecules that scavenge free radicals. Suitable antioxidants include those that are used as ingredients in dietary supplements. The antioxidant can be a natural antioxidant or a synthetic antioxidant.

Examples of antioxidants include, but are not limited to, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavanoid phenolics, isothiocyanates, vitamins and vitamin cofactors, such as vitamin A, vitamin C, vitamin E, vitamin E phosphate and ubiquinone (ubidecarenone, coenzyme Q, coenzyme Q10), ascorbic acid, citric acid, rosemary oil, minerals, such as mineral selenium and manganese, melatonin, α-carotene, β-carotene, lycopene, lutein, zeanthin, crypoxanthin, resveratrol, eugenol, quercetin, catechin, gossypol, hesperetin, curcumin, ferulic acid, thymol, hydroxytyrosol, tumeric, thyme, olive oil, lipoic acid, glutathione, glutamine, oxalic acid, tocopherol-derived compounds, di-alpha-tocopheryl phosphate, tocotrienols, butylated hydroxyanisole, butylated hydroxytoluene, ethylenediaminetetraacetic acid, tert-butylhydroquinone, acetic acid, pectin, tocotrienol, tocopherol, coenzyme Q10 (coQ10), zeaxanthin, astaxanthin, canthaxantin, saponins, limonoids, kaempferol, myricetin, isorhamnetin, proanthocyanidins, quercetin, rutin, luteolin, apigenin, tangeritin, hesperetin, naringenin, erodictyol, flavan-3-ols (e.g., anthocyanidins), green tea extract, gallocatechins, epicatechin and its gallate forms, epigallocatechin and its gallate forms, theaflavin and its gallate forms, thearubigins, isotlavone phytoestrogens, genistein, daidzein, glycitein, anythocyanins, cyaniding, delphinidin, malvidin, pelargonidin and peonidin. In one example, the antioxidant is vitamin C. In another example, the antioxidant is a coenzyme Q-containing compounds, such as ubiquinone (ubidecarenone, coenzyme Q, coenzyme Q10).

iv. Polar Solvents

The pre-spray emulsions provided herein include one or more polar solvents. Polar solvents are well known in the art. The polarity of a solvent generally indicates which compounds are soluble in the solvent, and with which other solvents/liquids the solvent is miscible. Generally speaking, polar compounds are more readily solubilized in water and other polar solvents than are non-polar ingredients and ingredients. Polar solvents are more likely to be miscible with water and other polar solvents and liquids.

The polarity of a solvent can be assessed by measuring a number of different parameters according to well-known methods (see, e.g., Przybitek, "High Purity Solvent Guide," Burdick and Jackson Laboratories, Inc., 1980), such as by determining a property of the solvent, such as the dielectric constant, the dipole moment or the polarity index. For example, polar solvents generally have high dielectric constants, typically dielectric constants greater than at or about 15 (see, e.g., Lowery et al., "Mechanism and Theory in Organic Chemistry," Harper Collins Publishers, 3rd ed., 1987, p. 177), such as at or about 15, 16, 17, 18, 19, 20, 21, 22, 23, 24, 25, 26, 27, 28, 29, 30, 31, 32, 33, 34, 35, 40, 45, 50, 55, 60, 65, 70, 75, 80 85, 90 or greater than 90. For example, the dielectric constant of water is at or about 80.10 at 20° C. Polar solvents generally have high polarity indices, typically greater than at or about 3 (see, e.g., Snyder, "Classification of the solvent properties of common liquids" (1974) J. Chromatog. A 92:223-230), such as at or about 3, 4, 5, 6, 7, 8 or 9 or greater than 9. Polar solvents generally have large dipole moments, typically greater than at or about 1.4 Debye, such as at or about 1.4, 1.5, 1.6, 1.7, 1.8, 1.9, 2.0, 2.1, 2.2, 2.3, 2.4, 2.5, 2.6, 3.0, 3.5, 4 or greater than 4 Debye (see, e.g., "CRC Handbook of Chemistry and Physics," Lide, ed., 82nd edition, CRC Press, 2001, p. 15(14)-15(18)). Other methods of assessing solvent polarity are known in the art, including, but not limited to, the Kosower Z scale (Kosower, "An introduction to physical organic chemistry," Wiley, 1969, p. 293), the donor number and donor acceptor scale (Gutmann, "Solvent effects on the reactivities of organometallic compounds" (1976) Coord. Chem. Rev. 18:225-255), and the Hildebrand solubility parameters (see, e.g., Giddings et al., "High pressure gas chromatography of nonvolatile species. Compressed gas is used to cause migration of intractable solutes" (1968) Science 162:67-73).

Polar solvents include polar protic solvents and polar aprotic solvents. A polar protic solvent (e.g., water, methanol, ethanol) contains a hydrogen atom attached to an electronegative atom, such that the hydrogen has a proton-like character and/or the bond between the hydrogen and electronegative atom is polarized. Polar aprotic solvents, on the other hand (e.g., acetone, acetonitrile), generally do not contain positively polarized hydrogen atoms.

The polar solvents in the provided compositions typically are polar protic solvents, including, but not limited to, water; alcohols, such as dihydric alcohols which contain two hydroxyl groups (for example, glycols, e.g., propylene glycol, ethylene glycol, tetraethylene glycol, triethylene glycol, trimethylene glycol), trihydric alcohols which contain three hydroxyl groups (e.g., glycerin, butane-1,2,3-triol, pentane-1,3,5-triol, 2-amino-2-hydroxymethyl-propane-1,3-diol), monohydric alcohols (e.g., methanol, ethanol, propanol, isopropanol, n-butanol and t-butanol) and other alcohols; and acids, such as acetic acid and formic acid. Other polar solvents include, but are not limited to, acetone, acetonitrile, butyl acetate, dimethylformamide, dimethyl sulfoxide, dioxane, ethyl acetate, tetrahydrofuran and hexamethylphosphoric triamide. Typically, the polar solvent is water, or is an alcohol that typically contains two or more hydroxyl groups, such as a trihydric or dihydric alcohol, such as, but not limited to, glycerol and propylene glycol. The polar solvents further include low molecular weight polyethylene glycols (PEGs), such as PEGs having a molecular weight not more than at or about 600 kDa, such as between or about between 200 kDa and 600 kDa, typically not more than at or about 400 kDa, for example, not more than 200 kDa.

In one example, the polar solvent has a dielectric constant greater than at or about 15, and typically between at or about 20 and at or about 80, such as at or about 80.1. In another example, the polar solvent has a polarity index between at or about 3 and at or about 9. In another example, the dipole moment of the polar solvent is between 1.5 and 3, and typically between at or about 1.8 and 2.8, such as 1.85 (for dielectric constants of solvents, see, for example, Landolt-Bornstein, New Series IV/17, "Static Dielectric Constants of Pure Liquids and Binary Liquid Mixtures," Springer, 2008; and "CRC Handbook of Chemistry and Physics," Lide, ed., 82nd edition, CRC Press, 2001; for dipole moment of solvents, see, for example, "CRC Handbook of Chemistry and Physics," Lide, ed., 82nd edition, CRC Press, 2001; and for polarity indices of solvents, see, for example, Snyder, "Classification of the solvent properties of common liquids," J. Chromatography A, 92:223-230, 1974).

When present, such as in the pre-spray emulsions, the amount of the polar solvent typically is present in a high concentration, for example, the total amount of polar solvent as a percentage (%) by weight of the liquid concentrate (wt %) can be, e.g., between or between about 25% and 70%, such as between or between about 35% and 65%, such as 35% to 40%, 35% to 45%, 35% to 50%, 35% to 55%, 35% to 60%, 35% to 65%, 40% to 45%, 40% to 50%, 40% to 55%, 40% to 60%, 40% to 65%, 45% to 50%, 45% to 55%, 45% to 60%, 45% to 65%, 50% to 55%, 50% to 60%, 50% to 65%, 55% to 60%, 55% to 65%, and 60% to 65% polar solvent, by weight, of the pre-spray emulsion. Exemplary concentrations of the polar solvent in the pre-spray emulsions are at or about 45%, 48%, 50%, 52%, 55%, 56%, 57%, 58%, 60%, 62%, 65%, 68%, and 70% (w/w) of the pre-spray emulsion.

In the provided methods for making the pre-spray emulsions, the polar solvent is added to the water phase. In one example, the polar solvent is water, e.g., purified water, such as water that is purified prior to adding it to the concentrate formula, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the concentrates.

v. Binders

The provided emulsions can further contain a binder. The binder can be any material capable of adhering other materials together, for example, during drying. Exemplary binders include, but are not limited to, polysaccharides, polyols, starches, and gums. For example, the binder can be, e.g., maltodextrin, lactose, sucrose, starch, polyethylene glycol, hypromellose, methylcellulose, macrocrystalline cellulose, polyethylene glycol, sorbitol, other sugars, and pectin. An exemplary binder is maltodextrin, a moderately sweet polysaccharide produced from starch as a creamy white hygroscopic powder. Maltodextrin is easily digestible, being absorbed as rapidly as glucose. Maltodextrin can be derived from any starch. In the U.S., this starch is usually corn or potato, whereas, elsewhere (e.g., Europe), it is commonly wheat.

When present, the amount of binder, e.g., maltodextrin, typically is present in an amount of between or between about 5% and 20% binder, such as between or between about 5% and 7%, 5% and 10%, 5% and 12%, 5% and 15%, 5% and 17%, 5% and 20%, 7% and 10%, 7% and 12%, 7% and 15%, 7% and 17%, 7% and 20%, 10% and 12%, 10% and 15%, 10% and 17%, 10% and 20%, 15% and 17%, 15% and 20%, and 17% and 20%, by weight of the emulsion.

Typically, when a binder, e.g., maltodextrin, is present, the total amount of binder, e.g., maltodextrin, and surfactant, for example, sugar fatty acid ester, e.g., sucrose fatty acid ester, is between about 5% and 40% binder and sugar fatty acid ester, such as between or between about 5% and 10%, 5% and 15%, 5% and 20%, 5% and 25%, 5% and 30%, 5% and 35%, 5% and 40%, 10% and 15%, 10% and 20%, 10% and 25%, 10% and 30%, 10% and 35%, 10% and 40%, 15% and 20%, 15% and 25%, 15% and 30%, 15% and 35%, 15% and 40%, 20% and 25%, 20% and 30%, 20% and 35%, 20% and 40%, 25% and 30%, 25% and 35%, 25% and 40%, 30% and 35%, 30% and 40%, and 35% and 40% total binder and surfactant, e.g., sucrose fatty acid ester, by weight of the emulsion.

vi. Co-Surfactants (Emulsifiers)

The pre-spray emulsions can further contain one or more co-surfactants (emulsifiers). For example, a co-surfactant can be included to improve emulsification of the non-polar compounds and/or the stability of the emulsion, for example, by preventing or slowing oxidation of the non-polar compounds and ingredients. Exemplary of a co-surfactant that can be used in the provided concentrates is a phospholipid, for example, phosphatidylcholine. Other exemplary co-surfactants include non-ionic surfactants, such as sugar-derived surfactants, including fatty acid esters of sugars and sugar derivatives, and PEG-derived surfactants, such as PEG derivatives of sterols, PEG derivatives of fat-soluble vitamins and PEG-sorbitan fatty acid esters. Other exemplary co-surfactants are fish collagen, for example, the fish collagen sold by Norland Products Inc. (Cranbury Township, N.J.) and saponin, such as saponin from quillaja bark, including the saponin from quillaja bark sold by Desert King International (San Diego, Calif.) and Sigma Aldrich (St. Louis, Mo.).

When present, the amount of the co-surfactant typically is present in a concentration less than or less than about 10%, typically less than or less than about 5%, for example, the total amount of co-surfactant as a percentage (%), by weight, of the emulsion (wt %) can be, e.g., less than or less than about 10%, such as less than or about 5%, 4.5%, 4%, 3.5%, 3.15%, 3%, 2.5%, 2%, 1.75%, 1.5%, 1.25%, 1%, 0.75%, 0.5%, 0.25%, 0.15% or less, by weight, of the emulsion.

(a) Phospholipids

Exemplary of the co-surfactants that can be used in the provided emulsions are phospholipids. Phospholipids are amphipathic lipid-like molecules, typically containing a hydrophobic portion at one end of the molecule and a hydrophilic portion at the other end of the molecule. A number of phospholipids can be used as co-surfactants in the provided compositions, for example, lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC (Newark, N.J.), for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids, Synthetic Phospholipids, PEGylated Phospholipids and phospholipid blends. Exemplary of the phosphatidylcholine that can be used as a co-surfactant in the provided compositions is the phosphatidylcholine composition sold by Lipoid, LLC, under the name Lipoid S100, which is derived from soy extract and contains greater than or greater than about 95% phosphatidylcholine.

(b) PEG-Derived Surfactants

Exemplary PEG-derived surfactants include, but are not limited to, PEG derivatives of sterols, e.g., a cholesterol or a sitosterol (including, for example, any of the PEG derivatives disclosed in U.S. Pat. No. 6,632,443); PEG derivatives of fat-soluble vitamins, for example, some forms of vitamin A (e.g., retinol) or vitamin D (e.g., vitamin D1-D5); and PEG-sorbitan fatty acid esters, such as polysorbates, including polyoxyethylene (20) sorbitan monooleate (also called polysorbate 80) and analogs (e.g., homologs) of polysorbate 80, such as, for example, polysorbate 20 (polyoxyethylene (20) sorbitan monolaurate), polysorbate 40 (polyoxyethylene (20) sorbitan monopalmitate) and polysorbate 60 (polyoxyethylene (20) sorbitan monostearate); and stearic acid derivatives, including, for example, polyethylene glycol 400 distearate (PEG 400 DS), such as the PEG 400 DS sold by Stepan Lipid Nutrition (Maywood, N.J.).

vii. Emulsion Stabilizers (Co-Emulsifiers)

The pre-spray emulsions can further contain one or more emulsion stabilizers (co-emulsifiers), which can be used to stabilize the emulsions containing the pre-emulsion concentrates. For example, the emulsion stabilizer can increase the viscosity of the concentrate. One or more emulsion stabilizers can be added, for example, during formulation after evaluation of an initial emulsion, particularly if the oil and water phases of the initial emulsion appear to be separating. Addition of the emulsion stabilizer can prevent separation of the oil and water phases.

Exemplary of an emulsion stabilizer that can be included in the provided emulsions is a composition containing a blend of gums, for example, gums used as emulsifying agents, for example, a blend containing one or more of xanthan gum, guar gum and sodium alginate. Exemplary of such an emulsion stabilizer includes the emulsion stabilizer sold under the brand name SALADIZER®, available from TIC Gums, Inc. (Belcamp, Md.). Other gums can be included in the emulsion stabilizer, for example, gum acacia, ester gums and sugar beet pectin. Exemplary emulsion stabilizers include modified food starches. These include the modified gum acacia sold under the name Tic Pretested® Ticamulsion A-2010 Powder, available from TIC Gums, Inc. (Belcamp, Md.). Other exemplary emulsion stabilizers containing an ester gum are, for example, the emulsion stabilizer sold under the name Tic Pretested® Ester Gum 8BG, available from TIC Gums, Inc. (Belcamp, Md.) or Ester Gum 8BG, available from Hercules/Pinova (Brunswick, Ga.). Others sold by Ingredion, Inc. (Westchester, Ill.) under the trademarks CAPSUL®, FIRMTEX®, THERMFLO®, THERMTEX®, and TEXTRA® and others, can be included in the compositions provided herein. Other blends of similar gums can also be used as emulsion stabilizers.

Also exemplary of an emulsion stabilizer is whey protein. Whey protein is a protein contained in the milk serum (whey) obtained by removing casein and other components from milk, and comprises lactoalbumin, lactoglobulin, and lactoferrin as main components. Whey protein is known to have such functions as a stamina improver, a fatigue reliever, and an immunity enhancer. In addition, it is used as a protein supplement material in athletic nutrient foods and diet foods. Whey proteins are often used in food emulsion systems because of their ability to stabilize oil-in-water (O/W) emulsions. An exemplary whey protein is the whey protein isolate sold by Marquez Brothers International (Hanford, Calif.).

Another exemplary emulsion stabilizer is green tea extract, which is high in epigallocatechin gallate (EGCG) and epicatechin gallate (ECG). Green tea extract is known to have high antioxidant activity and the ability to provide stability to emulsions. An exemplary green tea extract that can be used in the pre-spray emulsions provided herein is a green tea extract that contains 40% EGCG, sold by Guilin Layn Natural Ingredients, Corp. (Guilin, China).

When present, the emulsion stabilizer is typically present at a concentration of less than 10%, such as less than or less than about 10%, 9%, 8%, 7%, 6%, 5%, 4%, 3%, 2%, or 1%, by weight, of the emulsion. For example, the emulsion stabilizer can be added to the water phase at a concentration of between 0.01% or about 0.01% and 10% or about 10%, for example, 0.01%, 0.1%, 0.2%, 0.3%, 0.4%, 0.5%, 1%, 1.5%, 2%, 2.5%, 3%, 3.5%, 4%, 4.5%, 5%, 6%, 7%, 8%, 9% or 10% w/w of the emulsion.

viii. pH Adjusters

One or more pH adjusters can be added to the emulsions at an appropriate concentration to achieve a desired pH. One or more of a plurality of pH adjusting agents can be used. The pH adjusting agent typically is safe for human consumption, for example, GRAS certified. The pH adjuster can be citric acid. An exemplary pH adjuster includes the citric acid sold by Mitsubishi Chemical (Dublin, Ohio). Another exemplary pH adjuster is phosphoric acid, such as Food Grade 80% Phosphoric Acid, sold by Univar.

3. Powder Compositions Containing Non-Polar Compounds

The pre-spray emulsions containing the pre-emulsion concentrates provided herein are dried, such as by evaporation, spray drying, lyophilization, or other drying method, to produce the powders provided. The water-soluble powders are prepared by drying the pre-spray emulsions provided herein, i.e., removing all of the polar solvent, e.g., water, from the pre-spray emulsion, to form a powder that does not contain any, or only minimal amounts, of polar solvent, e.g., water. The resulting powders contain high concentrations of non-polar ingredients and display advantageous properties as compared to other powders containing high concentrations of non-polar ingredients, such as producing a free flowing, i.e., not sticky, powder rather than a sludge-like, oily substance. The powders provided herein typically contain the same ingredients as the corresponding pre-spray emulsion, with the exception of the polar solvent, e.g., water, that is removed during the drying process. Removal of the polar solvent, e.g., water, from the pre-spray emulsion results in an increased concentration (i.e., wt %) of each ingredient in the powder as compared to the corresponding emulsion. For example, the pre-spray emulsions provided herein contain between or between about 5 wt % and 30 wt % non-polar ingredient and produce powders that contain between or between about 10 wt % and 60 wt % non-polar ingredient after drying. The provided powders (and methods for making the powders) can be used to formulate any non-polar compound in a water-soluble powder, including the non-polar compounds (e.g., non-polar ingredients) described herein and other known non-polar compounds.

Methods of producing powders from liquid compositions, e.g., emulsions, are well known to the skilled artisan. Exemplary processes for producing powders include, but are not limited to spray drying, freeze drying, evaporation, lyophilization, or absorption plating. The methods for forming the powders include spray drying. Spray drying processes and spray drying equipment are described generally in Perry's Chemical Engineers' Handbook, pp. 20-57 (Sixth Edition 1984). More details on spray drying processes and equipment are reviewed by Marshall (1954) "Atomization and Spray-Drying," Chem. Eng. Prog. Monogr. 50:Series 2 and Masters, "Spray Drying Handbook" (Fourth Edition 1985). Methods for spray drying are well known (see, e.g. U.S. Pat. Nos. 5,430,021 and 6,534,085 and U.S. Publication No. US 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

The powder compositions provided herein can be made using any emulsion containing non-polar ingredients, a sugar fatty acid ester, and a polyalkylene glycol derivative of vitamin, such as the pre-spray emulsions provided herein.

a. Formulating the Powder Compositions

The powder compositions provided herein are water-soluble and have high concentrations of non-polar ingredients, for example, at least 10%, 20%, 30%, 40%, 50%, or more, such as 60%, and are stable and free-flowing, i.e., not sticky. The powders also contain a surfactant, for example, a sugar fatty acid ester, e.g., a sucrose fatty acid ester, that also acts as a binder and/or in combination with a binder, that does not contribute to the oil load of the powder, thus allowing for the high concentrations of non-polar ingredients. The sugar fatty acid esters, such as sucrose fatty acid esters, are present in the water-soluble powders in place of or in combination with a binder, and result in powders that are water-soluble, free flowing, i.e., not sticky, and contain high concentrations of non-polar ingredient.

The pre-emulsion concentrates and pre-spray emulsions provided herein are formulated such that drying the resulting emulsion yields a powder composition that contains high concentrations of non-polar ingredient, yet is free-flowing, i.e., not sticky, and water-soluble. A number of parameters of the concentrates and emulsions, including ingredients, their relative concentrations, and methods for making the concentrates and emulsions, affect the ability of emulsion to form a free-flowing, i.e., not sticky, powder when a high concentration of non-polar ingredient is present. By extension, these parameters of the concentrates and emulsions also affect the advantageous properties of the powders, for example, the solubility of the powder, for example, in an aqueous solution.

Thus, the pre-spray emulsions are formulated such that after drying, the resulting powder compositions display one or more advantageous properties, for example, the powder is free flowing, i.e., not sticky, and/or the powder is water-soluble. In one example, the advantageous property is the ability of the provided emulsions to yield powder compositions that have no or only a minimal amount of polar solvent, e.g., water and are free-flowing, i.e., not sticky, after drying, for example, spray drying. In another example, the advantageous property relates to the ability of the pre-spray emulsions to be dried, e.g., spray dried, to form a powder that contains a high concentration of non-polar ingredients and is water-soluble. In another example, it can be advantageous that the powder contains less than or equal to a particular concentration of one or more ingredients. In another example, it can be advantageous that the powder contains greater than or equal to a particular concentration of one or more ingredients.

b. Exemplary Ingredients and Concentration Ranges

Each of the provided powder compositions contains a pre-spray emulsion that has been dried to remove all or almost all of the polar solvent, e.g., water. The pre-spray emulsions, and thus, the powder compositions provided herein, contain the pre-emulsion concentrates provided herein that contain non-polar ingredients and a polyalkylene glycol surfactant, e.g., TPGS. In some examples, the pre-emulsion concentrate contains a preservative, e.g., benzyl alcohol. The pre-spray emulsions, and thus, the powder compositions provided herein additionally contain a surfactant, such as a sugar fatty acid ester, e.g., sucrose fatty acid ester, in place of or in combination with a binder, e.g., maltodextrin, and additional ingredients, including, but not limited to, stabilizers, e.g., bicarbonates or carbonates, acids, and/or antioxidants, co-surfactants (emulsifiers), e.g., phospholipids and/or PEG-derived surfactants, emulsion stabilizers (co-emulsifiers), pH adjusters, e.g., citric acid, and any of the ingredients provided herein in Section B.2.b., with the exception of polar solvents, e.g., water.

Each of the provided powder compositions contains a non-polar ingredient, including, but not limited to, the exemplary non-polar ingredients and compounds described herein above. Typically, the non-polar ingredient is or has one or more non-polar compound. The powder compositions provided herein can contain one non-polar compound or more than one non-polar ingredient, such as two, three, four, five, six, seven, eight, or more non-polar ingredients. The powder compositions provided herein can contain high amounts (i.e., concentrations) of non-polar ingredients (i.e., non-polar compounds that are or contain non-polar ingredients), such as up to at or about 60 wt % non-polar ingredient.

The powders provided herein contain high amounts of non-polar ingredient, e.g., non-polar ingredients that contain non-polar compounds, for example, between or between about 10 wt % and 60 wt % non-polar ingredient, such as between or between about 10% and 15%, 10% and 20%, 10% and 25%, 10% and 30%, 10% and 35%, 10% and 40%, 10% and 45%, 10% and 50%, 10% and 55%, 10% and 60%, 15% and 20%, 15% and 25%, 15% and 30%, 15% and 35%, 15% and 40%, 15% and 45%, 15% and 50%, 15% and 55%, 15% and 60%, 20% and 25%, 20% and 30%, 20% and 35%, 20% and 40%, 20% and 45%, 20% and 50%, 20% and 55%, 20% and 60%, 25% and 30%, 25% and 35%, 25% and 40%, 25% and 45%, 25% and 50%, 25% and 55%, 25% and 60%, 30% and 35%, 30% and 40%, 30% and 45%, 30% and 50%, 30% and 55%, 30% and 60%, 35% and 40%, 35% and 45%, 35% and 50%, 35% and 55%, 35% and 60%, 40% and 45%, 40% and 50%, 40% and 55%, 40% and 60%, 45% and 50%, 45% and 55%, 45% and 60%, 50% and 55%, 50% and 60%, and 55% and 60%, by weight of the powder. The powder compositions that contain high amounts of non-polar ingredient and a sugar fatty acid ester surfactant in place of or in combination with a binder, e.g., maltodextrin, exhibit desirable properties, for example, the powder is a free-flowing, i.e., not sticky, powder that is water-soluble.

Each of the provided powder compositions contain a pre-emulsion concentrate that contains at least one surfactant that is a polyethylene glycol derivative of vitamin E, for example, TPGS, TPGS analogs, TPGS homologs and TPGS derivatives described herein. The surfactant typically has an HLB value of between 12 or about 12 and 20 or about 20, for example, 12, 13, 14, 15, 16, 17, 18, 19 or 20, or about 12, about 13, about 14, about 15, about 16, about 17, about 18, about 19 or about 20, typically between at or about 12 and at or about 14. For example, TPGS, such as the TPGS described herein, has an HLB value of about 13.

The polyethylene glycol derivative of vitamin E, e.g., TPGS, is typically present in an amount as a percentage (%) by weight of the powder compositions (wt %), e.g., from at or about 0.1% to at or about 20%, such as 0.1% to 0.5%, 0.1% to 1%, 0.1% to 2%, 0.1% to 5%, 0.1% to 7%, 0.1% to 10%, 0.1% to 12%, 0.1% to 15%, 0.1% to 20%, 0.5% to 1%, 0.5% to 2%, 0.5% to 5%, 0.5% to 7%, 0.5% to 10%, 0.5% to 12%, 0.5% to 15%, 0.5% to 20%, 1% to 2%, 1% to 5%, 1% to 7%, 1% to 10%, 1% to 12%, 1% to 15%, 1% to 20%, 2% to 5%, 2% to 7%, 2% to 10%, 2% to 12%, 2% to 15%, 2% to 20%, 5% to 7%, 5% to 10%, 5% to 12%, 5% to 15%, 5% to 20%, 7% to 10%, 7% to 12%, 7% to 15%, 7% to 20%, 10% to 12%, 10% to 15%, 10% to 20%, 12% to 15%, 12% to 20%, and 15% to 20%, by weight, of the powder compositions. Exemplary concentrations of the polyethylene glycol derivative of vitamin E, e.g., TPGS, in the powder compositions are at or about 0.1%, 0.5%, 1%, 1.5%, 2%, 2.5%, 3%, 4%, 5%, 7%, 10%, 12%, 15%, 17% and 20% (wt %) of the powder compositions.

The powder compositions contain a sugar fatty acid ester surfactant in place of or in combination with a binder, e.g., maltodextrin. Typically, the sugar fatty acid ester is a sucrose fatty acid ester. The surfactant, e.g., sucrose fatty acid ester, does not contribute to the oil load of the composition, thus allowing the addition of high concentrations of non-polar ingredients and formation of a free-flowing, i.e., not sticky, powder. In one example, the powder contains a sugar fatty acid ester, e.g., sucrose fatty acid ester, in place of a binder, e.g., maltodextrin. In another example, the powder contains a sugar fatty acid ester, e.g., sucrose fatty acid ester, in combination with a binder, e.g., maltodextrin.

The powder compositions provided herein contain a surfactant, such as a sugar fatty acid ester, e.g., sucrose fatty acid ester, where the total amount of surfactant, e.g., sucrose fatty acid ester, is typically present in an amount as a percentage (%) by weight of the powder compositions (wt %), e.g., from at or about 5 wt % to at or about 30 wt %, such as between or between about 5% and 7%, 5% and 10%, 5% and 12%, 5% and 15%, 5% and 17%, 5% and 20%, 5% and 25%, 5% and 30%, 7% and 10%, 7% and 12%, 7% and 15%, 7% and 17%, 7% and 20%, 7% and 25%, 7% and 30%, 10% and 12%, 10% and 15%, 10% and 17%, 10% and 20%, 10% and 25%, 10% and 30%, 12% and 15%, 12% and 17%, 12% and 20%, 12% and 25%, 12% and 30%, 15% and 17%, 15% and 20%, 15% and 25%, 15% and 30%, 17% and 20%, 17% and 25%, 17% and 30%, 20% and 25%, 20% and 30%, and 25% and 30% sugar fatty acid ester, e.g., sucrose fatty acid ester, by weight of the powder compositions. Exemplary concentrations of the total amount of sugar fatty acid ester, e.g., sucrose fatty acid ester in the powder compositions are at or about 5%, 7%, 10%, 12%, 15%, 17%, 20%, 25% and 30% (wt %) of the powder compositions.

The powder compositions provided herein can contain a binder. Exemplary binders include, e.g., maltodextrin. Typically, when a binder, e.g., maltodextrin, is present in the powder composition, the total amount of binder, e.g., maltodextrin, and surfactant, such as a sugar fatty acid ester, e.g., sucrose fatty acid ester, is typically present in a total amount as a percentage (%) by weight of the powder compositions (wt %), e.g., from at or about 5 wt % to at or about 60 wt %, such as between or between about 5% and 10%, 5% and 15%, 5% and 20%, 5% and 25%, 5% and 30%, 5% and 35%, 5% and 40%, 5% and 45%, 5% and 50%, 5% and 55%, 5% and 60%, 10% and 15%, 10% and 20%, 10% and 25%, 10% and 30%, 10% and 35%, 10% and 40%, 10% and 45%, 10% and 50%, 10% and 55%, 10% and 60%, 15% and 20%, 15% and 25%, 15% and 30%, 15% and 35%, 15% and 40%, 15% and 45%, 15% and 50%, 15% and 55%, 15% and 60%, 20% and 25%, 20% and 30%, 20% and 35%, 20% and 40%, 20% and 45%, 20% and 50%, 20% and 55%, 20% and 60%, 25% and 30%, 25% and 35%, 25% and 40%, 25% and 45%, 25% and 50%, 25% and 55%, 25% and 60%, 30% and 35%, 30% and 40%, 30% and 45%, 30% and 50%, 30% and 55%, 30% and 60%, 35% and 40%, 35% and 45%, 35% and 50%, 35% and 55%, 35% and 60%, 40% and 45%, 40% and 50%, 40% and 55%, 40% and 60%, 45% and 50%, 45% and 55%, 45% and 60%, 50% and 55%, 50% and 60%, and 55% and 60% total amount of binder, e.g., maltodextrin, and sugar fatty acid ester, e.g., sucrose fatty acid ester, by weight of the powder compositions. Exemplary concentrations of the total amount of binder, e.g., maltodextrin, and sugar fatty acid ester, e.g., sucrose fatty acid ester in the powder compositions are at or about 5%, 7%, 10%, 12%, 15%, 17%, 20%, 25%, 30%, 35%, 40%, 45%, 50%, 55%, and 60% (wt %) of the powder compositions.

Typically, when the powder compositions provided herein contain a mixture of surfactant, such as a sugar fatty acid ester, e.g., sucrose fatty acid ester, and binder, e.g., maltodextrin, such as a mixture of surfactant, e.g., sucrose fatty acid ester, and binder, e.g., that is present in an amount between or about between 5 wt % and 60 wt %, the mixture contains at least or about at least 5% sugar fatty acid ester, e.g., sucrose fatty acid ester, e.g., at least or about at least 5%, 7%, 10%, 15%, 20%, or more, sugar fatty acid ester, e.g., sucrose fatty acid ester, by weight of the powder.

C. Exemplary Methods for Preparing Compositions Containing Non-Polar Compounds Methods for preparing compositions and powders containing a high amounts of non-polar ingredients and a sugar fatty acid ester-binder mixture are provided herein. Equipment for use in the methods and general steps of the methods are described below. The methods include bench-top manufacturing processes, which are used to make small quantities of the concentrates. The methods also include scaled-up manufacturing processes, which are used to make larger batches of the compositions and powders. Any of the bench-top processes can be scaled up to perform the methods using the scaled-up processes. Any of the provided compositions and powders can be made using either scaled-up or bench-top processes. The compositions provided herein can be made following the methods provided in U.S. Pat. No. 8,282,977 and U.S. Pub. Nos. 2009-0297491 and 2012-0016026.

1. Equipment Employed in the Methods

Equipment used in various steps of the provided methods for making the compositions and powders can include, for example, vessels, such as tanks, for mixing the water and oil phases and the product; scales; mixers, for example standard mixers and homogenizers; heating and cooling apparatuses, such as water-jacketed tanks, hot plates, water baths and chillers (coolers), including recirculating coolers; transfer apparatuses, for example, transfer devices, such as, pumps, hoses and sanitary fittings; ball valves; purifiers, for example, filters, such as carbon filters, ion exchange equipment, reverse osmosis equipment, end-point filters and end product filters; evaluation devices, for example, pH and temperature meters; and other equipment. The choice of equipment depends on a plurality of factors, including batch size and the manufacturing process.

a. Scales

One or more scales can be used to measure the amount of the ingredients before adding them to the appropriate vessel. Alternatively, the ingredients can be weighed in the vessel, for example, in a tank on top of a scale.

Any of a plurality of well-known, commercially-sold scales can be used to weigh the ingredients. The choice of scale(s) can depend on a number of factors, including the mass of the product being made (e.g., the batch size) and the ingredient being weighed. In one example, multiple scales are used to weigh the various ingredients of the compositions and products. In general, relatively larger capacity (i.e., weight) scale(s) are used in making larger batches of the products while relatively smaller capacity scale(s) are used in making smaller batches.

Exemplary of the scales used to weigh the ingredients using the provided methods are a Toledo Scale (Model GD13x/USA); a Sartorius Basic Analytical Scale (Model BA110S), which is a basic series analytical scale with a 110 g capacity and a resolution of 0.1 mg; and an OHAUS Scale (Model CS2000), which is a compact portable digital scale having a 2000 g capacity and a resolution of 1 g.

b. Purifiers

Purifiers, such as filters, are used in the provided methods to remove impurities from the ingredients prior to their addition to and/or from the composition or product or to and/or from a phase of the composition or product. For example, the water added to the water phase typically is purified water. In one example, one or more purifiers, for example, carbon filters, ion exchange purifiers, reverse osmosis purifiers, and/or end-point filters can be used to filter water, for example, city water, prior to its addition to the water phase. For example, the water can be filtered to remove impurities, such as sediment, from the water.

Purifiers that can be used with the provided methods include filters, for example, 100 micron filters and carbon filters, which are filters that use activated carbon to remove impurities by chemical adsorption. Carbon filtering typically is used for water purification and is particularly effective at filtering out chlorine, sediment, volatile organic compounds and other impurities. Typically, the particles removed by carbon filters are between about 0.5 microns and about 50 microns. Other filters are well known and can be used with the provided methods.

The purifiers also include reverse osmosis purifiers, which use mechanical pressure to purify liquids, for example, water. In one example, the pressure forces the water through a semi-permeable membrane to remove impurities.

The purifiers also include exchange purifiers, for example, an ion exchange purifier. The ion exchange purifier can use a resin bed, such as a zeolite resin bed, to replace salts, such as cations, e.g., magnesium and calcium, with other cations, such as sodium and potassium cations. Such purifiers can be purchased, for example, from Aqua-Pure Filters (Clarkston, Mich.).

In one example, the purifier is an end-product filter (e.g., a 100 micron filter; Product No. BPEM 100-5GP; FSI, Michigan City, Ind.). This filter is used to filter any impurities out of the final product (e.g., the final pre-emulsion composition). Other filters also are known and can be used with the provided methods.

c. Vessels

One or more, typically two or more, vessels, can be used in the methods to contain the ingredients of the provided compositions and powders, for example, during mixing and/or heating or cooling. The vessels can be tanks, for example, water-jacketed tanks; pots; and/or beakers, for example, Pyrex® beakers. Separate vessels (e.g., an oil phase tank and a water phase tank) can be used for mixing and heating the ingredients of the oil phase and the water phase prior to combining the two phases. In some examples, an additional vessel, for example, a holding and/or packaging tank, can be used for holding and/or packaging the compositions and powders and/or for addition/mixing of additional ingredients to the compositions and powders.

A number of vessels are available for mixing ingredients. Typically, the vessels are cleaned, for example, rinsed, soaped and/or sanitized, according to known procedures prior to use and between uses, such as with the cleaning procedures described below.

In the bench-top process, the vessel can be a container, for example, a bench-top container, such as a flask, beaker (e.g., a Pyrex® beaker), vial, measuring container, bottle and/or other bench-top container.

In the scaled-up manufacturing process, the vessels can be tanks, for example, water phase tanks, oil phase tanks and holding/packaging tanks Typically, the tanks are equipped with one or more mixers, for example, a standard mixer and/or homogenizer, which are used to mix the ingredients that are added to the tank. In one example, the tank is further equipped with a heating and/or cooling device. For example, the tank can be a water-jacketed tank. The temperature of the water-jacketed tank is controlled through the water jacket, for example, to heat the contents, such as during mixing.

Exemplary of the tanks that can be used with the provided methods are water-jacketed tanks, for example, the Overly 550 gallon water-jacketed tank (Model 10576501G), which has a 550 gallon capacity and typically is used as a water phase tank, the Schweitzer's 450 gallon tank (Model #5214-C), which has a 450 gallon capacity and typically is used as an oil phase tank and the Royal 190 gallon water-jacketed tank (Model 9977-5), which has a 190 gallon capacity and can be used as a water or oil phase tank when mixing smaller volumes. Other tanks are well known and can be used with the provided methods for mixing the compositions and powders, for example, the phases of the composition.

d. Mixers

Mixers are used in the methods to blend, mix and/or emulsify the compositions and ingredients, mixtures and phases of the compositions. In some examples, the mixers can be used to keep the ingredients and/or mixture circulating to maintain temperature, viscosity and/or other parameters of the mixture. Suitable mixers include, but are not limited to, standard mixers, for example, those that can be used to mix ingredients and maintain a homogeneous mixture, such as while heating a mixture of ingredients. Exemplary of the standard mixers are LIGHTNIN® mixers (LIGHTNIN, Rochester, N.Y.), for example, Model Numbers XJC117 and ND-2. In one example, the LIGHTNIN® mixers are fixed-mount, gear drive high-flow mixers, for use with closed tanks Another example of a standard mixer is a mixer sold by IKA®, for example, overhead IKA® mixers. Exemplary IKA® mixers include Model Nos. RW-14 Basic and RE-16S, which are laboratory stirrers that can be used to mix ingredients. In some examples, the mixer can be attached to the vessel, e.g., the tank, such as by mounting or clamping onto the tank, such as at the top of the tank. In other examples, the mixer can be placed in the vessel for mixing.

The mixer can be a homogenizer which can be used, for example, to emulsify mixtures, i.e., form an emulsion. The homogenizer can be used to mix phases of the compositions, e.g., oil and water phases, after combining the phases, in order to form an emulsion. The homogenizer provides high-shear dispersion of solids and emulsification of immiscible liquids at high shear rates. Suitable homogenizers include, but are not limited to, high-shear homogenizers, for example, reversible homogenizers sold by Arde Barinco, Inc. (Norwood, N.J.). Exemplary Arde Barinco, Inc. reversible homogenizers are Model CJ-50 (a 3600 rpm mixer having a 6-inch rotor diameter, tip speed of 5575 ft/minute, emersion depth of 33 inches, and six separate openings at the bottom and top, which concentrate the liquid into six chambers, reducing the surface volume and creating a shear effect); and Model CJ-4E (a 10,000 rpm mixer with fan-cooled motor, optimized for 1 to 5 gallon batch sizes, having a 1.875 inch rotor diameter, tip speed of 4920 rpm, and immersion depth of 16 inches). The homogenizers further include other homogenizers, for example, other reversible homogenizers sold by Arde Barinco, Inc.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from the top and bottom of the mixture, while upward "umbrella flow" controls mixing at the highest shear and recirculation rates without splashing or incorporating air. The reversible homogenizers typically are equipped with an adjustable baffle plate, which can be adjusted to control the type of mixing, for example at different times during mixing, e.g., during emulsification.

A number of other mixers are well known and can be used with the provided methods. Exemplary of suitable mixers that can be used with the provided methods are homogenizers, inline mixers, ribbon mixers, plow mixers, paddle mixers, Forberg® mixers, conveyors, bag dumps and compactors, V-blenders, blade mixers, double cone mixers, continuous mixers, speedflow mixers, batch mixers, double ribbon blenders, paddle and ribbon mixers with choppers, plow blenders, turbulent mixers, fluidizing Forberg-type mixers, air mixers, active mixers, passive mixers, top-entry mixers, side-entry mixers, static mixers, fixed-entry mixers, portable mixers (e.g., direct and gear drive), sanitary mixers, drum mixers, bulk container (IBC) mixers, lab stirrers, variable speed mixers, dough mixer, vertical mixer, spiral mixer, twin arm mixer, fork mixer, double spiral mixer, all agitators, agitator mixers, Banbury® mixers, rubber mixers, Blondheim mixers, churn mixers, conical mixers, continuous mixers, disperser mixers, pan mixers, emulsifier mixers, Hobart® mixers, liquifier mixers, Littleford mixers, meat mixers, plow mixers, Mix-Muller® Mixers, vertical screw mixers (e.g., Nauta mixers), Oakes mixers, planetary mixers, pony mixers, pug mixers, Ross mixers, rotary mixers, Sigma mixers, single arm mixers, tote bin mixers, tumble mixers, vacuum mixers, Turbolizer mixers, twin shell mixers, V-type mixers, zigzag mixers, side-arm mixers, hand-held mixers, stir rods, stir bars, magnetic mixers, overhead mixers (e.g., mechanical and/or electric overhead mixers), and any mixer known to those of skill in the art.

e. Heating/Cooling Apparatuses

Equipment that can be used in the methods includes heating and cooling apparatuses. The heating and cooling apparatuses can be used to control the temperature of the ingredients and combinations thereof, such as while generating the compositions and products.

Heating apparatuses that can be used in the provided methods are those that are capable of heating the mixture to between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. Typically, the heating apparatus is used to heat the mixtures to a temperature of between at or about 60° C. to at or about 70° C.

The heating apparatus can be a water jacket, for example, a water jacket on a water-jacketed tank, which can be controlled, for example, by a control panel, such as to adjust the temperature of the contents of the tank. Other suitable heating apparatuses are immersible and/or submersible heaters, for example, 12 KW or 13 KW sanitary heaters, including food-grade heaters, that can be immersed into the tanks, typically while mixing and typically when higher temperatures are required, such as when temperatures greater than 60° C. or about 60° C., or greater than 80° C. or about 80° C. are required. The heating apparatuses also include stoves, for example, propane stoves, and hot plates, for example, Thermolyne® hot plates (e.g., Model Nos. 846925 and SP46615).

The cooling apparatus can be any apparatus that can cool the ingredients and combinations thereof, such as rapidly cooling and/or cooling while mixing the ingredients. Typically, the cooling apparatus is capable of cooling the mixtures to a temperature between at or about 25° C. and at or about 45° C., for example, to at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C. or 45° C. In some examples, the cooling apparatus can cool the mixture to a temperature between at or about 30° C. and at or about 35° C. Typically, the cooling is rapid cooling. For example, the compositions can be cooled to a temperature between at or about 30° C. and at or about 35° C. in at or about 15 minutes to at or about 2 hours, for example, in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In an exemplary method, the compositions can be cooled to a temperature between at or about 30° C. to at or about 35° C. in at or about 30 minutes to at or about 60 minutes.

Suitable cooling apparatuses for use in the methods include chillers, for example, recirculating coolers. The cooling apparatuses can be attached to the vessel, such as remotely or by a tank mounted in the cooler, to repeatedly circulate fluid from the tank, through the chiller and back to the vessel, to rapidly cool and maintain the temperature of the mixture during mixing. Exemplary of cooling apparatuses that can be attached to the tank and used with the provided methods are open-loop chillers and closed-loop chillers, for example, those sold by Turmoil (West Swanzey, N.H.), such as Model No. OC-1000 RO. Suitable cooling apparatuses also include water baths and ice baths, for example, water baths and/or ice baths in which the vessel is placed, for example, during homogenizing. Other cooling apparatuses are well known by those of skill in the art and can be used with the provided methods.

f. Transfer Devices

Transfer devices can be used with the provided methods to transfer liquid from one vessel to another vessel. Transfer devices can be used in the methods to combine the phases and form the emulsion. For example, transfer device can be used to transfer the water phase from the water phase vessel to the oil phase vessel or to transfer the oil phase from the oil phase vessel to the water phase vessel. Transfer devices include, for example, transfer pumps and associated accessories (e.g., fittings), including ball valves, sanitary fittings (for example, sanitary fittings sold by Granger, Inc. (Lake Forrest, Ill.)) and transfer hoses (for example, hoses sold by Sani-Tech West (Oxnard, Calif.)), such as food grade hoses attached to a transfer pump, for example, the food grade Sani-Tech® STHT-R-HD Braid-Reinforced Heavy Duty Silicone Hose. Suitable transfer pumps include the Teel Pump (Model 2P377B; Granger, Inc., Lake Forrest Ill.), a self-priming pump having a power rating of 2 HP, 60 Hz voltage, 208-230/460 AC, speed of 3450 rpm; and other pumps, such as self-priming pumps from Granger, Inc. The transfer device can also include equipment for manually transferring the liquid to another vessel, for example, by pouring, pipetting and/or other well-known methods of manually transferring liquids.

g. Evaluation Equipment

Evaluation equipment includes equipment that can be used to evaluate properties of the products and/or phases of the products, such as the temperature, pH, clarity, color, activity, smell and/or taste of the products. Suitable evaluation equipment includes pH and temperature meters, such as the pH and temperature meter sold by Hanna Instruments (Model No. HI 8314; Ann Arbor, Mich.), which can be used to measure the temperature and the pH of the product. Temperature meters can also include temperature probes, for example, digital and/or water-proof temperature probes, such as temperature probes sold by Cooper-Atkins (Middlefield, Conn.), for example, the Cooper-Atkins digital waterproof temperature probe (Model # DPP400W). The products can be evaluated and analyzed to verify the amounts of the non-polar ingredients and to verify that the products meet industry standards, such as to verify that the products do not contain levels of microbials and heavy metals that are above acceptable levels. Typically, these tests are performed by sending a sample of the product to a commercial testing facility, as described in section D.2.h., below.

2. General Methods for Producing the Compositions

In general, the methods useful for making the concentrates provided herein are performed by generating an oil phase (e.g., the pre-emulsion concentrate) and generating a water phase and combining (e.g., using a transfer device) and mixing the phases to form emulsions, e.g., the pre-spray emulsions. The powders are generated from the pre-spray emulsions, for example, by drying the pre-spray emulsions. For example, the powders can be prepared by evaporation, spray drying, lyophilization, or any other drying method. The oil and water phases typically are generated in separate vessels. The vessels can be, for example, tanks Generation of the water phase and generation of the oil phase can be performed simultaneously or sequentially, in any order. Typically, both phases are heated to a desired temperature prior to combining the phases. For example, the phases can be heated to between 60° C. and 70° C. prior to combining the phases. The provided methods can include additional steps. In some examples, the additional steps include evaluating properties of the products, adding additional ingredients (e.g., taste-modifying agents), packaging and/or filtering.

The provided methods can be performed using a bench-top manufacturing process (for small batch sizes) or performed using a scaled-up manufacturing process (for larger batch sizes). Each of the provided products can be made with either the bench-top or scaled-up process. In one example, the product is first made with the bench-top process and then the method is scaled-up to make larger quantities of the product.

The bench-top process can be performed on a bench, counter, table or any other suitable surface. Typically, the bench-top process is used to make emulsions having relatively smaller volumes than those made with the scaled-up process. For example, volumes less than 1 L or about 1 L, or less than 1 gallon or about 1 gallon, for example, less than or about 500 mL, for example, less than or about 1000 mL, 900 mL, 800 mL, 700 mL, 600 mL, 500 mL, 450 mL, 400 mL, 350 mL, 300 mL, 250 mL, 200 mL, 150 mL, 100 mL, or 50 mL or less, can be made using the bench-top process.

For the bench-top process, the equipment can be sufficiently compact to be used on a bench-top or other similar surface, and can be sufficiently compact to be moved, for example, lifted, by the artisan using the methods. For example, the vessels, such as water phase vessels, oil phase vessels, holding vessels, and packaging vessels, can be bench-top vessels. Exemplary bench-top vessels include, for example, flasks, beakers, vials, measuring containers, bottles and/or other bench-top containers. In some examples, the vessel in the bench-top process is a Pyrex® beaker.

Typically, the mixers for use in the bench-top processes of the provided methods are mixers that can be used in the bench-top vessels. Mixers that can be used in the bench-top vessels include, for example, standard mixers, such as hand-held mixers, stir rods, stir bars, magnetic mixers and overhead mixers, including, for example, mechanical and/or electric overhead mixers, and any other mixer that is suitable for use in the bench-top vessel. Exemplary standard mixers include those sold by IKA®, for example, overhead IKA® mixers, such as Model Nos. RW-14 Basic and RE-16S, which are laboratory stirrers and can be used to mix ingredients, such as to generate the oil and water phases. Suitable bench-top mixers also include homogenizers, for example, reversible homogenizers. An exemplary reversible homogenizer is the Arde Barinco reversible homogenizer, Model no. CJ-4E, which can be used to emulsify the phases.

Typically, the heating and cooling apparatuses are those that can be used with the bench-top vessels, such as hot plates, ice baths and/or water baths, into (or onto) which the vessels can be placed, for example, for rapid cooling. The evaluation device used in the bench-top process, for example, the temperature and/or pH meters, typically are capable of being placed in the bench-top vessels.

For the bench-top process, combining the oil and water phases typically is carried out manually, e.g., by pouring, pipetting and/or another manual transfer device.

The scaled-up manufacturing process of the methods typically is used to make products of relatively larger volumes, such as volumes greater than 1 L or about 1 L, or greater than 1 gallon (gal) or about 1 gallon. For example, volumes greater than or about 0.5 L, for example, greater than or about 0.5 L, 1 L, or 2 L, or greater than or about 1 gal, 2 gal, 3 gal, 4 gal, 5 gal, 6 gal, 7 gal, 8 gal, 9 gal, 10 gal, 11 gal, 12 gal, 13 gal, 14 gal, 15 gal, 16 gal, 17 gal, 18 gal, 19 gal, 20 gal, 21 gal, 22 gal, 23 gal, 24 gal, 25 gal, 26 gal, 27 gal, 28 gal, 29 gal, 30 gal, 40 gal, 50 gal, 60 gal, 70 gal, 80 gal, 90 gal, 100 gal, 150 gal, 200 gal, 250 gal, 300 gal, 350 gal, 400 gal, 450 gal, 500 gal, 550 gal, 600 gal, 650 gal, 700 gal, 800 gal, 900 gal, or 1000 gal or more, can be made using the scaled-up manufacturing process.

In general, equipment used for the scaled-up process is compatible with larger volume batches (batch sizes). For example, the vessels for use in the scaled-up processes can be tanks, for example, water-jacketed tanks, which are equipped with water jackets that can be used as heating apparatuses to heat the oil and water phase ingredients during generation of the oil and water phases. The water jackets typically are controlled via control panels. The transfer device can include devices attached to and connecting the tanks, such as transfer pumps and associated fittings, for example, ball valves and hoses that are attached to the tanks Mixers for use in the scaled-up process can be standard mixers, for example, mounted mixers, such as LIGHTNIN® mixers, e.g., Model Nos. XJC117 (a fixed-mount, gear drive high-flow mixer) and ND2.

Prior to beginning the methods, the water jacket lines on any water-jacketed oil phase and water phase tank can be bled. The water jacket switches can then be turned on to maintain a pressure in the water jackets of between at or about 20 psi and at or about 40 psi (pounds per square inch). If the pressure in the water jacket falls below 20 psi during the method, the line can be bled and checked for bubbles while purging the line.

a. Oil Phase Ingredients

The oil phase includes the non-polar ingredients, for example, non-polar ingredients that contain the non-polar compounds and, in some examples, other oil phase ingredients, such as a surfactant, for example, a water-soluble vitamin E derivative surfactant, e.g., TPGS. Typically, oil phase ingredients include one or more lipophilic and/or amphipathic ingredients of the pre-emulsion concentrate. Oil phase ingredients typically do not include aqueous ingredients or hydrophilic ingredients. Certain ingredients, for example, ingredients having hydrophobic and hydrophilic moieties, for example, surfactants and co-surfactants, can be added to either the oil or the water phase, or to the oil and the water phase. Exemplary of ingredients used in the oil phase of the provided concentrates are non-polar ingredients, for example, non-polar compounds, including any of the non-polar compounds provided herein; pH adjusters, for example, citric acid; surfactants; co-surfactants, for example, sucrose fatty acid esters; preservatives, such as benzyl alcohol; and oils, for example, non-polar solvents and other oil phase ingredients.

Oil phase ingredients can be added to the oil phase simultaneously and/or sequentially, for example, in any order or in a specific order. In one example, one or more oil phase ingredients is added first, prior to addition of further ingredient(s). In one example, when the oil phase ingredients include a surfactant, a preservative, and a non-polar ingredient, these ingredients are added sequentially, in the following order: 1) surfactant; 2) preservative; and 3) non-polar ingredient. In another example, when the oil phase ingredients include a surfactant and a non-polar ingredient, the ingredients are added sequentially, in the following order: 1) surfactant and 2) non-polar compound. In another example, when the oil phase ingredients include a preservative and a non-polar compound, the ingredients are added sequentially, in the following order: 1) surfactant and 2) non-polar ingredient. Alternatively, the oil phase ingredients can be added in a different order, for example, any order. Two or more oil phase ingredients can be added simultaneously.

Typically, when the oil phase includes a surfactant, particularly when the surfactant is a surfactant that is solid at room temperature, for example, tocopherol polyethylene glycol succinate surfactant, the surfactant is the first oil phase ingredient added to the oil phase vessel. Typically, the non-polar ingredient is the last ingredient added to the oil phase vessel.

b. Oil Phase Production

To produce the oil phase, appropriate amounts of the oil phase ingredients are added to the oil phase vessel. Oil phase vessels can include tanks, for example, water-jacketed tanks, such as, but not limited to, the Royal 190 Gallon water-jacketed tank, or any other tank described herein. The amounts of the oil phase ingredients are measured, e.g., weighed, either prior to adding to the oil phase vessel or are weighed/measured in the oil phase vessel. In one example, the oil phase ingredients are measured by weighing the ingredients on a scale (e.g., one or more of the scales described herein; the choice of scale depends on the desired amount of the ingredient), before addition to the oil phase vessel. Typically, the appropriate amount of the oil phase ingredient is calculated based on the desired concentration (e.g., weight by weight (w/w), molarity (M), volume by weight (v/w) or volume by volume (v/v)), of the ingredient in the final product.

In general, the oil phase ingredients are added, mixed and/or heated in the oil phase vessel. Mixing the oil phase ingredients can be carried out with a standard mixer or other mixer, such as, but not limited to, the mixers described herein, for example, a Lightnin® mixer (e.g., Model No. XJC117, a fixed-mount gear drive high-flow mixer). Heating the oil phase ingredients is carried out using a heating apparatus, such as those described herein, typically a water jacket on a water-jacketed tank. In one example, the ingredients are heated to temperatures between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. In one example, the oil phase ingredients are heated to a temperature of between at or about 60° C. and 70° C., for example, by adjusting the temperature on a water-jacketed tank.

The oil phase ingredients can be added to the oil phase vessel simultaneously or sequentially in any order. In one example, one or more of the ingredients are added, mixed and/or heated, prior to the addition of the other ingredients to the vessel.

In an exemplary method provided herein, the oil phase is generated by heating a surfactant, such as a water-soluble vitamin E derivative surfactant, e.g., TPGS, in the oil phase vessel. The oil phase is then heated to the desired temperature, for example, to a temperature of between at or about 60° C. and 70° C., by adjusting the temperature on a water-jacketed tank, until dissolved. After the oil phase reaches the desired temperature, e.g., at or about 60° C. to 70° C., a non-polar ingredient, such as the non-polar ingredients described herein, is added to the oil phase. In some examples, the oil phase ingredients are mixed (e.g., using a mixer as provided herein) during generation of the oil phase.

Typically, the oil phase ingredients are mixed until combined and maintained at the desired temperature, e.g., between at or about 60° C. and 70° C., prior to combining with the water phase.

c. Water Phase Ingredients

The water phase includes one or more polar solvents, such as water, and other water phase ingredients. Typically, water phase ingredients are hydrophilic and/or amphipathic ingredients of the pre-spray emulsion. For example, oils and other lipophilic ingredients typically are not added to the water phase. Certain ingredients, for example, ingredients having hydrophobic and hydrophilic moieties, for example, surfactants and co-surfactants, can be added to either the oil or the water phase, or to the oil and the water phase. Exemplary water phase ingredients include, but are not limited to, polar solvents, e.g., water, typically filtered water; stabilizers, for example, bicarbonates, such as potassium bicarbonate, vitamins, such as vitamin C, green tea extract, such as a green tea extract that contains epigallocatechin gallate (EGCG), and fish collagen; binders, such as maltodextrin and fish collagen; emulsion stabilizers; pH adjusters, for example, citric acid; flavors; surfactants; co-surfactants, for example, sucrose fatty acid esters; co-emulsifiers; and preservatives.

Water phase ingredients can be added to the water phase simultaneously and/or sequentially, in a specific order. In one example, one or more water phase ingredients are added first and heated, prior to addition of further ingredient(s). In one example, when the water phase ingredients include a polar solvent and an emulsion stabilizer, these ingredients are added sequentially, in the following order: 1) polar solvent, and 2) emulsion stabilizer. In one example, when the water phase ingredients include water and an emulsion stabilizer, these ingredients are added sequentially, in the following order: 1) water, and 2) emulsion stabilizer. In another example, when the water phase ingredients include a surfactant, a polar solvent (e.g., water) and an emulsion stabilizer, these ingredients are added to the water phase vessel sequentially, in the following order: 1) surfactant; 2) polar solvent (e.g., water); 3) emulsion stabilizer. Alternatively, the water phase ingredients can be added in any other order. Typically, when the water phase includes a surfactant, particularly when the surfactant is a surfactant that is solid at room temperature, for example, tocopherol polyethylene glycol succinate surfactant, the surfactant is the first water phase ingredient added to the water phase vessel. Typically, when the water phase ingredients include an emulsion stabilizer, the emulsion stabilizer is the last ingredient added to the water phase vessel.

d. Water Phase Production

To produce the water phase, appropriate amounts of the water phase ingredients are added to the water phase vessel. Water phase vessels can include tanks, for example, water-jacketed tanks such as, but not limited to, the Overly 550 gallon water-jacketed tank, or any other tank described herein. The amounts of the water phase ingredients are measured, e.g., weighed, either prior to adding to the water phase vessel or are measured in the water phase vessel. In one example, the water phase ingredients are measured by weighing the ingredients on a scale (e.g., one or more of the scales described herein; the choice of scale depends on the desired amount of the ingredient), before addition to the water phase vessel. Typically, the appropriate amount of the water phase ingredient is calculated based on the desired concentration (e.g., weight by weight (w/w), molarity (M), volume by weight (v/w) or volume by volume (v/v)), of the ingredient in the final product.

Water phase ingredients can include water, typically purified water. In one example, unpurified water, for example, city water, is purified to remove impurities using one or more purifiers (e.g., purifiers described herein) prior to adding it to the water phase vessel. In another example, unpurified water, for example, city water, is purified by passing the water through the following purifiers, typically sequentially, in the following order: a carbon filter, an ion exchange purifier, a reverse osmosis purifier and an end-point filter, for example, a 100 micron end-point filter.

In general, the water phase ingredients are added, mixed and/or heated in the water phase vessel. The water phase vessel can be a water phase tank, for example, a water-jacketed tank, such as one of the tanks described herein (e.g., an Overly 550 gallon water-jacketed tank). In one example, ingredients are heated to temperatures between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. In one example, the water phase ingredients are heated to a temperature of between at or about 60° C. and 70° C., for example, by adjusting the temperature on a water-jacketed tank or using another heating apparatus.

The mixing can be carried out with a standard mixer, a homogenizer, or any other suitable mixer, such as, but not limited to, the mixers described herein. Exemplary mixers include standard mixers, such as Lightnin® mixers (e.g., Model No. XJC117, a fixed-mount gear drive high-flow mixer) and homogenizers, such as Arde Barinco reversible homogenizers (e.g., Model No. CJ-4E). The mixer can be attached to the top of the water phase vessel, for example, attached to the tank, such as mounted on the top of the tank.

The water phase ingredients can be added to the water phase simultaneously or sequentially in any order. Typically, the water, e.g., purified water, is added before adding the other water phase ingredients. In one example, one or more of the ingredients are mixed and/or heated in the water phase tank before adding the other water phase ingredients.

In an exemplary method provided herein, the water phase is generated by heating water, e.g., purified water, in the water phase vessel to the desired temperature, for example, to a temperature of between at or about 60° C. and 70° C. After the water phase reaches the desired temperature, e.g., between at or about 60° C. and 70° C., an emulsion stabilizer, such as the SALADIZER® brand emulsion stabilizer (blend of xanthan gum, guar gum and sodium alginate) is added to the water phase. The water phase is then mixed using a mixer such as a homogenizer, for example an Arde Barinco reversible homogenizer (e.g., Model No. CJ-4E), typically using the "reverse" setting. The homogenizer can be attached to the top of the water phase vessel. Additional water phase ingredients are then added to the water phase tank at a temperature of between at or about 60° C. and 70° C. The mixture is then mixed until the ingredients are dispersed, using a mixer, such as a standard water phase mixer, for example, a Lightnin® mixer (e.g., Model No. XJC117). Typically the heat is maintained at a temperature of between at or about 60° C. and 70° C. Typically, the ingredients are mixed until combined and maintained at the desired temperature e.g., between at or about 60° C. and 70° C., until combining with the oil phase.

e. Combining Phases

After the oil phase and the water phase are generated, the phases can be combined, for example, by using a transfer device, and mixed, e.g., homogenized, to form an emulsion. In one example, the oil phase is transferred from the oil phase vessel to the water phase vessel. In another example, the water phase is transferred from the water phase vessel to the oil phase vessel. In another example, the oil and water phases are transferred to another vessel, such as an emulsifying vessel.

Transfer devices can include any device for transferring the contents of one vessel to another vessel, as described above. For example, suitable transfer devices include transfer pumps and associated equipment, such as, but not limited to, combinations of sanitary fittings, hoses and/or ball valves; manual transfer devices, for example, pouring and/or pipetting device; and any other suitable transfer device known to those of skill in the art. Typically, the phases are kept clean, e.g., sterile, during transfer. Sterility of the phases can be maintained, for example, by transfer devices having sanitary fittings and/or by combining the phases in a sterile environment. In one example, the transfer device include a transfer pump, for example, a Teel pump (Model No. 2P377B; Granger, Inc.), sanitary fittings, transfer hoses, for example, food grade hoses, such as those sold by Sani-Tech West, and ball valves, which are attached to the tanks and connect the tanks.

Simultaneous with and/or subsequent to the combination of the phases, a mixer, for example, a homogenizer (e.g., a reversible homogenizer), can be used to emulsify the water and oil phases. In one example, a homogenizer, e.g., a homogenizer mounted on one of the tanks, is turned on, the ball valves are opened, and the transfer pump is turned on to effect transfer of the contents of one tank to another, for example, to transfer the contents of the oil phase tank to the water phase tank. As the phases are combined, they can be mixed by the homogenizer to form an emulsion. The position of the homogenizer in the tank can be adjusted, for example, by adjusting a baffle plate, e.g., moving the baffle plate further into/out of the mixture, in order to achieve and maintain the emulsion. Typically, the phases are homogenized (i.e., emulsified) by operating the mixer, e.g., homogenizer, at a speed sufficient to form an emulsion. In one example, the homogenizer is operated at a speed of between at or about 1000 and at or about 1500 rpm. Mixing typically is continued until the phases are combined, typically in an emulsion.

f. Cooling

The emulsion can be cooled during and/or after mixing to promote stability and emulsification, for example, by preventing or minimizing oxidization. The cooling can be rapid cooling and can be performed using one or more cooling apparatuses, for example, any of the cooling apparatuses described herein or any cooling apparatus known to those of skill in the art. Suitable cooling apparatuses for use with the methods include recirculating coolers and water and ice baths. An exemplary cooling apparatus is a recirculating cooler, such as those sold by Turmoil (Model No. OC-1000 RO; West Swanzey, N.H.). When the cooling apparatus is a recirculating cooler, fluid from the vessel containing the combined oil and water phases is circulated through the cooler, typically while mixing, and then back to the vessel, to rapidly cool and maintain the temperature of the mixture during mixing. Typically, the phases are mixed and cooled until the phases are emulsified and the temperature of the emulsification reaches between at or about 25° C. and at or about 43° C., typically between at or about 30° C. and at or about 35° C. For example, the emulsification can be cooled to a temperature of at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C. or 43° C. Typically, when the cooling is rapid cooling, the temperature can be reached in less than or about 2 hours, typically less than or about 1 hour. For example, the emulsification can be cooled to the desired temperature, e.g., between at or about 25° C. and at or about 43° C., in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

Cooling can be performed before or after additional steps, such as adding additional ingredients and/or evaluation of the product. In one example, the cooling is carried out after the addition of additional ingredients, for example, taste-modifying agents, and/or pH adjusting agents.

g. Spray Drying

After combining the oil phase and water phase to form the emulsion, the emulsion can be dried into a powder. An exemplary method of drying includes spray drying. In the methods provided herein, the powder formed is a free-flowing, i.e., not sticky, powder. Free-flowing powders can be obtained using techniques well known in the art, such as, but not limited to, spray drying, freeze drying or absorption plating. Typically, the emulsion is dried, for example, spray dried, into a powder after the emulsion has been cooled to a desired temperature, e.g., between or between about 25° C. and 43° C., such as at or about 30° C.

The methods for forming the powders include spray drying. Spray drying processes and spray drying equipment are described generally in Perry's Chemical Engineers' Handbook, pp. 20-57 (Sixth Edition 1984). More details on spray drying processes and equipment are reviewed by Marshall (1954) "Atomization and Spray-Drying," Chem. Eng. Prog. Monogr. 50:Series 2 and Masters, "Spray Drying Handbook" (Fourth Edition 1985). Methods for spray drying are well known (see, e.g., U.S. Pat. Nos. 5,430,021 and 6,534,085 and U.S. Publication No. 2007/0184117). In general, spray drying is used to dry a heated liquid by passing it through hot gas. One or more spray nozzles is used to atomize the liquid in a cooling tower or chamber. As the material is atomized (sprayed), the surface tension causes a uniform spherical particle to form, which is passed through the cooling chamber and hardens into a solid intact sphere. The spray dried particles can be between at or about 0.5 microns and at or about 100 microns, and typically are less than at or about 10 microns, typically less than at or about 5 microns, and typically less than at or about, or at or about, 1 micron.

Exemplary of a spray dryer is a cyclone spray dryer. During spray drying with a cyclone spray dryer, the homogenized mixture is pumped into an atomizing device where it is broken into small droplets. Upon contact with a stream of hot air, the moisture is removed very rapidly from the droplets while still suspended in the drying air. The dry powder is separated from the moist air in cyclones by centrifugal action. The centrifugal action is caused by the great increase in air speed when the mixture of particles and air enters the cyclone system. The dense powder particles are forced toward the cyclone walls while the lighter, moist air is directed away through the exhaust pipes. The powder settles to the bottom of the cyclone where it is removed through a discharging device. Sometimes the air-conveying ducts for the dry powder are connected with cooling systems which admit cold air for transport of the product through conveying pipes. Cyclone dryers have been designed for large production schedules capable of drying ton-lots of powder per hour.

The methods provided herein produce powders using a standard spray dryer. The liquid to be dried, for example a solution, suspension or emulsion, may be fed into an atomizer to generate the powder. The atomizer may be, for example, a rotary (wheel) atomizer or nozzle atomizer. In some examples, a fluid bed dryer may also be used. The atomizer is typically an open-mode design with single-point powder discharge, an open-mode design with dual-point powder discharge, or a closed-cycle design with single-point powder discharge, or an alternative form of atomizer. In some examples, the atomizer is contained within a dryer consisting of a feed pump to funnel in the liquid, for example the emulsion, an atomizer, an air heater, an air dispenser, a drying chamber, systems for powder recovery, and process control systems.

In order to prepare the dry powder using a spray drier, the liquid, e.g., emulsion, is fed into a rotary wheel or high pressure nozzle atomizer at a uniform rate, and thereby converted into a spray of droplets. The pattern of the resultant droplets may be largely dependent on the properties of the liquid to be spray dried, including its bulk density, in conjunction with the speed and configuration of the atomizer wheel. In desirable conditions, rotation of the atomizer wheel occurs with minimal vibration, at high peripheral speeds and with smooth internal surfaces, for maximum efficacy. The optimum speed and wheel configuration for a specific liquid can be determined empirically by one of skill in the art. In some examples, the spray of droplets contacts the hot air, for example air at a temperature of about 180° C., present in the drying chamber, triggering the formation of dry particles and cooling of the hot air due to the evaporation of water or chemical solvent from the concentrated liquid sample. The resultant powder and cooler, humid air are separately, and continuously, discharged from the chamber. In some examples, the dry powder is cooled and bagged after separation from the cooler, humid air. After powder recovery, some powders are rewet by re-dissolving the powder in water or a solvent and the composition is subject to a second round of spray drying and collection. In some examples the powders are then sifted, for example through a 60-80 μm mesh screen.

As will be appreciated by one of skill in the art, the inlet temperature and the outlet temperature of the spray drier are not critical but will be of such a level to provide the desired particle size, of less than at or about 1 micron, and to result in a powder that has a desired property. The inlet and outlet temperatures can be adjusted depending on the melting characteristics and composition of the emulsion. The inlet temperature typically is between at or about 60° C. and at or about 170° C. with outlet temperatures between at or about 40° C. to at or about 120° C. Typical inlet temperatures are from at or about 90° C. to at or about 120° C. and typical outlet temperatures are from at or about 60° C. to at or about 90° C. The flow rate which is used in the spray drying equipment will generally be at or about 3 mL per minute to at or about 15 mL per minute. The atomizer air flow rate will vary between values of at or about 25 L per minute to at or about 50 L per minute. Commercially available spray dryers are well known to those of skill in the art, and suitable settings for any particular dispersion can be readily determined by one of skill in the art without undue experimentation. Operating conditions such as inlet temperature and outlet temperature, feed rate, atomization pressure, flow rate of the drying air, and nozzle configuration can be adjusted in accordance with the manufacturer's guidelines.

In some examples, a processing aid, such as additional solvent, for example, water, is added to the emulsion. The processing aid, e.g., water, allows the emulsion to pass through the pump of the dryer more easily, for example, by making the emulsion less thick. The processing aid, for example, water, is evaporated during the drying process and is not present in the final dry powder.

In some examples, the dry powder is stored into a capsule form or is pressed into a tablet. For use as tablets, the compositions typically contain multiple other excipients. These excipients include tablet disintegrants, such as corn starch, glidants, such as silicon dioxide, and lubricants such as magnesium stearate. Ordinarily these compositions contain minor amounts by weight of glidants and lubricants, e.g., each two percent (2%) or less by weight. Tablet disintegrants are optionally present and, if present, are included in sufficient amounts to assure that the tablet disintegrates upon ingestion. For example, disintegrants, such as corn starch, can be employed at concentrations of from about zero to about 30 percent by weight of the composition.

Free flowing, i.e., not sticky, powders also can be used to administer the non-polar ingredients by inhalation using a dry powder inhaler (DPI). Such dry powder inhalers typically administer the ingredient as a free-flowing powder that is dispersed in the air-stream during inspiration. In order to achieve a free flowing powder, the ingredients are typically formulated with a suitable excipient such as lactose or starch. For example, such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

h. Filtration, Additions, Evaluation and Packaging

After combining the oil and water phases to form a mixture, i.e., emulsion, or after drying the emulsion to form a dry powder, one or more additional steps can be carried out to modify, evaluate, analyze and/or package the product. Typically, taste-modifying agents are added to the emulsion, such as flavoring agents (e.g., flavoring agents that confer fruit flavors, such as peach, or other flavors, such as pina colada) and sweetening agents (e.g., sucralose). Other ingredients can be added, such as masking agents (e.g., NAT masking agent) and pH adjusting agents (e.g., acids, such as, but not limited to citric acid). The pH adjusting agent can be used to adjust the pH of the emulsion, for example, to a pH of between at or about 2 and at or about 5, e.g., to at or about 2 and at or about 3.5. Thus, the provided products typically have a pH of between at or about 2 and at or about 5, e.g., at or about 2 and at or about 3.5, such as a pH of at or about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.

Before and/or after adding additional ingredients, the product can be evaluated, such as by measuring the pH and/or the temperature. Measurements can be taken using an instrument such as those described herein. In one example, additional ingredients (e.g., pH adjusters) are added based on information obtained by evaluating the product. The product can be analyzed and evaluated to verify and/or determine other properties of the product, for example, to verify that the product contains the appropriate amounts of the non-polar ingredients and other ingredients. For example, the products can be evaluated to verify that microbial and heavy metal (e.g., arsenic, cadmium, mercury, lead and others) levels are within the acceptable range according to food and beverage standards. In one example, the acceptable microbial levels are not more than 1,000 cfu/g microbes (e.g., yeast, bacteria, mold and other microbes) and negative for *E. coli* and *Salmonella*. In another example, the acceptable heavy metal levels are not more than 10 ppm heavy metals and not more than 0.2 ppm lead and 2 ppm arsenic. When a standard exists for a particular amount and/or property, the amount/property is verified by tests in accordance with U.S. Pharmacopeia (USP) and/or AOAC (Association of Analytical Communities) standards. Samples can be analyzed in accordance with these standards by sending a sample of the product to a commercial testing facility, such as Eurofins U.S. (Des Moines, Iowa) or Advanced Botanical Consulting & Testing, Inc. (Tustin, Calif.), or any other facility that performs tests in accordance with these standards.

For example, the amount of some non-polar ingredients, such as caffeine anhydrous, chromium picolinate and vitamin B12, typically is verified according to USP standards. The density and pH of the composition and the level of microbes, e.g., yeast, mold, *E. coli* and *Salmonella*, also typically are verified according to USP standards. The amount of fatty acids can be verified according to AOAC standards, for example, by gas chromatography (GC), gas liquid chromatography (GLC) or other fatty acid profiling methods. The levels of heavy metals, such as lead and arsenic, are tested using inductively coupled plasma mass spectrometry (ICP-MS), or by sending a sample of the composition for testing to a testing facility, such as Eurofins U.S. (Des Moines, Iowa) or Advanced Botanical Consulting & Testing, Inc. (Tustin, Calif.), or any other facility capable of performing such tests. Additionally, Fourier transform infrared spectroscopy (FTIR) typically is used to obtain a fingerprint of the product, to verify that no other compounds except the desired ingredients are present in the product.

The emulsifications can be purified, for example, filtered, prior to use or drying, using any of purification device described herein or any other suitable purification device. Water can be added in the case of evaporation, to bring the product up to the appropriate volume. HPLC, GC, GLC, FTIR and ICP-MS can be performed according to well-known methods (see, for example, Analytical Chemistry: An Introduction, 6th Ed., Douglas A. Skoog et al. (1994) Chapters 22 (FTIR) and 27 (GC/GLC, HPLC) and U.S. Pat. No. 6,265,717 (ICP-MS)).

After evaluation, purification, and/or addition of all the ingredients, the product, e.g., emulsion or dry powder, can be packaged, for example, into large containers for storage or into smaller containers for administration, such as bottles or ampoules (as described below). The products can be transferred to the packaging containers using a transfer device, such as the transfer device described herein, including transfer pumps and fittings as described above or by manual transfer. For example, the product can be packaged for storage in containers, such as totes, e.g., 275 gallon totes (such as the 275 gallon bottle with a reconditioned CageTote tank IBC, Item No. REN275; Qualserv Enterprises, Inc. (www.qualservcontainer.com)), by transferring the mixture using a food grade hose (Sani-Tech® STHT-R-HD braid-reinforced heavy duty silicone hose; Sani-Tech West). After transfer, the tote can be closed and sealed, e.g., tied, such as with a cable tie.

i. Cleaning the Equipment

The equipment used in the provided methods can be cleaned prior to and/or after use, such as in a sink and/or rinsing the vessels, e.g., tanks, and hose lines. The tanks can be cleaned by filling with hot water, washing with soap and water, and rinsing with water. The pH of the water can be checked before discharging the water from the vessel. The water can be adjusted to the desired pH, for example to a pH between 6 and 9, by adding a pH adjusting agent, such as soda ash, citric acid and/or $H_3PO_4$. After discharging the water from the vessel, the tanks can be sanitized, such as with isopropyl alcohol (IPA), and let dry.

D. Examples

Example 1

A. Method of Producing TPGS Compositions d-α-Tocopheryl polyethylene glycol 1000 succinate (TPGS 1000) was synthesized from vitamin E succinate according to the following general procedure. See also, U.S. patent application Ser. No. 14/207,310 and International Patent Application No. PCT/US14/25006.

Polyethylene glycol (PEG) 1000 (168.7 kg) was added to a reaction flask containing 1430 L of toluene, followed by the addition of 71.5 kg of vitamin E (α-tocopheryl acid) succinate and 2.86 kg of p-toluene sulfonic acid. The reaction mixture was heated to 110-112° C. and refluxed for up to 6.5 hours, removing the water formed during the esterification reaction by azeotropic distillation. The reaction was terminated when the desired amounts of TPGS monomer and TPGS dimer were formed, as indicated by high performance liquid chromatography (HPLC) and thin layer chromatography (TLC), resulting in the TPGS compositions set forth in Table 1a below. Each TPGS composition in Table 1a was formed by terminating the reaction at a different time point, up to 6.5 hours, and contained various amounts of TPGS monomer and TPGS dimer. The remainder of the TPGS composition was made up of unreacted starting materials, such as vitamin E and PEG The reaction was terminated by cooling the reaction mixture to room temperature, followed by washing with 25 L of a 10% solution of $NaHCO_3$. The solution stirred for 10 minutes, and after stirring was allowed to separate into layers. The organic (toluene) layer was removed, 6 kg of activated carbon (charcoal) was added, and the solution was heated to 55-60° C. and maintained at this temperature for 1 hour. The solution was then cooled to room temperature, filtered through 10 kg of Celite® Hyflo® filter aid (Sigma Aldrich, St. Louis, Mo.) and then washed with 100 L of toluene. The filtered toluene solution was concentrated by vacuum distillation below 60° C. to remove the toluene. Water (140 L) was added to remove traces of toluene and was then removed via vacuum distillation below 60° C. to obtain ~180 kg of a crude α-tocopheryl polyethylene glycol 1000 succinate composition that contained a mixture of TPGS monomer and TPGS dimer, along with unreacted PEG 1000 and α-tocopherol.

TABLE 1a

Amounts of TPGS monomer and TPGS dimer formed during reaction

| TPGS composition | Monomer (%) | Dimer (%) | Total (% monomer + % dimer) |
|---|---|---|---|
| 1 | 43.90 | 53.90 | 97.80 |
| 2 | 42.80 | 48.80 | 91.60 |
| 3 | 40.95 | 53.15 | 94.10 |
| 4 | 43.52 | 49.80 | 93.32 |
| 5 | 55.88 | 29.27 | 85.15 |
| 6 | 52.92 | 33.70 | 86.62 |
| 7 | 42.76 | 51.10 | 93.86 |
| 8 | 40.39 | 54.90 | 95.29 |
| 9 | 57.70 | 40.40 | 98.10 |
| 10 | 39.35 | 35.56 | 74.91 |
| 11 | 60.00 | 38.10 | 98.10 |

A series of extractions were performed on the crude TPGS composition. The crude TPGS composition (~180 kg) was dissolved in 360 L of methanol and then 540 L of cyclohexane was added. The solution was stirred and then allowed to separate into layers. The cyclohexane layer was removed and an additional 540 L of cyclohexane was added to the remaining methanol layer. The solution was stirred and then allowed to separate into layers. The cyclohexane layer was again removed and an additional 540 L of cyclohexane was added to the remaining methanol layer. The solution was again stirred and allowed to separate into layers. The cyclohexane layer was removed, and the remaining methanol layer was further diluted with an additional 270 L of methanol. Activated carbon (18 kg) was added and the solution was heated to 55-60° C. and maintained at this temperature for 1 hour. The solution was then cooled to room temperature, filtered through 30 kg of Celite® Hyflo® filter aid, and washed with 100 L of methanol. The methanol solution was passed through a micron filter, then concentrated via vacuum distillation below 60° C. to obtain ~98-102 kg of a TPGS composition. All traces of solvent were then removed by purging with nitrogen at 55° C. for two hours to obtain ~98-102 kg of a purified TPGS composition that contained TPGS monomer and TPGS dimer.

One typical batch of TPGS prepared to contain a high dimer concentration, and used in the Examples below, had the following components:
TPGS monomer: 48%
TPGS dimer: 51%
Vitamin E: 0.42%
Vitamin E succinate: 0.46%.

Other typical batches contained:
TPGS monomer: 46.09%-43.15% w/w
TPGS dimer: 39.07%-50.28% w/w
Other: up to about 3%-3.2% w/w For example, the batches used in Example 11, below, contained:
TPGS monomer: 46.55%-48.72% w/w
TPGS dimer: 46.88%-47.33% w/w
Other: up to about 3.95%-6.55% w/w B. Evaluation of the Clarity of the TPGS-Containing Compositions by a Turbidity Analysis The clarity of the TPGS compositions prepared above was evaluated by a turbidity analysis. TPGS compositions 1-11 were formulated as 1 g concentrates and each were dissolved in 8 oz. of water. The resulting aqueous liquid dilution compositions then were evaluated for clarity by measuring turbidity using a nephelometer. Results of the evaluation are set forth in Table 1b below.

Each of the eleven TPGS compositions listed in Table 1a above was diluted in water (purified according to the provided methods) using the following steps.

Eight ounces of water was heated in a Pyrex® beaker by placing the beaker on a Thermolyne hot plate (Model #846925) until the water reached 49.8° C. The TPGS composition concentrate was then added to the heated water and stirred with a stir rod until dispersed. The resulting aqueous TPGS composition was cooled to room temperature (about 25° C.). The cooled aqueous TPGS composition was added to an amber-glass screw-top vial (Alcon) for evaluation.

The vials containing the aqueous TPGS compositions were sent to ACZ Laboratories, Inc. (Steamboat Springs, Colo.) for turbidity analysis using a nephelometer. Results are listed in the form of Nephelometric Turbidity Units (NTU) and are indicated in Table 1b below.

TABLE 1b

Turbidity (NTU) of aqueous TPGS compositions

| TPGS composition | Monomer (%) | Dimer (%) | Total (% monomer + % dimer) | Turbidity (NTU) |
|---|---|---|---|---|
| 1 | 43.90 | 53.90 | 97.80 | 8 |
| 2 | 42.80 | 48.80 | 91.60 | 8.2 |
| 3 | 40.95 | 53.15 | 94.10 | 10 |
| 4 | 43.52 | 49.80 | 93.32 | 10 |
| 5 | 55.88 | 29.27 | 85.15 | 14 |
| 6 | 52.92 | 33.70 | 86.62 | 14 |
| 7 | 42.76 | 51.10 | 93.86 | 18.5 |
| 8 | 40.39 | 54.90 | 95.29 | 39.4 |
| 9 | 57.70 | 40.40 | 98.10 | 71 |
| 10 | 39.35 | 35.56 | 74.91 | 80 |
| 11 | 60.00 | 38.10 | 98.10 | 80 |

Example 2

Preparation of Pre-Emulsion Concentrates Containing TPGS and Non-Polar Compounds Pre-emulsion concentrates were prepared according to the method described below with the ingredients detailed in Tables 2-18. The pre-emulsion concentrates contained between 31.5% and 97.43% by weight (of the concentrate) of one or more non-polar compounds and TPGS (α-tocopheryl polyethylene glycol succinate) or benzyl alcohol, or TPGS and benzyl alcohol. The TPGS was prepared as described in Example 1, above.

The pre-emulsion concentrates contained as much as about 97% non-polar compounds. The remainder was TPGS or benzyl alcohol, or TPGS and benzyl alcohol. Non-polar compounds included: a fish oil that contains 50% of the non-polar ingredients DHA/EPA (sold as VivoMega 3322 TG by GC Rieber Oils, Kristiansund, Norway); an algal oil that contains 40% of the non-polar ingredient DHA (sold by GC Rieber Oils, Kristiansund, Norway); an algal oil that contains 35% of the non-polar ingredient DHA and contains 350 mg DHA/g oil (life's DHA™ S35-0300, sold by DSM Nutritional Products Inc., Kaiseraugst, Switzerland); a conjugated linoleic acid (CLA) that contains 79.6% CLA (Clarinol® G-80, sold by Stepan Lipid Nutrition, Maywood, N.J.); a medium chain triglyceride (MCT) oil that contains 98% MCT (sold by Abitec, Janesville, Wis. and Stepan Lipid Nutrition, Maywood, N.J.); a flaxseed oil that contains 50% C:18-3 alpha-linolenic acid (ALA) (sold by San Mark Ltd., Greensboro, N.C.); resveratrol (sold by Maxsun Industries Inc., Walnut, Calif.); vinpocetine (sold by Cyvex Nutrition, Irvine, Calif.); sesamin (sold by KEB Nutraceutical USA, Inc., Minneapolis, Minn.); a turmeric/curcumin composition that contains 95% curcumin (sold by Siddharth International, Mumbai, India); a phosphatidylserine (PS) composition that contains 40% phosphatidylserine and lesser amounts of phosphatidylinositol and phosphatidylethanolamine (sold by Doosan Corporation and distributed by Perrimondo LLC); vitamin E acetate that contains 1360 IU tocopheryl/g vitamin E oil (sold by DSM Nutritional Products Inc., Kaiseraugst, Switzerland); alpha-lipoic acid (sold by Pure Assay Ingredients, Walnut, Calif.); quercetin (sold by Pure Assay Ingredients, Walnut, Calif.); pyrroloquinoline quinone (PQQ; Nascent Health Sciences, Allentown, N.J.); and mixtures thereof. Ingredients marked with a "*" were added in overage to ensure the stated amount of non-polar compound was in the final product.

Each of the pre-emulsion concentrates set forth in Tables 2-18, below, were prepared using a bench-top process. Larger amounts of the pre-emulsion concentrates can be made by scaling up the bench-top process or using a scaled-up manufacturing process, for example, to make larger batch sizes of the pre-emulsion concentrates. Accordingly, each of the pre-emulsion concentrates in Tables 2-18 also can be made with the provided methods as described and a scaled-up process. Further details for each pre-emulsion concentrate are provided in each individual Table.

The bench-top process for making the pre-emulsion concentrates was performed using the following general steps. For each of the pre-emulsion concentrates set forth in Tables 2-18, below, the indicated amount of each ingredient was weighed using a Toledo Scale (Model GD13x/USA), Sartorius Basic Analytical Scale (Model BA110S) or an OHAUS Scale (Model CS2000). Selection of scale depended on the weight of each ingredient being weighed.

The initial ingredients (all ingredients except the non-polar compounds) were added in the indicated amounts (g/batch) to a vessel (a Pyrex® beaker), and mixed with a standard mixer (IKA® model No. RE-16 S1, an overhead mixer (laboratory stirrer) compatible with the bench-top process). While mixing, the ingredients were heated by a Thermolyne hot plate (Model # SP46615) to reach a temperature of between 60° C. and 70° C.

After the initial ingredients dissolved, e.g., formed a homogeneous mixture, and reached the desired temperature, e.g., 60° C., the non-polar compounds were added. The ingredients then were homogenized by placing a reversible homogenizer (Arde Barinco, Inc.; Model CJ-4E) in the vessel (beaker) and turning on at 850-1200 RPM. Mixing with the homogenizer was continued while maintaining the temperature using the hot plate. The baffle plate on the homogenizer was adjusted to achieve and maintain an emulsion, for example, by moving the baffle plate further into and/or out of the ingredient mixture. Homogenization continued at between 60° C. and 70° C. until the mixture became homogeneous. For the preparation of some pre-emulsion concentrates, an additional solvent, such as ethanol, tetrahydrofuran or hexanes, was added to aid in dissolving the non-polar compound. The additional solvent was then evaporated before further use of the solid phase composition.

Unless otherwise indicated, when the ingredients include a surfactant, a preservative and one or more non-polar compounds, these ingredients were added sequentially, in the following order: 1) surfactant; 2) preservative; 3) non-polar compound. When the ingredients include a surfactant, a preservative, a solvent and one or more non-polar compounds, these ingredients were added sequentially, in the following order: 1) surfactant; 2) preservative; 3) solvent; 4) non-polar compound. The ingredients were heated with the hot plate until the temperature reached between 60° C. and 70° C. A temperature probe (Model # DPP400W, Cooper-Atkins) was used to measure the temperature of the mixing ingredients.

The composition then was filtered, through a 100 micron end-product filter, and packaged (transferred) by filling into one or more storage containers, for example, plastic bottles or 5 gallon pails, where it was cooled to room temperature (about 25° C.). Alternatively, the composition was packaged into a bag-in-a-box-type storage container. Depending on the particular ingredients, the resulting concentrates either were a solid to semi-solid composition at room-temperature (having a waxy consistency) or remained as a liquid.

TABLE 2

Pre-emulsion concentrate containing fish oil (50% DHA/EPA) and TPGS

| Ingredient | wt % of composition |
|---|---|
| Fish oil (50% DHA/EPA blend)* (non-polar ingredient) | 39.50 |
| TPGS | 60.50 |
| Total | 100.00 |

TABLE 3

Pre-emulsion concentrate containing algal oil (40% DHA) and TPGS

| Ingredient | wt % of composition |
|---|---|
| Algal oil (40% DHA) (non-polar ingredient) | 84.00 |
| TPGS | 16.00 |
| Total | 100.00 |

TABLE 4

Pre-emulsion concentrate containing algal oil (35% DHA) and TPGS

| Ingredient | wt % of composition |
|---|---|
| Algal oil (35% DHA) (non-polar ingredient) | 97.35 |
| TPGS | 2.65 |
| Total | 100.00 |

TABLE 5

Pre-emulsion concentrate containing CLA oil (79.6% CLA) and TPGS

| Ingredient | wt % of composition |
|---|---|
| CLA oil (79.6% CLA) (non-polar ingredient) | 97.43 |
| TPGS | 2.57 |
| Total | 100.00 |

TABLE 6

Pre-emulsion concentrate containing MCT oil (98% MCT) and TPGS

| Ingredient | wt % of composition |
|---|---|
| MCT oil (98% MCT) (non-polar ingredient) | 97.42 |
| TPGS | 2.58 |
| Total | 100.00 |

TABLE 7

Pre-emulsion concentrate containing resveratrol and TPGS

| Ingredient | wt % of composition |
|---|---|
| Resveratrol (non-polar ingredient) | 35.00 |
| TPGS | 65.00 |
| Total | 100.00 |

TABLE 8

Pre-emulsion concentrate containing vinpocetine and TPGS

| Ingredient | wt % of composition |
|---|---|
| Vinpocetine (non-polar ingredient) | 35.00 |
| TPGS | 65.00 |
| Total | 100.00 |

TABLE 9

Pre-emulsion concentrate containing sesamin and TPGS

| Ingredient | wt % of composition |
|---|---|
| Sesamin (non-polar ingredient) | 35.00 |
| TPGS | 65.00 |
| Total | 100 |

TABLE 10

Pre-emulsion concentrate containing turmeric/curcumin (95% curcumin) and TPGS

| Ingredient | wt % of composition |
|---|---|
| Turmeric/curcumin (95% curcumin) (non-polar ingredient) | 31.50 |
| TPGS | 68.50 |
| Total | 100.00 |

TABLE 11

Pre-emulsion concentrate containing turmeric/curcumin (95% curcumin) and TPGS

| Ingredient | wt % of composition |
|---|---|
| Turmeric/curcumin (95% curcumin) (non-polar ingredient) | 37.10 |
| TPGS | 62.90 |
| Total | 100.00 |

TABLE 12

Pre-emulsion concentrate containing phosphatidylserine (40% phosphatidylserine) and TPGS

| Ingredient | wt % of composition |
|---|---|
| Phosphatidylserine (40% PS) (non-polar ingredient) | 68.40 |
| TPGS | 31.60 |
| Total | 100.00 |

TABLE 13

Pre-emulsion concentrate containing phosphatidylserine (40% phosphatidylserine), MCT oil (98% MCT) and TPGS

| Ingredient | wt % of composition |
|---|---|
| Phosphatidylserine (40% PS) (non-polar ingredient) | 68.50 |
| MCT oil (98% MCT) (non-polar ingredient) | 17.80 |
| TPGS | 13.70 |
| Total | 100.00 |

TABLE 14

Pre-emulsion concentrate containing vitamin E acetate, TPGS, and benzyl alcohol

| Ingredient | wt % of composition |
|---|---|
| Vitamin E acetate (1360 IU tocopheryl/g oil) (non-polar ingredient) | 95.43 |
| TPGS | 4.07 |
| Benzyl alcohol (preservative) | 0.50 |
| Total | 100.00 |

TABLE 15

Pre-emulsion concentrate containing alpha-lipoic acid, TPGS and benzyl alcohol

| Ingredient | wt % of composition |
|---|---|
| Alpha-lipoic acid (non-polar ingredient) | 70.00 |
| TPGS | 20.00 |
| Benzyl alcohol (preservative) | 10.00 |
| Total | 100.00 |

TABLE 16

Pre-emulsion concentrate containing quercetin, TPGS, and benzyl alcohol

| Ingredient | wt % of composition |
|---|---|
| Quercetin (non-polar ingredient) | 35.00 |
| TPGS | 64.50 |
| Benzyl alcohol (preservative) | 0.50 |
| Total | 100.00 |

TABLE 17

Pre-emulsion concentrate containing PQQ, TPGS, and benzyl alcohol

| Ingredient | wt % of composition |
|---|---|
| PQQ (non-polar ingredient) | 35.00 |
| TPGS | 64.50 |
| Benzyl alcohol (preservative) | 0.50 |
| Total | 100.00 |

TABLE 18

Pre-emulsion concentrate containing fish oil (50% DHA/EPA), flaxseed oil (50% ALA), TPGS, and benzyl alcohol

| Ingredient | wt % of composition |
|---|---|
| Flaxseed oil (50% ALA) (non-polar ingredient) | 79.02 |
| Fish oil (50% DHA/EPA) (non-polar ingredient) | 0.40 |
| TPGS | 20.08 |
| Benzyl alcohol (preservative) | 0.50 |
| Total | 100.00 |

Example 3

Preparation of Pre-Spray Emulsions Containing TPGS and Non-Polar Compounds

The pre-emulsion concentrates of Tables 2-18 were used to prepare pre-spray emulsions. The pre-spray emulsions were prepared by combining a pre-emulsion concentrate with the ingredients detailed in Tables 19-39, below, according to the general procedure described below. The resulting pre-spray emulsions contained between 5.25% and 19.49% by weight non-polar compound(s), as shown in Table 40, below.

The ingredients in the pre-spray emulsions included: a pre-emulsion concentrate prepared as described above in Example 2 (see Tables 2-18); an emulsion stabilizer that is blend of xanthan gum, guar gum and sodium alginate, sold under the product name SALADIZER®, available from TIC Gums, Inc. (Belcamp, Md.); a binder, maltodextrin (Archer Daniels Midland Company, Decatur, Ill.); a sucrose fatty acid ester (SFAE) sold under the trade name DK Ester® (produced by Dai-Ichi Kogyo Seiyaku Co., Ltd of Japan) in place of some or all of the maltodextrin; citric acid, a pH adjuster; stabilizers, including vitamin C (Pure Assay Ingredients, Walnut, Calif.), potassium bicarbonate (Armand Products, Princeton, N.J.), a green tea extract that contains 40% EGCG (epigallocatechin gallate) (Guilin Layn Natural Ingredients Corp., Guilin, China); one or more co-emulsifiers such as fish collagen (Norland Products Inc., Cranbury Township, N.J.), a whey protein isolate (Marquez Brothers International, Hanford, Calif.), and saponin from quillaja bark (sold by Desert King and Sigma Aldrich, St. Louis, Mo.); and a polar solvent, water, which was purified city water, purified as described below. Before adding to the appropriate phase, as described below, the correct amount of each ingredient (as indicated in Tables 19-39) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Production of the Water Phase

The water phase was prepared in a 1500 mL Pyrex beaker. The appropriate amount of city water was purified by passing the water through the following purifiers, sequentially, in the following order: a carbon filter, an ion exchange purifier, a reverse osmosis purifier and a 100 micron endpoint filter. The water (amount indicated in Tables 19-39, below) finally was passed through a UV sterilizer before it was measured and added to the beaker. The switch controlling the pump and UV sterilizer was then turned off.

The beaker containing the water was placed onto a Thermolyne hot plate (Model No. SP46615). An Arde Barinco reversible homogenizer (Model No. CJ-4E; Arde Barinco, Inc., Norwood, N.J.) was immersed in the water and turned on, using the "forward" setting, at a speed of 30 rpm. The water phase then was heated to between 60° C. and 70° C. using the Thermolyne hot plate while slowly mixing at 30 rpm. The Arde Barinco mixer then was raised and switched to the "reverse" setting to create a vortex.

The indicated amount of the "water phase" ingredients were added to the water phase beaker at 60-70° C. When a stabilizer was present, such as $KHCO_3$, the ingredients were added in the following order: 1) emulsion stabilizer; 2) co-emulsifier; 3) co-surfactant(s); and 4) stabilizer(s). Mixing was continued at 60-70° C. until the emulsion stabilizer was mostly dispersed in the water phase and until the water phase was ready to be combined with the solid phase. Temperatures were measured with a pH and temperature meter (Hanna Instruments, Model No. HI 8314).

Combining the Water and Oil Phases

Once the water phase had been prepared and was at 60-70° C., the Arde Barinco homogenizer was turned on the "forward" setting at 30 rpm in the water phase beaker and the oil phase (i.e., pre-emulsion concentrate) was transferred to the water phase beaker. Mixing with the homogenizer at 30 rpm continued until the phases had combined.

The ingredients were mixed and cooled in a water bath until the mixture reached 50° C. The indicated amount of pH adjuster was then added and the mixture was continuously mixed at 30 rpm using the Arde Barinco mixer on "forward" and further cooled to 30° C. Additional water was added to account for any evaporation that had occurred during the process. Temperatures and pH were measured with a temperature and pH meter (Hanna Instruments, Model No. HI 8314). The pH of each mixture was measured to confirm that it was around 2.76.

Tables 19-39, below, indicate the amount (g) of each ingredient per batch of the pre-spray emulsion, the phase each ingredient was added, and the percentage by weight (wt %) of each ingredient.

TABLE 19

Pre-spray emulsion containing fish oil (50% DHA/EPA) and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 54.507268 | Water | 10.90 |
| SFAE (co-surfactant) | 41.3388 | Water | 8.27 |
| SALADIZER ® emulsifier (emulsion stabilizer) | 0.33 | Water | 0.07 |
| Vitamin C (stabilizer) | 10.00 | Water | 2.00 |
| Saponin (co-emulsifier) | 3.03 | Water | 0.61 |
| Pre-emulsion concentrate containing fish oil (50% DHA/EPA) and TPGS (Table 2 above) | 83.34 | Oil | 16.67 |
| Totals | 500.00 | | 100.00 |

TABLE 20

Pre-spray emulsion containing algal oil (40% DHA) and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 46.172823 | Water | 9.24 |
| SFAE (co-surfactant) | 33.0044 | Water | 6.60 |
| SALADIZER ® (emulsion stabilizer) | 0.33 | Water | 0.07 |
| Vitamin C (stabilizer) | 10.00 | Water | 2.00 |
| Saponin (co-emulsifier) | 3.03 | Water | 0.61 |
| Pre-emulsion concentrate containing algal oil (40% DHA) and TPGS (Table 3 above) | 100.01 | Oil | 20.00 |
| Totals | 500.00 | | 100.00 |

TABLE 21

Pre-spray emulsion containing algal oil (35% DHA) and TPGS

| Ingredient | g/batch | Phase | wt % of composition |
|---|---|---|---|
| Water (polar solvent) | 284.37 | Water | 56.87 |
| KHCO$_3$ (stabilizer) | 16.66889 | Water | 3.33 |
| Green tea extract (40% EGCG) (stabilizer) | 44.239232 | Water | 8.85 |
| SFAE (co-surfactant) | 41.3388 | Water | 8.27 |
| SALADIZER ® (emulsion stabilizer) | 0.33 | Water | 0.07 |
| Vitamin C (stabilizer) | 10.00 | Water | 2.00 |
| Saponin (co-emulsifier) | 3.03 | Water | 0.61 |
| Pre-emulsion concentrate containing algal oil (35% DHA) and TPGS (Table 4 above) | 100.01 | Oil | 20.00 |
| Totals | 500.00 | | 100.00 |

TABLE 22

Pre-spray emulsion containing CLA oil (79.6% CLA) and TPGS

| Ingredient | g/batch | Phase | wt % of composition |
|---|---|---|---|
| Water (polar solvent) | 170.62 | Water | 56.87 |
| KHCO$_3$ (stabilizer) | 10.00133 | Water | 3.33 |
| Fish collagen (binder) | 26.543539 | Water | 8.85 |
| SFAE (co-surfactant) | 24.8033 | Water | 8.27 |
| SALADIZER ® (emulsion stabilizer) | 0.20 | Water | 0.07 |
| Vitamin C (stabilizer) | 6.00 | Water | 2.00 |
| Saponin (co-emulsifier) | 1.82 | Water | 0.61 |
| Pre-emulsion concentrate containing CLA oil (79.6% CLA) and TPGS (Table 5 above) | 60.01 | Oil | 20.00 |
| Totals | 300.00 | | 100.00 |

TABLE 23

Pre-spray emulsion containing CLA oil (79.6% CLA) and TPGS

| Ingredient | g/batch | Phase | wt % of composition |
|---|---|---|---|
| Water (polar solvent) | 86.23 | Water | 57.48 |
| KHCO$_3$ (stabilizer) | 5.00 | Water | 3.33 |
| Whey protein (co-emulsifier) | 13.27 | Water | 8.85 |
| SFAE (co-surfactant) | 12.40 | Water | 8.27 |
| SALADIZER ® (emulsion stabilizer) | 0.10 | Water | 0.07 |
| Vitamin C (stabilizer) | 3.00 | Water | 2.00 |
| Pre-emulsion concentrate containing CLA oil (79.6% CLA) and TPGS (Table 5 above) | 30.00 | Oil | 20.00 |
| Totals | 150.00 | | 100.00 |

TABLE 24

Pre-spray emulsion containing MCT oil (98% MCT) and TPGS

| Ingredient | g/batch | Phase | wt % of composition |
|---|---|---|---|
| Water (polar solvent) | 568.74 | Water | 56.87 |
| KHCO$_3$ (stabilizer) | 33.33778 | Water | 3.33 |
| Green tea extract (40% EGCG) (stabilizer) | 88.478464 | Water | 8.85 |
| SFAE (co-surfactant) | 82.6777 | Water | 8.27 |
| SALADIZER ® (emulsion stabilizer) | 0.67 | Water | 0.07 |
| Vitamin C (stabilizer) | 20.00 | Water | 2.00 |
| Saponin (co-emulsifier) | 6.07 | Water | 0.61 |
| Pre-emulsion concentrate containing MCT oil (98% MCT) and TPGS (Table 6 above) | 200.03 | Oil | 20.00 |
| Totals | 1000.00 | | 100.00 |

TABLE 25

Pre-spray emulsion containing MCT oil (98% MCT) and TPGS

| Ingredient | g/batch | Phase | wt % of composition |
|---|---|---|---|
| Water (polar solvent) | 170.62 | Water | 56.87 |
| KHCO$_3$ (stabilizer) | 10.00133 | Water | 3.33 |
| Fish collagen (binder) | 26.543539 | Water | 8.85 |
| SFAE (co-surfactant) | 24.8033 | Water | 8.27 |
| SALADIZER ® (emulsion stabilizer) | 0.20 | Water | 0.07 |
| Vitamin C (stabilizer) | 6.00 | Water | 2.00 |
| Saponin (co-emulsifier) | 1.82 | Water | 0.61 |
| Pre-emulsion concentrate containing MCT oil (98% MCT) and TPGS (Table 6 above) | 60.01 | Oil | 20.00 |
| Totals | 300.00 | | 100.00 |

TABLE 26

Pre-spray emulsion containing MCT oil (98% MCT) and TPGS

| Ingredient | g/batch | Phase | wt % of composition |
|---|---|---|---|
| Water (polar solvent) | 170.62 | Water | 56.87 |
| KHCO$_3$ (stabilizer) | 10.00133 | Water | 3.33 |
| Whey protein (co-emulsifier) | 26.543539 | Water | 8.85 |
| SFAE (co-surfactant) | 24.8033 | Water | 8.27 |
| SALADIZER ® (emulsion stabilizer) | 0.20 | Water | 0.07 |
| Vitamin C (stabilizer) | 6.00 | Water | 2.00 |
| Saponin (co-emulsifier) | 1.82 | Water | 0.61 |
| Pre-emulsion concentrate containing MCT oil (98% MCT) and TPGS (Table 6 above) | 60.01 | Oil | 20.00 |
| Totals | 300.00 | | 100.00 |

TABLE 27

Pre-spray emulsion containing MCT oil (98% MCT) and TPGS

| Ingredient | g/batch | Phase | wt % of composition |
|---|---|---|---|
| Water (polar solvent) | 1437.166 | Water | 57.48 |
| KHCO$_3$ (stabilizer) | 83.333 | Water | 3.33 |
| Whey protein (co-emulsifier) | 221.166 | Water | 8.85 |
| SFAE (co-surfactant) | 206.666 | Water | 8.27 |
| SALADIZER ® (emulsion stabilizer) | 1.666 | Water | 0.07 |
| Vitamin C (stabilizer) | 50.00 | Water | 2.00 |
| Pre-emulsion concentrate containing MCT oil (98% MCT) and TPGS (Table 6 above) | 500.00 | Oil | 20.00 |
| Totals | 2500.00 | | 100.00 |

TABLE 28

Pre-spray emulsion containing resveratrol and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing resveratrol and TPGS (Table 7 above) | 83.34 | Oil | 16.67 |
| Totals | 500.00 | | 100.00 |

TABLE 29

Pre-spray emulsion containing vinpocetine and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |

TABLE 29-continued

Pre-spray emulsion containing vinpocetine and TPGS

| Ingredient | g/batch | Phase | wt % of composition |
|---|---|---|---|
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing vinpocetine and TPGS (Table 8 above) | 83.34 | Oil | 16.67 |
| Totals | 500.00 | | 100.00 |

TABLE 30

Pre-spray emulsion containing sesamin and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing sesamin and TPGS (Table 9 above) | 83.34 | Oil | 16.67 |
| Totals | 500.00 | | 100.00 |

TABLE 31

Pre-spray emulsion containing turmeric/curcumin (95% curcumin) and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing turmeric/curcumin (95% curcumin) and TPGS (Table 10 above) | 83.34 | Oil | 16.67 |
| Totals | 500.00 | | 100.00 |

TABLE 32

Pre-spray emulsion containing turmeric/curcumin (95% curcumin) and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing turmeric/curcumin (95% curcumin) and TPGS (Table 11 above) | 83.34 | Oil | 16.67 |
| Totals | 500.00 | | 100.00 |

TABLE 33

Pre-spray emulsion containing phosphatidylserine (40% phosphatidyl serine) and TPGS

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 64.508601 | Water | 12.90 |
| SFAE (co-surfactant) | 41.3388 | Water | 8.27 |
| SALADIZER ® (emulsion stabilizer) | 0.33 | Water | 0.07 |
| Saponin (co-emulsifier) | 3.03 | Water | 0.61 |
| Pre-emulsion concentrate containing phosphatidylserine (40% phosphatidylserine) and TPGS (Table 12 above) | 83.34 | Oil | 16.67 |
| Totals | 500.00 | | 100.00 |

TABLE 34

Pre-spray emulsion containing phosphatidylserine (40% phosphatidylserine), MCT oil (98% MCT), and TPGS

| Ingredient | g/batch | Phase | wt % of composition |
|---|---|---|---|
| Water (polar solvent) | 170.62 | Water | 56.87 |
| KHCO$_3$ (stabilizer) | 13.84 | Water | 4.61 |
| Maltodextrin (binder/carrier) | 38.71 | Water | 12.90 |
| SFAE (co-surfactant) | 24.80 | Water | 8.27 |
| SALADIZER ® (emulsion stabilizer) | 0.20 | Water | 0.07 |
| Saponin (co-emulsifier) | 1.82 | Water | 0.61 |

TABLE 34-continued

Pre-spray emulsion containing phosphatidylserine (40% phosphatidylserine), MCT oil (98% MCT), and TPGS

| Ingredient | g/batch | Phase | wt % of composition |
|---|---|---|---|
| Pre-emulsion concentrate containing phosphatidylserine (40% phosphatidylserine), MCT oil (98% MCT), and TPGS (Table 13 above) | 50.01 | Oil | 16.67 |
| Totals | 300.00 | | 100.00 |

TABLE 35

Pre-spray emulsion containing vitamin E acetate, TPGS, and benzyl alcohol

| Ingredient | g/batch | Phase | wt % of composition |
|---|---|---|---|
| Water (polar solvent) | 85.31 | Water | 56.87 |
| Maltodextrin (binder/carrier) | 23.273103 | Water | 15.51 |
| SFAE (co-surfactant) | 12.4017 | Water | 8.27 |
| SALADIZER ® (emulsion stabilizer) | 0.10 | Water | 0.07 |
| Vitamin C (stabilizer) | 3.00 | Water | 2.00 |
| Saponin (co-emulsifier) | 0.91 | Water | 0.61 |
| Pre-emulsion concentrate containing vitamin E acetate, TPGS, and benzyl alcohol (Table 14 above) | 25.00 | Oil | 16.67 |
| Totals | 150.00 | | 100.00 |

TABLE 36

Pre-spray emulsion containing alpha-lipoic acid, TPGS, and benzyl alcohol

| Ingredient | g/batch | Phase | wt % of composition |
|---|---|---|---|
| Water (polar solvent) | 284.33 | Water | 56.86 |
| KHCO$_3$ (stabilizer) | 23.06667 | Water | 4.61 |
| Maltodextrin (binder/carrier) | 87.900 | Water | 17.58 |
| SFAE (co-surfactant) | 41.3333 | Water | 8.27 |
| SALADIZER ® (emulsion stabilizer) | 0.33 | Water | 0.07 |
| Vitamin C (stabilizer) | 10.00 | Water | 2.00 |
| Saponin (co-emulsifier) | 3.03 | Water | 0.61 |
| Pre-emulsion concentrate containing alpha-lipoic acid, TPGS, and benzyl alcohol (Table 15 above) | 50.00 | Oil | 10.00 |
| Totals | 500.00 | | 100.000 |

TABLE 37

Pre-spray emulsion containing quercetin, TPGS, and benzyl alcohol

| Ingredient | g/batch | Phase | wt % of composition |
|---|---|---|---|
| Water (polar solvent) | 170.60 | Water | 56.86 |
| Citric acid (pH adjuster) | 0.4000 | Water | 0.13 |
| Maltodextrin (binder/carrier) | 54.20 | Water | 18.07 |
| SFAE (co-surfactant) | 24.80 | Water | 8.27 |
| Pre-emulsion concentrate containing quercetin, TPGS, and benzyl alcohol (Table 16 above) | 50.00 | Oil | 16.67 |
| Totals | 300.00 | | 100.00 |

TABLE 38

Pre-spray emulsion containing PQQ, TPGS, and benzyl alcohol

| Ingredient | g/batch | Phase | wt % of composition |
|---|---|---|---|
| Water (polar solvent) | 85.3 | Water | 56.86 |
| Citric acid (pH adjuster) | 0.20 | Water | 0.13 |
| Maltodextrin (binder/carrier) | 27.1 | Water | 18.07 |
| SFAE (co-surfactant) | 12.400 | Water | 8.27 |
| Pre-emulsion concentrate containing PQQ, TPGS, and benzyl alcohol (Table 17 above) | 25.0 | Oil | 16.67 |
| Totals | 150.00 | | 100.00 |

TABLE 39

Pre-spray emulsion containing fish oil (50% DHA/EPA), flaxseed oil (50% ALA), TPGS, and benzyl alcohol

| Ingredient | g/batch | Phase | wt % of composition |
|---|---|---|---|
| Water (polar solvent) | 284.37 | Water | 56.87 |
| KHCO$_3$ (stabilizer) | 23.06974 | Water | 4.61 |
| Maltodextrin (binder/carrier) | 54.507268 | Water | 10.90 |
| SFAE (co-surfactant) | 41.3388 | Water | 8.27 |
| SALADIZER ® (emulsion stabilizer) | 0.33 | Water | 0.07 |
| Vitamin C (stabilizer) | 10.00 | Water | 2.00 |
| Saponin (co-emulsifier) | 3.03 | Water | 0.61 |
| Pre-emulsion concentrate containing fish oil (50% DHA/EPA), flaxseed oil (50% ALA), TPGS, and benzyl alcohol (Table 18 above) | 83.34 | Oil | 16.67 |
| Totals | 500.00 | | 100.00 |

The pre-spray emulsions of Tables 18-36, above, contained between 5.25% and 19.49% by weight non-polar compound(s), as shown in Table 37, below.

TABLE 40

Amount of non-polar compound(s) in pre-spray emulsions

| Non-polar compound | wt % of pre-emulsion concentrate in pre-spray emulsion | wt % of non-polar compound in pre-spray emulsion |
|---|---|---|
| Fish oil (Table 19 above) | 16.67 | 6.58 |
| Algal oil (Table 20 above) | 20.00 | 16.80 |
| Algal oil (Table 21 above) | 20.00 | 19.47 |
| CLA oil (Table 22 above) | 20.00 | 19.49 |
| CLA oil (Table 23 above) | 20.00 | 19.49 |
| MCT oil (Table 24 above) | 20.00 | 19.48 |
| MCT oil (Table 25 above) | 20.00 | 19.48 |
| MCT oil (Table 26 above) | 20.00 | 19.48 |
| MCT oil (Table 27 above) | 20.00 | 19.48 |
| Resveratrol (Table 28 above) | 16.67 | 5.83 |
| Vinpocetine (Table 29 above) | 16.67 | 5.83 |
| Sesamin (Table 30 above) | 16.67 | 5.83 |
| Turmeric/curcumin (Table 31 above) | 16.67 | 5.25 |
| Turmeric/curcumin (Table 32 above) | 16.67 | 6.18 |
| Phosphatidylserine (Table 33 above) | 16.67 | 11.40 |
| Phosphatidylserine/ MCT oil (Table 34 above) | 16.67 | 14.39 |
| Vitamin E acetate (Table 35 above) | 16.67 | 15.91 |
| Alpha-lipoic acid (Table 36 above) | 10.00 | 7.00 |
| Quercetin (Table 37 above) | 16.67 | 5.83 |
| PQQ (Table 38 above) | 16.67 | 5.83 |
| Fish oil/flaxseed oil (Table 39 above) | 16.67 | 13.24 |

Example 4

Preparation of Dry Powders Containing TPGS and Non-Polar Compounds

The pre-spray emulsions described above in Example 3 and indicated in Tables 19-39 were then spray dried into dry powders. The final dry powders contained between 12.18% and 45.83% non-polar compound, as summarized in Table 62 below, and were prepared according to the following procedure. Tables 41-61 below indicate the percentage by weight (wt %) of each ingredient per batch of the final dry powder after spray drying the pre-spray emulsions.

The dry powders were prepared using a standard spray dryer equipped with a rotary atomizer nozzle or a standard spray nozzle. Alternatively, a fluid bed dryer can be used. A pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature of 180° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g of powder was dissolved in 100 g of water) and spray drying a second time. The powders then were sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion.

TABLE 41

Dry powder containing fish oil (50% DHA/EPA) and TPGS

| Ingredient | wt % of composition |
|---|---|
| KHCO$_3$ (stabilizer) | 10.62 |
| Maltodextrin (binder/carrier) | 25.85 |
| SFAE (co-surfactant) | 19.02 |
| SALADIZER ® (emulsion stabilizer) | 0.15 |
| Vitamin C (stabilizer) | 4.60 |
| Saponin (co-emulsifier) | 1.40 |
| Pre-emulsion concentrate containing fish oil (50% DHA/EPA) and TPGS (Table 2 above) | 38.36 |
| Total | 100.00 |

TABLE 42

Dry powder containing algal oil (40% DHA) and TPGS

| Ingredient | wt % of composition |
|---|---|
| KHCO$_3$ (stabilizer) | 10.70 |
| Maltodextrin (binder/carrier) | 21.41 |
| SFAE (co-surfactant) | 15.31 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing algal oil (40% DHA) and TPGS (Table 3 above) | 46.38 |
| Total | 100.00 |

TABLE 43

Dry powder containing algal oil (35% DHA) and TPGS

| Ingredient | wt % of composition |
|---|---|
| KHCO$_3$ (stabilizer) | 7.73 |
| Green tea extract (40% EGCG) (stabilizer) | 20.52 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing algal oil (35% DHA) and TPGS (Table 4 above) | 46.38 |
| Total | 100.00 |

TABLE 44

Dry powder containing CLA oil (79.6% CLA) and TPGS

| Ingredient | wt % of composition |
|---|---|
| KHCO$_3$ (stabilizer) | 7.73 |
| Fish collagen (binder) | 20.52 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing CLA oil (79.6% CLA) and TPGS (Table 5 above) | 46.38 |
| Total | 100.00 |

TABLE 45

Dry powder containing CLA oil (79.6% CLA) and TPGS

| Ingredient | wt % of composition |
|---|---|
| KHCO$_3$ (stabilizer) | 7.85 |
| Whey protein (co-emulsifier) | 20.81 |
| SFAE (co-surfactant) | 19.44 |
| SALADIZER ® (emulsion stabilizer) | 0.16 |
| Vitamin C (stabilizer) | 4.70 |
| Pre-emulsion concentrate containing CLA oil (79.6% CLA) and TPGS (Table 5 above) | 47.04 |
| Total | 100.00 |

TABLE 46

Dry powder containing MCT oil (98% MCT) and TPGS

| Ingredient | wt % of composition |
|---|---|
| KHCO$_3$ (stabilizer) | 7.73 |
| Green tea extract (40% EGCG) (stabilizer) | 20.52 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing MCT oil (98% MCT) and TPGS (Table 6 above) | 46.38 |
| Total | 100.00 |

TABLE 47

Dry powder containing MCT oil (98% MCT) and TPGS

| Ingredient | wt % of composition |
|---|---|
| KHCO$_3$ (stabilizer) | 7.73 |
| Fish collagen (binder) | 20.52 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing MCT oil (98% MCT) and TPGS (Table 6 above) | 46.38 |
| Total | 100.00 |

TABLE 48

Dry powder containing MCT oil (98% MCT) and TPGS

| Ingredient | wt % of composition |
|---|---|
| KHCO$_3$ (stabilizer) | 7.73 |
| Whey protein (co-emulsifier) | 20.52 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing MCT oil (98% MCT) and TPGS (Table 6 above) | 46.38 |
| Total | 100.00 |

TABLE 49

Dry powder containing MCT oil (98% MCT) and TPGS

| Ingredient | wt % of composition |
|---|---|
| KHCO$_3$ (stabilizer) | 7.84 |
| Whey protein (co-emulsifier) | 20.81 |
| SFAE (co-surfactant) | 19.45 |
| SALADIZER ® (emulsion stabilizer) | 0.16 |
| Vitamin C (stabilizer) | 4.70 |
| Pre-emulsion concentrate containing MCT oil (98% MCT) and TPGS (Table 6 above) | 47.04 |
| Total | 100.00 |

TABLE 50

Dry powder containing resveratrol and TPGS

| Ingredient | wt % of composition |
|---|---|
| KHCO$_3$ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing resveratrol and TPGS (Table 7 above) | 38.65 |
| Total | 100.00 |

TABLE 51

Dry powder containing vinpocetine and TPGS

| Ingredient | wt % of composition |
|---|---|
| KHCO$_3$ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing vinpocetine and TPGS (Table 8 above) | 38.65 |
| Total | 100.00 |

TABLE 52

Dry powder containing sesamin and TPGS

| Ingredient | wt % of composition |
|---|---|
| KHCO₃ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing sesamin and TPGS (Table 9 above) | 38.65 |
| Total | 100.00 |

TABLE 53

Dry powder containing turmeric/curcumin (95% curcumin) and TPGS

| Ingredient | wt % of composition |
|---|---|
| KHCO₃ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing turmeric/curcumin (95% curcumin) and TPGS (Table 10 above) | 38.65 |
| Total | 100.00 |

TABLE 54

Dry powder containing turmeric/curcumin (95% curcumin) and TPGS

| Ingredient | wt % of composition |
|---|---|
| KHCO₃ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing turmeric/curcumin (95% curcumin) and TPGS (Table 11 above) | 38.65 |
| Total | 100.00 |

TABLE 55

Dry powder containing phosphatidylserine (40% phosphatidyl serine) and TPGS

| Ingredient | wt % of composition |
|---|---|
| KHCO₃ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing phosphatidylserine (40% PS) and TPGS (Table 12 above) | 38.65 |
| Total | 100.00 |

TABLE 56

Dry powder containing phosphatidylserine (40% phosphatidylserine), MCT oil (98% MCT), and TPGS

| Ingredient | wt % of composition |
|---|---|
| KHCO₃ (stabilizer) | 10.70 |
| Maltodextrin (binder/carrier) | 29.92 |
| SFAE (co-surfactant) | 19.17 |
| SALADIZER ® (emulsion stabilizer) | 0.15 |
| Saponin (co-emulsifier) | 1.41 |
| Pre-emulsion concentrate containing phosphatidylserine (40% PS), MCT oil (98% MCT) and TPGS (Table 13 above) | 38.65 |
| Total | 100.00 |

TABLE 57

Dry powder containing vitamin E acetate, TPGS, and benzyl alcohol

| Ingredient | wt % of composition |
|---|---|
| Maltodextrin (binder/carrier) | 35.98 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing vitamin E acetate, TPGS, and benzyl alcohol (Table 14 above) | 38.65 |
| Total | 100.00 |

TABLE 58

Dry powder containing alpha-lipoic acid, TPGS, and benzyl alcohol

| Ingredient | wt % of composition |
|---|---|
| KHCO₃ (stabilizer) | 10.70 |
| Maltodextrin (binder/carrier) | 40.76 |
| SFAE (co-surfactant) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing alpha-lipoic acid, TPGS, and benzyl alcohol (Table 15 above) | 23.18 |
| Total | 100.00 |

TABLE 59

Dry powder containing quercetin, TPGS, and benzyl alcohol

| Ingredient | wt % of composition |
|---|---|
| Citric acid (pH adjuster) | 0.31 |
| Maltodextrin (binder/carrier) | 41.89 |
| SFAE (co-surfactant) | 19.17 |
| Pre-emulsion concentrate containing quercetin, TPGS, and benzyl alcohol (Table 16 above) | 38.64 |
| Total | 100.00 |

TABLE 60

Dry powder containing PQQ, TPGS, and benzyl alcohol

| Ingredient | wt % of composition |
|---|---|
| Citric acid (pH adjuster) | 0.31 |
| Maltodextrin (binder/carrier) | 41.89 |
| SFAE (co-surfactant) | 19.17 |
| Pre-emulsion concentrate containing PQQ, TPGS, and benzyl alcohol (Table 17 above) | 38.64 |
| Total | 100.00 |

TABLE 61

Dry powder containing fish oil (50% DHA/EPA), flaxseed oil (50% ALA), TPGS, and benzyl alcohol

| Ingredient | wt % of composition |
|---|---|
| KHCO$_3$ (stabilizer) | 10.62 |
| Maltodextrin (binder/carrier) | 25.85 |
| SFAE (co-surfactant) | 19.02 |
| SALADIZER ® (emulsion stabilizer) | 0.15 |
| Vitamin C (stabilizer) | 4.60 |
| Saponin (co-emulsifier) | 1.40 |
| Pre-emulsion concentrate containing fish oil (50% DHA/EPA), flaxseed oil (50% ALA), TPGS, and benzyl alcohol (Table 18 above) | 38.36 |
| Total | 100.00 |

The dry powders depicted above in Tables 41-61 that contained the pre-emulsion concentrates described in Example 2 contained between 12.18% and 45.83% by weight non-polar compound(s), as shown in Table 62, below.

TABLE 62

Amount of non-polar compound(s) in dry powders

| Non-polar compound | wt % of pre-emulsion concentrate in dry powder | wt % of non-polar compound in dry powder |
|---|---|---|
| Fish oil (Table 41 above) | 38.36 | 15.15 |
| Algal oil (Table 42 above) | 46.38 | 38.96 |
| Algal oil (Table 43 above) | 46.38 | 45.15 |
| CLA oil (Table 44 above) | 46.38 | 45.19 |
| CLA oil (Table 45 above) | 47.04 | 45.83 |
| MCT oil (Table 46 above) | 46.38 | 45.18 |
| MCT oil (Table 47 above) | 46.38 | 45.18 |
| MCT oil (Table 48 above) | 46.38 | 45.18 |
| MCT oil (Table 49 above) | 47.04 | 45.83 |
| Resveratrol (Table 50 above) | 38.65 | 13.53 |
| Vinpocetine (Table 51 above) | 38.65 | 13.53 |
| Sesamin (Table 52 above) | 38.65 | 13.53 |
| Turmeric/curcumin (Table 53 above) | 38.65 | 12.18 |
| Turmeric/curcumin (Table 54 above) | 38.65 | 14.34 |
| Phosphatidylserine (Table 55 above) | 38.65 | 26.44 |
| Phosphatidylserine/MCT oil (Table 56 above) | 38.65 | 33.35 |
| Vitamin E acetate (Table 57 above) | 38.65 | 36.88 |
| Alpha-lipoic acid (Table 58 above) | 23.18 | 16.23 |
| Quercetin (Table 59 above) | 38.64 | 13.52 |
| PQQ (Table 60 above) | 38.64 | 13.52 |
| Fish oil/flaxseed oil (Table 61 above) | 38.36 | 30.46 |

Example 5

Preparation of Another Dry Powder Containing Non-Polar Compounds

A. Preparation of the Pre-Emulsion Concentrate

A pre-emulsion concentrate was prepared according to the method described above in Example 2 using the ingredients detailed in Table 63, below. The pre-emulsion concentrate contained benzyl alcohol, a natural preservative, and 99.5% by weight (of the concentrate) of fish oil, a non-polar compound which contains 50% of the non-polar ingredients DHA/EPA (sold as VivoMega 3322 TG by GC Rieber Oils, Kristiansund, Norway).

The pre-emulsion concentrate set forth in Table 63, below, was made using a bench-top process according to the provided methods (see Example 2). The pre-emulsion concentrate can alternatively be made by scaling up the bench-top process, using a scaled-up manufacturing process of the provided methods, for example, to make larger batch sizes of the pre-emulsion concentrate.

TABLE 63

Pre-emulsion concentrate containing fish oil (50% DHA/EPA) and benzyl alcohol

| Ingredient | wt % of composition |
| --- | --- |
| Benzyl alcohol | 0.5 |
| Fish oil (50% DHA/EPA blend)* (non-polar ingredient) | 99.5 |
| Total | 100.00 |

B. Preparation of the Pre-Spray Emulsion

The pre-emulsion concentrate described above and shown in Table 63 was used in the preparation of a pre-spray emulsion. The pre-spray emulsion was prepared by combining the pre-emulsion concentrate that contained 99.5% of the non-polar compound fish oil (50% DHA/EPA blend), described in Table 63, above, with the ingredients detailed in Table 64, below, according to the general procedure described above in Example 3. The resulting pre-spray emulsion thus contained 16.669% by weight pre-emulsion concentrate containing 99.5% of the non-polar compound fish oil (i.e., the resulting pre-spray emulsion contained a total of 16.59% by weight non-polar compound).

The ingredients in the pre-spray emulsion included the pre-emulsion concentrate containing the non-polar compound fish oil, prepared as described above (see Table 63); a surfactant, a sucrose fatty acid ester (SFAE; sold under the trade name DK Ester®, produced by Dai-Ichi Kogyo Seiyaku Co., Ltd of Japan); an emulsion stabilizer that was a blend of xanthan gum, guar gum and sodium alginate, sold under the product name SALADIZER®, available from TIC Gums, Inc. (Belcamp, Md.); the binder maltodextrin (sold by Archer Daniels Midland Company, Decatur, Ill.); stabilizers, including vitamin C (sold by Pure Assay Ingredients, Walnut, Calif.) and potassium bicarbonate; a co-emulsifier that was saponin from quillaja bark (sold by Desert King, San Diego, Calif., and Sigma Aldrich, St. Louis, Mo.); and a polar solvent, water, which was purified city water, purified as described above (see Example 3). Before adding to the appropriate phase, as described above, the correct amount of each ingredient (as indicated in Table 64) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Table 64, below, indicates the amount (g) of each ingredient per batch of the pre-spray emulsion, the phase each ingredient was added, and the percentage by weight (wt %) of each ingredient.

TABLE 64

Pre-spray emulsion containing fish oil (50% DHA/EPA), benzyl alcohol, and SFAE

| Ingredient | g/batch | Phase | wt % of composition |
| --- | --- | --- | --- |
| Water (polar solvent) | 284.37 | Water | 56.874 |
| KHCO$_3$ (stabilizer) | 23.06974 | Water | 4.614 |
| Maltodextrin (binder/carrier) | 54.507268 | Water | 10.901 |
| SFAE (co-surfactant) | 41.3388 | Water | 8.268 |
| SALADIZER ® emulsifier (emulsion stabilizer) | 0.33 | Water | 0.067 |
| Vitamin C (stabilizer) | 10.00 | Water | 2.000 |
| Saponin (co-emulsifier) | 3.03 | Water | 0.607 |
| Pre-emulsion concentrate containing fish oil (50% DHA/EPA) and benzyl alcohol (Table 63 above) | 83.34 | Oil | 16.669 |
| Totals | 500.00 | | 100.000 |

C. Preparation of the Dry Powder

The pre-spray emulsion described above and indicated in Table 64 was then spray dried into a dry powder according to the procedure detailed in Example 4. The addition of extra water (i.e., evaporation water) to the pre-spray emulsion was required as a processing aid to make the emulsion thinner and able to pass through the dryer pump more easily. The extra water was added to the pre-spray emulsion at 35° C. and was evaporated during the spray dry process, along with the rest of the water in the pre-spray emulsion.

The final dry powder contained 38.36% of the pre-emulsion concentrate containing 99.5% fish oil (i.e., 38.17% non-polar compound). Table 65, below, indicates the percentage by weight (wt %) of each ingredient per batch of the final dry powder after spray drying the pre-spray emulsion.

TABLE 65

Dry powder containing fish oil (50% DHA/EPA), benzyl alcohol, and SFAE

| Ingredient | wt % of composition |
| --- | --- |
| KHCO$_3$ (stabilizer) | 10.62 |
| Maltodextrin (binder/carrier) | 25.85 |
| SFAE (co-surfactant) | 19.02 |
| SALADIZER ® (emulsion stabilizer) | 0.15 |
| Vitamin C (stabilizer) | 4.60 |
| Saponin (co-emulsifier) | 1.40 |
| Pre-emulsion concentrate containing fish oil (50% DHA/EPA) and benzyl alcohol (Table 63 above) | 38.36 |
| Total | 100.00 |

The final dry powder thus contained 38.17% of the non-polar compound fish oil.

Example 6

Comparison Example of Preparation of Dry Powders Containing Non-Polar Compounds and No Sucrose Fatty Acid Ester This example is provided to show that addition of a sucrose (or other sugar) fatty acid ester in place of maltodextrin or other such binder in a pre-spray emulsion permits production of powders with a higher concentration of non-polar compounds. In order to produce powders for spray drying, it is necessary to include a threshold amount of solids for forming the powder. To achieve this, the TPGS is reduced in amount, and SFAE is added in its place. In the absence of the added SFAE, the emulsions, and particularly the emulsions with higher amounts of non-polar compound, when dried, do not form dry free-flowing powders, but are sludge-like and oily and have too high a moisture content.

A series of pre-emulsion concentrates containing increasing concentrations of non-polar compound, as set forth in Tables 66-69, were prepared and used to prepare pre-spray emulsions that contained a binder (maltodextrin), but no SFAE. Preparation of dry powders from each pre-spray emulsion was attempted. If successful, the resulting dry powders would have contained 5.5%, 11.62%, 27.5% and 45.18% non-polar compound. As shown below, it was possible to produce dry powders that contained less than about 15% (5.5%, 11.62%) non-polar compound, but it was not possible to produce dry powders from the pre-spray emulsions containing the pre-emulsion concentrates with the highest amount of non-polar compounds, and powders with the lower amounts (between about 15%-30%) exhibited undesirable properties. A dry powder could not be produced from the pre-spray emulsion with the highest concentration of non-polar compound (45.18%) and no SFAE. For all concentrations of non-polar compounds, the presence of SFAE in place of a binder, such as maltodextrin, in the pre-spray emulsions improved the properties of the resulting powders, and permitted preparation of powders with very high concentrations (above 30%, 35%, or 40%) of non-polar compounds.

A. Preparation of the Pre-Emulsion Concentrates

Pre-emulsion concentrates were prepared according to the bench-top process described in Example 2, above, with the ingredients detailed in Tables 66-69, below. The pre-emulsion concentrates contained between 16.84% and 97.42% by weight (of the concentrate) of a non-polar compound, with the remainder of the concentrate containing TPGS or TPGS and benzyl alcohol. The non-polar compounds included a conjugated linoleic acid (CLA) that contains 70% CLA (Clarinol® CLA, sold by Stepan Lipid Nutrition, Maywood, N.J.); a coenzyme Q10 (coQ10) compound that contains greater than 98% ubidicarenone (ubiquinone), sold under the name Kaneka Q10™ (USP Ubidicarenone; Kaneka Nutrients, L.P., Pasadena, Tex.); and an algal oil that contains 35% of the non-polar ingredient DHA and contains 350 mg DHA/g oil (life's DHA™ S35-0300, sold by DSM Nutritional Products Inc., Kaiseraugst, Switzerland).

TABLE 66

Pre-emulsion concentrate containing coQ10, TPGS, and benzyl alcohol

| Ingredient | wt % of composition |
|---|---|
| TPGS | 82.66 |
| Benzyl alcohol (preservative) | 0.50 |
| CoQ10 (non-polar ingredient) | 16.84 |
| Total | 100.00 |

TABLE 67

Pre-emulsion concentrate containing coQ10, TPGS, and benzyl alcohol

| Ingredient | wt % of composition |
|---|---|
| TPGS | 65.82 |
| Benzyl alcohol (preservative) | 0.50 |
| CoQ10 (non-polar ingredient) | 33.68 |
| Total | 100.00 |

TABLE 68

Pre-emulsion concentrate containing CLA oil (70% CLA) and TPGS

| Ingredient | wt % of composition |
|---|---|
| TPGS | 16.58 |
| CLA oil (70% CLA) (non-polar ingredient) | 83.42 |
| Total | 100.00 |

TABLE 69

Pre-emulsion concentrate containing the non-polar compound algal oil (35% DHA) and TPGS

| Ingredient | wt % of composition |
|---|---|
| TPGS | 2.58 |
| Algal oil (35% DHA) (non-polar ingredient) | 97.42 |
| Total | 100.00 |

B. Preparation of the Pre-Spray Emulsions

Pre-spray emulsions were prepared from the pre-emulsion concentrates of Tables 66-69, above, by combining the pre-emulsion concentrate with the ingredients detailed in Tables 70-73, below, according to the general procedure described above in Example 3. The pre-spray emulsions contained between about 14.21% and 20.003% of a pre-emulsion concentrate, resulting in pre-spray emulsions that contained between 2.39% and 19.48% non-polar compound. None of the pre-spray emulsions contained SFAE.

In addition to the pre-emulsion concentrates prepared as described above (see Tables 66-69), the pre-spray emulsions also contained: maltodextrin (sold by Archer Daniels Midland Company, Decatur, Ill.); the emulsion stabilizer SALADIZER® (TIC Gums, Inc.; Belcamp, Md.); stabilizers, including vitamin C (Pure Assay Ingredients, Walnut, Calif.), potassium bicarbonate (Armand Products, Princeton, N.J.), and a green tea extract that contains 40% EGCG (epigallocatechin gallate) (Guilin Layn Natural Ingredients Corp., Guilin, China); a co-emulsifier, saponin from quillaja bark (sold by Desert King and Sigma Aldrich, St. Louis, Mo.); citric acid, a pH adjuster; and a polar solvent, water, which was purified city water, purified as described above.

Before adding to the appropriate phase, as described above in Example 2, the correct amount of each ingredient (as indicated in Tables 70-73) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Tables 70-73 set forth the ingredients included in each pre-spray emulsion, the amount (g) of each ingredient per batch of the pre-spray emulsion, the phase to which each ingredient was added, and the percentage by weight (wt %) of each ingredient.

TABLE 70

Pre-spray emulsion containing coQ10, TPGS, and benzyl alcohol and maltodextrin in place of SFAE

| Ingredient | g/batch | Phase | wt % of composition |
|---|---|---|---|
| Water (polar solvent) | 23051.31282 | Water | 56.86 |
| Citric acid (pH adjuster) | 54.05 | Water | 0.13 |
| Maltodextrin (binder/carrier) | 11578.4 | Water | 28.56 |
| SALADIZER ® (emulsion stabilizer) | 96.4750 | Water | 0.24 |
| Pre-emulsion concentrate containing coQ10, TPGS, and benzyl alcohol (Table 66 above) | 5761.5 | Oil | 14.21 |
| Totals | 40541.67 | | 100.000 |

TABLE 71

Pre-spray emulsion containing coQ10, TPGS, and benzyl alcohol and maltodextrin in place of SFAE

| Ingredient | g/batch | Phase | wt % of composition |
|---|---|---|---|
| Water (polar solvent) | 23051.31282 | Water | 56.86 |
| Citric acid (pH adjuster) | 54.05 | Water | 0.13 |
| Maltodextrin (binder/carrier) | 11578.4 | Water | 28.56 |
| SALADIZER ® (emulsion stabilizer) | 96.4750 | Water | 0.24 |
| Pre-emulsion concentrate containing coQ10, TPGS, and benzyl alcohol (Table 67 above) | 5761.5 | Oil | 14.21 |
| Totals | 40541.67 | | 100.000 |

TABLE 72

Pre-spray emulsion containing CLA oil (70% CLA) and TPGS and maltodextrin in place of SFAE

| Ingredient | g/batch | Phase | wt % of composition |
|---|---|---|---|
| Water (polar solvent) | 284.38 | Water | 56.876 |
| Citric acid (pH adjuster) | 0.6668 | Water | 0.133 |
| Maltodextrin (binder/carrier) | 142.69 | Water | 28.538 |
| SALADIZER ® (emulsion stabilizer) | 1.18 | Water | 0.237 |
| Pre-emulsion concentrate containing CLA oil (70% CLA) and TPGS (Table 68 above) | 71.08 | Oil | 14.216 |
| Totals | 500.00 | | 100.000 |

TABLE 73

Pre-spray emulsion containing algal oil (35% DHA) and TPGS and maltodextrin in place of SFAE

| Ingredient | g/batch | Phase | wt % of composition |
|---|---|---|---|
| Water (polar solvent) | 284.3712 | Water | 56.874 |
| $KHCO_3$ (stabilizer) | 16.6689 | Water | 3.334 |
| Green tea extract (40% EGCG) (stabilizer) | 44.2392 | Water | 8.848 |
| Maltodextrin (binder/carrier) | 41.3388 | Water | 8.268 |
| SALADIZER ® (emulsion stabilizer) | 0.333378 | Water | 0.067 |
| Vitamin C (stabilizer) | 10.001 | Water | 2.000 |
| Saponin (co-emulsifier) | 3.03373 | Water | 0.607 |
| Pre-emulsion concentrate containing algal oil (35% DHA) and TPGS (Table 69 above) | 100.0134 | Oil | 20.003 |
| Totals | 500.00 | | 100.000 |

C. Attempted Preparation of Dry Powders

Preparation of a dry powder was attempted from each of the pre-spray emulsions that contained a binder (maltodextrin) in place of sucrose fatty acid esters (described above and in Tables 70-73) according to the procedure detailed in Example 4, above. The final compositions contained between 32.94% and 46.38% of a pre-emulsion concentrate, resulting in final compositions that contained between 5.5% and 45.18% non-polar compound. A dry powder was not formed from the composition that contained the highest amount of non-polar compound (45.18%) and no SFAE (see Table 77). Dry powders were formed from the compositions containing lower amounts of non-polar compound (see Tables 74-76).

Tables 74-77, below, indicate the percentage by weight (wt %) of each ingredient per batch of the composition after attempting to spray dry the pre-spray emulsion.

TABLE 74

Dry powder containing coQ10, TPGS, and benzyl alcohol and maltodextrin inplace of SFAE

| Ingredient | wt % of composition |
|---|---|
| Citric acid (pH adjuster) | 0.31 |
| Maltodextrin (binder/carrier) | 66.20 |
| SALADIZER ® (emulsion stabilizer) | 0.55 |
| Pre-emulsion concentrate containing coQ10, TPGS, and benzyl alcohol (Table 66 above) | 32.94 |
| Total | 100.00 |

TABLE 75

Dry powder containing coQ10, TPGS, and benzyl alcohol and maltodextrin in place of SFAE

| Ingredient | wt % of composition |
|---|---|
| Citric acid (pH adjuster) | 0.31 |
| Maltodextrin (binder/carrier) | 64.66 |
| SALADIZER ® (emulsion stabilizer) | 0.55 |
| Pre-emulsion concentrate containing coQ10, TPGS, and benzyl alcohol (Table 67 above) | 34.49 |
| Total | 100.00 |

TABLE 76

Dry powder containing CLA oil (70% CLA) and TPGS and maltodextrin in place of SFAE

| Ingredient | wt % of composition |
|---|---|
| Citric acid (pH adjuster) | 0.31 |
| Maltodextrin (binder/carrier) | 66.18 |
| SALADIZER ® (emulsion stabilizer) | 0.55 |
| Pre-emulsion concentrate containing CLA oil (70% CLA) and TPGS (Table 68 above) | 32.96 |
| Total | 100.00 |

TABLE 77

Attempted dry powder containing algal oil (35% DHA) and TPGS and maltodextrin in place of SFAE

| Ingredient | wt % of composition |
|---|---|
| KHCO$_3$ (stabilizer) | 7.73 |
| Green tea extract (40% EGCG) (stabilizer) | 20.52 |
| Maltodextrin (binder/carrier) | 19.17 |
| SALADIZER ® (emulsion stabilizer) | 0.15 |
| Vitamin C (stabilizer) | 4.64 |
| Saponin (co-emulsifier) | 1.41 |
| Pre-emulsion concentrate containing algal oil (35% DHA) and TPGS (Table 69 above) | 46.38 |
| Total | 100.00 |

Example 7

Preparation and Comparison of Dry Powders Containing Non-Polar Compounds and TPGS with and without Sucrose Fatty Acid Esters Two dry powders were prepared from pre-spray emulsions that each contained a pre-emulsion concentrate containing the non-polar compound fish oil (50% DHA/EPA blend), TPGS and benzyl alcohol. One powder contained the binder maltodextrin, while the other contained maltodextrin and SFAE in place of some of the maltodextrin.

Table 78, below, lists the ingredients used in each pre-emulsion concentrate, prepared according to the general procedure described in Example 2, above. The pre-emulsion concentrates contained either 40.025% (Composition 12A) or 79.42% (Composition 13A) of the non-polar compound fish oil that contains 50% of the non-polar ingredients DHA/EPA (sold as VivoMega 3322 TG by GC Rieber Oils, Kristiansund, Norway).

TABLE 78

Preparation of two pre-emulsion concentrates containing fish oil (50% DHA/EPA) and TPGS

| Ingredient | wt % of Composition 12A | wt % of Composition 13A |
|---|---|---|
| TPGS | 59.475 | 20.08 |
| Benzyl alcohol (preservative) | 0.50 | 0.50 |
| Fish oil (50% DHA/EPA) (non-polar ingredient) | 40.025 | 79.42 |
| Total | 100.00 | 100.00 |

Compositions 12A and 13A (Table 78) were used to prepare pre-spray emulsions 12B and 13B, respectively, with the ingredients detailed in Table 79, below, according to the general procedure described above in Example 3. Composition 12B, which contained maltodextrin and no SFAE, contained 14.21% of the pre-emulsion concentrate 12A containing 40.025% fish oil (i.e., 5.69% non-polar compound). Composition 13B, which contained SFAE in place of some of the maltodextrin, contained 16.67% of the pre-emulsion concentrate 13A containing 79.42% fish oil (i.e., 13.24% non-polar compound).

TABLE 79

Pre-spray emulsions containing fish oil (50% DHA/EPA) and TPGS, with and without SFAE

| Ingredient | wt % of Composition 12B | wt % of Composition 13B |
|---|---|---|
| Water (polar solvent) | 56.86 | 56.87 |
| Citric acid (pH adjuster) | 0.13 | — |
| Maltodextrin (binder/carrier) | 28.80 | 10.90 |
| KHCO$_3$ (stabilizer) | — | 4.61 |
| SFAE (co-surfactant) | — | 8.27 |
| SALADIZER ® (emulsion stabilizer) | — | 0.07 |
| Vitamin C (stabilizer) | — | 2.00 |

TABLE 79-continued

Pre-spray emulsions containing fish oil
(50% DHA/EPA) and TPGS, with and without SFAE

| Ingredient | wt % of Composition 12B | wt % of Composition 13B |
|---|---|---|
| Saponin (co-emulsifier) | — | 0.61 |
| Pre-emulsion concentrate containing fish oil (50% DHA/EPA) and TPGS (Table 78 above) | 14.21 | 16.67 |
| Total | 100.00 | 100.00 |

The pre-spray emulsions described above in Table 79 (Compositions 12B and 13B) were then spray dried into dry powders 12C and 13C, respectively, according to the general procedure described above in Example 4. Final dry powder 12C, which contained maltodextrin and no SFAE, contained 32.94% of the pre-emulsion concentrate 12A containing 40.025% fish oil (i.e., 13.18% non-polar compound). Composition 13C, which contained SFAE in place of some of the maltodextrin, contained 38.36% of the pre-emulsion concentrate 13A containing 79.42% fish oil (i.e., 30.47% non-polar compound). Table 80, below, indicates the percentage by weight (wt %) of each ingredient per batch of the final dry powders after spray drying the pre-spray emulsions.

TABLE 80

Dry powders containing fish oil (50% DHA/EPA), with and without SFAE

| Ingredient | wt % of Composition 12C | wt % of Composition 13C |
|---|---|---|
| Citric acid (pH adjuster) | 0.31 | — |
| Maltodextrin (binder/carrier) | 66.75 | 25.85 |
| KHCO$_3$ (stabilizer) | — | 10.62 |
| SFAE (co-surfactant) | — | 19.02 |
| SALADIZER ® (emulsion stabilizer) | — | 0.15 |
| Vitamin C (stabilizer) | — | 4.60 |
| Saponin (co-emulsifier) | — | 1.40 |
| Pre-emulsion concentrate containing fish oil (50% DHA/EPA) and TPGS (Table 78 above) | 32.94 | 38.36 |
| Total | 100.00 | 100.00 |

The composition containing SFAE in place of some of the maltodextrin (Composition 13C) formed a more free-flowing dry powder and was able to incorporate a higher amount of non-polar compound (i.e., 30.47% vs. 13.18%) than the composition that did not contain SFAE, but contained maltodextrin (Composition 12C).

Example 8

Preparation and Comparison of Dry Powders Containing Non-Polar Compounds and TPGS with and without Sucrose Fatty Acid Esters This example is provided to show that addition of a sucrose (or other sugar) fatty acid ester in place of maltodextrin or other such binder in a pre-spray emulsion permits production of powders with a higher concentration of non-polar compounds. Pre-emulsion concentrates were prepared containing non-polar compounds, TPGS, and sucrose fatty acid ester. Pre-spray emulsions that contained SFAE were prepared from the pre-emulsion concentrates. Comparative pre-emulsion concentrates were used to prepare comparative pre-spray emulsions in which the sucrose fatty acid ester was omitted. Preparation of dry powders from each was attempted. Dry powders could not be produced from the compositions containing maltodextrin in place of sucrose fatty acid ester (i.e., compositions not containing any sucrose fatty acid ester). Thus, the presence of SFAE in place of a binder, such as maltodextrin, in the pre-spray emulsions improves the properties of the resulting powders, and permits preparation of powders with high concentrations (above 30%, 35%, or 40%) of non-polar compounds.

A. Preparation of the Pre-Emulsion Concentrates

Pre-emulsion concentrates were prepared according to the bench-top process described above in Example 2, with the ingredients detailed in Tables 81-84 below. The pre-emulsion concentrates contained a non-polar compound, with the remainder of the concentrate containing TPGS or TPGS and benzyl alcohol. The non-polar compounds included a conjugated linoleic acid (CLA) that contains 70% CLA (Clarinol® CLA, sold by Stepan Lipid Nutrition, Maywood, N.J.); a medium chain triglyceride (MCT) oil that contains 98% MCT (sold by Abitec, Janesville, Wis. and Stepan Lipid Nutrition, Maywood, N.J.); pyrroloquinoline quinone (PQQ; Nascent Health Sciences, Allentown, N.J.); and an algal oil that contains 35% of the non-polar ingredient DHA and contains 350 mg DHA/g oil (life'sDHA™ S35-0300, sold by DSM Nutritional Products Inc., Kaiseraugst, Switzerland).

TABLE 81

Preparation of two pre-emulsion concentrates containing algal oil (35% DHA) and TPGS

| Ingredient | wt % of Composition 14A | wt % of Composition 15A |
|---|---|---|
| TPGS | 2.65 | 2.58 |
| Algal oil (35% DHA) (non-polar ingredient) | 97.35 | 97.42 |
| Total | 100.00 | 100.00 |

TABLE 82

Preparation of two pre-emulsion concentrates
containing CLA oil (79.6% CLA) and TPGS

| Ingredient | wt % of Composition 16A | wt % of Composition 17A |
|---|---|---|
| TPGS | 2.57 | 2.58 |
| CLA oil (79.6% CLA) (non-polar ingredient) | 97.43 | 97.42 |
| Total | 100.00 | 100.00 |

TABLE 83

Preparation of two pre-emulsion concentrates
containing MCT oil (98% MCT) and TPGS

| Ingredient | wt % of Composition 18A | wt % of Composition 19A |
|---|---|---|
| TPGS | 2.58 | 2.58 |
| MCT oil (98% MCT) (non-polar ingredient) | 97.42 | 97.42 |
| Total | 100.00 | 100.00 |

TABLE 84

Preparation of two pre-emulsion
concentrates containing PQQ and TPGS

| Ingredient | wt % of Composition 20A | wt % of Composition 21A |
|---|---|---|
| TPGS | 64.50 | 69.50 |
| Benzyl alcohol (preservative) | 0.50 | 0.50 |
| PQQ (non-polar ingredient) | 35.00 | 30.00 |
| Total | 100.00 | 100.00 |

B. Preparation of the Pre-Spray Emulsions

Pre-spray emulsions were prepared from the pre-emulsion concentrates of Tables 81-84, above, by combining a pre-emulsion concentrate with the ingredients detailed in Tables 85-88, below, according to the general procedure described above in Example 3. The pre-spray emulsions contained a pre-emulsion concentrate containing a non-polar compound and TPGS, and were formulated either with sucrose fatty acid ester, or with maltodextrin in place of sucrose fatty acid ester.

In addition to the pre-emulsion concentrates prepared as described above (see Tables 81-84), the pre-spray emulsions also contained: maltodextrin (sold by Archer Daniels Midland Company, Decatur, Ill.); the emulsion stabilizer SALADIZER® (TIC Gums, Inc.; Belcamp, Md.); stabilizers, including vitamin C (Pure Assay Ingredients, Walnut, Calif.), potassium bicarbonate (Armand Products, Princeton, N.J.), and a green tea extract that contains 40% EGCG (epigallocatechin gallate) (Guilin Layn Natural Ingredients Corp., Guilin, China); a co-emulsifier, saponin from quillaja bark (sold by Desert King and Sigma Aldrich, St. Louis, Mo.); citric acid, a pH adjuster; and a polar solvent, water, which was purified city water, purified as described above.

Before adding to the appropriate phase, as described above in Example 3, the correct amount of each ingredient (as indicated in Tables 85-88) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Tables 85-88 set forth the ingredients included in each pre-spray emulsion, the amount (g) of each ingredient per batch of the pre-spray emulsion, the phase to which each ingredient was added, and the percentage by weight (wt %) of each ingredient.

TABLE 85

Pre-spray emulsions containing algal oil
(35% DHA), with and without SFAE

| Ingredient | wt % of Composition 14B | wt % of Composition 15B |
|---|---|---|
| Water (polar solvent) | 56.87 | 56.87 |
| Maltodextrin (binder/carrier) | — | 8.27 |
| KHCO$_3$ (stabilizer) | 3.33 | 3.33 |
| Green tea extract (40% EGCG) (stabilizer) | 8.85 | 8.85 |
| SFAE (co-surfactant) | 8.27 | — |
| SALADIZER ® (emulsion stabilizer) | 0.07 | 0.07 |
| Vitamin C (stabilizer) | 2.00 | 2.00 |
| Saponin (co-emulsifier) | 0.61 | 0.61 |
| Pre-emulsion concentrate containing algal oil (35% DHA) and TPGS (Table 81 above) | 20.00 | 20.00 |
| Total | 100.00 | 100.00 |

TABLE 86

Pre-spray emulsions containing CLA oil (79.6% CLA),
with and without SFAE

| Ingredient | wt % of Composition 16B | wt % of Composition 17B |
|---|---|---|
| Water (polar solvent) | 57.48 | 57.48 |
| Maltodextrin (binder/carrier) | — | 8.27 |
| KHCO$_3$ (stabilizer) | 3.33 | 3.33 |
| Whey protein (co-emulsifier) | 8.85 | 8.85 |
| SFAE (co-surfactant) | 8.27 | — |
| SALADIZER ® (emulsion stabilizer) | 0.07 | 0.07 |
| Vitamin C (stabilizer) | 2.00 | 2.00 |
| Pre-emulsion concentrate containing CLA oil (79.6% CLA) and TPGS (Table 82 above) | 20.00 | 20.00 |
| Total | 100.00 | 100.00 |

TABLE 87

Pre-spray emulsions containing MCT oil (98% MCT), with and without SFAE

| Ingredient | wt % of Composition 18B | wt % of Composition 19B |
|---|---|---|
| Water (polar solvent) | 57.48 | 57.48 |
| Maltodextrin (binder/carrier) | — | 8.27 |
| $KHCO_3$ (stabilizer) | 3.33 | 3.33 |
| Whey protein (co-emulsifier) | 8.85 | 8.85 |
| SFAE (co-surfactant) | 8.27 | — |
| SALADIZER ® (emulsion stabilizer) | 0.07 | 0.07 |
| Vitamin C (stabilizer) | 2.00 | 2.00 |
| Pre-emulsion concentrate containing MCT oil (98% MCT) and TPGS (Table 83 above) | 20.00 | 20.00 |
| Total | 100.00 | 100.00 |

TABLE 88

Pre-spray emulsions containing PQQ, with and without SFAE

| Ingredient | wt % of Composition 20B | wt % of Composition 21B |
|---|---|---|
| Water (polar solvent) | 56.86 | 58.87 |
| Maltodextrin (binder/carrier) | 18.07 | 26.33 |
| Citric acid (pH adjuster) | 0.13 | 0.13 |
| SFAE (co-surfactant) | 8.27 | — |
| Pre-emulsion concentrate containing PQQ, benzyl alcohol and TPGS (Table 84 above) | 16.67 | 16.67 |
| Total | 100.00 | 100.00 |

C. Preparation of Dry Powders

Formation of a dry powder from each of the pre-spray emulsions described above (Tables 85-88), was attempted, according to the procedure detailed in Example 4, above. Tables 89-92, below, indicate the percentage by weight (wt %) of each ingredient per batch of the final composition after spray drying of the pre-spray emulsions was attempted. During preparation of the dry powders, the emulsions were continuously mixed in order to keep the mixture homogenous. Dry powders were obtained from all of the pre-spray emulsions containing sucrose fatty acid ester (Compositions 14B, 16B, 18B and 20B), but dry powders were not formed when maltodextrin was used as a binder in place of sucrose fatty acid ester (Compositions 15C, 17C, 19C and 21C). When maltodextrin was included in place of the SFAE, the end compositions were sludge-like materials, not dry powders. Hence, this Example demonstrates that addition of SFAE in place of some of the binder, such as maltodextrin, in pre-spray emulsions permits preparation of dry powders containing rather high amounts of non-polar compounds.

TABLE 89

Dry powders containing algal oil (35% DHA), with and without SFAE

| Ingredient | wt % of Composition 14C | wt % of Composition 15C |
|---|---|---|
| $KHCO_3$ (stabilizer) | 7.73 | 7.73 |
| Green tea extract (40% EGCG) (stabilizer) | 20.52 | 20.52 |
| SFAE (co-surfactant) | 19.17 | — |
| Maltodextrin (binder/carrier) | — | 19.17 |
| SALADIZER ® (emulsion stabilizer) | 0.15 | 0.15 |
| Vitamin C (stabilizer) | 4.64 | 4.64 |
| Saponin (co-emulsifier) | 1.41 | 1.41 |
| Pre-emulsion concentrate containing algal oil (35% DHA) and TPGS (Table 81 above) | 46.38 | 46.38 |
| Total | 100.00 | 100.00 |

TABLE 90

Dry powders containing CLA oil (79.6% CLA), with and without SFAE

| Ingredient | wt % of Composition 16C | wt % of Composition 17C |
|---|---|---|
| $KHCO_3$ (stabilizer) | 7.85 | 7.85 |
| Whey protein (co-emulsifier) | 20.81 | 20.81 |
| SFAE (co-surfactant) | 19.44 | — |
| SALADIZER ® (emulsion stabilizer) | 0.16 | 0.16 |
| Maltodextrin (binder/carrier) | — | 19.44 |
| Vitamin C (stabilizer) | 4.70 | 4.70 |
| Pre-emulsion concentrate containing CLA oil (79.6% CLA) and TPGS (Table 82 above) | 47.04 | 47.04 |
| Total | 100.00 | 100.00 |

TABLE 91

Dry powders containing MCT oil (98% MCT), with and without SFAE

| Ingredient | wt % of Composition 18C | wt % of Composition 19C |
|---|---|---|
| $KHCO_3$ (stabilizer) | 7.84 | 7.84 |
| Whey protein (co-emulsifier) | 20.81 | 20.81 |
| SFAE (co-surfactant) | 19.45 | — |
| Maltodextrin (binder/carrier) | — | 19.45 |
| SALADIZER ® (emulsion stabilizer) | 0.16 | 0.16 |
| Vitamin C (stabilizer) | 4.70 | 4.70 |

TABLE 91-continued

Dry powders containing MCT oil
(98% MCT), with and without SFAE

| Ingredient | wt % of Composition 18C | wt % of Composition 19C |
|---|---|---|
| Pre-emulsion concentrate containing MCT oil (98% MCT) and TPGS (Table 83 above) | 47.04 | 47.04 |
| Total | 100.00 | 100.00 |

TABLE 92

Dry powders containing PQQ, with and without SFAE

| Ingredient | wt % of Composition 20C | wt % of Composition 21C |
|---|---|---|
| Citric acid (pH adjuster) | 0.31 | 0.31 |
| Maltodextrin (binder/carrier) | 41.89 | 61.06 |
| SFAE (co-surfactant) | 19.17 | — |
| Pre-emulsion concentrate containing PQQ, TPGS, and benzyl alcohol (Table 84 above) | 38.64 | 38.64 |
| Total | 100.00 | 100.00 |

Example 9

Preparation of Dry Powders Containing TPGS and Non-Polar Compounds

A. Preparation of Pre-Emulsion Concentrates

Pre-emulsion concentrates were prepared according to the method described above in Example 2 using the ingredients detailed in Tables 93-97, below. The pre-emulsion concentrates contained between 37.1% and 97.42% by weight (of the concentrate) of one or more non-polar compounds and either TPGS (α-tocopheryl polyethylene glycol succinate) or TPGS and benzyl alcohol. The TPGS was prepared as described in Example 1.

The pre-emulsion concentrates contained as much as about 97% non-polar compound. The remainder was TPGS or TPGS and benzyl alcohol. Non-polar compounds in the concentrates included fish oils that contain 500 mg of the non-polar ingredients DHA/EPA (sold as AlaskOmega® TG300200 M EU by Organic Technologies, Coshocton, Ohio); a carotenoid-containing compound, astaxanthin (an oil containing 10% astaxanthin sold as AstaPure® by Alga Technologies, Hevel Eilot, Israel); a dihydrocapsiate compound naturally found in CH-19 Sweet peppers (sold as CapsiAtra™ by Glanbia Nutritionals, Carlsbad, Calif.); vitamin K2 that contains 97% of the MK-7 form (sold as MenaQ7® by NattoPharma®, Metuchen, N.J.); a medium chain triglyceride (MCT) oil that contains 98% MCT (sold by Abitec, Janesville, Wis. and Stepan Lipid Nutrition, Maywood, N.J.); and combinations thereof.

The pre-emulsion concentrates set forth in Tables 93-97, below, were prepared using a bench-top process according to the provided methods (see Example 2). The pre-emulsion concentrates can alternatively be made by scaling up the bench-top process, using a scaled-up manufacturing process of the provided methods, for example, to make larger batch sizes of the pre-emulsion concentrates.

TABLE 93

Pre-emulsion concentrate containing
fish oil (60% DHA/EPA) and TPGS

| Ingredient | wt % of composition |
|---|---|
| Fish oil (60% DHA/EPA blend) (non-polar ingredient) | 97.42 |
| TPGS | 2.58 |
| Total | 100.00 |

TABLE 94

Pre-emulsion concentrate containing
fish oil (60% DHA/EPA) and TPGS

| Ingredient | wt % of composition |
|---|---|
| Fish oil (60% DHA/EPA blend) (non-polar ingredient) | 97.42 |
| TPGS | 2.58 |
| Total | 100.00 |

TABLE 95

Pre-emulsion concentrate containing astaxanthin
(10% astaxanthin) and TPGS

| Ingredient | wt % of composition |
|---|---|
| Astaxanthin (10%) (non-polar ingredient) | 80 |
| TPGS | 20 |
| Total | 100.00 |

TABLE 96

Pre-emulsion concentrate containing
dihydrocapsiate and TPGS

| Ingredient | wt % of composition |
|---|---|
| Dihydrocapsiate (non-polar ingredient) | 37.1 |
| TPGS | 62.9 |
| Total | 100.00 |

TABLE 97

Pre-emulsion concentrate containing MCT oil (98% MCT),
vitamin K2 (97% MK-7), benzyl alcohol and TPGS

| Ingredient | wt % of composition |
|---|---|
| MCT oil (98% MCT) (non-polar ingredient) | 31.99 |
| Vitamin K2 (MK-7) (non-polar ingredient) | 3.99 |
| TPGS | 58.0 |
| Benzyl alcohol (preservative) | 6.02 |
| Total | 100.00 |

B. Preparation of the Pre-Spray Emulsions

The pre-emulsion concentrates described above and shown in Tables 93-97 were used in the preparation of pre-spray emulsions. The pre-spray emulsions were prepared by combining the pre-emulsion concentrate with the ingredients detailed in Tables 98-102, below, according to the general procedure described above in Example 3. The resulting pre-spray emulsions contained between 6.18% and 19.49%, by weight, non-polar compound.

The ingredients in the pre-spray emulsions included: the pre-emulsion concentrates containing non-polar compounds, prepared as described above (see Tables 93-97); a surfactant, a sucrose fatty acid ester (SFAE) (sold as DK Ester® by Dai-Ichi Kogyo Seiyaku Co., Ltd, Japan); a co-emulsifier, saponin from quillaja bark (Desert King International, San Diego, Calif.; Sigma Aldrich, St. Louis, Mo.); an emulsion stabilizer that was a blend of xanthan gum, guar gum and sodium alginate, sold under the product name SALADIZER®, available from TIC Gums, Inc. (Belcamp, Md.); the binders maltodextrin (sold by Archer Daniels Midland Company, Decatur, Ill.) and a highly branched cyclic dextrin (HBCD) (sold as Cluster Dextrin® by Glico Nutrition, Japan); stabilizers, including vitamin C (sold by Pure Assay Ingredients, Walnut, Calif.), potassium bicarbonate, and green tea extracts that contained 40% or 50% epigallocatechin gallate (EGCG) (Guilin Layn Natural Ingredients, Corp., Guilin, China); sweeteners that included erythritol, stevia (sold as Stevia Leaf Powder Extract, Product code STE091, by MiniStar International Inc.), and sorbitol; flavor agents that included pink grapefruit, natural mandarin orange (346316), natural watermelon (600171), and natural sour yuzu (347528), all sold by Gold Coast Ingredients, Inc. (Commerce, Calif.), natural fresh orange (L-17283), natural blueberry (BL-238), natural watermelon (WM-122), and natural sour yuzu (L-20609), all sold by Mission Flavors and Fragrances, Inc. (Foothill Ranch, Calif.), natural orange tangerine (DABJ826) and natural blueberry pomegranate (DABJ831), sold by Wild Flavors (Erlanger, Ky.), and green tea flavor, sold by Kerry, Inc. (Beloit, Wis.); a pH adjuster, citric acid; and a polar solvent, water, which was purified city water, purified as described above (see Example 3). Ingredients marked with a * were added in the indicated amount of overage to ensure the final composition contained the stated amount of this ingredient.

Before adding to the appropriate phase, as described above, the correct amount of each ingredient (as indicated in Tables 98-102) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Tables 98-102, below, indicate the amount (g) of each ingredient per batch of the pre-spray emulsion, the phase each ingredient was added, and the percentage by weight (wt %) of each ingredient.

TABLE 98

Pre-spray emulsion containing fish oil
(50% DHA/EPA) and TPGS

| Ingredient | g/batch | Phase | wt % of composition |
|---|---|---|---|
| Water (polar solvent) | 268.42 | Water | 44.74 |
| KHCO$_3$ (stabilizer) | 10.99 | Water | 1.83 |
| Green tea extract (50% EGCG) (stabilizer) | 27.50 | Water | 4.58 |
| Vitamin C (stabilizer) | 14.04 | Water | 2.34 |

TABLE 98-continued

Pre-spray emulsion containing fish oil
(50% DHA/EPA) and TPGS

| Ingredient | g/batch | Phase | wt % of composition |
|---|---|---|---|
| SALADIZER ® emulsifier (emulsion stabilizer) | 0.22 | Water | 0.04 |
| SFAE (co-surfactant) | 10.34 | Water | 1.72 |
| Maltodextrin (binder/carrier) | 49.50 | Water | 8.25 |
| Highly branched cyclic dextrin (HBCD) (binder/carrier) | 29.50 | Water | 4.92 |
| Erythritol (sweetener) | 10.99 | Water | 1.83 |
| Stevia (sweetener) | 15.46 | Water | 2.58 |
| Pink grapefruit flavor (flavor) | 54.99 | Water | 9.17 |
| Natural mandarin orange (flavor) | 2.67 | Water | 0.45 |
| Natural fresh orange (flavor) | 3.37 | Water | 0.56 |
| Natural blueberry (flavor) | 3.57 | Water | 0.60 |
| Natural watermelon (flavor) | 1.20 | Water | 0.20 |
| Natural sour yuzu (flavor) | 6.96 | Water | 1.16 |
| Citric acid (pH adjuster) | 7.77 | Water | 1.29 |
| Pre-emulsion concentrate containing fish oil (50% DHA/EPA) and TPGS (Table 93 above) | 82.49 | Oil | 13.75 |
| Totals | 600.00 | | 100.00 |

TABLE 99

Pre-spray emulsion containing fish oil
(50% DHA/EPA) and TPGS

| Ingredient | g/batch | Phase | wt % of composition |
|---|---|---|---|
| Water (polar solvent) | 279.37 | Water | 55.87 |
| KHCO$_3$ (stabilizer) | 16.67 | Water | 3.33 |
| Green tea extract (40% EGCG) (stabilizer) | 44.23 | Water | 8.85 |
| Vitamin C (stabilizer) | 10.00 | Water | 2.00 |
| SALADIZER ® emulsifier (emulsion stabilizer) | 0.33 | Water | 0.07 |
| SFAE (co-surfactant) | 41.33 | Water | 8.27 |
| Saponin (co-emulsifier) | 3.03 | Water | 0.61 |
| Green tea flavor (flavor) | 5.00 | Water | 1.00 |
| Pre-emulsion concentrate containing fish oil (50% DHA/EPA) and TPGS (Table 94 above) | 100.01 | Oil | 20.00 |
| Totals | | | 100.00 |

TABLE 100

Pre-spray emulsion containing astaxanthin (10% astaxanthin) and TPGS

| Ingredient | g/batch | Phase | wt % of composition |
|---|---|---|---|
| Water (polar solvent) | 6255.33 | Water | 56.87 |
| KHCO$_3$ (stabilizer) | 507.47 | Water | 4.61 |
| Vitamin C (stabilizer) | 220.00 | Water | 2.00 |
| SALADIZER ® emulsifier (emulsion stabilizer) wt % | 7.33 | Water | 0.07 |
| SFAE (co-surfactant) | 909.33 | Water | 8.27 |
| Saponin (co-emulsifier) | 26.77 | Water | 0.24 |
| Highly branched cyclic dextrin (HBCD) (binder/carrier) | 1240.43 | Water | 11.28 |
| Pre-emulsion concentrate containing astaxanthin and TPGS (Table 95 above) | 1833.33 | Oil | 16.67 |
| Totals | | | 100.00 |

TABLE 101

Pre-spray emulsion containing dihydrocapsiate and TPGS

| Ingredient | g/batch | Phase | wt % of composition |
|---|---|---|---|
| Water (polar solvent) | 85.31 | Water | 56.87 |
| SALADIZER ® emulsifier (emulsion stabilizer) | 0.10 | Water | 0.07 |
| SFAE (co-surfactant) | 12.40 | Water | 8.27 |
| Saponin (co-emulsifier) | 0.91 | Water | 0.61 |
| Maltodextrin (binder/carrier) | 19.35 | Water | 12.90 |
| Citric acid (pH adjuster) | 6.92 | Water | 4.61 |
| Pre-emulsion concentrate containing dihydrocapsiate and TPGS (Table 96 above) | 25.00 | Oil | 16.67 |
| Totals | 150.00 | | 100.00 |

TABLE 102

Pre-spray emulsion containing MCT oil (98% MCT), vitamin K2 (97% MK-7), benzyl alcohol, and TPGS

| Ingredient | g/batch | Phase | wt % of composition |
|---|---|---|---|
| Water (polar solvent) | 49.47 | Water | 56.87 |
| SALADIZER ® emulsifier (emulsion stabilizer) | 0.06 | Water | 0.07 |
| SFAE (co-surfactant) | 3.89 | Water | 4.47 |
| Highly branched cyclic dextrin (HBCD) (binder/carrier) | 8.874 | Water | 10.20 |
| Sorbitol (sweetener) | 1.45 | Water | 1.67 |

TABLE 102-continued

Pre-spray emulsion containing MCT oil (98% MCT), vitamin K2 (97% MK-7), benzyl alcohol, and TPGS

| Ingredient | g/batch | Phase | wt % of composition |
|---|---|---|---|
| Pre-emulsion concentrate containing MCT oil, vitamin K2 (MK-7), benzyl alcohol and TPGS* (20% overage) (Table 97 above) | 23.26 | Oil | 26.73 |
| Totals | 87.00 | | 100.00 |

The pre-spray emulsions of tables 98-102, above, contained between 6.18% and 19.49%, by weight, non-polar compound(s), as shown in Table 103, below.

TABLE 103

Amount of non-polar compound(s) in pre-spray emulsions

| Non-polar compound | wt % of pre-emulsion concentrate in pre-spray emulsion | wt % of non-polar compound in pre-spray emulsion |
|---|---|---|
| Fish oil (Table 98 above) | 13.75 | 13.39 |
| Fish oil (Table 99 above) | 20.00 | 19.49 |
| Astaxanthin (Table 100 above) | 16.67 | 13.33 |
| Dihydrocapsiate (Table 101 above) | 16.67 | 6.18 |
| MCT oil/vitamin K2 (MK-7) (Table 102 above) | 26.73 | 9.62 |

C. Preparation of the Dry Powder

The pre-spray emulsions described above and indicated in Tables 98-102 were then spray dried into dry powders according to the procedure detailed in Example 4. The addition of extra water (i.e., evaporation water) to the pre-spray emulsions was required as a processing aid to make the emulsions thinner and able to pass through the dryer pump more easily. The extra water was added to the pre-spray emulsions at 35° C. and was evaporated during the spray dry process, along with the rest of the water in the pre-spray emulsions.

Tables 104-108, below, indicate the percentage by weight (wt %) of each ingredient per batch of the final dry powders after spray drying the pre-spray emulsions.

TABLE 104

Dry powder containing fish oil (50% DHA/EPA) and TPGS

| Ingredient | wt % of composition |
|---|---|
| KHCO$_3$ (stabilizer) | 4.25 |
| Green tea extract (50% EGCG) (stabilizer) | 10.62 |
| Vitamin C (stabilizer) | 5.42 |
| SALADIZER ® emulsifier (emulsion stabilizer) | 0.08 |
| SFAE (co-surfactant) | 3.99 |
| Maltodextrin (binder/carrier) | 19.12 |
| Highly branched cyclic dextrin (HBCD) (binder/carrier) | 11.40 |
| Erythritol (sweetener) | 4.25 |

TABLE 104-continued

Dry powder containing fish oil (50% DHA/EPA) and TPGS

| Ingredient | wt % of composition |
|---|---|
| Stevia (sweetener) | 5.98 |
| Citric acid (pH adjuster) | 3.00 |
| Pre-emulsion concentrate containing fish oil (50% DHA/EPA) and TPGS (Table 98 above) | 31.87 |
| Totals | 100.000 |

TABLE 105

Dry powder containing fish oil (50% DHA/EPA) and TPGS

| Ingredient | wt % of composition |
|---|---|
| KHCO$_3$ (stabilizer) | 7.73 |
| Green tea extract (40% EGCG) (stabilizer) | 18.96 |
| Vitamin C (stabilizer) | 4.64 |
| SALADIZER ® emulsifier (emulsion stabilizer) | 0.15 |
| SFAE (co-surfactant) | 14.53 |
| Saponin (co-emulsifier) | 1.41 |
| Green tea flavor (flavor) | |
| Pre-emulsion concentrate containing fish oil (50% DHA/EPA) and TPGS (Table 99 above) | 52.58 |
| Totals | 100.00 |

TABLE 106

Dry powder containing astaxanthin (10% astaxanthin) and TPGS

| Ingredient | wt % of composition |
|---|---|
| KHCO$_3$ (stabilizer) | 10.70 |
| Vitamin C (stabilizer) | 4.64 |
| SALADIZER ® emulsifier (emulsion stabilizer) | 0.15 |
| SFAE (co-surfactant) | 19.17 |
| Saponin (co-emulsifier) | 0.56 |
| Highly branched cyclic dextrin (HBCD) (binder/carrier) | 26.14 |
| Pre-emulsion concentrate containing astaxanthin and TPGS (Table 100 above) | 38.64 |
| Totals | 100.00 |

TABLE 107

Dry powder containing dihydrocapsiate and TPGS

| Ingredient | wt % of composition |
|---|---|
| SALADIZER ® emulsifier (emulsion stabilizer) | 0.15 |

TABLE 107-continued

Dry powder containing dihydrocapsiate and TPGS

| Ingredient | wt % of composition |
|---|---|
| SFAE (co-surfactant) | 19.17 |
| Saponin (co-emulsifier) | 1.41 |
| Maltodextrin (binder/carrier) | 29.92 |
| Citric acid (pH adjuster) | 10.70 |
| Pre-emulsion concentrate containing dihydrocapsiate and TPGS (Table 101 above) | 38.65 |
| Totals | 100.00 |

TABLE 108

Dry powder containing MCT oil (98% MCT), vitamin K2 (97% MK-7), benzylalcohol, and TPGS

| Ingredient | wt % of composition |
|---|---|
| SALADIZER ® emulsifier (emulsion stabilizer) | 0.15 |
| SFAE (co-surfactant) | 10.36 |
| Highly branched cyclic dextrin (HBCD) (binder/carrier) | 39.10 |
| Sorbitol (sweetener) | 19.32 |
| Pre-emulsion concentrate containing MCT oil, vitamin K2 (MK-7), benzyl alcohol and TPGS (Table 102 above) | 31.07 |
| Totals | 100.00 |

The dry powders depicted above in Tables 104-108 that contained the pre-emulsion concentrates described in Tables 93-97, above, contained between 11.18% and 51.22% by weight non-polar compound(s), as shown in Table 109, below.

TABLE 109

Amount of non-polar compound in dry powders

| Non-polar compound | wt % of pre-emulsion concentrate in dry powder | wt % of non-polar compound in dry powder |
|---|---|---|
| Fish oil (Table 104 above) | 31.87 | 31.05 |
| Fish oil (Table 105 above) | 52.58 | 51.22 |
| Astaxanthin (Table 106 above) | 38.64 | 30.91 |
| Dihydrocapsiate (Table 107 above) | 38.65 | 14.34 |
| MCT oil/vitamin K2 (MK-7) (Table 108 above) | 31.07 | 11.18 |

Example 10

Preparation of a Dry Powder by Instantization

A. Preparation of the Pre-Emulsion Concentrate

A pre-emulsion concentrate was prepared according to the method described above in Example 2 using the ingredients detailed in Table 110, below. The pre-emulsion concentrate contained TPGS, prepared as described in Example 1, above, and a total of 93.42% by weight (of the concentrate) non-polar compounds that included a coenzyme Q10 (coQ10) compound that contains 99% ubidicarenone (ubiquinone) sold under the name Kaneka Q10™ (USP Ubidicarenone; Kaneka Nutrients, L.P., Pasadena, Tex.); astaxanthin (an oil containing 10% astaxanthin sold as AstaPure® by Alga Technologies, Hevel Eilot, Israel); pyrroloquinoline quinone (PQQ) (sold by Nascent Health Sciences, Allentown, N.J.); and a medium chain triglyceride (MCT) that contains 95% MCT (sold as Captex® 300 by Abitec, Columbus, Ohio).

The pre-emulsion concentrate set forth in Table 110, below, was made using a bench-top process according to the provided methods (see Example 2). The pre-emulsion concentrate can alternatively be made by scaling up the bench-top process, using a scaled-up manufacturing process of the provided methods, for example, to make larger batch sizes of the pre-emulsion concentrate.

TABLE 110

Pre-emulsion concentrate containing coQ10, astaxanthin, PQQ, MCT,and TPGS

| Ingredient | wt % of composition |
|---|---|
| CoQ10 (99% ubiquinone) | 1.21 |
| Astaxanthin (10% astaxanthin) | 4.00 |
| PQQ (99% PQQ) | 0.70 |
| MCT (95% MCT) | 87.51 |
| TPGS | 6.58 |
| Total | 100.00 |

B. Preparation of the Pre-Spray Emulsion

The pre-emulsion concentrate described above and shown in Table 110 was used in the preparation of a pre-spray emulsion. The pre-spray emulsion was prepared by combining the pre-emulsion concentrate that contained 93.42% of the non-polar compounds coQ10, astaxanthin, PQQ and MCT, described in Table 110, above, with the ingredients detailed in Table 111, below, according to the general procedure described above in Example 3. The resulting pre-spray emulsion thus contained 16.75% by weight pre-emulsion concentrate containing 93.42% of the non-polar compounds coQ10, astaxanthin, PQQ and MCT (i.e., the resulting pre-spray emulsion contained a total of 15.65% by weight non-polar compound).

The ingredients in the pre-spray emulsion included the pre-emulsion concentrate prepared as described above (see Table 110); a surfactant, a sucrose fatty acid ester (SFAE; sold under the trade name DK Ester®, produced by Dai-Ichi Kogyo Seiyaku Co., Ltd of Japan); an emulsion stabilizer that was a blend of xanthan gum, guar gum and sodium alginate, sold under the product name SALADIZER®, available from TIC Gums, Inc. (Belcamp, Md.); the binders maltodextrin (sold by Archer Daniels Midland Company, Decatur, Ill.) and a highly branched cyclic dextrin (HBCD) (sold as Cluster Dextrin® by Glico Nutrition, Japan); stabilizers, including potassium bicarbonate and green tea extract that contained 60% epigallocatechin gallate (EGCG) (Guilin Layn Natural Ingredients, Corp., Guilin, China); sweeteners, including pure cane sugar; active ingredients, including citicholine (sold as Cognizin® Citicholine by Kyowa Hakko USA, New York, N.Y.) and caffeine (sold as Caffeine Anhydrous powder (white, crystalline powder), by Pacific Rainbow International, Inc., City of Industry, Calif.); silicon dioxide; and a polar solvent, water, which was purified city water, purified as described above (see Example 3). Before adding to the appropriate phase, as described above, the correct amount of each ingredient (as indicated in Table 111) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Table 111, below, indicates the amount (g) of each ingredient per batch of the pre-spray emulsion, the phase each ingredient was added, and the percentage by weight (wt %) of each ingredient.

TABLE 111

Pre-spray emulsion containing coQ10, astaxanthin, PQQ, MCT, and TPGS

| Ingredient | g/batch | Phase | wt % of composition |
|---|---|---|---|
| Water (polar solvent) | 287.5 | Water | 57.50 |
| KHCO₃ (stabilizer) | 14.67 | Water | 2.93 |
| Green tea extract (60% EGCG) (stabilizer) | 13.33 | Water | 2.67 |
| SALADIZER ® emulsifier (emulsion stabilizer) | 0.33 | Water | 0.07 |
| SFAE (co-surfactant) | 6.67 | Water | 1.33 |
| Highly branched cyclic dextrin (HBCD) (binder/carrier) | 14.23 | Water | 2.85 |
| Maltodextrin (binder/carrier) | 21.67 | Water | 4.33 |
| Silicon dioxide (anticaking agent) | 2.17 | Water | 0.43 |
| Citicholine (active ingredient) | 12.50 | Water | 2.50 |
| Caffeine (active ingredient) | 4.73 | Water | 0.95 |
| Cane sugar (sweetener) | 38.45 | Water | 7.69 |
| Pre-emulsion concentrate containing coQ10, astaxanthin, PQQ, MCT and TPGS (Table 110 above) | 83.75 | Oil | 16.75 |
| Totals | 500.00 | | 100.000 |

C. Preparation of the Dry Powder

The pre-spray emulsion described above and indicated in Table 111 then was spray dried into an initial dry powder according to the procedure detailed in Example 4. The addition of extra water (i.e., evaporation water) to the pre-spray emulsion was required as a processing aid to make the emulsion thinner and able to pass through the dryer pump more easily. The extra water was added to the pre-spray emulsion at 35° C. and was evaporated during the spray dry process, along with the rest of the water in the pre-spray emulsion.

The initial dry powder contained 39.41% of the pre-emulsion concentrate containing 93.42% coQ10, astaxanthin, PQQ, and MCT (i.e., 36.82% non-polar compounds). Table 112, below, indicates the percentage by weight (wt %) of each ingredient per batch of the initial dry powder after spray drying the pre-spray emulsion.

TABLE 112

Initial dry powder containing coQ10,
astaxanthin, PQQ, MCT, and TPGS

| Ingredient | wt % of composition |
|---|---|
| KHCO$_3$ (stabilizer) | 6.90 |
| Green tea extract (60% EGCG) (stabilizer) | 6.27 |
| SALADIZER ® emulsifier (emulsion stabilizer) | 0.16 |
| SFAE (co-surfactant) | 3.14 |
| Highly branched cyclic dextrin (HBCD) (binder/carrier) | 6.70 |
| Maltodextrin (binder/carrier) | 10.20 |
| Silicon dioxide (anticaking agent) | 1.02 |
| Citicholine (active ingredient) | 5.88 |
| Caffeine (active ingredient) | 2.23 |
| Cane sugar (sweetener) | 18.09 |
| Pre-emulsion concentrate containing coQ10, astaxanthin, PQQ, MCT and TPGS (Table 110 above) | 39.41 |
| Total | 100.00 |

The initial dry powder thus contained 36.82% of the non-polar compounds coQ10, astaxanthin, PQQ, and MCT.

The initial dry powder was then instantized to form a final dry powder. The initial dry powder was instantized by first rewetting the surface of the individual particles (by adding water), allowing the particles to come into contact and stick together, and then drying to remove the water, causing individual particles to stick together as agglomerates. Agglomerization was facilitated by addition of sugars and/or sugar alcohols. Silicon dioxide and maltodextrin were also added to facilitate the drying process. Table 113, below, indicates the amount (g) of each ingredient per batch and the percentage by weight (wt %) of each ingredient of the rewetted powder.

TABLE 113

Rewetted powder containing the initial dry powder
containing coQ10, astaxanthin, PQQ, MCT, and TPGS

| Ingredient | wt % of composition |
|---|---|
| Water | 35.00 |
| Pure cane sugar | 9.42 |
| Silicon dioxide (anticaking agent) | 0.66 |
| Maltodextrin (binder/carrier) | 9.42 |
| Initial dry powder containing non-polar compound coQ10, astaxanthin, PQQ, MCT, and TPGS (Table 110 above) | 45.50 |
| Total | 100.00 |

The rewetted powder depicted above in Table 113 then was dried by fluidized bed drying to form the final instantized dry powder. The resulting final dry powder was a more granular product with improved wettability of the powder (i.e., the powder gets wet quickly and disperses in water quickly without any lumping). Table 114, below, indicates the percentage by weight (wt %) of each ingredient per batch of the final dry powder after instantization of the rewetted powder.

TABLE 114

Rewetted powder containing the initial dry powder
containing coQ10, astaxanthin, PQQ, MCT, and TPGS

| Ingredient | wt % of composition |
|---|---|
| Pure cane sugar | 14.49 |
| Silicon dioxide (anticaking agent) | 1.01 |
| Maltodextrin (binder/carrier) | 14.49 |
| Initial dry powder containing non-polar compound coQ10, astaxanthin, PQQ, MCT, and TPGS (Table 110 above) | 70.00 |
| Total | 100.00 |

The final dry powder, after instantization, thus contained 25.77% of the non-polar compounds coQ10, astaxanthin, PQQ, and MCT and was a more granular powder than the initial dry powder.

Since modifications will be apparent to those of skill in this art, it is intended that this invention be limited only by the scope of the appended claims.

The invention claimed is:

1. A water-soluble powder, comprising:
   a) a water-soluble vitamin E derivative mixture present in an amount of from between 0.1% and 25%, by weight of the powder, wherein:
      the water-soluble vitamin E derivative mixture is a high dimer mixture;
      the high dimer mixture comprises at least 13 wt % water-soluble vitamin E derivative dimer and up to 87 wt % water-soluble vitamin E derivative monomer; and
      the vitamin E derivative is a polyalkylene glycol derivative of vitamin E;
   b) a mixture of sugar fatty acid ester and a binder, wherein:
      the total amount of sugar fatty acid ester and binder is between 5% and 60%, by weight of the powder; and
      the mixture of sugar fatty acid ester and binder contains at least 5% sugar fatty acid ester; and
   c) a non-polar ingredient, other than the polyalkylene glycol derivative of vitamin E, present in an amount of from between 15% and 60%, by weight of the powder; wherein the non-polar ingredient is a non-polar compound or contains a mixture of non-polar compounds.

2. The powder of claim 1, wherein the amount of the mixture of sugar fatty acid ester and binder is between 15% and 60%, by weight of the powder.

3. The powder of claim 1, wherein the polyalkylene glycol derivative of vitamin E contains a polyethylene glycol (PEG) moiety having a molecular weight of from between or between about 100 Da and 20,000 Da.

4. The powder of claim 1, wherein the polyalkylene glycol derivative of vitamin E is selected from among tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate, TPGS analogs and TPGS homologs.

5. The powder of claim 1, wherein the polyalkylene glycol derivative of vitamin E is tocopheryl polyethylene glycol succinate (TPGS).

6. The powder of claim 5, wherein the polyalkylene glycol derivative of vitamin E is tocopheryl polyethylene glycol succinate 1000 (TPGS 1000).

7. The powder of claim 1, wherein the polyalkylene glycol derivative of vitamin E is present in an amount between 1% and 15%, inclusive, by weight of the powder.

8. The powder of claim 1, wherein the sugar fatty acid ester is a sucrose fatty acid ester or a sucrose fatty acid ester blend.

9. The powder of claim 1, wherein the total amount of sugar fatty acid ester, by weight, of the powder is between about 5% and about 40%, inclusive.

10. The powder of claim 1, wherein the binder is selected from among polysaccharides, polyols, starches and gums.

11. The powder of claim 1, wherein the binder is a dextrin.

12. The powder of claim 1, wherein the binder is maltodextrin, fish collagen, lactose, sucrose, starch, polyethylene glycol, hypromellose, methylcellulose, macrocrystalline cellulose, sorbitol or pectin.

13. The powder of claim 1, wherein the powder contains from 20% to 60%, by weight, of the mixture of sugar fatty acid ester and a binder.

14. The powder of claim 1, wherein the non-polar ingredient is or contains a non-polar compound selected from among polyunsaturated fatty acids (PUFAs), medium chain triglycerides, phospholipids, coenzyme Q compounds, phytosterols, resveratrol, pyrroloquinoline quinone (PQQ), *Boswellia serrata* extract, astaxanthin, a cannabinoid, alpha lipoic acid, oil-soluble vitamins, flavonoids, carotenoids, micronutrients, alkaloids, antioxidants, and mixtures thereof.

15. The powder of claim 1, wherein the non-polar ingredient is selected from among one or more of: a flavonoid that is selected from among resveratrol and quercetin; an alkaloid that is vinpocetine; a coenzyme Q10 that is selected from among ubiquinol, ubidecarenone, and ubisemiquinone; an oil-soluble vitamin that is selected from among vitamin B12, vitamin D3, vitamin A palmitate, vitamin E, vitamin B1, vitamin B3, vitamin B5, vitamin B6, vitamin C, vitamin K2, and mixtures thereof; a carotenoid-containing compound that is selected from among astaxanthin, lycopene, lutein, zeaxanthin, and mixtures thereof; an antioxidant that is selected from among sesamin, alpha-lipoic acid, pyrroloquinoline quinone (PQQ), a turmeric/curcumin composition that is 95% curcumin, and mixtures thereof; an omega-5 fatty acid derivative that is cetyl myristoleate (CMO); *cannabis*; a micronutrient-containing compound that is selected from among yerba mate, *ginkgo biloba* and *ginseng*; and a phospholipid that is a phosphatidylserine.

16. The powder of claim 1, wherein the non-polar ingredient is present in an amount between 30% and 60%.

17. The powder of claim 1, further comprising a stabilizer selected from among a carbonate, bicarbonate, vitamin C, and green tea extract and mixtures thereof.

18. The powder of claim 1, further comprising an emulsion stabilizer selected from among one or more of a blend of xanthan gum, guar gum and sodium alginate; modified gum acacia; ester gum; whey protein; and green tea extract containing epigallocatechin gallate (EGCG) and epicatechin gallate (ECG).

19. A water-soluble powder, comprising:
a) a water-soluble vitamin E derivative mixture present in an amount of from between 1% and 13%, inclusive, by weight of the powder, wherein:
the water-soluble vitamin E derivative mixture is a high dimer tocopheryl poly-ethylene glycol succinate (TPGS) mixture;
the high dimer mixture comprises at least 13 wt % TPGS dimer, and up to 87 wt % TPGS monomer;
b) a mixture of sugar fatty acid ester and a binder, wherein:
the sugar fatty acid ester is sucrose fatty acid ester;
the binder is maltodextrin;
the total amount of sucrose fatty acid ester and maltodextrin in the mixture is between 36% and 60%, inclusive, by weight of the powder;
the mixture of sugar fatty acid ester and binder contains at least 7% sucrose fatty acid ester;
c) a non-polar ingredient, other than the polyalkylene glycol derivative of vitamin E, wherein:
the non-polar ingredient is a non-polar compound or contains a mixture of non-polar compounds; and
the non-polar ingredient is in an amount between 12% and 39%, inclusive, by weight of the powder; and
d) a stabilizer selected from among potassium bicarbonate, vitamin C, and mixtures thereof.

20. The powder of claim 19, wherein the water-soluble vitamin E derivative mixture contains at least 29%, by weight, water-soluble vitamin E derivative dimer.

21. The powder of claim 20, wherein the amount of dimer is greater than 29% and the total amount of dimer and monomer in the water-soluble vitamin E derivative mixture is greater than 95%, by weight.

22. The powder of claim 19, wherein the monomer in the water-soluble vitamin E derivative mixture comprises between about 30% and 69%, by weight, of the water-soluble vitamin E derivative mixture.

23. The powder of claim 1, further comprising a stabilizer, wherein:
the sugar fatty acid ester is sucrose fatty acid ester and the total amount of sucrose fatty acid ester and binder in the mixture is between 18% and 56%, inclusive, by weight of the powder;
the binder is a maltodextrin or fish collagen or whey protein or mixture thereof, and the mixture contains at least 7% sucrose fatty acid ester;
the water-soluble vitamin E derivative mixture is a high dimer TPGS mixture, in an amount between 1% and 13%, inclusive, by weight of the powder; and
the stabilizer is potassium bicarbonate or a mixture of potassium bicarbonate and vitamin C.

24. The powder of claim 23, wherein the monomer in the water-soluble vitamin E derivative mixture comprises between about 30% and 69%, by weight, of the water-soluble vitamin E derivative mixture.

25. The powder of claim 1, wherein the mixture of sugar fatty acid ester and a binder is at least 19%, 20%, 25%, 30%, 35%, 40%, 44%, 45%, 46%, 49%, 50%, or 55% inclusive, by weight of the powder.

26. The powder of claim 25, wherein the monomer comprises between or between about 35% and 65%, inclusive, by weight, of the water-soluble vitamin E derivative mixture and the dimer comprises between or between about 25% and 65%, by weight, of the water-soluble vitamin E derivative mixture, or the dimer comprises between or between about 29% and 61% or 62%, by weight, of the water-soluble vitamin E derivative mixture, and the monomer and dimer together comprise at least 70%, by weight, of the water-soluble vitamin E derivative mixture.

27. The powder of claim 25, wherein:
the polyalkylene glycol derivative of vitamin E is a tocopheryl polyethylene glycol succinate (TPGS); and
the monomer in the water-soluble vitamin E derivative mixture comprises between about 30% and 69%, by weight, of the water-soluble vitamin E derivative mixture.

28. The powder of claim 1, wherein the water-soluble vitamin E derivative mixture:
contains 29%-69%, inclusive, by weight water-soluble vitamin E derivative dimer; and/or
contains less than 65%, by weight, water-soluble vitamin E derivative monomer.

29. The powder of claim 28, wherein the vitamin E derivative is a polyalkylene glycol derivative of vitamin E that is tocopheryl polyethylene glycol succinate (TPGS).

30. The powder of claim 1, wherein the polyalkylene glycol derivative of vitamin E contains at least 30wt % and up to 55 wt % polyalkylene glycol derivative of vitamin E derivative dimer; and contains less than 70 wt % vitamin E derivative monomer.

31. The powder of claim 1, wherein:
the amount of dimer in the water-soluble vitamin E derivative mixture is greater than 29 wt %; and
the total amount of the dimer and monomer in the water-soluble vitamin E derivative mixture is at least 95 wt % of the mixture.

32. The powder of claim 1, wherein the monomer in the water-soluble vitamin E derivative mixture comprises between about 30% and 69%, by weight, of the water-soluble vitamin E derivative mixture.

* * * * *

UNITED STATES PATENT AND TRADEMARK OFFICE
CERTIFICATE OF CORRECTION

PATENT NO. : 10,016,363 B2
APPLICATION NO. : 14/866717
DATED : July 10, 2018
INVENTOR(S) : Philip J. Bromley It is certified that error appears in the above-identified patent and that said Letters Patent is hereby corrected as shown below:

On the Title Page

In Item (71) Applicant, 1st column, Line 5, please replace "Walnut" with —Pomona—;

In Item (56) References Cited, in U.S. PATENT DOCUMENTS, on page 2, 2nd column, Line 42, please replace "2611/0117184" with the Patent Publication No. —2011/0117184—;

In Item (56) References Cited, in U.S. PATENT DOCUMENTS, on page 2, 2nd column, Line 45, please replace "Bed" with the inventor —Berl—;

In Item (56) References Cited, in U.S. PATENT DOCUMENTS, please include the following reference: U.S. Patent Publication No. 2015/0173410, published Jun. 25, 2015, by inventor James et al., U.S. classification 426/72;

In Item (56) References Cited, in OTHER PUBLICATIONS, on page 5, 2nd column, Line 41, please replace "ganuna-tocotrienyl" with —gamma-tocotrienyl—;

In Item (56) References Cited, in OTHER PUBLICATIONS, on page 5, 2nd column, Line 53, please replace "inhibitorby" with —inhibitor by—.

In the Specification

At Column 28, Line 55, please replace "last (w) carbon" with —last (ω) carbon—;

At Column 58, Line 4, please replace "Type OL®)." with —Type OL®.—;

At Column 61, Line 17, please replace "Type OL®)." with —Type OL®.—;

At Column 64, Line 62, please replace "linoleic acid (18:20ω6)" with —linoleic acid (18:2ω6)—;

Signed and Sealed this
Fifteenth Day of January, 2019

Andrei Iancu
*Director of the United States Patent and Trademark Office*

CERTIFICATE OF CORRECTION (continued)
U.S. Pat. No. 10,016,363 B2

At Column 64, Line 63, please replace "gamma-linoleic acid (GLA; 18:30ω6)" with —gamma-linoleic acid (GLA; 18:3ω6)—;

At Column 66, Line 25, please replace "w (or omega, or n)" with —ω (or omega, or n)—;

At Column 66, Line 41, please replace "a carbon" with —α carbon—;

At Column 72, Line 32, please replace "18:3ω3-6" with —18:3ω-6—;

At Column 72, Line 32, please replace "18:3ω3-5" with —18:3ω-5—;

At Column 118, Line 59, please replace "DHA™ S35-0300" with —DHA™ S35-O300—;

At Column 143, Line 49, please replace "DHA™ S35-0300" with —DHA™ S35-O300—;

At Column 150, Line 38, please replace "life'sDHA™ S35-0300" with —life'sDHA™ S35-O300—;

At Column 159, Lines 2-24, please replace Table 100 with the following amended Table:

| Pre-spray emulsion containing astaxanthin (10% astaxanthin) and TPGS | | | |
|---|---|---|---|
| Ingredient | g/batch | Phase | wt% of composition |
| Water (polar solvent) | 6255.33 | Water | 56.87 |
| KHCO₃ (stabilizer) | 507.47 | Water | 4.61 |
| Vitamin C (stabilizer) | 220.00 | Water | 2.00 |
| SALADIZER® emulsifier (emulsion stabilizer) | 7.33 | Water | 0.07 |
| SFAE (co-surfactant) | 909.33 | Water | 8.27 |
| Saponin (co-emulsifier) | 26.77 | Water | 0.24 |
| Highly branched cyclic dextrin (HBCD) (binder/carrier) | 1240.43 | Water | 11.28 |
| Pre-emulsion concentrate containing astaxanthin and TPGS (Table 95 above) | 1833.33 | Oil | 16.67 |
| Totals | | | 100.00 |

—;

At Column 162, Line 18, please replace "benzylalcohol" with —benzyl alcohol—;

At Column 163, Line 22, please replace "MCT,and TPGS" with —MCT, and TPGS—.

CERTIFICATE OF CORRECTION (continued)
U.S. Pat. No. 10,016,363 B2

In the Claims

At Column 167, Lines 66-67, please replace Claim 16 with the following amended claim:
—16. The powder of claim 1, wherein the non-polar ingredient is present in an amount between 30% and 60%, by weight.—;

At Column 168, Lines 10-35, please replace Claim 19 with the following amended claim:
—19. A water-soluble powder, comprising:
    a) a water-soluble vitamin E derivative mixture present in an amount of from between 1% and 13%, inclusive, by weight of the powder, wherein:
    the water-soluble vitamin E derivative mixture is a high dimer tocopheryl polyethylene glycol succinate (TPGS) mixture; and
    the high dimer mixture comprises at least 13 wt % TPGS dimer, and up to 87 wt % TPGS monomer;
    b) a mixture of sugar fatty acid ester and a binder, wherein:
    the sugar fatty acid ester is sucrose fatty acid ester;
    the binder is maltodextrin;
    the total amount of sucrose fatty acid ester and maltodextrin in the mixture is between 36% and 60%, inclusive, by weight of the powder; and
    the mixture of sugar fatty acid ester and binder contains at least 7% sucrose fatty acid ester;
    c) a non-polar ingredient, other than the polyalkylene glycol derivative of vitamin E, wherein:
    the non-polar ingredient is a non-polar compound or contains a mixture of non-polar compounds; and
    the non-polar ingredient is in an amount between 12% and 39%, inclusive, by weight of the powder; and
    d) a stabilizer selected from among potassium bicarbonate, vitamin C, and mixtures thereof.—;

At Column 169, Lines 22-23, to Column 170, Lines 1-4, please replace Claim 28 with the following amended claim:
—28. The powder of claim 1, wherein the water-soluble vitamin E derivative mixture:
    contains 29%-69%, inclusive, by weight, water-soluble vitamin E derivative dimer; and/or
    contains less than 65%, by weight, water-soluble vitamin E derivative monomer.—;

At Column 170, Lines 8-12, please replace Claim 30 with the following amended claim:
—30. The powder of claim 1, wherein the polyalkylene glycol derivative of vitamin E contains at least 30 wt % and up to 55 wt % polyalkylene glycol derivative of vitamin E derivative dimer; and contains less than 70 wt % vitamin E derivative monomer.—.